(12) United States Patent
Mortezaei

(10) Patent No.: US 12,358,904 B2
(45) Date of Patent: *Jul. 15, 2025

(54) INHIBITORS OF TYK2

(71) Applicant: Atomwise Inc., San Francisco, CA (US)

(72) Inventor: Shahab Mortezaei, San Francisco, CA (US)

(73) Assignee: Atomwise Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/732,301

(22) Filed: Jun. 3, 2024

(65) Prior Publication Data

US 2024/0417396 A1 Dec. 19, 2024

Related U.S. Application Data

(60) Provisional application No. 63/618,980, filed on Jan. 9, 2024, provisional application No. 63/505,969, filed on Jun. 2, 2023.

(51) Int. Cl.

| C07D 413/14 | (2006.01) |
| A61K 31/506 | (2006.01) |
| A61K 31/5377 | (2006.01) |
| A61K 31/675 | (2006.01) |
| A61P 1/00 | (2006.01) |
| A61P 17/06 | (2006.01) |
| A61P 37/02 | (2006.01) |
| A61P 37/06 | (2006.01) |

(Continued)

(52) U.S. Cl.
CPC .......... *C07D 413/14* (2013.01); *A61K 31/506* (2013.01); *A61K 31/5377* (2013.01); *A61K 31/675* (2013.01); *A61P 1/00* (2018.01); *A61P 17/06* (2018.01); *A61P 37/02* (2018.01); *A61P 37/06* (2018.01); *C07D 239/48* (2013.01); *C07D 401/12* (2013.01); *C07D 401/14* (2013.01); *C07D 403/12* (2013.01); *C07D 405/14* (2013.01); *C07D 491/048* (2013.01); *C07D 491/107* (2013.01); *C07F 9/65583* (2013.01)

(58) Field of Classification Search
CPC .. C07D 413/14; C07D 401/12; C07D 401/14; C07D 403/12; C07D 405/14; C07D 491/048; C07D 491/107; C07F 9/65583; A61K 31/506; A61K 31/5377; A61K 31/675; A61P 1/00; A61P 17/06; A61P 37/02

See application file for complete search history.

(56) References Cited

U.S. PATENT DOCUMENTS

2020/0317705 A1 10/2020 Wang et al.

FOREIGN PATENT DOCUMENTS

EP 4206196 A1 * 7/2023 ............. A61P 17/06

OTHER PUBLICATIONS

U.S. Appl. No. 18/732,048, filed Jun. 3, 2024.
International Search Report and Written Opinion mailed on Oct. 16, 2024.

* cited by examiner

*Primary Examiner* — Sarah Pihonak
*Assistant Examiner* — Padmaja S Rao

(57) ABSTRACT

In exemplary embodiments, inhibitors of Tyrosine Kinase 2 (TYK2), pharmaceutical formulations comprising these compounds, methods of using these compounds to inhibit TYK2, and treat diseases such as autoimmune and inflammatory diseases are provided.

18 Claims, 26 Drawing Sheets

(51) Int. Cl.
*C07D 239/48* (2006.01)
*C07D 401/12* (2006.01)
*C07D 401/14* (2006.01)
*C07D 403/12* (2006.01)
*C07D 405/14* (2006.01)
*C07D 491/048* (2006.01)
*C07D 491/107* (2006.01)
*C07F 9/6558* (2006.01)

INHIBITORS OF TYK2

CROSS-REFERENCE TO RELATED APPLICATIONS

This U.S. patent application claims priority to Provisional Patent Application No. 63/505,969, filed on Jun. 2, 2023, and to Provisional Patent Application No. 63/618,980, filed on Jan. 9, 2024, the entire contents of which are incorporated herein for all purposes.

FIELD OF THE INVENTION

The invention resides in the field of potent and selective small molecule inhibitors of Tyrosine Kinase 2 (TYK2), pharmaceutical formulations containing these compounds and methods of using these compounds to treat or prevent a disease in which TYK2 is implicated.

BACKGROUND OF THE INVENTION

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons, and interleukins (e.g., IL-4, IL-6, IL-10, IL-11, IL-12, IL-13, L-22, IL-23, IL-27, IL-31, oncostatin M, ciliary neurotrophic factor, cardiotrophin 1, cardiotrophin-like cytokine, and LIF). The activated TYK2 then goes on to phosphorylate further signaling proteins such as members of the STAT family, including STAT, STAT2, STAT4, and STATE. These cytokines are implicated in the pathogenesis of numerous autoimmune diseases, e.g., psoriasis, inflammatory bowel disease (IBD) and lupus.

Janus kinase (JAK) is a cytoplasmic tyrosine kinase that transduces cytokine signals from membrane receptors to STAT transcription factors. Four JAK family members are recognized: JAK1, JAK2, JAK3 and TYK2. When cytokines bind to their receptors, JAK family members are autophosphorylated and/or transphos-phorylated with each other, then STATs phosphorylated, and then migrate into the nucleus to regulate transcription. JAK-STAT intracellular signal transduction is applicable to interferon, most of interleukins, and a variety of cytokines and endocrine factors, such as EPO, TPO, GH, OSM, LIF, CNTF, GM-CSF and PRL.

TYK2 is important in the signaling of type I interferons (IFNa, INFb), IL-6, IL-10, IL-12 and IL-23. Thus, TYK2 signals with other members of the JAK kinase family in the following combinations: TYK2/JAK1, TYK2/JAK2, TYK2/JAK1/JAK2. TYK2 has shown importance in the differentiation and function of multiple cell types important for inflammatory and autoimmune diseases, including natural killer cells, B and T helper cell types.

Certain autoimmune diseases are believed to be mediated by TYK2 signaling of certain proinflammatory cytokines (See e.g., J. S. Tokarski, et al., *J. Biol. Chem.*, vol. 290(17): 11061 11074 (2015); and, L. Marroqui, et al., *Diabetes*, vol. 64: 3808-3817 (2015)). Psoriasis and other autoimmune diseases, such as diabetes, are believed to be mediated by TYK2 signaling of certain proinflammatory cytokines. TYK2 is implicated as a therapeutic target for psoriasis-like skin inflammation (Ishizaki, et al., *Int Immunol.* 2014 26(5): 257-67), psoriatic arthritis (Mease et al., *Ann Rheum Dis.* 2022 81(6):815-822), and inflammatory bowel disease (IBD) (Nielsen, et al., *Trends Pharmacol Sci.* 2022 43(5): 424-436).

TYK2 mediates signaling through the IL-12 family receptors (IL-12R and IL23R). The interleukin-23 (IL-23) cytokine has been implicated as playing a crucial role in the pathogenesis of autoimmune inflammation and related diseases and disorders, such as multiple sclerosis, asthma, rheumatoid arthritis, psoriasis, and inflammatory bowel diseases (IBD), e.g., ulcerative colitis and Crohn's disease. Studies in acute and chronic mouse models of IBD revealed a primary role of IL-23R and downstream effector cytokines in disease pathogenesis.

IL-12 and IL-23, which encompass subunits p40/p35 and p40/p 19, respectively, signal through the receptor complexes of IL-12Rβ1/IL-12Rβ2 and IL-12Rβ1/IL-23R, respectively. IL-12 is essential for the differentiation of IFN-γ producing T helper (Th) 1 cells and for the development of TH 1 immune response, while IL-23 sustains the survival, expansion and effector function of Th17 cells. Activated Th17 cells produce a variety of effector cytokines, including IL-17A and IL 17F.

Inhibiting the IL-23 pathway has been shown to be efficacious in treating IL-23-related diseases and disorders. A number of antibodies that bind to IL-23 or IL-23R have been approved for the treatment of moderate to severe plaque psoriasis, active psoriatic arthritis, moderately to severely active Crohn's disease and moderately to severely active ulcerative colitis. Clinical trials in Crohn's Disease or psoriasis with briakinumab (which also target the common p40 subunit) and tildrakizumab, guselkumab, MEDI2070, and BI-655066 (which target the unique p19 subunit of IL-23) highlight the potential of IL-23 signaling blockade in treatment of human inflammatory diseases. While these findings are promising, challenges remain with respect to identifying stable and selective agents that preferentially target one or more component of the IL-23 pathway.

JAK inhibitors have been successfully used in clinical development, initially for organ transplantation rejection, but later for other immunoinflammatory indications as well, such as inflammatory bowel disease (IBD), allergic dermatitis (AD), rheumatoid arthritis (RA), psoriasis and Crohn's disease (http://clinicaltrials.gov/). TYK2 is a target for treating autoimmune and inflammatory diseases, which has been confirmed by human genetics and mouse knockout studies.

The search for potent and selective compounds useful in treating autoimmune and inflammatory diseases is ongoing. Clearly, there remains a need in the art for new therapeutics for these diseases, and agents targeting JAK family protein kinases, especially TYK2 are promising candidates. Compounds inhibiting TYK2 should be readily synthesizable in acceptable yields, stable, bioavailable and druggable with high potency, selectivity for TYK2 and excellent pharmacokinetic properties. The present disclosure sets forth such compounds and methods of using them to treat and prevent autoimmune and inflammatory diseases.

SUMMARY OF THE INVENTION

The present invention provides a novel class of potent and selective small molecule modulators of TYK2 activity. Exemplary compounds set forth in the present disclosure are potent and selective inhibitors of TYK2 and, on binding to TYK2, they reduce the activity of this kinase and, in some embodiments, this reduction in TYK2 activity results in a concomitant decrease in certain cytokine signaling, e.g. IL-23 signaling. In some embodiments, compounds are selective for TYK2 over other JAKs.

In an exemplary embodiment, the invention provides a compound according to Formula I:

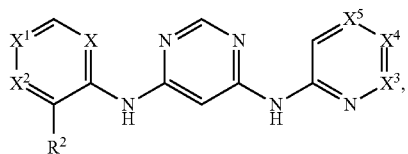

or a solvate, hydrate, pharmaceutically acceptable salt, tautomer or prodrug thereof.

In Formula I, $X^1$ is selected from N and $CR^1$. $R^1$ is a member selected from H, halogen, substituted or unsubstituted straight- or branched-chain $C_1$-$C_6$ alkyl, and substituted or unsubstituted straight- or branched-chain $C_1$-$C_6$ alkoxy. X and $X^2$ are independently selected from N and CH. $R^2$ is a member selected from:

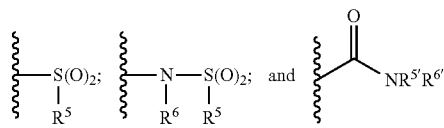

in which $R^5$ is substituted or unsubstituted alkyl, e.g., substituted or unsubstituted $C_1$-$C_6$ alkyl ($C_1$, $C_2$, $C_3$, $C_4$, $C_5$ or $C_6$). $R^{5'}$, $R^6$, and $R^{6'}$ are members independently selected from H and substituted or unsubstituted alkyl, e.g., substituted or unsubstituted $C_1$-$C_6$ alkyl. $X^3$ is selected from N and $CR^7$. $X^4$ is selected from N and $CR^8$. $X^5$ is selected from N and $CR^9$. The moieties $R^7$, $R^8$, $R^9$ and $R^{10}$ are each independently selected from H, substituted or unsubstituted $C_1$-$C_6$ alkyl ($C_1$, $C_2$, $C_3$, $C_4$, $C_5$ or $C_6$), and substituted or unsubstituted $C_1$-$C_6$ aminoalkyl ($C_1$, $C_2$, $C_3$, $C_4$, $C_5$ or $C_6$), wherein $R^7$ and $R^8$ or $R^8$ and $R^9$, together with the carbon atoms to which they are joined, are optionally joined to form a ring selected from substituted or unsubstituted cycloalkyl and substituted or unsubstituted heterocycloalkyl.

In an exemplary embodiment, when neither $R^7$ and $R^8$ nor $R^8$ and $R^9$, together with the carbons to which they are attached, is joined to form a ring, and not more than one member selected from $R^7$, $R^8$ and $R^9$ is other than H, $R^9$ does not comprise the moiety:

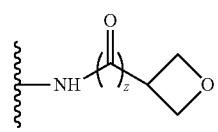

in which z is 0 or 1.

In an exemplary embodiment, when at least one member selected from $R^1$, $R^8$ and $R^9$ is Me, $R^2$ is:

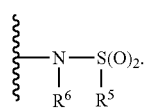

Also provided herein are pharmaceutical formulations incorporating a compound of the invention and/or a solvate, hydrate, pharmaceutically acceptable salt, tautomer or prodrug thereof, in combination with a pharmaceutically acceptable carrier.

In some embodiments, there is a provided a method of using a compound of the invention or a solvate, hydrate, pharmaceutically acceptable salt, tautomer or prodrug thereof to inhibit TYK2. The method can be performed in vitro or in vivo and generally involves contacting TYK2 with a compound of the invention which is a TYK2 inhibitor in an amount sufficient to inhibit TYK2. Exemplary methods further include detecting and/or quantifying the degree of TYK2 inhibition. In some embodiments, the inhibition takes place in the body of a subject and is the basis of a method of treating a subject in need of such treatment for a disease susceptible to treatment with a TYK2 inhibitor.

Additional objects and embodiments of the invention will be apparent from the Detailed Description which follows.

DESCRIPTION OF THE DRAWINGS

FIG. 6A-6L Exemplary compounds of the invention demonstrated dose-dependent inhibition of (A) colon weight-to-length ratio and (B) colon histopathology scores in a 7-day anti-CD40-induced mouse model of inflammatory bowel disease (IBD). (C) Representative sections of H&E-stained colon tissue show gland loss (*) and improvement in animals treated with Atomwise exemplary compound. Improvement in disease also seen with colon tissue proinflammatory cytokine/chemokine levels for (D) IFNγ (pg/mL); (E) IL-1β (pg/mL); (F) TNF-α (pg/mL); (G) IL-6 (pg/mL); (H) IL-22 (pg/mL); and (I) IP-10 (pg/mL). **$p<0.0001$; *$p<0.001$ v. Naive (two-tailed t-test); ††††$<0.0001$; †††$p<0.001$; ††$p<0.01$; †$p<0.05$ v. Vehicle (one-way ANOVA with Dunnett's multiple comparisons test).

DETAILED DESCRIPTION

A. Introduction

Figure 1A:
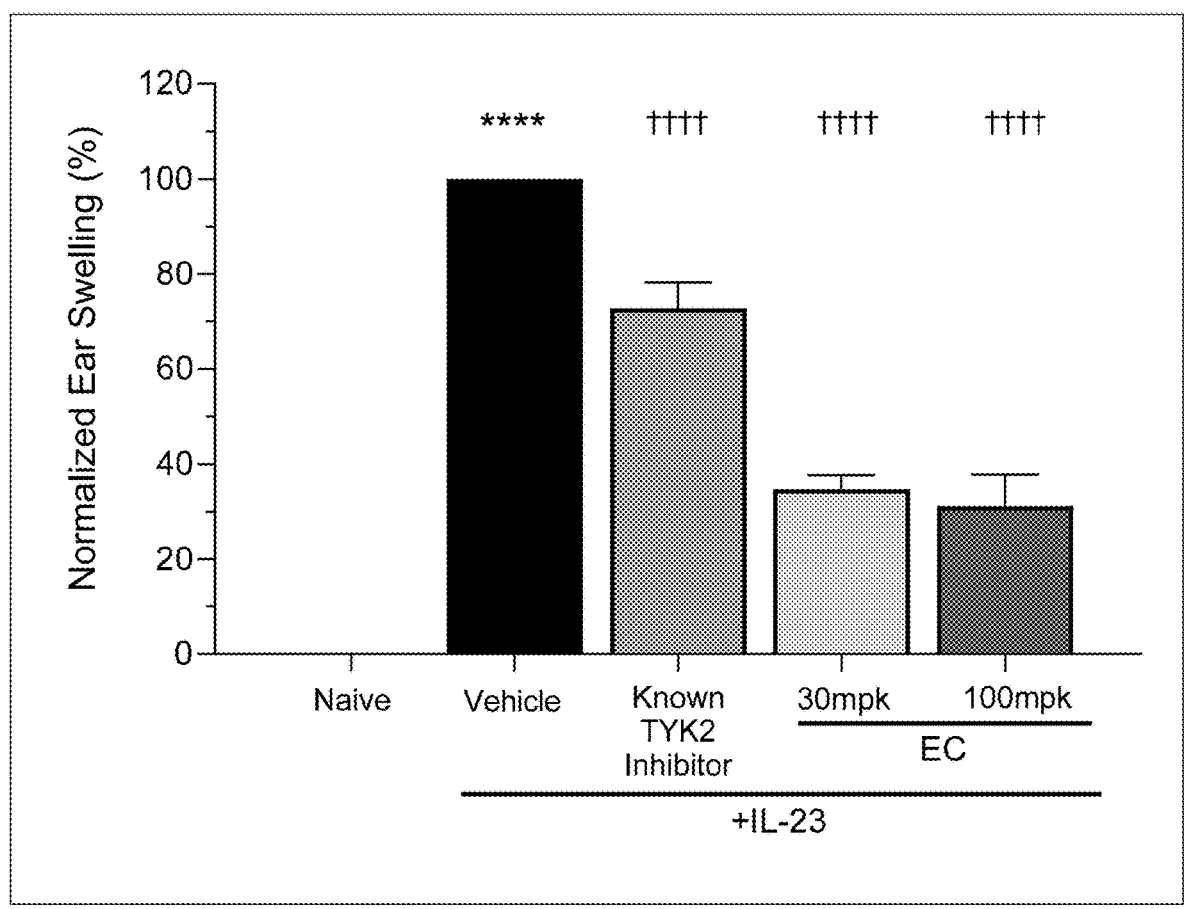
FIG. 1A-FIG. 1B. Exemplary compound (EC) of the invention demonstrated dose-dependent inhibition of ear swelling and skin IL-17A levels in an IL-23-induced PD model of inflammation. (A) Ear swelling. (B) Ear skin IL-17A. ****$p<0.0001$ v. Naive (two-tailed t-test); ††††$p<0.0001$ v. Vehicle (one-way ANOVA with Dunnett's multiple comparisons test).

The compounds of the invention, their solvates, hydrates, pharmaceutically acceptable salts, tautomers and prodrugs thereof, are potent and selective TYK2 inhibitors. The TYK2 kinase inhibiting activity and the selectivity towards this target of the compounds provided herein are readily determined using art-recognized assays such as the assays set forth in the Examples hereinbelow.

The TYK2 kinase-modulating activities of the compounds can be leveraged to advantage in various methods of treating diseases where TYK2 plays a role in the development or progression of the disease, e.g., autoimmune and inflammatory diseases. The various uses of the compounds typically involve bringing the compounds in an therapeutically effective amount into contact with a TYK2 kinase, thereby modulating the activity of TYK2. The modulation of the TYK2 kinase may take place either in vitro to study a disease or treatment thereof, or in vivo to treat a disease. In an exemplary embodiment, the modulating is inhibiting a TYK2 kinase.

The potency and selectivity of the compounds of the invention are beneficial in chronic and acute treatment of inflammatory and autoimmune diseases. In the context of the present invention, an autoimmune disease is a disease which is at least partially provoked by an immune reaction of the body against its own components, for example proteins, lipids or DNA. In various embodiments, the disease treated is mediated by IL-12 and/or IL-23, and TYK2 plays a role in the signaling pathway of these cytokines.

Exemplary diseases treatable by compounds, formulations and methods of the invention include, without limitation, Psoriasis, Plaque Psoriasis, Psoriatic Arthritis, Inflammatory Bowel Disease (e.g., Crohn's and Ulcerative Colitis), and Lupus.

Psoriasis is a chronic inflammatory dermatosis that affects approximately 2% of the population. It is characterized by red, scaly skin patches that are usually found on the scalp, elbows, and knees, and may be associated with severe arthritis. The lesions are caused by abnormal keratinocyte proliferation and infiltration of inflammatory cells into the dermis and epidermis (Schon et al, 2005, *New Engl. J. Med.* 352: 1899-1912).

The suitability of the compounds for use in treating psoriasis can be determined by testing the effect of the compounds on imiquimod-induced psoriasis-like skin inflammation in mice: see for example Mori et al., *Kobe J. Med. Sci.*, Vol. 62, No. 4, pp. E79-E88, 2016; van der Fits et al., *The Journal of Immunology*, 2009; 182: 5836-5845; and Lin et al., PLOS ONEIDOI:10.1371/journal.pone. 0137890 Sep. 10, 2015. Thus, imiquimod can be applied topically to mice (for example to the back skin of a mouse) to induce psoriasis-like inflammation and scaling, and a comparison made between the levels of inflammation and scaling in mice (or areas of the body of mice) that have also been treated with a compound of the invention or a control containing no imiquimod.

Inflammatory bowel disease (IBD) is characterized by a chronic relapsing intestinal inflammation. IBD is sub-divided into Crohn's disease and ulcerative colitis phenotypes. Crohn's disease involves most frequently the terminal ileum and colon, is transmural and discontinuous. In contrast, in ulcerative colitis, the inflammation is continuous and limited to rectal and colonic mucosal layers. In approximately 10% of cases confined to the rectum and colon, definitive classification of Crohn's disease or ulcerative colitis cannot be made and are designated indeterminate colitis'. Both diseases include extraintestinal inflammation of the skin, eyes, or joints. Neutrophil-induced injuries may be prevented by the use of neutrophil migration inhibitors (Asakura et al., 2007, *World J. Gastroenterol.* 13(15):2145-9).

Systemic lupus erythematosus (SLE) is a chronic inflammatory disease generated by T cell-mediated B-cell activation, which results in glomerulonephritis and renal failure. Human SLE is characterized at early stages by the expansion of long-lasting autoreactive CD4+ memory cells (D'Cruz et al, 2007, Lancet 369(9561):587-596).

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, and components have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For instance, a first property could be termed a second property, and, similarly, a second property could be termed a first property, without departing from the scope of the present disclosure. The first property and the second property are both properties, but they are not the same property.

B. Definitions

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, but do not preclude the presence or addition of one or more other features, integers, steps, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range off ±20%, ±10%, ±5%, or ±1% of a given value. Where particular values are described in the application and claims, unless otherwise stated, the term "about" means within an acceptable error range for the particular value. The term "about" can have the meaning as commonly understood by one of ordinary skill in the art. The term "about" can refer to ±10%. The term "about" can refer to ±5%.

"Substantially", as used herein refers to at least about 80%, at least about 85%, at least about 90%, at least about 92%, at least about 94%, at least about 96%, at least about 98%, or at least about 90% of the total weight of the ganglioside in the composition.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

In an exemplary embodiment, a pharmaceutical formulation of the invention comprises a therapeutically effective amount a compound of the invention. As used herein, "therapeutically effective amount" or "an amount effective" refers to an amount of the pharmaceutical formulation of the invention which is effective, upon single or multiple dose administrations to a subject, in treating a cell, or curing, alleviating, relieving or improving a symptom of a disorder. An effective amount of the composition may vary according to factors such as the disease state, age, sex, and weight of the individual, and the ability of the compound to elicit a desired response in the individual. The term also applies to a dose that will induce a particular response in target cells. The specific dose will vary depending on the particular compounds chosen, the dosing regimen to be followed, whether the compound is administered in combination with other compounds, timing of administration, the tissue to which it is administered, and the physical delivery system in which the compound is carried. An effective amount is also one in which any toxic or detrimental effects of the composition are outweighed by the therapeutically beneficial effects.

In various embodiments, the term "therapeutically effective amount" relates to an amount of compound which, when administered according to a desired dosing regimen, provides the desired therapeutic effect. Dosing may occur at intervals of minutes, hours, days, weeks, months or years or continuously over any one of these periods. Exemplary suitable dosages may lie within the range of about 0.1 ng per kg of body weight to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

In an exemplary embodiment, a composition of the invention is of use when administered to a subject in an effective amount to prevent a disease or symptoms of a disease. As used herein, the terms "prevent" or "preventing" as used in the context of the administration of an agent to a subject, refers to subjecting the subject to a regimen, e.g., the administration of a pharmaceutical formulation of the invention such that the onset of at least one symptom of the disorder is delayed as compared to what would be seen in the absence of the regimen.

In various embodiments, the compositions of the invention are administered to a subject to treat or prevent a disease or the symptoms of a disease. As used herein, the term "subject" is intended to include human and non-human animals. Exemplary human subjects include a human patient having a disorder, e.g., a disorder described herein, or a normal subject. The term "non human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

As used herein, the terms "treat" or "treating" a subject having a disorder refers to subjecting the subject to a regimen, e.g., the administration of a pharmaceutical formulation of the invention such that at least one symptom of the disorder is cured, healed, alleviated, relieved, altered, remedied, ameliorated, or improved. Treating includes administering an amount effective to alleviate, relieve, alter, remedy, ameliorate, improve or affect the disorder or the symptoms of the disorder. The treatment may inhibit deterioration or worsening of a symptom of a disorder.

In various embodiments, a compound of the invention is administered to a subject in a therapeutically effective amount, achieving a therapeutic effect, thereby treating or preventing a disease, ameliorating or preventing the symptoms of the disease. As used herein, the terms "administer," "administration" or "administering" refer to (1) providing, giving, dosing, and/or prescribing by either a health practitioner or authorized agent, or under the direction a health practitioner or authorized agent, according to the disclosure; and/or (2) putting into, taking or consuming by the mammal, according to the disclosure.

In various embodiments, the compound of the invention is co-administered to a subject with a second compound, either of the invention or otherwise, to achieve, augment or regulate the therapeutic effect of the compound of the invention. The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

The neutral forms of the compounds are optionally regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

It will be appreciated that any compound that is a prodrug of the compound the invention is also within the scope and spirit of the invention. Thus, the compound of the invention can be administered to a subject in the form of a pharmaceutically acceptable prodrug. The term "prodrug" is used in its broadest sense and encompasses those derivatives that are converted in vivo to the compound of the invention. Such derivatives would readily occur to those skilled in the art. Other texts which generally describe prodrugs (and the preparation thereof) include: *Design of Prodrugs*, 1985, H. Bundgaard (Elsevier); *The Practice of Medicinal Chemistry*, 1996, Camille G. Wermuth et al., Chapter 31 (Academic Press); and *A Textbook of Drug Design and Development*, 1991, Bundgaard et al., Chapter 5, (Harwood Academic Publishers). For example, the N atom on the oxindole ring may be reacted with an acid (for example acetic acid). An exemplary pharmaceutically acceptable prodrug is a pharmaceutically acceptable ester.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The term "solvate" refers to a physical association of one of the present compounds with one or more solvent molecules. This physical association includes hydrogen bonding. In certain instances, the solvate will be capable of isolation, for example when one or more solvent molecules are incorporated in the crystal lattice of a crystalline solid. "Solvate" encompasses both solution-phase and insoluble solvates. Exemplary solvates include, without limitation, hydrates, hemihydrates, ethanolates, hemiethanolates, n-propanolates, iso-propanolates, 1-butanolates, 2-butanolate, and solvates of other physiologically acceptable solvents, such as the Class 3 solvents described in the International Conference on Harmonization (ICH), Guide for Industry, Q3C Impurities: Residual Solvents (1997). The compounds as herein described also include each of their solvates and mixtures thereof.

"Pharmaceutically acceptable excipients", as used herein, refers to recognized additives in pharmaceutical formulations of active pharmaceutical agents. Exemplary excipients include buffers, salts (e.g., NaCl), sugars, sugar alcohols, and amino acids (e.g., arginine, glycine). They are generally safe for administering to humans according to established governmental standards, including those promulgated by the United States Food and Drug Administration. Representative, non-limiting examples include, agar-agar, algins, calcium carbonate, carboxymethylcellulose, cellulose, gums, low substituted hydroxypropylcellulose, sodium starch glycolate, carbonate, calcium phosphate, dibasic calcium phosphate, tribasic calcium sulfate, calcium carboxymethylcellulose, cellulose, dextrin derivatives, dextrin, dextrose, fructose, lactitol, lactose, magnesium carbonate, magnesium oxide, maltitol, maltodextrins, maltose, sorbitol, starch, sucrose, sugar, xylitol, calcium stearate, ethyl oleate, ethyl laureate, glycerin, glyceryl palmitostearate, mannitol, poloxamer, glycols, sodium benzoate, and sodium lauryl sulfate.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). $^2H$ may be present in a compound of the invention at one or more site. All isotopic variations of the compounds of the present invention, whether radioactive or not, are intended to be encompassed within the scope of the present invention.

The expression "pharmaceutically acceptable carrier, adjuvant, or vehicle" and equivalent expressions, refer to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sothic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester, prodrug, salt of a prodrug, or other derivative of a compound of the present description that, upon administration to a recipient, is capable of providing, either directly or indirectly, a compound of the present description or an inhibitory active metabolite or residue thereof.

An "exemplary compound" or "EC", as this term is used herein refers to compounds which were test articles in the Examples, and for which data are provided in the Figures appended hereto, and to closely structurally related analogues such as compounds 1-80 displayed in Table 1.

A "known TYK2 inhibitor" refers to a small molecule therapeutic recognized in the art as an inhibitor of TYK2 and having been demonstrated to have favorable biological, pharmacological and, in certain examples, therapeutic properties in indications in which TYK2 inhibition is implicated.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

The compounds and method of the invention are particularly useful in treating or preventing inflammatory diseases and autoimmune diseases. An "inflammatory disease" as used herein is a disease in which lymphoproliferation contributes to tissue or organ damage leading to disease. For instance, excessive T-cell proliferation at the site of a tissue or organ will cause damage to the tissue or organ. Inflammatory processes are well known in the art and have been described extensively in medical textbooks (See, e.g., Harrison's Principles of Experimental Medicine, 13th Edition, McGraw-Hill, Inc., N.Y.). An "autoimmune disease" is a disease which is at least partially provoked by an immune reaction of the body against its own compo-nents, for example proteins, lipids or DNA.

In an exemplary embodiment, the present invention provides a method for treating or preventing an inflammatory process, involving administering to a subject suffering from an inflammatory process a therapeutically effective amount of a compound of the invention.

Many diseases are associated with abnormalities of the inflammatory process.

"Alkyl" refers to a straight or branched hydrocarbon chain radical consisting solely of carbon and hydrogen atoms, containing no unsaturation, having from one to ten carbon atoms (e.g., ($C_{1-10}$)alkyl or $C_{1-10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where alkyl and aryl are as disclosed herein and which are optionally substituted by one or more of the substituents described as suitable substituents for alkyl and aryl respectively.

"Alkylheteroaryl" refers to an -(alkyl)heteroaryl radical where alkyl and heteroaryl are as disclosed herein and which are optionally substituted by one or more of the substituents described as suitable substituents for alkyl and heteroaryl respectively.

"Alkylheterocycloalkyl" refers to an -(alkyl)heterocycloalkyl radical where alkyl and heterocycloalkyl are as disclosed herein and which are optionally substituted by one or more of the substituents described as suitable substituents for alkyl and heterocycloalkyl respectively.

"Alkenyl" or "alkene" refers to a straight or branched hydrocarbon chain radical group consisting solely of carbon and hydrogen atoms, containing at least one double bond, and having from two to ten carbon atoms (i.e., ($C_{2-10}$) alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —SC(O)R$^a$, —N(R$^a$)$_2$, —C(O)R$^a$, —C(O)OR$^a$, —C(O)SR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S (O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" or "alkyne" refers to a straight or branched hydrocarbon chain radical group consisting solely of carbon and hydrogen atoms, containing at least one triple bond, having from two to ten carbon atoms (i.e., (C$_{2-10}$)alkynyl or C$_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or —PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Aromatic" or "aryl" or "Ar," by itself or as part of another substituent, refers to an aromatic ring system (e.g., aromatic radical) which has at least one ring having a conjugated pi electron system which is carbocyclic (e.g., phenyl, fluorenyl, and naphthyl). Aryl groups can have any suitable number of carbon ring atoms and any suitable number of rings. Aryl groups can include any suitable number of carbon ring atoms, such as C$_6$, C$_7$, C$_8$, C$_9$, C$_{10}$, C$_{11}$, C$_{12}$, C$_{13}$, C$_{14}$, C$_{15}$ or C$_{16}$, as well as C$_{6-12}$, C$_{6-10}$, or C$_{6-14}$. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" (e.g., C$_6$-C$_{10}$ aromatic or C$_6$-C$_{10}$ aryl) refers to each integer in the given range; e.g., "6 to 10 ring atoms" means that the aryl group may consist of 6 ring atoms, 7 ring atoms, etc., up to and including 10 ring atoms. Aryl groups can be monocyclic, fused (i.e., rings which share adjacent pairs of ring atoms) to form bicyclic (e.g., benzocyclohexyl) or tricyclic groups or polycyclic groups, or linked by a bond to form a biaryl group. Representative aryl groups include phenyl, naphthyl and biphenyl. Other aryl groups include benzyl, having a methylene linking group. Unless stated otherwise specifically in the specification, an aryl moiety is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)W, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)—OR$^a$ (where t is 1 or 2), —S(O)$_t$N(R$^a$)$_2$ (where t is 1 or 2), or —PO(OR$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein, and which are optionally substituted by one or more of the substituents described as suitable substituents for aryl and alkyl respectively.

The term "aryloxy" refers to the group —O-aryl.

The term "substituted aryloxy" refers to aryloxy wherein the aryl substituent is substituted (i.e., —O-(substituted aryl)). Unless stated otherwise specifically in the specification, the aryl moiety of an aryloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —SC(O)R$^a$, —N(R$^a$)$_2$, —C(O)R$^a$, —C(O)OR$^a$, —C(O)SR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)—OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e., (C$_{3-10}$)cycloalkyl or C$_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, acylsulfonamido, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO(OR$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C=O)— attached through the carbonyl carbon wherein the alkoxy group has the indicated number of carbon atoms. Thus a (C$_{1-6}$)alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —SC(O)R$^a$, —N(R$^a$)$_2$, —C(O)R$^a$, —C(O)OR$^a$, —C(O)SR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —SC(O)R$^a$, —N(R$^a$)$_2$, —C(O)R$^a$, —C(O)OR$^a$, —C(O)SR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or —PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —SC(O)R$^a$, —N(R$^a$)$_2$, —C(O)R$^a$, —C(O)OR$^a$, —C(O)SR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or —PO$_3$(R$^a$)$_2$, where each R$^a$ is independently hydrogen, alkyl, fluoroalkyl, cathocyclyl, carbocyclylalkyl, aryl, aralkyl, heterocycloalkyl, heterocycloalkylalkyl, heteroaryl or heteroarylalkyl.

"Acylsulfonamide" refers a —S(O)$_2$—N(R$^a$)—C(=O)— radical, where R$^a$ is hydrogen, alkyl, fluoroalkyl, carbocyclyl, carbocyclylalkyl, aryl, aralkyl, heterocycloalkyl, heterocycloalkylalkyl, heteroaryl or heteroarylalkyl. Unless stated otherwise specifically in the specification, an acylsulfonamide group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —SC(O)R$^a$, —N(R$^a$)$_2$, —C(O)R$^a$, —C(O)OR$^a$, —C(O)SR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S —S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or 1PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ substituents other than hydrogen, they can be combined with the nitrogen atom to form a 4-, 5-, 6- or 7-membered ring. For example, —N(Rah is intended to include, but is not limited to, -pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or —PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^a$, and NR$^a$R$^a$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)NI$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$_2$ of —NI$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or —PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heteroaryl" or "heteroaromatic" or "HetAr" or "Het" refers to a 5- to 18-membered aromatic radical (e.g., $C_5$-$C_{13}$ heteroaryl) that includes one or more ring heteroatoms selected from nitrogen, oxygen, and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_2$R$^a$ (where t is 1 or 2), —S(O)$_t$R$^a$ (where t is 1 or 2), —S(O)—OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heterocycloalkyl" refers to a stable 3- to 18-membered non-aromatic ring radical that comprises two to twelve carbon atoms and from one to six heteroatoms selected from nitrogen, oxygen, and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic, or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)—OR$^a$ (where t is 1 or 2), —S(O)$_t$N(R$^a$)$_2$ (where t is 1 or 2), or —PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., $C_1$-$C_4$ heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —SC(O)R$^a$, —N(R$^a$)$_2$, —C(O)R$^a$, —C(O)OR$^a$, —C(O)SR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroarylalkyl" refers to a moiety having an aryl moiety, as described herein, connected to an alkylene moiety, as described herein, wherein the connection to the remainder of the molecule is through the alkylene group.

"Oxa" refers to the —O— radical.

"Oxo" refers to the =O radical.

"Nitro" refers to the —NO$_2$ radical.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

"Moiety" refers to a specific segment or functional group of a molecule of the invention. Chemical moieties are often recognized chemical entities embedded in or appended to a molecule.

"Isomers" are different compounds of the invention that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either I or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as I or (S). The present chemical entities, pharmaceutical compositions and methods are meant to include all such possible isomers, including racemic mixtures, optically pure forms and intermediate mixtures. Optically active I- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer of a compound of the invention relative to the other enantiomer. For example, if a compound, which may potentially have an I- or an (S)-isomeric configuration, is present as a racemic mixture, the enantiomeric purity is about 50% with respect to either the I- or (S)-isomer. If that compound has one isomeric form predominant over the other, for example, 80% (S)-isomer and 20% I-isomer, the enantiomeric purity of the compound with respect to the (S)-isomeric form is 80%. The enantiomeric purity of a compound of the invention can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In some embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York (1981); E. L. Eliel, Stereochemistry of Carbon Compounds, McGraw-Hill, New York (1962); and E. L. Eliel and S. H. Wilen, Stereochemistry of Organic Compounds, Wiley-Interscience, New York (1994).

The terms "enantiomerically enriched" and "non-racemic," as used herein, refer to compositions of compounds of the invention in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the I-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Tautomers" are structurally distinct isomers of compounds of the invention that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of 32yridine-4-ol and 32yridine-4 (1H)-one tautomers.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

"Solvate" refers to a compound in physical association with one or more molecules of a pharmaceutically acceptable solvent.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, Protective Groups in Organic Synthesis, Third Edition, John Wiley & Sons, New York (1999).

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, 33yridine33, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

For the avoidance of doubt, it is intended herein that particular features (for example integers, characteristics, values, uses, diseases, formulae, compounds, or groups) described in conjunction with a particular aspect, embodiment or example of the invention are to be understood as applicable to any other aspect, embodiment or example described herein unless incompatible therewith. Thus, such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

When ranges are used herein to describe, for example, physical or chemical properties such as molecular weight or chemical formulae, all combinations and subcombinations of ranges and specific embodiments therein are intended to be included.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" 34yridines any element, step or material other than those specified In the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All embodiments of the invention can, in the alternative, be more specifically defined by any of the transitional terms "comprising," "consisting essentially of," and "consisting of." The term "comprising" (and related terms such as "comprise" or "comprises" or "having" or "including") includes those embodiments such as, for example, an embodiment of any composition of matter, method or process that "consist of" or "consist essentially of" the described features.

C. The Embodiments

1. The Compounds

In an exemplary embodiment, the invention provides a compound according to Formula I:

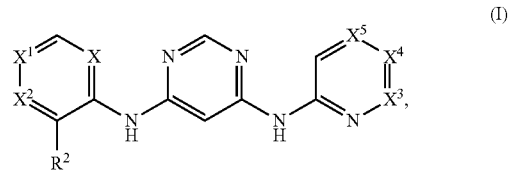

or a solvate, hydrate, pharmaceutically acceptable salt, tautomer or prodrug thereof.

In Formula I, $X^1$ is selected from N and $CR^1$. $R^1$ is a member selected from H, halogen, substituted or unsubstituted straight- or branched-chain $C_1$-$C_6$ alkyl, and substituted or unsubstituted straight- or branched-chain $C_1$-$C_6$ alkoxy. X and $X^2$ are independently selected from N and CH. $R^2$ is a member selected from:

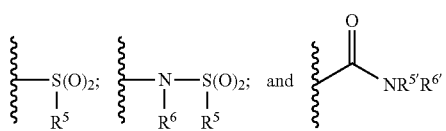

in which $R^5$ is substituted or unsubstituted alkyl, e.g., substituted or unsubstituted $C_1$-$C_6$ alkyl ($C_1$, $C_2$, $C_3$, $C_4$, $C_5$ or $C_6$). $R^{5'}$, $R^6$, and $R^{6'}$ are members independently selected from H and substituted or unsubstituted alkyl, e.g., substituted or unsubstituted $C_1$-$C_6$ alkyl. $X^3$ is selected from N and $CR^7$. $X^4$ is selected from N and $CR^8$. $X^5$ is selected from N and $CR^9$. The moieties $R^7$, $R^8$, $R^9$ and $R^{10}$ are each independently selected from H, substituted or unsubstituted $C_1$-$C_6$ alkyl ($C_1$, $C_2$, $C_3$, $C_4$, $C_5$ or $C_6$), and substituted or unsubstituted $C_1$-$C_6$ aminoalkyl ($C_1$, $C_2$, $C_3$, $C_4$, $C_5$ or $C_6$), wherein $R^7$ and $R^8$ or $R^8$ and $R^9$, together with the carbon atoms to which they are joined, are optionally joined to form a ring selected from substituted or unsubstituted cycloalkyl and substituted or unsubstituted heterocycloalkyl.

In an exemplary embodiment, when neither $R^7$ and $R^8$ nor $R^8$ and $R^9$, together with the carbons to which they are attached, is joined to form a ring, and not more than one member selected from $R^7$, $R^8$ and $R^9$ is other than H, $R^9$ does not comprise the moiety:

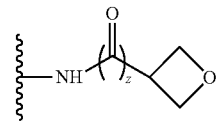

in which z is 0 or 1.

In an exemplary embodiment, when at least one member selected from $R^7$, $R^8$ and $R^9$ is Me, $R^2$ is:

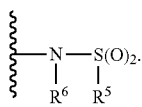

Also provided herein are pharmaceutical formulations incorporating a compound of the invention and/or a solvate, hydrate, pharmaceutically acceptable salt, tautomer or prodrug thereof, in combination with a pharmaceutically acceptable carrier.

In some embodiments, $R^2$ is is $S(O)_2Me$.

In an exemplary embodiment, X is N; $X^1$ and $X^2$ are CH; and $X^3$ and $X^4$ are $CR^7$ and $CR^8$, respectively.

In some embodiments, $R^1$ is fluoro.

In an exemplary embodiment, when neither $R^7$ and $R^8$ nor $R^8$ and $R^9$, together with the carbons to which they are attached, is joined to form a ring, and not more than one member selected from $R^7$, $R^8$ and $R^9$ is other than H, $R^9$ does not comprise the moiety:

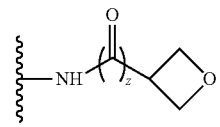

in which z is 0 or 1.

In an exemplary embodiment, when at least one member selected from $R^7$, $R^8$ and $R^9$ is Me, $R^2$ is:

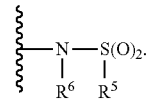

In various embodiments, $X^3$, $X^4$ and $X^5$ are $CR^7$, $CR^8$ and $CR^9$, respectively.

In some embodiments, at least one of $CR^7$, $CR^8$ and $CR^9$ comprises a ring system selected from a monocyclic or bicyclic ring system with 1 or 2 heteroatoms and 4, 5, 6, or 7 carbon atoms. The ring system optionally includes an oxygen, a nitrogen or both an oxygen and a nitrogen.

In son embodiments, in which $R^7$, $R^8$ and $R^9$ are independently select rd from H,

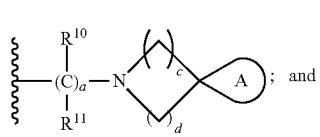

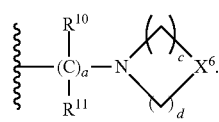

One or more carbon atom of a ring in Formula II or Formula III is optionally substituted with a member independently selected from halogen, and substituted or unsubstituted alkyl. The index a is selected from the integers 0 and 1. $R^{10}$ and $R^{11}$ are independently selected from H, halogen and substituted or unsubstituted $C_1$-$C_6$ alkyl. The indices c and d are independently selected from the integers 0, 1, 2, 3 and 4 with the proviso that the sum c+d is selected from the integers 3, 4, 5, and 6. A is a ring system selected from substituted or unsubstituted cycloalkyl and substituted or unsubstituted heterocylcoalkyl. $X^6$ is selected from O, $NR^{12}$, and $CR^{12}R^{13}$ in which $R^{12}$ and $R^{13}$ are independently selected from H and substituted or unsubstituted alkyl.

In various embodiments at least one of $R^7$, $R^8$ and $R^9$ is selected from Formula II and III. In an exemplary embodiment, not more than one, or not more than two of $R^7$, $R^8$ and $R^9$ is selected from Formula II or Formula III. In certain embodiments, not more than one, or not more than two of $R^7$, $R^8$ and $R^9$ is H.

In an exemplary embodiment, there is provided a compound according to Formula IV:

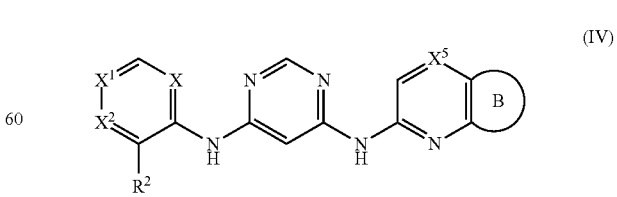

wherein ring system B is cycloalkyl substituted with at least one moiety selected from Formula II and Formula III. Ring system B is substituted or unsubstituted cycloalkyl or substituted or unsubstituted heterocycloalkyl, and is optionally selected from substituted or unsubstituted cyclopentylamine and substituted or unsubstituted cyclohexylamine.
In an exemplary embodiment, there is provided a compound of the invention in which $R^7$, $R^8$ and $R^9$ are independently selected from:
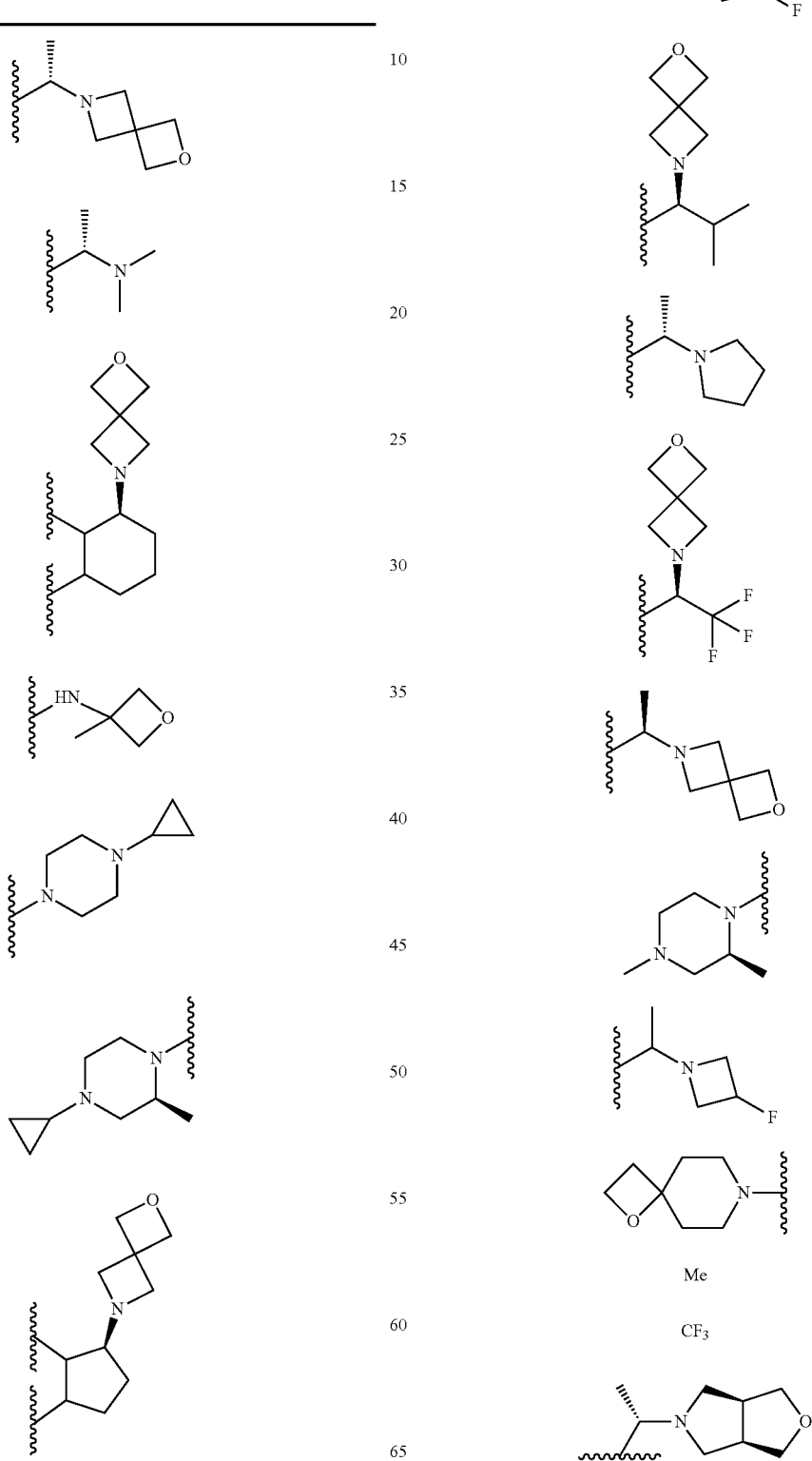

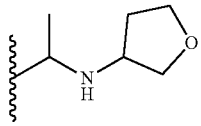 [SMILES: *C(C)NC1CCOC1]
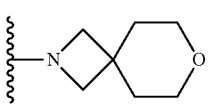
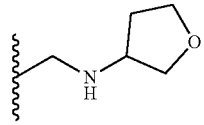 [SMILES: *CNC1CCOC1]
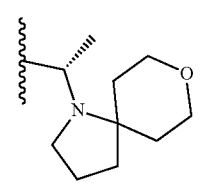 [SMILES: *[C@H](C)N1CCCC12CCOCC2]
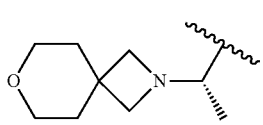 [SMILES: *[C@H](C)N1CC2(CCOCC2)C1]
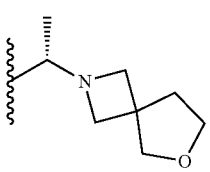 [SMILES: *[C@H](C)N1CC2(CCOC2)C1]
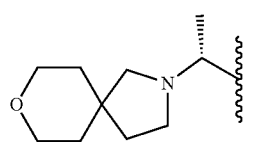 [SMILES: *[C@@H](C)N1CCC2(CCOCC2)C1]
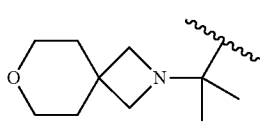 [SMILES: *C(C)(C)N1CC2(CCOCC2)C1]
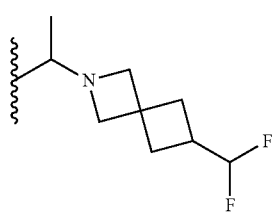 [SMILES: *C(C)N1CC2(CC(C(F)F)C2)C1]
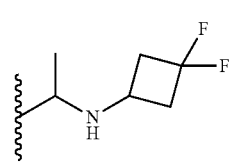 [SMILES: *C(C)NC1CC(F)(F)C1]
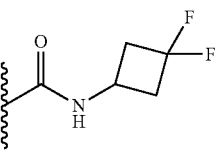 [SMILES: *C(=O)NC1CC(F)(F)C1]
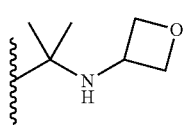 [SMILES: *C(C)(C)NC1COC1]
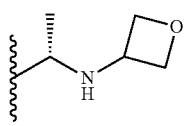
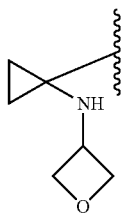 [SMILES: *C1(NC2COC2)CC1]
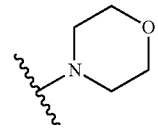
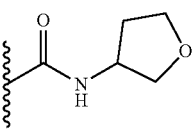 [SMILES: *C(=O)NC1CCOC1]
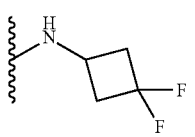 [SMILES: *NC1CC(F)(F)C1]
In various embodiments, there is provided a compound according to Formula V:
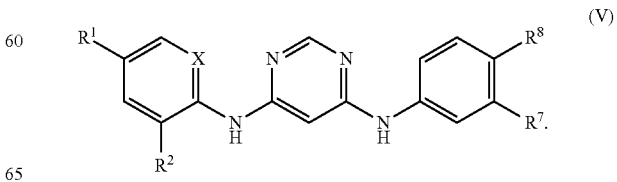

In an exemplary embodiment, there is provided a compound according to Formula VI:

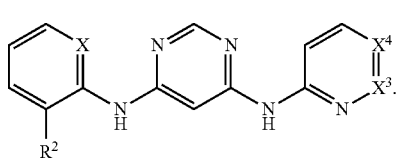
(VI)

X is selected from N and CH. $R^2$ is selected from:

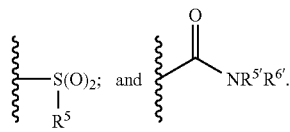

$R^5$ is $C_1$-$C_6$ alkyl. $R^{5'}$, $R^6$, and $R^{6'}$ are members independently selected from H and $C_1$-$C_6$ alkyl. $X^3$ and $X^4$ are $CR^7$, and $CR^a$, respectively. $R^7$ and $R^8$ are independently selected from H and

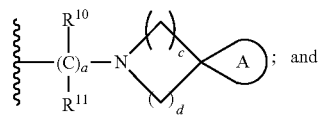
(II)

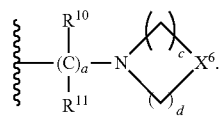
(III)

One or more carbon atom of a ring in Formula II or Formula III is optionally substituted with a member independently selected from halogen, and substituted or unsubstituted alkyl. The index a is selected from the integers 0 and 1. $R^{10}$ and $R^{11}$ are independently selected from H, halogen and substituted or unsubstituted $C_1$-$C_6$ alkyl. The indices c and d are independently selected from the integers 0, 1, 2, 3 and 4 with the proviso that the sum c+d is selected from the integers 3, 4, 5, and 6. A is a ring system selected from substituted or unsubstituted cycloalkyl and substituted or unsubstituted heterocylcoalkyl. $X^6$ is selected from O, $NR^{12}$, and $CR^{12}R^{13}$ in which $R^{12}$ and $R^{13}$ are independently selected from H and substituted or unsubstituted alkyl.

In various embodiments, the invention provides a compound according to Formula VI, wherein $R^9$ does not comprise the moiety:

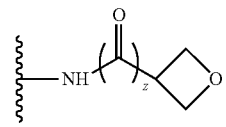

in which z is selected from 0 and 1.

In an exemplary embodiment one of $R^{10}$ and $R^{11}$ is $CF_3$.

In various embodiments, there is provided a compound of Formula Ib:

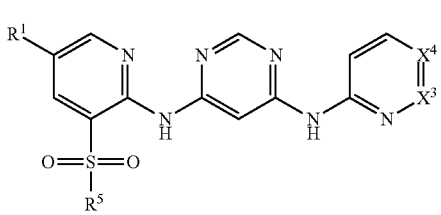
(Ib)

wherein $R^1$ is a member selected from H, halogen, substituted or unsubstituted straight- or branched-chain $C_1$-$C_6$ alkyl, and substituted or unsubstituted straight- or branched-chain $C_1$-$C_6$ alkoxy; $R^5$ is $C_1$-$C_6$ alkyl; $X^3$ is selected from N and $CR^7$; $X^4$ is selected from N and $CR^8$; $R^7$, and $R^8$, are independently selected from H, substituted or unsubstituted $C_1$-$C_6$ alkyl, and substituted or unsubstituted $C_1$-$C_6$ aminoalkyl, wherein $R^7$ and $R^8$, together with the carbon atoms to which they are joined, are optionally joined to form a ring selected from substituted or unsubstituted cycloalkyl and substituted or unsubstituted heterocycloalkyl, wherein, when $R^7$ and $R^8$, together with the carbons to which they are attached, are not joined to form a ring not more than one member selected from $R^7$, and $R^8$ and $R^9$ is other than H.

In an exemplary embodiment, there is provided a compound according to Formula Ib, wherein $CR^8$ comprises a ring system selected from a monocyclic or bicyclic ring system with 1 or 2 heteroatoms and 4, 5, 6, or 7 carbon atoms.

In some embodiments, there is provided a compound according to Formula Ib wherein the ring system includes an oxygen and a nitrogen.

In some embodiments, there is provided a compound according to Formula Ib wherein $R^8$ is selected from H,

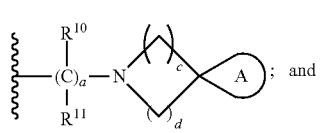
(II)

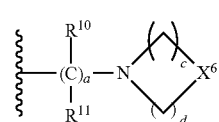
(III)

wherein A is a ring system selected from substituted or unsubstituted cycloalkyl and substituted or unsubstituted heterocycloalkyl, wherein one or more carbon atom is substituted with halogen; $R^{10}$ and $R^{11}$ are independently selected from H, halogen and substituted or unsubstituted $C_1$-$C_6$ alkyl; a is selected from the integers 0 and 1; c and d are independently selected from the integers 0, 1, 2, 3 and 4 with the proviso that the sum c+d is selected from the integers 3, 4, 5, and 6; and $X^6$ is selected from O, $NR^{12}$, and $CR^{12}R^{13}$, in which $R^{12}$ and $R^{13}$ are independently selected from H, halogen, and substituted or unsubstituted alkyl.

In some embodiments, there is provided a compound according to Formula Ib wherein $R^{13}$ is selected from H and halogen.

In various embodiments, there is provided a compound according to Formula IV:

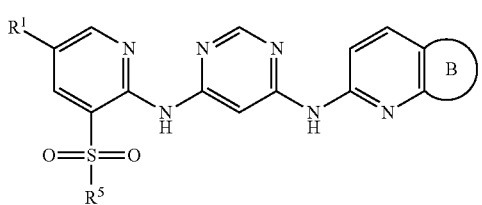

wherein ring system B is cycloalkyl substituted with at least one moiety selected from Formula II and Formula III.

In some embodiments, there is provided a compound according to Formula Ib wherein wherein ring system B is selected from substituted or unsubstituted cyclopentyl amine and substituted or unsubstituted cyclohexylamine.

Exemplary compounds of the invention include those of the formula:

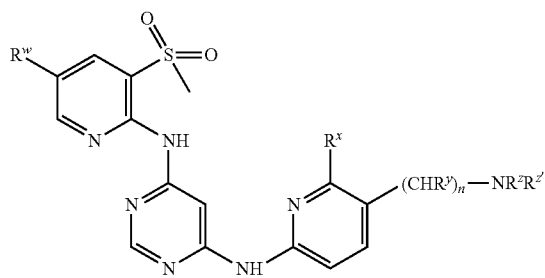

in which $R^w$ is selected from H and halogen; $R^x$ is H, or $C_1$-$C_3$ alkyl, which optionally bonds with $R^y$ to form a 5- or 6-membered cycloalkyl ring fused to the pyridyl ring; $R^y$ is H, Me, or a bond with $R^x$; the index n is selected from 0, 1, 2, and 3; $R^z$ is H or, with $R^{z'}$, which is $C_1$-$C_3$ alkyl, and the nitrogen to which both $R^z$ and $R^{z'}$ are bound, forms a first 3-, 4-, or 5-member substituted or unsubstituted heterocyclic ring. In an exemplary compound, the heterocyclic ring is substituted with a second 3-, 4-, or 5-member substituted or unsubstituted heterocyclic ring. In an exemplary compound, the first and second heterocyclic ring are in a spiro configuration. In an exemplary compound, the second heterocyclic ring includes an oxygen atom.

An exemplary compound of the invention has a ligand efficiency in the TYK-JH2 binding assay of at least about 0.39 (⅜ ⅜ ⅜).

An exemplary compound of the invention has a potency towards TYK2 of less than about 1000 nm, preferably less than about 500 nm, more preferably less than about 250 nm, and still more preferably less than about 100 nm, less than about 50 nm, less than about 25 nm or less than about 10 nm.

An exemplary compound of the invention has a potency against TYK2 of less than about 100 nm (IL-12/pSTAT4), and a cellular selectivity for TYK2 over JAK 1/2 of greater than about 10,000 nM (IL-6/pSTAT3). An exemplary compound of the invention exhibits a ligand efficiency of greater than about 0.39 (TYK-JH2 binding assay) and a potency against TYK2 of less than about 100 nm (IL-12/pSTAT4), or a cellular selectivity for TYK2 of greater than about 10,000 nM (IL-6/pSTAT3, or GM-CSF/pSTAT5).

An exemplary compound of the invention is characterized by a $C_{max}$ of at least about 1500 (ng/mL). An exemplary compound of the invention is characterized by an AUCinf (hr*ng/mL) of at least about 2000. In some embodiments, the compound has a T½ of greater than about one hour, e.g., greater than about 1.5 h. Exemplary compounds of the invention can be demonstrated to have these properties in a mouse PO PK experiment with dosing at about 10-15 mg/kg. An exemplary compound of the invention is characterized by two or more of these parameters having the enumerated quantities.

An exemplary compound of the invention has similar or improved properties in one or more of the assays set forth herein relative to one or more known TYK2 inhibitors at an equivalent dosage. Exemplary known TYK2 inhibitors useful as comparators with the exemplary compounds of the invention include ritlecitinib, deucravacitinib, upadacitinib, and abrocitinib.

Exemplary compounds having the properties set forth above are the exemplary compound test articles in the examples and figures incorporated herein.

As will be apparent to one of skill in the art, an exemplary compound of the invention can have the above enumerated properties and parameters in any combination. The examples provided above are merely illustrative and are not limiting.

In various embodiments, the invention provides a compound selected from those set forth in Table 1.

TABLE 1

| TYK2 inhibitors |
| --- |

| Compound No. | Structure |
| --- | --- |
| 1 | 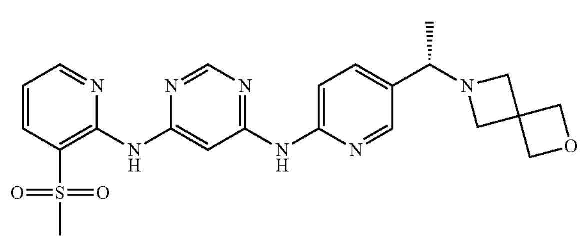 [SMILES: C[C@@H](c1ccc(Nc2cc(Nc3ncccc3S(C)(=O)=O)ncn2)nc1)N1CC2(COC2)C1] |

TABLE 1-continued
TYK2 inhibitors
| Compound No. | Structure |
|---|---|
| 2 | 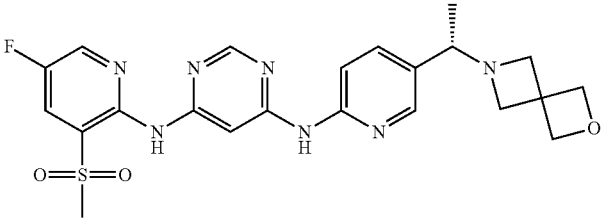 |
| 3 | 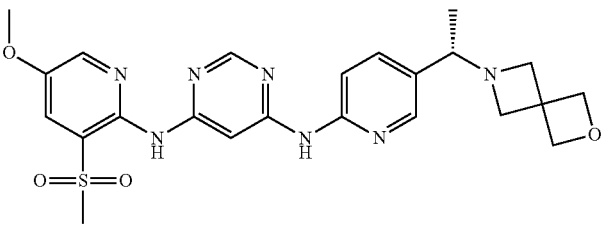 [SMILES: C[C@@H](c1ccc(Nc2cc(Nc3ncc(F)cc3S(C)(=O)=O)ncn2)nc1)N1CC2(COC2)C1] |
| 4 | 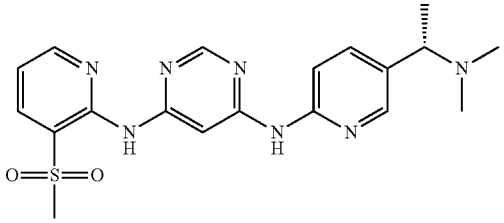 [SMILES: C[C@@H](c1ccc(Nc2cc(Nc3ncccc3S(C)(=O)=O)ncn2)nc1)N(C)C] |
| 5 | 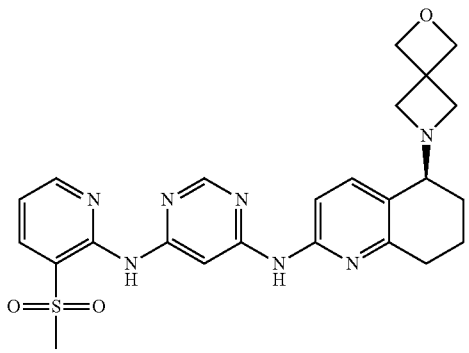 [SMILES: CS(=O)(=O)c1cccnc1Nc1cc(Nc2ccc3c(n2)CCC[C@@H]3N2CC3(COC3)C2)ncn1] |
| 6 | 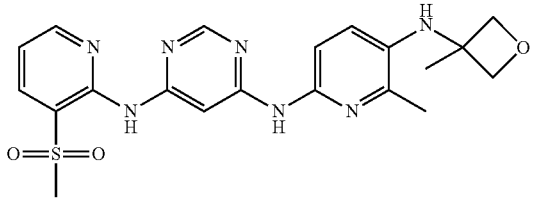 [SMILES: Cc1nc(Nc2cc(Nc3ncccc3S(C)(=O)=O)ncn2)ccc1NC1(C)COC1] |
| 7 | 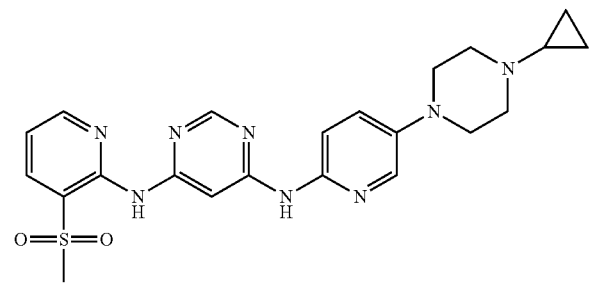 [SMILES: CS(=O)(=O)c1cccnc1Nc1cc(Nc2ccc(N3CCN(C4CC4)CC3)cn2)ncn1] |

TABLE 1-continued
TYK2 inhibitors
| Compound No. | Structure |
|---|---|
| 8 | 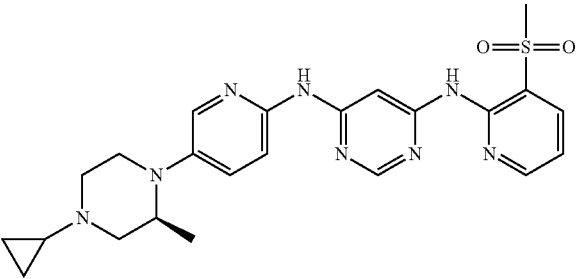 [SMILES: C[C@H]1CN(C2CC2)CCN1c1ccc(Nc2cc(Nc3ncccc3S(C)(=O)=O)ncn2)nc1] |
| 9 | 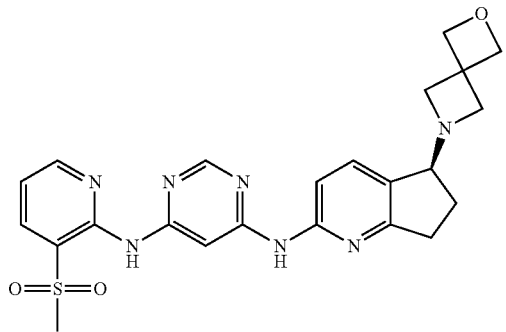 [SMILES: CS(=O)(=O)c1cccnc1Nc1cc(Nc2ccc3c(n2)CC[C@@H]3N2CC3(COC3)C2)ncn1] |
| 10 | 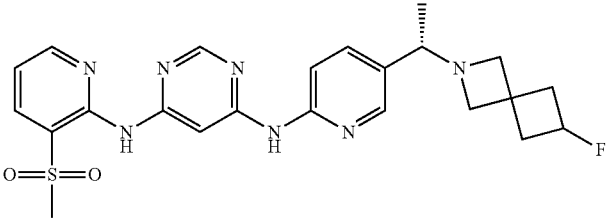 [SMILES: C[C@@H](c1ccc(Nc2cc(Nc3ncccc3S(C)(=O)=O)ncn2)nc1)N1CC2(CC(F)C2)C1] |
| 11 | 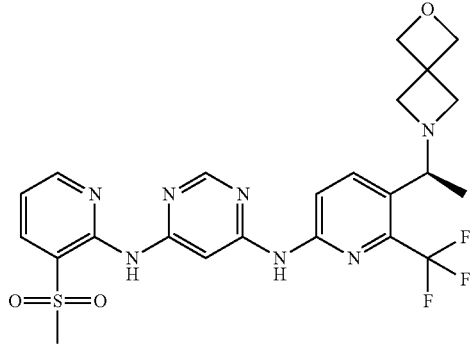 [SMILES: C[C@@H](c1ccc(Nc2cc(Nc3ncccc3S(C)(=O)=O)ncn2)nc1C(F)(F)F)N1CC2(COC2)C1] |
| 12 | 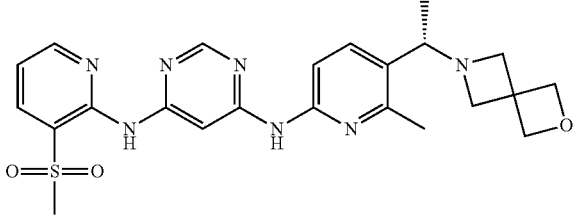 [SMILES: Cc1nc(Nc2cc(Nc3ncccc3S(C)(=O)=O)ncn2)ccc1[C@H](C)N1CC2(COC2)C1] |

TABLE 1-continued
TYK2 inhibitors
| Compound No. | Structure |
|---|---|
| 13 | 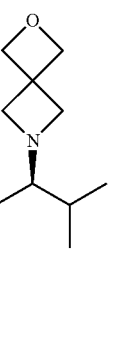 |
| 14 | 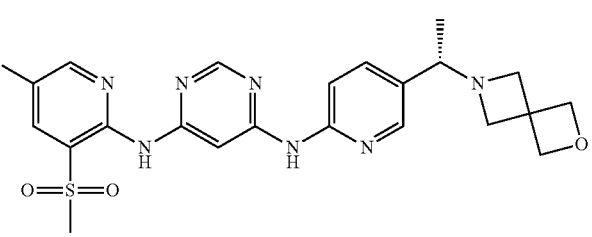 |
| 15 | 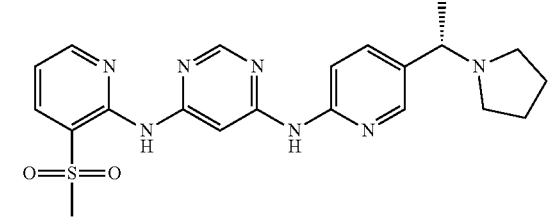 [SMILES: C[C@@H](c1ccc(Nc2cc(Nc3ncccc3S(C)(=O)=O)ncn2)nc1)N1CCCC1] |
| 16 | 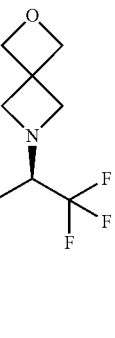 |
| 17 | 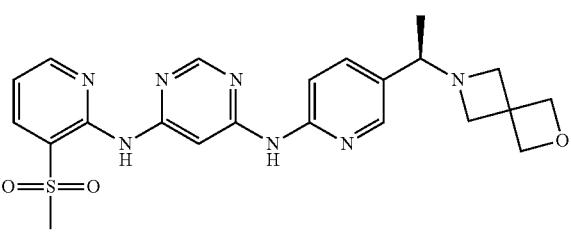 [SMILES: C[C@H](c1ccc(Nc2cc(Nc3ncccc3S(C)(=O)=O)ncn2)nc1)N1CC2(COC2)C1] |

TABLE 1-continued

TYK2 inhibitors

| Compound No. | Structure |
|---|---|
| 18 | 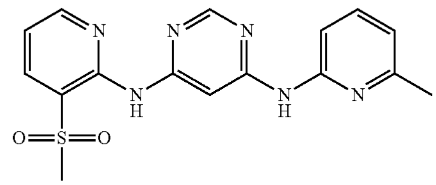 [SMILES: Cc1cccc(Nc2cc(Nc3ncccc3S(C)(=O)=O)ncn2)n1] |
| 19 | 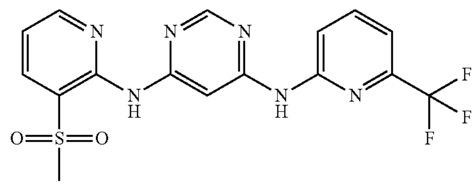 [SMILES: CS(=O)(=O)c1cccnc1Nc1cc(Nc2cccc(C(F)(F)F)n2)ncn1] |
| 20 | 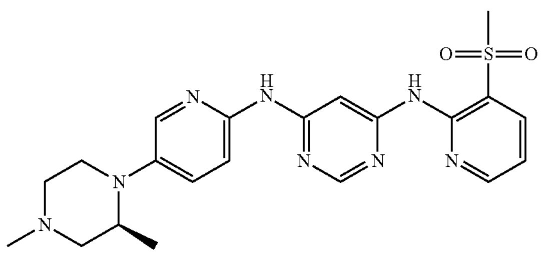 [SMILES: C[C@H]1CN(C)CCN1c1ccc(Nc2cc(Nc3ncccc3S(C)(=O)=O)ncn2)nc1] |
| 21 | 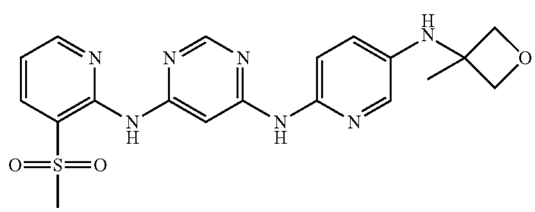 [SMILES: CC1(Nc2ccc(Nc3cc(Nc4ncccc4S(C)(=O)=O)ncn3)nc2)COC1] |
| 22 | 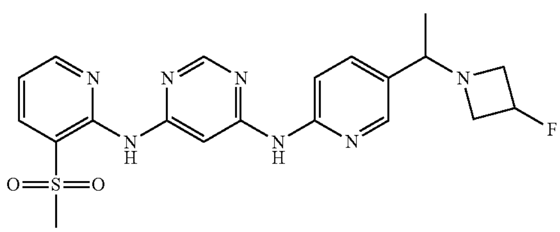 [SMILES: CC(c1ccc(Nc2cc(Nc3ncccc3S(C)(=O)=O)ncn2)nc1)N1CC(F)C1] |
| 23 | 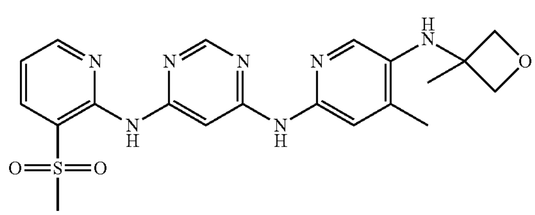 [SMILES: Cc1cc(Nc2cc(Nc3ncccc3S(C)(=O)=O)ncn2)ncc1NC1(C)COC1] |
| 24 | 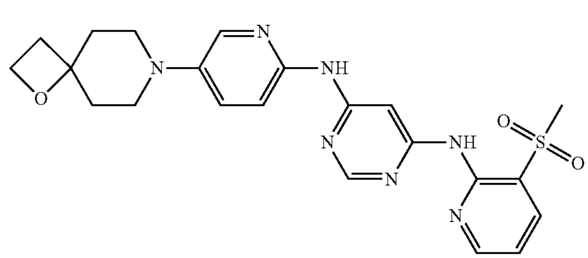 [SMILES: CS(=O)(=O)c1cccnc1Nc1cc(Nc2ccc(N3CCC4(CCO4)CC3)cn2)ncn1] |

TABLE 1-continued

TYK2 inhibitors

| Compound No. | Structure |
|---|---|
| 25 | 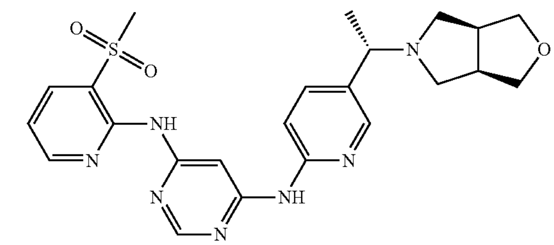 [SMILES: C[C@@H](c1ccc(Nc2cc(Nc3ncccc3S(C)(=O)=O)ncn2)nc1)N1C[C@H]2COC[C@H]2C1] |
| 26 | 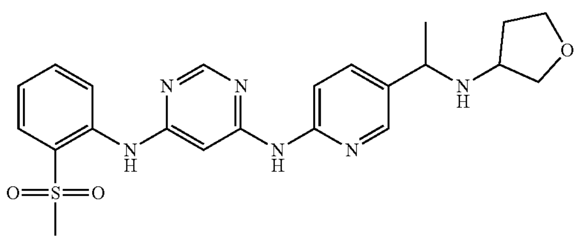 [SMILES: CC(NC1CCOC1)c1ccc(Nc2cc(Nc3ccccc3S(C)(=O)=O)ncn2)nc1] |
| 27 | 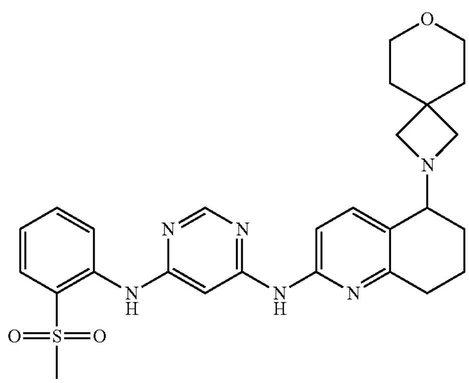 [SMILES: CS(=O)(=O)c1ccccc1Nc1cc(Nc2ccc3c(n2)CCCC3N2CC3(CCOCC3)C2)ncn1] |
| 28 | 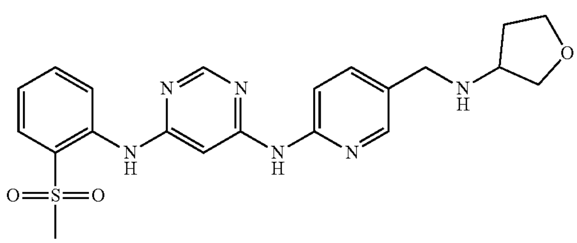 [SMILES: CS(=O)(=O)c1ccccc1Nc1cc(Nc2ccc(CNC3CCOC3)cn2)ncn1] |
| 29 | 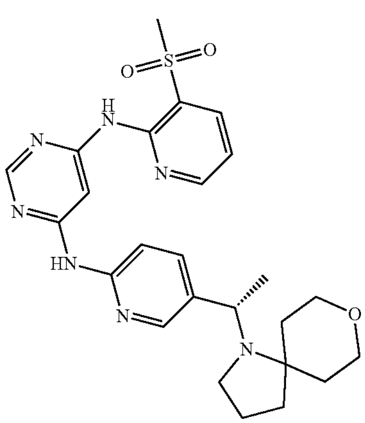 [SMILES: C[C@@H](c1ccc(Nc2cc(Nc3ncccc3S(C)(=O)=O)ncn2)nc1)N1CCCC12CCOCC2] |

TABLE 1-continued

TYK2 inhibitors

| Compound No. | Structure |
|---|---|
| 30 | 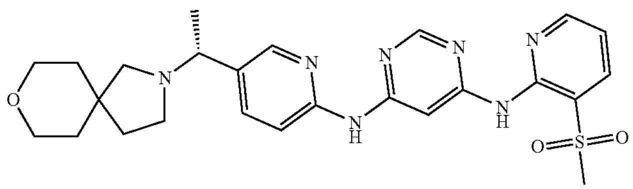 [SMILES: C[C@H](c1ccc(Nc2cc(Nc3ncccc3S(C)(=O)=O)ncn2)nc1)N1CCC2(CCOCC2)C1] |
| 31 | 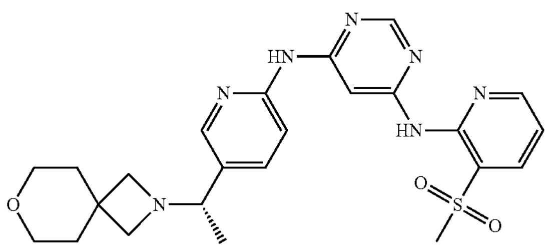 [SMILES: C[C@@H](c1ccc(Nc2cc(Nc3ncccc3S(C)(=O)=O)ncn2)nc1)N1CC2(CCOCC2)C1] |
| 32 | 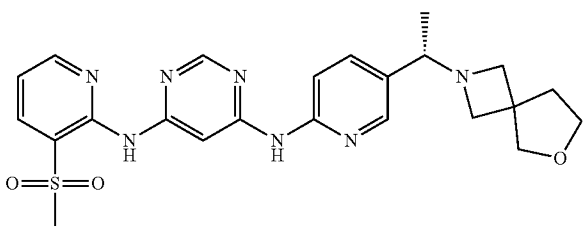 [SMILES: C[C@@H](c1ccc(Nc2cc(Nc3ncccc3S(C)(=O)=O)ncn2)nc1)N1CC2(CCOC2)C1] |
| 33 | 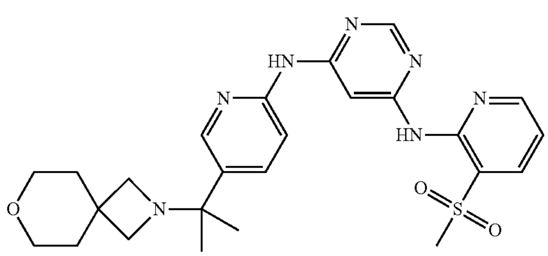 [SMILES: CC(C)(c1ccc(Nc2cc(Nc3ncccc3S(C)(=O)=O)ncn2)nc1)N1CC2(CCOCC2)C1] |
| 34 | 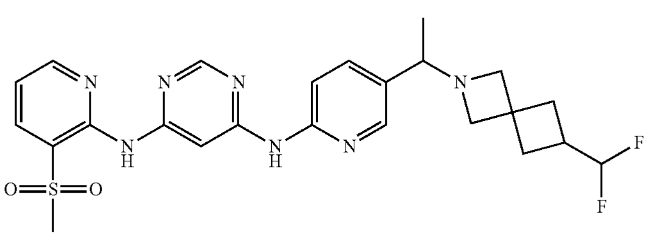 [SMILES: CC(c1ccc(Nc2cc(Nc3ncccc3S(C)(=O)=O)ncn2)nc1)N1CC2(CC(C(F)F)C2)C1] |
| 35 | 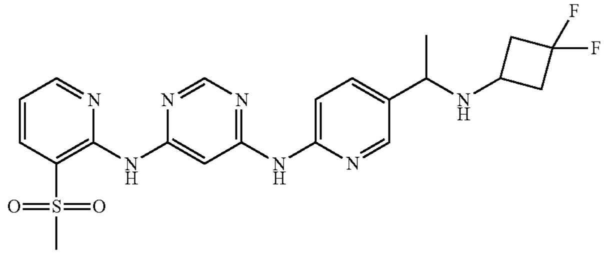 [SMILES: CC(NC1CC(F)(F)C1)c1ccc(Nc2cc(Nc3ncccc3S(C)(=O)=O)ncn2)nc1] |

TABLE 1-continued
TYK2 inhibitors
| Compound No. | Structure |
|---|---|
| 36 | 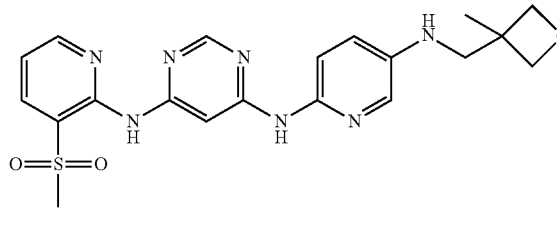 |
| 37 | 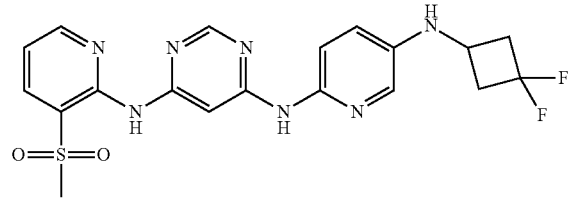 [SMILES: CS(=O)(=O)c1cccnc1Nc1cc(Nc2ccc(NC3CC(F)(F)C3)cn2)ncn1] |
| 38 | 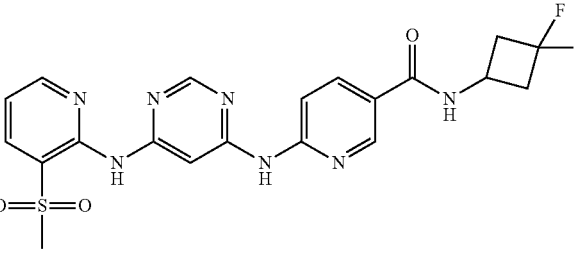 |
| 39 | 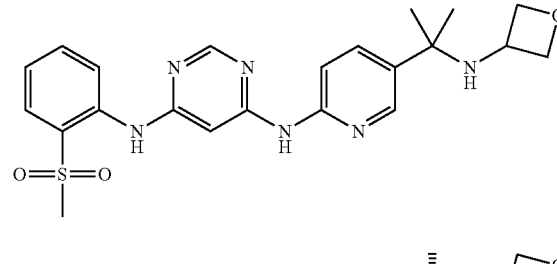 |
| 40 | 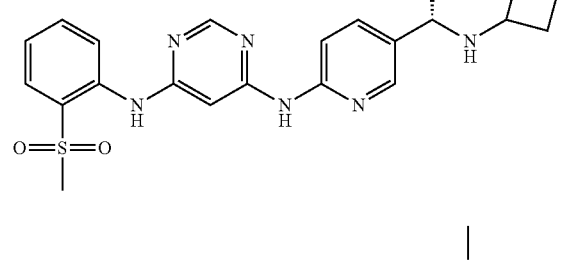 |
| 41 | 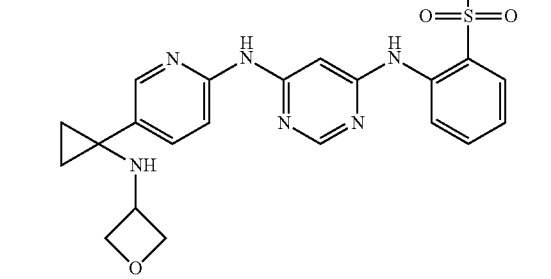 |

TABLE 1-continued

TYK2 inhibitors

| Compound No. | Structure |
|---|---|
| 42 | 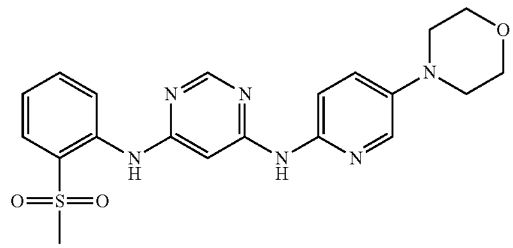 [SMILES: CS(=O)(=O)c1ccccc1Nc1cc(Nc2ccc(N3CCOCC3)cn2)ncn1] |
| 43 | 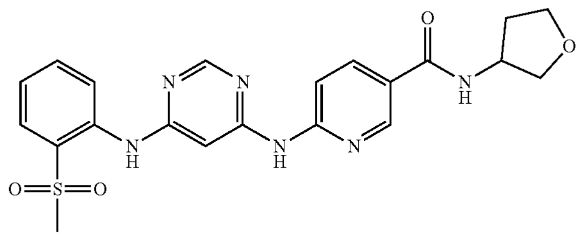 [SMILES: CS(=O)(=O)c1ccccc1Nc1cc(Nc2ccc(C(=O)NC3CCOC3)cn2)ncn1] |
| 44 | 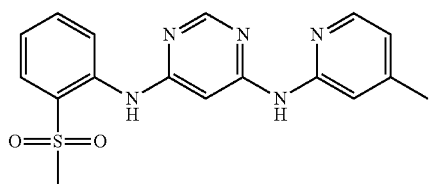 [SMILES: Cc1ccnc(Nc2cc(Nc3ccccc3S(C)(=O)=O)ncn2)c1] |
| 45 | 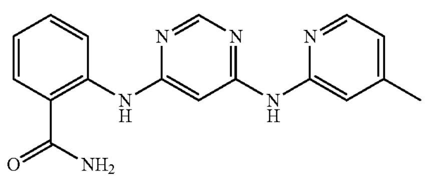 [SMILES: Cc1ccnc(Nc2cc(Nc3ccccc3C(N)=O)ncn2)c1] |
| 46 | 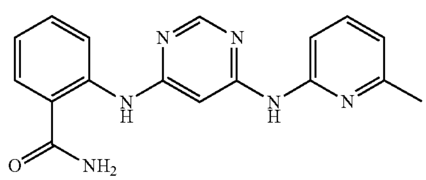 [SMILES: Cc1cccc(Nc2cc(Nc3ccccc3C(N)=O)ncn2)n1] |
| 47 | 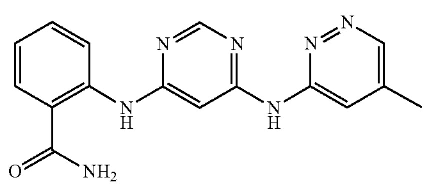 [SMILES: Cc1cnnc(Nc2cc(Nc3ccccc3C(N)=O)ncn2)c1] |
| 48 | 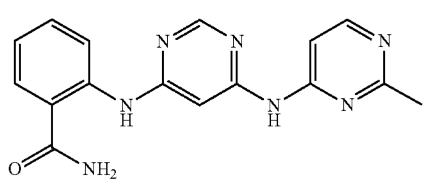 [SMILES: Cc1nccc(Nc2cc(Nc3ccccc3C(N)=O)ncn2)n1] |

TABLE 1-continued

TYK2 inhibitors

| Compound No. | Structure |
|---|---|
| 49 | 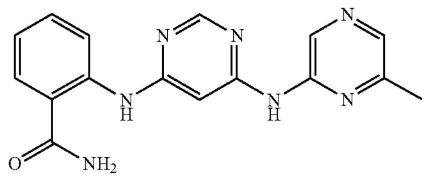 [SMILES: Cc1cncc(Nc2cc(Nc3ccccc3C(N)=O)ncn2)n1] |
| 50 | 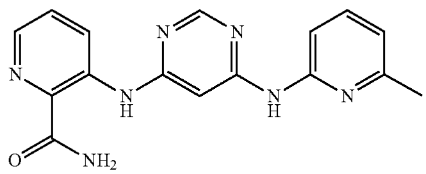 |
| 51 | 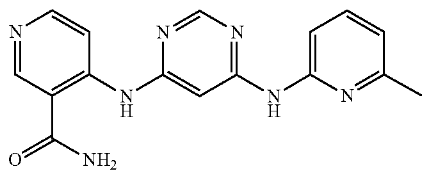 [SMILES: Cc1cccc(Nc2cc(Nc3ccncc3C(N)=O)ncn2)n1] |
| 52 | 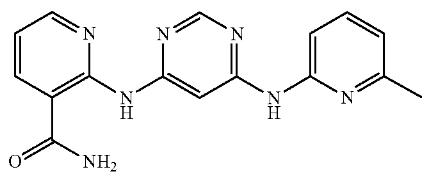 [SMILES: Cc1cccc(Nc2cc(Nc3ncccc3C(N)=O)ncn2)n1] |
| 53 | 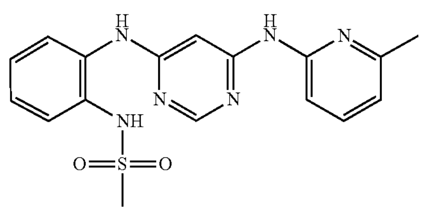 [SMILES: Cc1cccc(Nc2cc(Nc3ccccc3NS(C)(=O)=O)ncn2)n1] |
| 54 | 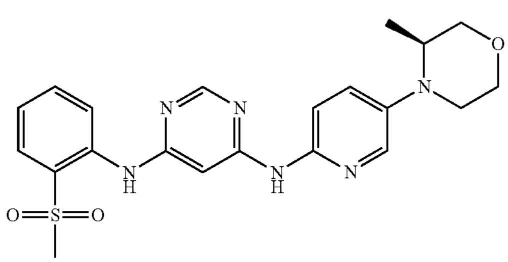 [SMILES: C[C@H]1COCCN1c1ccc(Nc2cc(Nc3ccccc3S(C)(=O)=O)ncn2)nc1] |
| 55 | 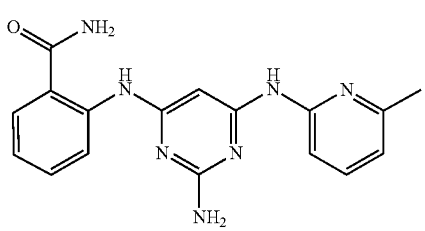 [SMILES: Cc1cccc(Nc2cc(Nc3ccccc3C(N)=O)nc(N)n2)n1] |

TABLE 1-continued

TYK2 inhibitors

| Compound No. | Structure |
|---|---|
| 56 | 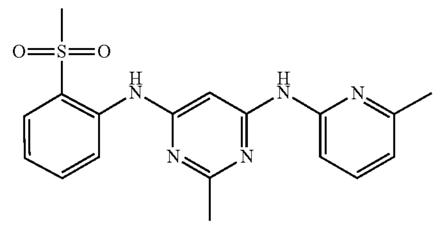 [SMILES: Cc1cccc(Nc2cc(Nc3ccccc3S(C)(=O)=O)nc(C)n2)n1] |
| 57 | 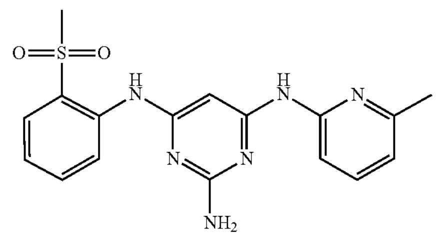 [SMILES: Cc1cccc(Nc2cc(Nc3ccccc3S(C)(=O)=O)nc(N)n2)n1] |
| 58 | 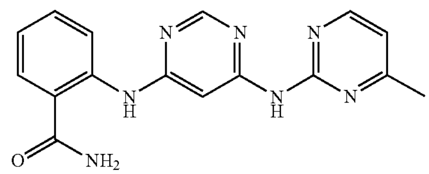 [SMILES: Cc1ccnc(Nc2cc(Nc3ccccc3C(N)=O)ncn2)n1] |
| 59 | 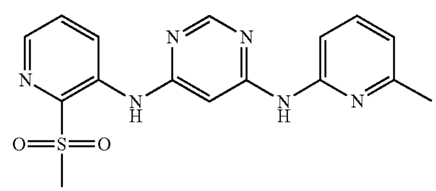 [SMILES: Cc1cccc(Nc2cc(Nc3cccnc3S(C)(=O)=O)ncn2)n1] |
| 60 | 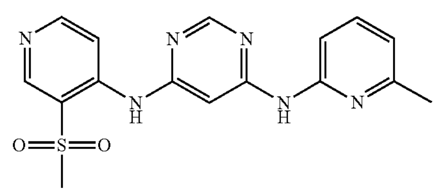 [SMILES: Cc1cccc(Nc2cc(Nc3ccncc3S(C)(=O)=O)ncn2)n1] |
| 61 | 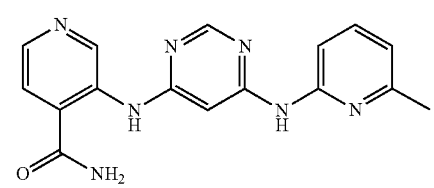 [SMILES: Cc1cccc(Nc2cc(Nc3cnccc3C(N)=O)ncn2)n1] |
| 62 | 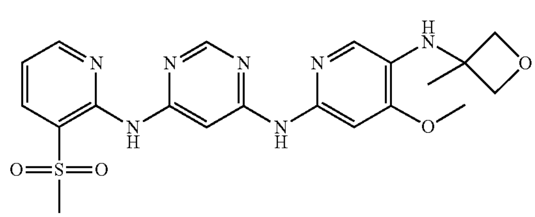 [SMILES: COc1cc(Nc2cc(Nc3ncccc3S(C)(=O)=O)ncn2)ncc1NC1(C)COC1] |

TABLE 1-continued
TYK2 inhibitors
| Compound No. | Structure |
|---|---|
| 63 | 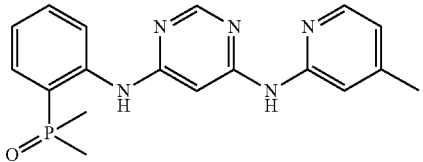 [SMILES: Cc1ccnc(Nc2cc(Nc3ccccc3P(C)(C)=O)ncn2)c1] |
| 64 | 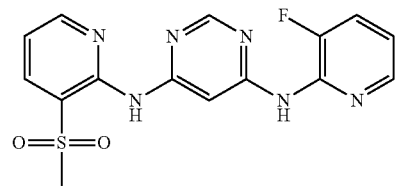 [SMILES: CS(=O)(=O)c1cccnc1Nc1cc(Nc2ncccc2F)ncn1] |
| 65 | 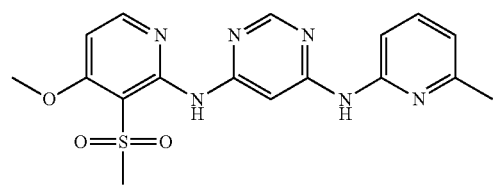 |
| 66 | 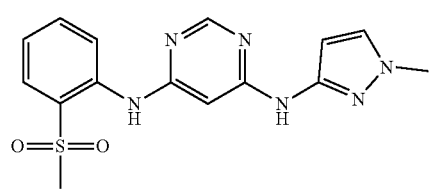 [SMILES: Cn1ccc(Nc2cc(Nc3ccccc3S(C)(=O)=O)ncn2)n1] |
| 67 | 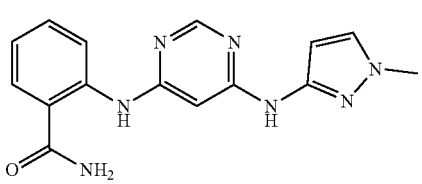 [SMILES: Cn1ccc(Nc2cc(Nc3ccccc3C(N)=O)ncn2)n1] |
| 68 | 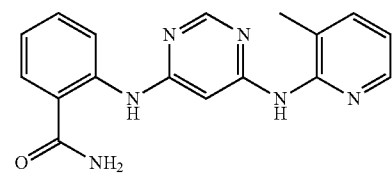 [SMILES: Cc1cccnc1Nc1cc(Nc2ccccc2C(N)=O)ncn1] |
| 69 | 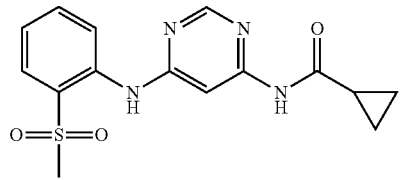 [SMILES: CS(=O)(=O)c1ccccc1Nc1cc(NC(=O)C2CC2)ncn1] |
| 70 | 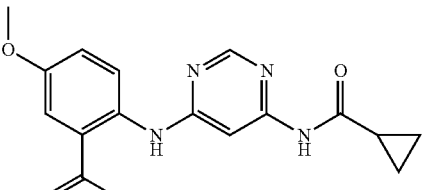 |

TABLE 1-continued

TYK2 inhibitors

| Compound No. | Structure |
|---|---|
| 71 | 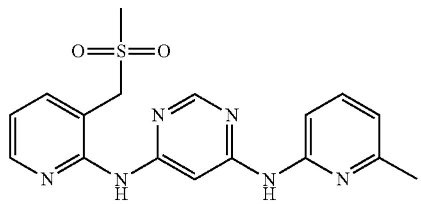 [SMILES: Cc1cccc(Nc2cc(Nc3ncccc3CS(C)(=O)=O)ncn2)n1] |
| 72 | 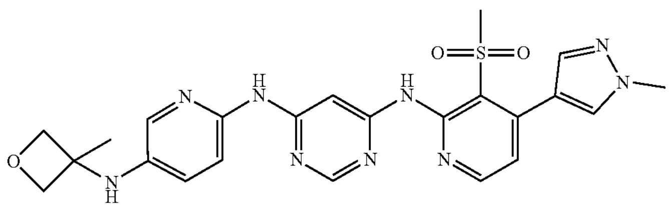 [SMILES: Cn1cc(-c2ccnc(Nc3cc(Nc4ccc(NC5(C)COC5)cn4)ncn3)c2S(C)(=O)=O)cn1] |
| 73 | 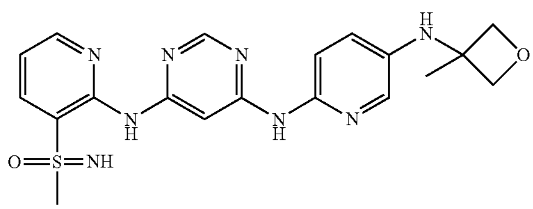 [SMILES: CC1(Nc2ccc(Nc3cc(Nc4ncccc4S(C)(=N)=O)ncn3)nc2)COC1] |
| 74 | 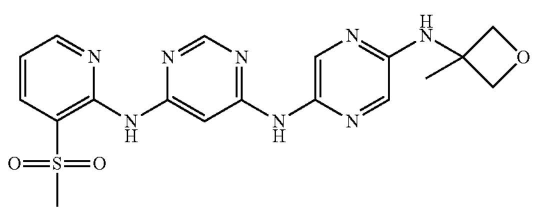 [SMILES: CC1(Nc2cnc(Nc3cc(Nc4ncccc4S(C)(=O)=O)ncn3)cn2)COC1] |
| 75 | 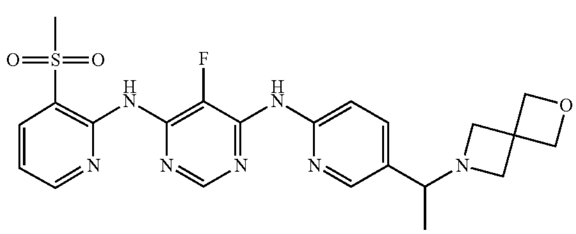 [SMILES: CC(c1ccc(Nc2ncnc(Nc3ncccc3S(C)(=O)=O)c2F)nc1)N1CC2(COC2)C1] |
| 76 | 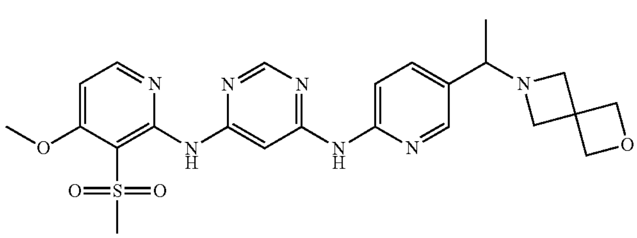 [SMILES: COc1ccnc(Nc2cc(Nc3ccc(C(C)N4CC5(COC5)C4)cn3)ncn2)c1S(C)(=O)=O] |

TABLE 1-continued

TYK2 inhibitors

| Compound No. | Structure |
|---|---|
| 77 | 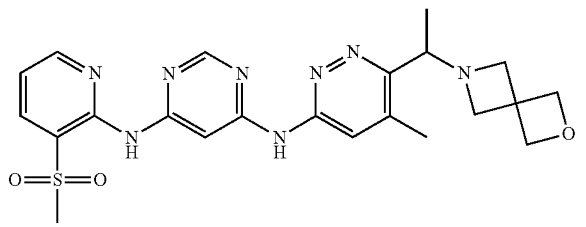 [SMILES: Cc1cc(Nc2cc(Nc3ncccc3S(C)(=O)=O)ncn2)nnc1C(C)N1CC2(COC2)C1] |
| 78 | 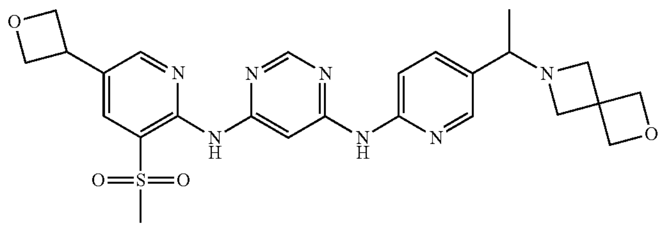 [SMILES: CC(c1ccc(Nc2cc(Nc3ncc(C4COC4)cc3S(C)(=O)=O)ncn2)nc1)N1CC2(COC2)C1] |
| 79 | 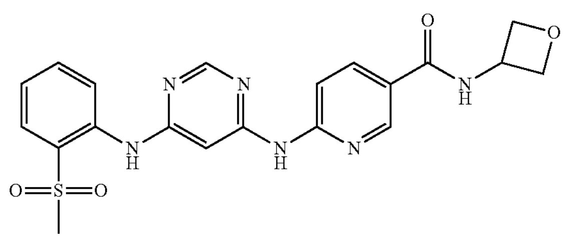 [SMILES: CS(=O)(=O)c1ccccc1Nc1cc(Nc2ccc(C(=O)NC3COC3)cn2)ncn1] |
| 80 | | a. Ligand Efficiency

In an exemplary embodiment, the invention provides a TYK2 inhibitor displaying excellent ligand efficiency. Optimization of ligand efficiency is generally achieved by optimization of both molecular size and lipophilicity. For example, ligand efficiency, is the binding free energy per heavy atom count (LE=ΔG/HA) and lipophilic ligand efficiency (LLE=pIC50 or Ki–c Log PID). Ligand efficiency is measured by art-recognized techniques. In one embodiment, the ligand efficiency is measured using TYK-JH2 binding assay set forth in Example 2.

Exemplary compounds of the invention have a ligand efficiency in the TYK-JH2 binding assay of at least about 0.39 (†††). In various embodiments, the compounds of the invention display a ligand efficiency of from about 0.37 to about 0.39 (††). In an exemplary embodiment, the compounds of the invention display a ligand efficiency of less than about 0.37 (†).

b. Compound Potency

The invention provides compounds that are highly potent inhibitors of TYK2. Potency of a TYK2 inhibitor is readily assessed using the assay set forth in Example 3a. In an exemplary embodiment, the compound of the invention has a potency against TYK2 of less than about 100 nm (†††). In various embodiments, the compound has a potency of from about 100 nm to about 1000 nm (††). In some embodiments, the compounds of the invention have a potency of greater than about 1,000 nm (†). In various embodiments, compounds having a potency towards TYK2 of less than about 1000 nm, preferably less than about 500 nm, more preferably less than about 250 nm, and still more preferably less than about 100 nm, less than about 50 nm, less than about 25 nm or less than about 10 nm are judged to be sufficiently potent to be clinically-relevant TYK2 inhibitors.

c. Compound Selectivity

For compounds to act as pharmaceutically useful TYK2 inhibitors, candidate compounds ideally demonstrate excellent cellular selectivity towards the target TYK2. Compound selectivity is conveniently assessed by the IL-6/pSTAT3 assay provided in Example 3b.

In various embodiments, the compounds of the invention exhibit a selectivity for TYK2 of at least about 10,000 nM (†††). In some embodiments, the compounds of the invention exhibit a selectivity of from about 4000 nM to about 10,000 nM (††). In some embodiments, the selectivity is less than about 4000 nM. Compounds having a selectivity of from about 4,000, e.g., about 5,000, about 6,000, about 7,000, about 8,000, about 9,000, about 10,000 nM or greater than about 10,000 nM are of use as clinically-relevant TYK2 inhibitors.

In various embodiments, the compounds of the invention exhibit an excellent cellular selectivity as measured by the GM-CSF/pSTAT5 assay. Using this assay, in various embodiments, the compounds of the invention exhibit a selectivity for TYK2 of at least about 10,000 nM (†††). In some embodiments, the compounds of the invention exhibit a selectivity of from about 4000 nM to about 10,000 nM (††). In some embodiments, the selectivity is less than about 4000 nM. Compounds having a selectivity of from about 4,000, e.g., about 5,000, about 6,000, about 7,000, about 8,000, about 9,000, about 10,000 nM or greater than about 10,000 nM are of use as clinically-relevant TYK2 inhibitors. See, Example 5.

D. Compound Toxicity

The ratio between toxicity and therapeutic effect for a particular compound is its therapeutic index and can be expressed as the ratio between LD50 (the amount of compound lethal in 50% of the population) and ED50 (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the ED50 with little or no toxicity. The dosage may vary within this range depending upon the dosage form employed and the route of administration utilized. See, e.g., *In The Pharmacological Basis of Therapeutics*, Ch. 1, p. 1, 1975. The exact formulation, route of administration and dosage can be chosen by the individual physician in view of the patient's condition and the particular method in which the compound is used.

Exemplary compounds according to the invention are characterized by an acceptable therapeutic index.

e. CNS Penetration

Exemplary compounds of the invention are characterized by CNS penetration sufficient to afford to these compounds therapeutic efficacy in treating diseases of the CNS, e.g., autoimmune and inflammatory diseases of the CNS. Such compounds are further characterized by an acceptable therapeutic index when administered to a subject in a therapeutically effective dosage and via a route appropriate to target the subject's CNS. An exemplary subject is a human subject having a disease which can be ameliorated by administering to the subject an exemplary compound of the invention.

f. Pharmacokinetics

Exemplary compounds of the invention are characterized by their favorable pharmacokinetics in mice. An exemplary pharmacokinetic study characterizing the compounds includes administering to a mouse about 5 mg/kg. In some embodiments, the compound of the invention has a $C_{max}$ of at least about 1500 (ng/mL). Selected compounds are characterized by an AUCinf (hr*ng/mL) of at least about 2000. In some embodiments, the compound has a T½ of greater than about one hour, e.g., greater than about 1.5 h. See, Example 6.

g. Selected Compounds

In various embodiments, compounds characterized by specific combinations of ranges of pharmacological parameters are provided. These compounds have excellent combinations of properties rendering them excellent clinical candidates.

Thus, in one embodiment, the invention provides a compound with a potency against TYK2 of less than about 100 nm (IL-12/pSTAT4), and a cellular selectivity for TYK2 of greater than about 10,000 nM (IL-6/pSTAT3). In various embodiments, the invention provides a compound with a ligand efficiency of greater than about 0.39 (TYK-JH2 binding assay) and a potency against TYK2 of less than about 100 nm (IL-12/pSTAT4), or a cellular selectivity for TYK2 of greater than about 10,000 nM (IL-6/pSTAT3, or GM-CSF/pSTAT5). In some embodiments, the invention provides a compound in which the ligand efficiency is greater than about 0.39 (TYK-JH2 binding assay), the potency against TYK2 is less than about 100 nm (IL-12/pSTAT4), and the cellular selectivity for TYK2 is greater than about 10,000 nM (IL-6/pSTAT3, or GM-CSF/pSTAT5).

In an exemplary embodiment, selected compounds of the invention are characterized by a C of at least about 1500 (ng/mL). Selected compounds are characterized by an AUCinf (hr*ng/mL) of at least about 2000. In some embodiments, the compound has a T½ of greater than about one hour, e.g., greater than about 1.5 h. Exemplary compounds of the invention can be demonstrated to have these properties in a mouse PO PK experiment with dosing at about 5 mg/kg. Certain selected compounds are characterized by two or more of these parameters having the enumerated quantities.

As will be apparent to one of skill in the art, the selected compounds can have the above enumerated properties and parameters in any combination. The examples provided above are merely illustrative and are not limiting.

2. Pharmaceutical Formulations

The invention further provides a pharmaceutical formulation comprising a compound of the invention according to Formula (I), a pharmaceutically acceptable salt, solvate, hydrate, tautomer or prodrug thereof, admixed with a pharmaceutically acceptable excipient. In an exemplary embodiment, the compounds are those according to Formula (II) and more preferably according to Formula (III).

In an exemplary embodiment, the compound of the invention, a pharmaceutically acceptable salt, solvate, hydrate, tautomer or prodrug thereof, is used for preparing a medicament of use in the treatment or prevention of a TYK2-mediated disease or condition in a subject in need thereof.

The compounds described herein, or pharmaceutically acceptable addition salts or hydrates thereof, can be formulated so as to be delivered to a patient using a wide variety of routes or modes of administration. Suitable routes of administration include, but are not limited to, inhalation, transdermal, oral, ocular, rectal, transmucosal, intestinal and parenteral administration, including intramuscular, subcutaneous and intravenous injections. In one embodiment, the formulation is formatted for parenteral or oral administration. In an exemplary embodiment, the formulation is formatted for intravenous, subcutaneous, intrathecal, intracerebral ventricular, or intraperitoneal injection.

The compounds described herein, or pharmaceutically acceptable salts and/or hydrates thereof, may be administered singly, in combination with other compounds of the invention, and/or in cocktails combined with other therapeutic agents. The choice of therapeutic agents that can be co-administered with the compounds of the invention will depend, in part, on the condition being treated.

For example, when administered to patients suffering from an autoimmune or inflammatory process, the compounds of the invention can be administered in cocktails containing agents used to treat the pain, infection and other symptoms and side effects commonly associated with an inflammatory process. Such agents include, e.g. analgesics, antibiotics, etc. The compounds can also be administered in cocktails containing other agents that are commonly used in treating inflammatory process, including butyrate and butyrate derivatives (Perrin et al., *N. Engl. J. Med.* 328(2): 81-86 (1993)); hydroxyurea (Charache et al., *N. Engl. J. Med.* 323(20): 1317-1322 (1995)); erythropoietin (Goldberg et al, *N. Engl. J. Med.* 323(6): 366-372 (1990)); and dietary salts such as magnesium (De Franceschi et al., *Blood* 88 (648a): 2580 (1996)).

Pharmaceutical compositions for use in accordance with the present invention can be formulated in a conventional manner using one or more physiologically acceptable carriers comprising excipients and auxiliaries, which facilitate processing of the active compounds into preparations which can be used pharmaceutically. Proper formulation is dependent upon the route of administration chosen.

For injection, the agents of the invention can be formulated in aqueous solutions, preferably in physiologically compatible buffers such as Hanks's solution, Ringer's solution, or physiological saline buffer. In an exemplary embodiment, the formulation includes water and an alcohol and/or glycol. Other useful components of this formulation include, for example, surfactant, emulsifiers and materials such as ethoxylated oils. An exemplary formulation includes a compound of the invention, poly(ethyleneglycol) 400, ethanol and water in a 1:1:1 ratio. Another exemplary formulation includes a compound of the invention, water, poly(ethyleneglycol) 400 and Cremophor-EL.

For transmucosal administration (e.g., buccal, rectal, nasal, ocular, etc.), penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be combined with a solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium cathoxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum 66yridi, talc, polyvinyl pyrrolidone, 66yridine gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form, such as those described above for intravenous administration. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium cathoxymethyl cellulose, sothitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In addition to the formulations described previously, the compounds may also be formulated as a depot preparation. Such long-acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may include suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

a. Effective Dosages

Pharmaceutical compositions suitable for use with the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to reduce the occurrence of psoriasis, or IBD (Crohn's, ulcerative colitis), such compositions will contain an amount of active ingredient effective to achieve this result. Determination of an effective amount is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of inducing inhibition of TYK2. In exemplary embodiments, TYK2 activity is at least 25% inhibited. Target plasma concentrations of active compound(s) that are capable of inducing at least about 50%, 75%, or even 90% or higher inhibition of TYK2 are within the scope of the instant disclosure. The percentage of inhibition of TYK2 in the subject can be monitored to assess the appropriateness of the plasma drug concentration achieved, and the dosage can be adjusted upwards or downwards to achieve the desired percentage of inhibition and the concomitant therapeutic effect.

In an exemplary embodiment, a single dose of a compound of the invention maintains an $IC_{50}$, $IC_{60}$, $IC_{70}$, $IC_{80}$ or $IC_{90}$ for at least about 15 hours, at least about 20 hours or at least about 24 hours. In an exemplary embodiment, the compound of the invention is administered to a subject in a therapeutically effective dosage sufficient to maintain $IC_{90}$ for at least about 24 hours.

As is well known in the art, therapeutically effective amounts for use in humans can also be determined from animal models. For example, a dose for humans can be formulated to achieve a circulating concentration that has been found to be effective in animals. The dosage in humans can be adjusted by monitoring IK1 channel inhibition and adjusting the dosage upwards or downwards, as described above.

Adjusting the dose to achieve maximal efficacy in humans based on the methods described above and other methods as are well-known in the art is well within the capabilities of the ordinarily skilled artisan. In the case of local administration, the systemic circulating concentration of administered compound will not be of particular importance. In such instances, the compound is administered so as to achieve a concentration at the local area effective to achieve the intended result.

Patient doses for oral administration of the compounds described herein, which is the preferred mode of administration for prophylaxis and for treatment of inflammatory process episodes, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day.

For any mode of administration, dosage amount and interval can be adjusted individually to provide plasma levels of the administered compound effective for the particular clinical indication being treated. For example, if acute inflammatory processes are the most dominant clinical manifestation, in one embodiment, a compound according to the invention can optionally be administered in relatively high concentrations one or multiple times per day. Alternatively, if the subject exhibits only periodic inflammatory crises on an infrequent, periodic or irregular basis, in one embodiment, it may be more desirable to administer a compound of the invention at minimal effective concentrations and to use a less frequent administration regimen. This will provide a therapeutic regimen that is commensurate with the severity of the individual's inflammatory disease.

Utilizing the teachings provided herein, an effective prophylactic or therapeutic treatment regimen can be planned which does not cause substantial toxicity and yet is effective to treat the clinical symptoms demonstrated by the particular subject. This planning should involve the careful choice of active compound by considering factors such as compound potency, relative bioavailability, patient body weight, presence and severity of adverse side effects, preferred mode of administration and the toxicity profile of the selected agent.

3. Methods

The present invention also provides methods of using the compounds of the invention to investigate autoimmune and inflammatory diseases, and to treat these diseases in a subject in need of such treatment.

In an exemplary embodiment, there is provided a method of treating a TYK2-mediated disease in a subject in need thereof by administering to the subject a therapeutically effective amount of the compound of the invention, a pharmaceutically acceptable salt, solvate or hydrate thereof, wherein the autoimmune disease is susceptible to treatment with a TYK2 inhibitor. In an exemplary embodiment, the inhibitor is administered in the form of a pharmaceutical formulation.

In some embodiments, the invention provides a method of treating a disease in a subject, which is an autoimmune or inflammatory disease. The method comprises inhibiting TYK2 kinase in the subject by administering to the subject a therapeutically effective amount of a compound of the invention, wherein the autoimmune or inflammatory disease is susceptible to treatment with a TYK2 inhibitor.

Exemplary diseases treatable by a method of the invention include Psoriasis, Plaque Psoriasis, Psoriatic Arthritis, and Inflammatory Bowel Disease (Crohn's, ulcerative colitis).

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

EXAMPLES

Example 1: Synthesis of TYK2 Inhibitor Compounds

The following example describes the preparation of compounds 1-80.

Example 1a: Preparation of Compound 1 and Compound 17

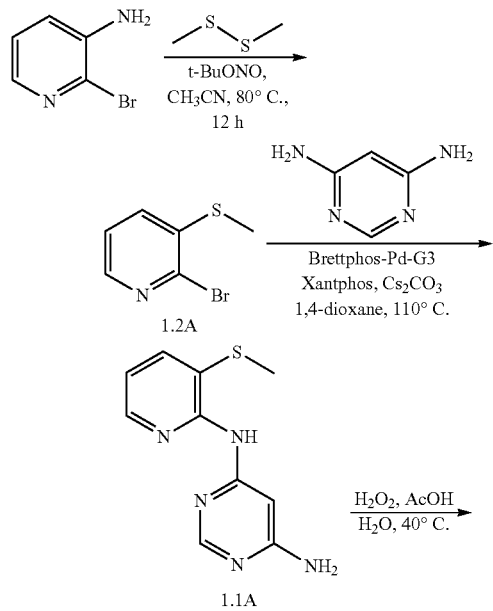

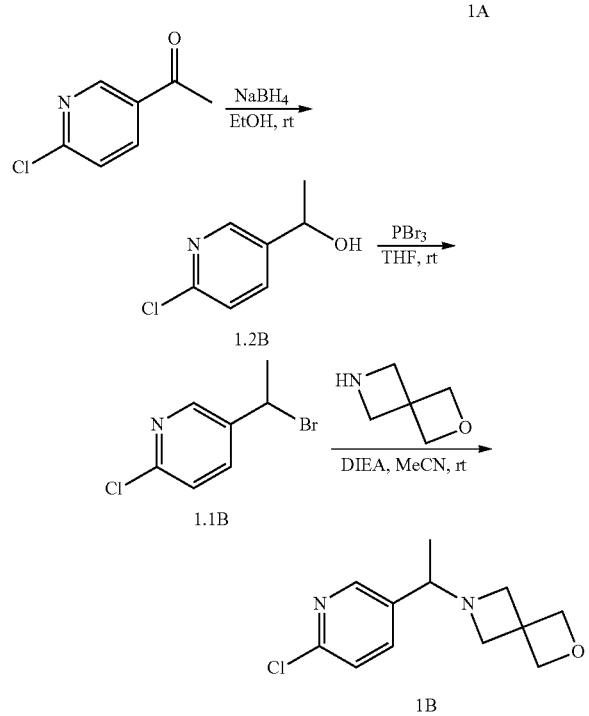

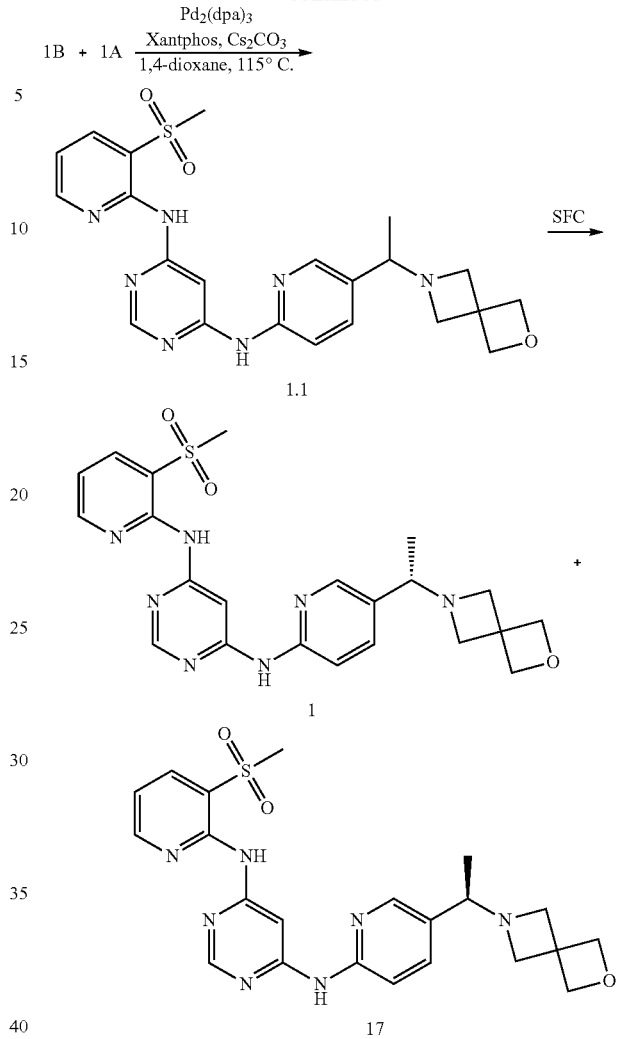

2-bromo-3-(methylthio)pyridine (1.2A). To a solution of 2-bromopyridin-3-amine (30.0 g, 173.40 mmol) and 1,2-dimethyldisulfane (32.60 g, 346.82 mmol) in MeCN (500 mL) was added t-BuONO (35.72 g, 346.82 mmol). The mixture was stirred at 80° C. for 12 hours. After the reaction was completed, the mixture was concentrated and purified by column chromatography on silica gel (hexane: EtOAc=10:1) to give 1.2A (23.50 g, 66.4% yield) as a yellow solid. LC-MS m/z: 204.0 [M+H]$^+$. LCMS purity (254 nm): 99.2%; $t_R$=1.445 min.

$N^4$-(3-(methylthio)71yridine-2-yl)pyrimidine-4,6-diamine (1.1A). A mixture of 1.2A (23.50 g, 115.20 mmol), pyrimidine-4,6-diamine (15.20 g, 138.24 mmol), Brettphos-Pd-G3 (5.21 g, 5.76 mmol), Xantphos (3.33 g, 5.76 mmol) and Cs$_2$CO$_3$ (75.11 g, 230.39 mmol) in 1,4-dioxane (400 mL) was stirred at 110° C. for 8 hours under argon atmosphere. After the reaction was completed, the mixture was filtered, concentrated and purified by column chromatography on silica gel (CH$_2$Cl$_2$:MeOH=20:1) to give 1.1A (19.50 g, 72.6% yield) as a yellow solid. LC-MS m/z: 234.2[M+H]$^+$. LCMS purity (214 nm): 96.96%; $t_R$=1.200 min.

$N^4$-(3-(methylsulfonyl)71yridine-2-yl)pyrimidine-4,6-diamine (1A). To a solution of 1.1A (19.50 g, 83.59 mmol) in AcOH (200 mL) and H$_2$O (200 mL) was added 30% H$_2$O$_2$ (195 mL), the mixture was stirred at 40° C. for 8 hours. After the reaction was completed, the mixture was poured into water (500 mL) and adjusted the pH to 7~8 with aqueous Na$_2$CO$_3$ solution, then the mixture was filtered and the filter cake was dried to give 1A (15.50 g, 69.9% yield) as a yellow solid. LC-MS m/z: 266.2[M+H]$^+$. LCMS purity (214 nm): 89.47%; t$_R$=1.083 min.

1-(6-chloropyridin-3-yl)ethanol (1.2B). To a mixture of 1-(6-chloropyridin-3-yl)72yridine (3.0 g, 19.28 mmol) in EtOH (40 mL) was added NaBH$_4$ (1.46 g, 38.46 mmol), the reaction mixture was stirred at room temperature overnight. After the reaction was completed, the mixture was concentrated, diluted by H$_2$O (40 mL) and extracted with EtOAc (30 mL×3). The combined organic layers were washed with brine (150 mL), dried over Na$_2$SO$_4$, concentrated and purified by column chromatography on silica gel (EtOAc: hexane=2:3) to give 1.2B (2.80 g, 92.2% yield) as colorless liquid. LC-MS m/z: 158.2 [M+1]$^+$; LCMS purity (214 nm): 99.4%, t$_R$=1.106 min.

5-(1-bromoethyl)-2-chloropyridine (1.1B). To a mixture of 1.2B (2.80 g, 17.77 mmol) in THF (40 mL) was added PBr$_3$ (4.80 g, 17.72 mmol), then it was stirred at room temperature overnight. After the reaction was completed, the mixture was concentrated, diluted by H$_2$O (40 mL) and extracted with EtOAc (30 mL×3). The combined organic layers were washed by brine (100 mL), dried over Na$_2$SO$_4$, concentrated and purified by column chromatography on silica gel (EtOAc:hexane=1:11) to give 1.1B (2.60 g, 66.4% yield) as a light-yellow liquid. LC-MS m/z: 221.9 [M+1]$^+$; purity (214 nm): 87.2%, t$_R$=1.624 min.

6-(1-(6-chloropyridin-3-yl)ethyl)-2-oxa-6-azaspiro[3.3]heptane (1B). To a mixture of 1.1B (2.60 g, 11.79 mmol) and 2-oxa-6-azaspiro[3.3]heptane (1.29 g, 13.00 mmol) in MeCN (50 mL) was added 72yri (6 mL), the reaction mixture was stirred at 80° C. overnight under argon atmosphere. After the reaction was completed, the mixture was concentrated, diluted by H$_2$O (30 mL) and extracted with EtOAc (30 mL×3). The combined organic layers were washed with brine (100 mL), dried over Na$_2$SO$_4$, concentrated and purified by column chromatography on silica gel (EtOAc) to give 1B (2.0 g, 71% yield) as a light-yellow liquid. LC-MS m/z: 239.2 [M+1]$^+$; purity (214 nm) 80%, t$_R$=1.232 min.

N$^4$-(5-(1-(2-oxa-6-azaspiro[3.3]heptan-6-yl)ethyl)72yridine-2-yl)-N$^6$-(3-(methylsulfonyl)72yridine-2-yl)pyrimidine-4,6-diamine (1.1). A mixture of 1B (268 mg, 1.12 mmol), 1A (200 mg, 0.75 mmol), Pd$_2$(dba)$_3$ (73 mg, 0.08 mmol), Xantphos (87 mg, 0.15 mmol) and Cs$_2$CO$_3$ (734 mg, 2.25 mmol) in 1,4-dioxane (20 mL) was stirred at 115° C. overnight under argon atmosphere. The reaction was repeated three times with the same scale in parallel. After the reaction was completed, three reaction mixtures were combined and concentrated, diluted by H$_2$O (50 mL) and extracted with EtOAc (50 mL×3). The combined organic layers were washed by brine (100 mL), dried over Na$_2$SO$_4$, concentrated and purified by column chromatography on silica gel (CH$_2$Cl$_2$:MeOH=11:1) to give crude 1.1 (550 mg). The crude product (150 mg) was further purified by reversed phase prep-HPLC to give pure 1.1 (90 mg, 31.0% yield) as a white solid. $^1$H NMR (400 MHz, DMSO-d$_6$) δ 10.12 (s, 1H), 9.43 (s, 1H), 8.76 (s, 1H), 8.67 (dd, J=4.8, 1.6 Hz, 1H), 8.40 (s, 1H), 8.27 (dd, J=7.6, 1.6 Hz, 1H), 8.19 (d, J=1.6 Hz, 1H), 7.67 (d, J=8.4 Hz, 1H), 7.62 (dd, J=8.4, 2.0 Hz, 1H), 7.27 (dd, J=8.0, 4.8 Hz, 1H), 4.59 (t, J=6.4 Hz, 4H), 3.39 (s, 3H), 3.25 (d, J=7.2 Hz, 2H), 3.20 (q, J=6.4 Hz, 1H), 3.13 (d, J=6.8 Hz, 2H), 1.11 (d, J=6.4 Hz, 3H). LC-MS m/z: 468.3 [M+H]$^+$. HPLC purity (214 nm): >99.9%; t$_R$=7.172 min.

(S)—N$^4$-(5-(1-(2-oxa-6-azaspiro[3.3]heptan-6-yl)ethyl)73yridine-2-yl)-N$^6$-(3-(methylsulfonyl)73yridine-2-yl)pyrimidine-4,6-diamine (1) and I—N$^4$-(5-(1-(2-oxa-6-azaspiro[3.3]heptan-6-yl)ethyl) 73yridine-2-yl)-N$^6$-(3-(methylsulfonyl)73yridine-2-yl)pyrimidine-4,6-diamine (17). Crude 1.1 (400 mg) was further purified by SFC to give 1 (154 mg, 19.9% yield) and 17 (148 mg, 19.2% yield) as a white solid. Compound 1: $^1$H NMR (400 MHz, DMSO-d$_6$) δ 10.12 (s, 1H), 9.43 (s, 1H), 8.76 (s, 1H), 8.67 (dd, J=4.8, 2.0 Hz, 1H), 8.40 (s, 1H), 8.27 (dd, J=7.6, 1.6 Hz, 1H), 8.19 (d, J=2.4 Hz, 1H), 7.67 (d, J=8.8 Hz, 1H), 7.62 (dd, J=8.4, 2.0 Hz, 1H), 7.27 (dd, J=8.0, 4.8 Hz, 1H), 4.59 (t, J=6.8 Hz, 4H), 3.39 (s, 3H), 3.25 (d, J=6.8 Hz, 2H), 3.21 (q, J=6.4 Hz, 1H), 3.13 (d, J=7.2 Hz, 2H), 1.11 (d, J=6.4 Hz, 3H). LC-MS m/z: 468.3 [M+H]$^+$. HPLC purity (214 nm): >99.9%; t$_R$=7.178 min. Chiralpak AS-3: >99.9% ee, t$_R$=1.154 min. Compound 17: $^1$H NMR (400 MHz, DMSO-d$_6$) δ 10.12 (s, 1H), 9.44 (s, 1H), 8.76 (s, 1H), 8.67 (dd, J=4.8, 1.6 Hz, 1H), 8.40 (s, 1H), 8.27 (dd, J 7.6, 1.6 Hz, 1H), 8.19 (d, J=2.0 Hz, 1H), 7.67 (d, J=8.0 Hz, 1H), 7.62 (dd, J=8.4, 2.0 Hz, 1H), 7.27 (dd, J=8.0, 4.8 Hz, 1H), 4.59 (s, 4H), 3.39 (s, 3H), 3.25 (d, J=7.2 Hz, 2H), 3.21 (q, J=6.4 Hz, 1H), 3.13 (d, J=7.2 Hz, 2H), 1.11 (d, J=6.4 Hz, 3H). LC-MS m/z: 468.2 [M+H]$^+$. HPLC purity (214 nm): >99.9%; t$_R$=7.182 min. Chiralpak AS-3:99.8% ee, t$_R$=1.524 min.

Example 1b: Preparation of Compound 2

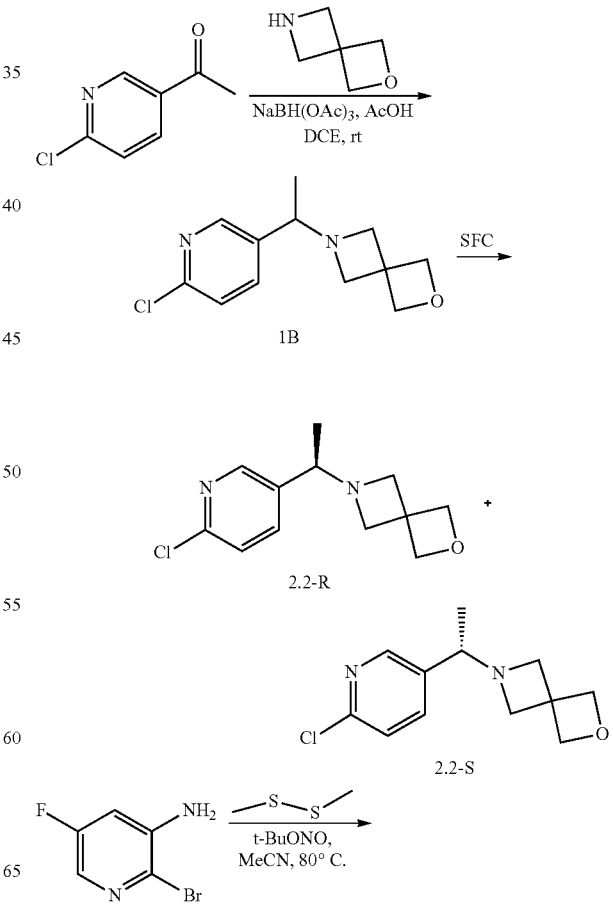

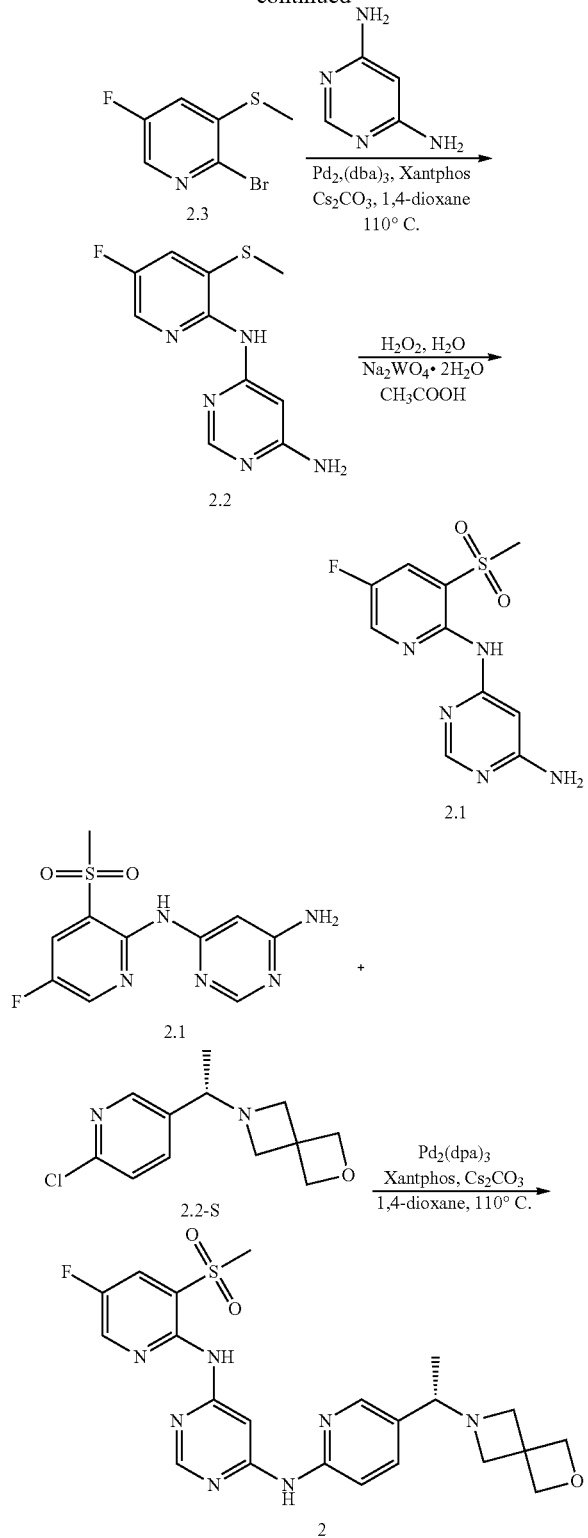

room temperature overnight. The reaction was repeated with the same scale in parallel. After the reaction was completed, the mixture was concentrated, diluted by H$_2$O (200 mL), adjusted pH to 8~9 with aqueous K$_2$CO$_3$ and extracted with CH$_2$Cl$_2$ (100 mL×3). The combined organic layers were washed with brine (150 mL), dried over Na$_2$SO$_4$, concentrated and purified by column chromatography on silica gel (EtOAc) and then reversed phase column chromatography (MeOH:H$_2$O=1:3) to give 1B (24.0 g for 3 batches, 52.2% yield) as a light-yellow liquid. LC-MS m/z: 239.4 [M+1]$^+$, purity (in 214 nm): 94.1%; $t_R$=1.424 min.

(S)-6-(1-(6-chloropyridin-3-yl)ethyl)-2-oxa-6-azaspiro[3.3]heptane (2.2-S). The 1B product was further purified by SFC to give pure 2.2-R (11.4 g) and 2.2-S (11.6 g) as light-yellow liquid. 2.2-R: Chiralpak AS-3, MeOH (0.2% 7M NH$_3$): >99.9% ee, $t_R$=1.103 min. 2.2-S: Chiralpak AS-3, MeOH (0.2% 7M NH$_3$): 99.8% ee, $t_R$=1.650 min.

2-bromo-5-fluoro-3-(methylthio)pyridine (23). To a solution of 2-bromo-5-fluoropyridin-3-amine (15.0 g, 78.53 mmol) and 1,2-dimethyldisulfane (20 mL, 235.59 mmol) in MeCN (150 mL) was added t-BuONO (25 mL, 235.59 mmol) carefully, the mixture was stirred at 80° C. overnight. After the reaction was completed, the mixture was concentrated and purified by column chromatography on silica gel (EtOAc:hexane=1:19) to give 2.3 (11.7 g, 67.1% yield) as a yellow solid. LC-MS m/z: 222.2 [M+1]$^+$. LCMS purity (254 nm): 94.2%; $t_R$=1.827 min.

N$^4$-(5-fluoro-3-(methylthio)75yridine-2-yl)pyrimidine-4,6-diamine (2.2). A mixture of 23 (6.70 g, 30.17 mmol), pyrimidine-4,6-diamine (6.64 g, 60.36 mmol), Pd$_2$(dba)$_3$ (1.93 g, 2.11 mmol), Xantphos (2.44 g, 4.22 mmol) and Cs$_2$CO$_3$ (29.52 g, 90.54 mmol) in 1,4-dioxane (100 mL) was stirred at 110° C. overnight under argon atmosphere. After the reaction was completed, the mixture was concentrated and purified by column chromatography on silica gel (CH$_2$Cl$_2$:MeOH=19:1) to give 2.2 (3.95 g, 52.1% yield) as a yellow solid. LC-MS m/z: 252.3 [M+1]$^+$. LCMS purity (214 nm): 93.0%; $t_R$=1.444 min.

N$^4$-(5-fluoro-3-(methylsulfonyl)75yridine-2-yl)pyrimidine-4,6-diamine (2.1). To a solution of 2.2 (5.90 g, 23.48 mmol) in AcOH (40 mL) and H$_2$O (40 mL) was added 30% H$_2$O$_2$ (40 mL), the mixture was stirred was stirred at room temperature overnight. LCMS showed the MS 268.2 (M-15) was detected. Then to the mixture was added additional 30% H$_2$O$_2$ (40 mL) and Na$_2$WO$_4$·2H$_2$O (7.75 g, 23.50 mmol), the resulting mixture was stirred was stirred at room temperature for 2 h. After the reaction was completed, the mixture was poured into water (200 mL) and adjusted the pH to 7~8 with aqueous K$_2$CO$_3$ solution carefully to give a precipitate. The mixture was filtered and the filter cake was dried to give 2.1 (5.60 g, 84.2% yield) as a yellow solid. LC-MS m/z: 284.2 [M+H]$^+$. LCMS purity (214 nm): 82.2%; $t_R$=1.345 min.

(S)—N$^4$-(5-(1-(2-oxa-6-azaspiro[3.3]heptan-6-yl)ethyl)75yridine-2-yl)-N$^6$-(5-fluoro-3-(methylsulfonyl)75yridine-2-yl)pyrimidine-4,6-diamine (2). A mixture of 2.1 (3.0 g, 10.59 mmol), 2.2-S (2.53 g, 10.59 mmol), Pd$_2$(dba)$_3$ (0.97 g, 1.06 mmol), Xantphos (1.23 g, 2.12 mmol) and Cs$_2$CO$_3$ (10.37 g, 31.80 mmol) in 1, 4-dioxane (100 mL) was stirred at 110° C. overnight under argon atmosphere. LCMS showed 2.1 and 2.2-S were not completely consumed. The reaction was repeated with the same scale In parallel. The mixture was diluted by H$_2$O (100 mL) and extracted with EtOAc (70 mL×3). The combined organic layers were washed with brine (150 mL), dried over Na$_2$SO$_4$, concentrated and purified by column chromatography on silica gel (CH$_2$Cl$_2$:MeOH=15:1) and then reversed phase prep-HPLC 6-(1-(6-chloropyridin-3-yl)ethyl)-2-oxa-6-azaspiro[3.3]heptane (1B). To a mixture of 1-(6-chloropyridin-3-yl)74yridine (10.0 g, 64.10 mmol) and 2-oxa-6-azaspiro[3.3]heptane (7.61 g, 76.92 mmol) in 1,2-dichloroethane (200 mL) was added 30% AcOH (3.85 g, 64.10 mmol) and NaBH(Oac)$_3$ (27.18 g, 128.20 mmol), the reaction mixture was stirred at to give 2 (2.6 g for 2 batches, 25.3% yield) as a white solid. ¹H NMR (400 MHz, DMSO-d₆) δ 10.13 (s, 1H), 9.30 (brs, 1H), 8.76 (d, J=2.8 Hz, 1H), 8.72 (s, 1H), 8.39 (s, 1H), 8.25 (dd, J=7.6, 2.8 Hz, 1H), 8.23 (s, 1H), 7.64-7.58 (m, 2H), 4.60-4.57 (m, 4H), 3.45 (s, 3H), 3.25 (d, J=6.8 Hz, 2H), 3.20 (q, J=6.4 Hz, 1H), 3.13 (d, J=6.8 Hz, 2H), 1.11 (d, J=6.8 Hz, 3H). LC-MS m/z: 486.2 [M+1]⁺. HPLC purity (214 nm): >99.9%; $t_R$=7.106 min. Chiralpak OJ-3, MeOH (0.2% 7M NH₃): 99.72% ee, $t_R$=2.461 min.

Example 1c: Preparation of Compound 3

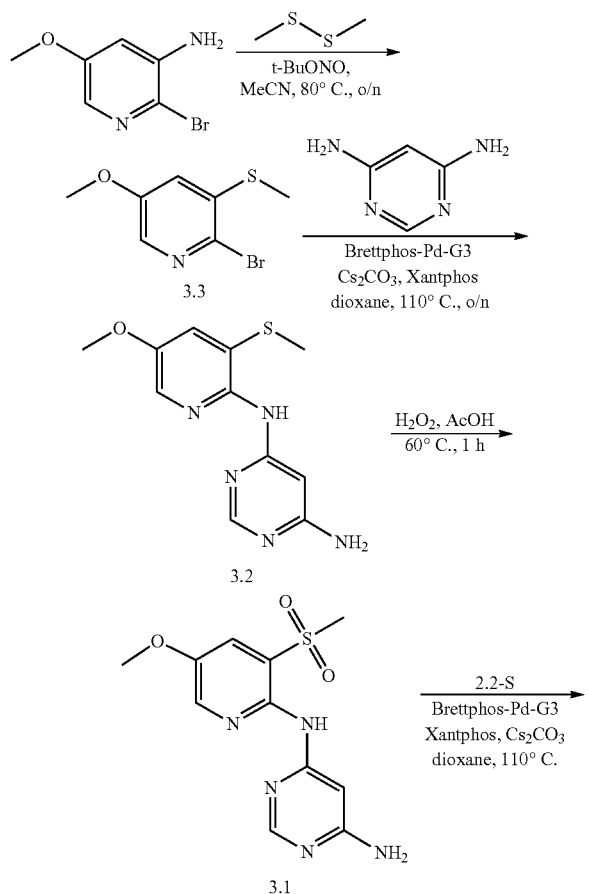

Methyl 2-bromo-5-methoxy-3-(methylthio)pyridine (3.3). To a solution of 2-bromo-5-methoxypyridin-3-amine (2 g, 9.85 mmol) in CH₃CN (60 mL) was added 1,2-dimethyldisulfane (1856 mg, 19.7 mmol) and t-BuONO (2031 mg, 19.7 mmol). The reaction mixture was stirred at 80° C. overnight. After the reaction was completed, the mixture was evaporated in vacuo to give crude product. Further purification with chromatography (EtOAc:Hexane=3:7) gives title product 3.3 (800 mg, 34.7% yield) as a yellow solid. LC-MS m/z: 235.2 [M+H]⁺. LCMS purity (254 nm): 95.06%; $t_R$=0.684 min.

N⁴-(5-methoxy-3-(methylthio)77yridine-2-yl)pyrimidine-4,6-diamine (3.2). To a solution of 3.3 (800 mg, 3.42 mmol) in dioxane (40 mL) was added pyrimidine-4,6-diamine (377 mg, 3.42 mmol), Cs₂CO₃ (2229 mg, 6.84 mmol) and Brettphos-Pd-G3 (154 mg, 0.17 mmol), Xantphos (98 mg, 0.17 mmol). The reaction was heated to 110° C. and stirred at 110° C. overnight under nitrogen atmosphere. After the reaction was completed, the mixture was evaporated in vacuo to give crude product. Further purification with Chromatography (CH₂Cl₂:MeOH=10/1) to give title product 3.2 (550 mg, 61.1% yield) as a green solid. LC-MS m/z: 264.2 [M+H]⁺. LCMS purity (254 nm): 95.14%; $t_R$=0.411 min.

N⁴-(5-methoxy-3-(methylsulfonyl)77yridine-2-yl)pyrimidine-4,6-diamine (3.1). To a solution of 3.2 (150 mg, 0.57 mmol) in AcOH (2 mL) was added H₂O₂ (30% wt, 0.5 mL). The reaction was stirred at 60° C. for 1 hour. After the reaction was completed, the reaction mixture was diluted with water (70 mL). The mixture was adjusted pH to 7-8 with NaHCO₃ solution. The mixture was extracted with CH₂Cl₂:MeOH (10:1, 80 mL). The organic phase was evaporated in vacuo to give crude product. Further purification with chromatography (CH₂Cl₂:MeOH=20:1) gives 3.1 (200 mg, 59.5% yield) as a yellow solid. LC-MS m/z: 296.2 [M+H]⁺. LCMS purity (254 nm): 78.04%; $t_R$=0.397 min.

(S)—N⁴-(5-(1-(2-oxa-6-azaspiro[3.3]heptan-6-yl)ethyl)pyridine-2-yl)-N⁶-(5-methoxy-3-(methylsulfonyl)77yridine-2-yl)pyrimidine-4,6-diamine (3). A solution of 2.2-S (80 mg, 0.27 mmol), 3.1 (65 mg, 0.27 mmol), Brettphos-Pd-G3 (25 mg, 0.027 mmol), Xantphos (31 mg, 0.054 mmol) and Cs₂CO₃ (177 mg, 0.54 mmol) in dry 1,4-dioxane (10 mL) was stirred at 110° C. overnight under nitrogen. After the reaction was completed, the mixture was cooled down to room temperature and filtered. The filtrate was concentrated in vacuo. The residue was purified by column chromatography on silica gel (MeOH/CH₂Cl₂=1/20) and reversed phase HPLC to give 3 (50.63 mg, 37.6% yield) as a white solid. ¹H NMR (400 MHz, DMSO-d₆) δ 10.03 (br, 1H), 9.20 (br, 1H), 8.54 (br, 1H), 8.44 (d, J=3.2 Hz, 1H), 8.34 (s, 1H), 8.19 (s, 1H), 7.83 (d, J=2.8 Hz, 1H), 7.61 (s, 2H), 4.59 (s, 4H), 3.93 (s, 3H), 3.40 (s, 3H), 3.26 (d, J=7.2 Hz, 2H), 3.22-3.19 (m, 1H), 3.13 (d, J=7.2 Hz, 2H), 1.11 (d, J=6.4 Hz, 3H). LC-MS m/z: 498.0 [M+H]⁺. HPLC purity (214 nm): >99.9%; $t_R$=2.708 min.

Example 1d: Preparation of Compound 4

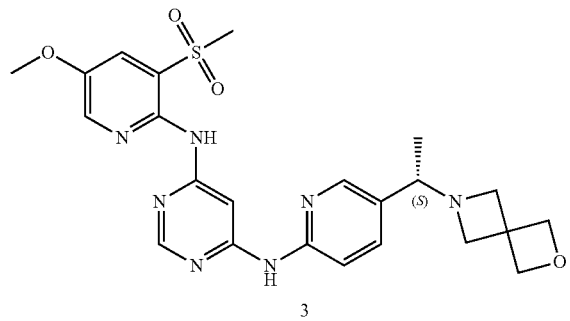

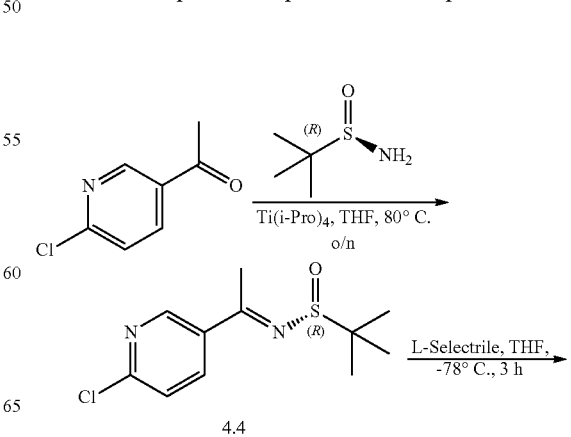

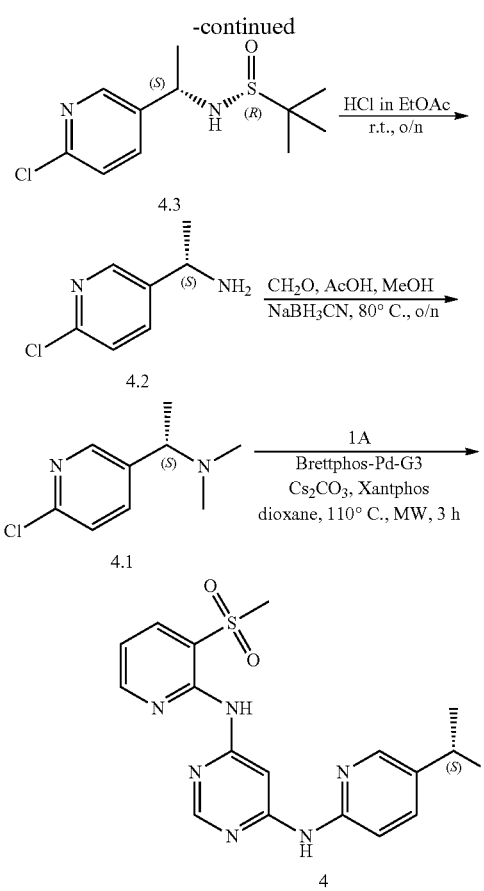

(R,E)-N-(1-(6-chloropyridin-3-yl)ethylidene)-2-methylpropane-2-sulfinamide (4.4). A stirred solution of 1-(6-chloropyridin-3-yl)ethan-1-one (1.00 g, 6.43 mmol), I-2-methylpropane-2-sulfinamide (1.56 g, 12.85 mmol) and Ti(i-PrO)$_4$ (5.44 g, 19.29 mmol) in MeCN (60 mL) was stirred at 80° C. overnight under nitrogen. After consumption of the starting material (monitored by LCMS), the mixture was added H$_2$O (100 mL), the solid was filtered and the filtrate was extracted with EtOAc (100 mL) and washed with water (50 mL×2) then brine (50 mL×2). The organic layer was dried over anhydrous sodium sulfate and concentrated in vacuo to give the crude product. The target product was purified by column chromatography on silica gel (EtOAc/Hexane=5/1) to give 4.4 (1.4 g, 84.2% yield) as a yellow oil. LC-MS m/z: 259.1 [M+1]$^+$. LCMS purity (214 nm): 94.01%; $t_R$=1.812 min.

I-N—((S)-1-(6-chloropyridin-3-yl)ethyl)-2-methylpropane-2-sulfinamide (4.3). A stirred solution of 4.4 (1.4 g, 5.41 mmol) in THF (30 mL) was added L-Selectrile (6 mL, 5.95 mmol) under −78° C. The mixture was stirred at −78° C. for 3 h under nitrogen. After consumption of the starting material (monitored by LCMS), the mixture was added H$_2$O (100 mL) and extracted with EtOAc (100 mL) and washed with water (50 mL×2) then brine (50 mL×2). The organic layer was dried over anhydrous sodium sulfate and concentrated in vacuo to give the crude product. The target product was purified by column chromatography on silica gel (EtOAc/Hexane=1/1) to give 4.3 (800 mg, 56.7% yield) as an off-white solid. LC-MS m/z: 261.2 [M+1]$^+$. LCMS purity (254 nm): 88.98%; $t_R$=0.320 min.

(S)-1-(6-chloropyridin-3-yl)ethanamine (4.2). A stirred solution of 4.3 (20 g, 76.69 mmol) in 4 N HCl/EtOAc (400 mL) was stirred at room temperature overnight. After consumption of the starting material (monitored by LCMS), the mixture was filtered and the filter cake was washed with EtOAc (50 mL). The filter cake was dried to give 4.2 (11.0 g, 91.6% yield) as a yellow solid. LC-MS m/z: 157.4 [M+1]$^+$. LCMS purity (214 nm): 85.50%; $t_R$=0.709 min.

3-bromoquinoline-8-carboxylic acid (4.1). To a solution of 4.2 (550 mg, 3.51 mmol) in MeOH (30 mL) was added CH$_2$O (949 mg, 10.53 mmol), AcOH (3 drops) and NaBH$_3$CN (662 mg, 10.53 mmol). The reaction was stirred at 80° C. overnight. After the reaction was completed, the mixture was evaporated in vacuo and purified by reversed phase prep-HPLC give 4.1 (150 mg, 23.1% yield) as a yellow oil. LC-MS m/z: 185.4 [M+1]$^+$. LCMS purity (214 nm): 94.33%; $t_R$=0.381 min.

(S)—N$^4$-(5-(1-(dimethylamino)ethyl)79yridine-2-yl)-N$^6$-(3-(methylsulfonyl)79yridine-2-yl) pyrimidine-4,6-diamine (4). To a solution of 4.1 (150 mg, 0.81 mmol) in dioxane (5 mL) was added N$^4$-(3-(methylsulfonyl)79yridine-2-yl)pyrimidine-4,6-diamine (1A, 215 mg, 0.81 mmol), Cs$_2$CO$_3$ (528 mg, 1.62 mmol) and Brettphos-Pd-G3 (73 mg, 0.081 mmol), Xantphos (47 mg, 0.081 mmol). The reaction was heated to 110° C. and stirred at 110° C. MW 3 h under nitrogen atmosphere. After the reaction was completed, the mixture was filtered via diatomite. The filtrate was concentrated and purified by reversed phase prep-HPLC to give 4 (31.32 mg, 9.4% yield) as a yellow solid. $^1$H NMR (400 MHz, DMSO-d$_6$) δ10.14 (s, 1H), 9.44 (s, 1H), 8.77 (s, 1H), 8.66 (dd, J=4.8, 1.6 Hz, 1H), 8.40 (d, J=0.8 Hz, 1H), 8.27 (dd, J=7.6, 1.6 Hz, 1H), 8.21 (d, J=1.6 Hz, 1H), 7.70 (d, J=8.4 Hz, 1H), 7.66 (dd, J=8.8, 2.4 Hz, 1H), 7.27 (dd, J=8.0, 5.2 Hz, 1H), 3.39 (s, 3H), 3.37-3.35 (m, 1H), 2.10 (s, 6H), 1.30 (d, J=6.8 Hz, 3H). LC-MS m/z: 414.2 [M+H]$^+$. HPLC purity (254 nm): 99.29%, $t_R$=6.961 min.

Example 1e: Preparation of Compound 5

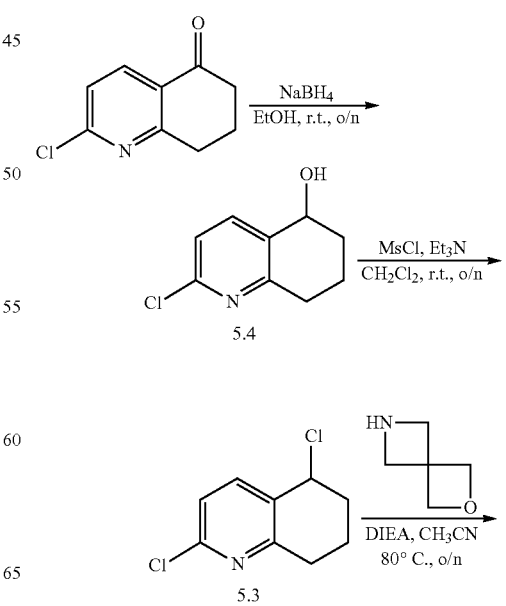

-continued

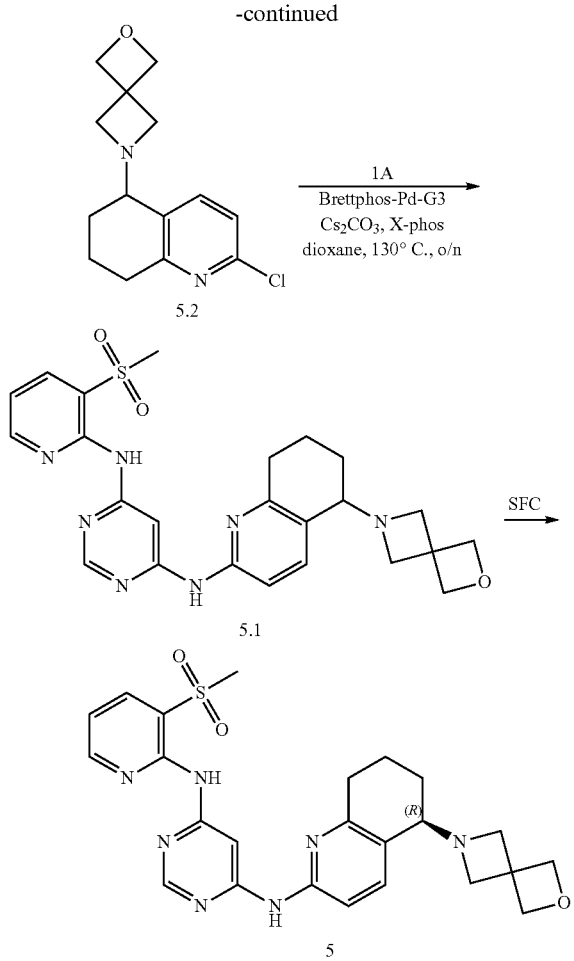

2-chloro-5,6,7,8-tetrahydroquinolin-5-ol (5.4). A stirred solution of 2-chloro-7,8-dihydroquinolin-5 (6H)-one (200 mg, 1.10 mmol) added NaBH$_4$ (42 mg, 1.10 mmol) in EtOH (5 mL). The mixture was stirred at room temperature overnight. After consumption of the starting material (monitored by LCMS), the mixture was diluted with water (20 mL) and extracted with EtOAc (20 mL×3). The combined organic layers were washed with brine (20 mL×3), dried over sodium and concentrated in vacuo to give 5.4 (200 mg, 99% yield) as yellow oil. LC-MS m/z: 184.2 [M+1]$^+$. LCMS purity (254 nm): >99.9%; $t_R$=1.391 min.

2,5-dichloro-5,6,7,8-tetrahydroquinoline (5.3). A stirred solution of 5.4 (200 mg, 1.09 mmol) added MsCl (250 mg, 2.18 mmol) and Et$_3$N (331 mg, 3.27 mmol) in CH$_2$Cl$_2$ (5 mL). The mixture was stirred at room temperature overnight. After consumption of the starting material (monitored by LCMS), the mixture was concentrated in vacuo. The residue was purified by column chromatography on silica gel (petroleum ether/EtOAc=10/1) to give 5.3 (150 mg, 68% yield) as yellow oil. LC-MS m/z: 202.2 [M+1]$^+$. LCMS purity (254 nm): 78.40%; $t_R$=2.085 min.

6-(2-chloro-5,6,7,8-tetrahydroquinolin-5-yl)-2-oxa-6-azaspiro [3.3]heptane (5.2). A stirred solution of 5.3 (130 mg, 0.64 mmol) added 2-oxa-6-azaspiro [3.3] heptane (64 mg, 0.64 mmol) and 80yri (250 mg, 1.94 mmol) in CH$_3$CN (6 mL). The mixture was stirred at 80° C. overnight. After consumption of the starting material (monitored by LCMS), the mixture was concentrated in vacuo. The residue was purified by column chromatography on silica gel (CH$_2$Cl$_2$/CH$_3$OH=20/1) to give 5.2 (100 mg, 59% yield) as yellow oil. LC-MS m/z: 265.2 [M+1]$^+$. LCMS purity (254 nm): >99.9%; $t_R$=1.554 min.

I-N$^4$-(5-(2-oxa-6-azaspiro[3.3]heptan-6-yl)-5,6,7,8-tetrahydroquinolin-2-yl)-N$^6$-(3-(methylsulfonyl)81yridine-2-yl)pyrimidine-4,6-diamine (5). A stirred solution of 5.2 (100 mg, 0.38 mmol) added 1A (100 mg, 0.38 mmol), Brettphos-Pd-G3 (36 mg, 0.04 mmol), X-phos (19 mg, 0.04 mmol), Cs$_2$CO$_3$ (248 mg, 0.76 mmol) in dioxane (5 mL). The mixture was stirred at 130° C. overnight. After consumption of the starting material (monitored by LCMS), the mixture was filtered and the filtrate was concentrated at reduced pressure. The residue was dissolved in EtOAc (20 mL) and washed with water (20 mL×2) then brine (20 mL×2). The organic layer was dried over anhydrous sodium sulfate and concentrated in vacuo. The residue was purified by column chromatography on silica (CH$_2$Cl$_2$/CH$_3$OH=10/1) and reversed-phase Prep-HPLC to give 5.1 (59 mg, 32% yield) as a white solid. Then 5.1 (59 mg, 0.12 mmol) was further purified by SFC to give 5 (21 mg, 36% yield) as a white solid. $^1$H NMR (400 MHz, DMSO-d$_6$) δ 10.06 (s, 1H), 9.46 (s, 1H), 9.04 (br, 1H), 8.63 (dd, J=4.8, 2.0 Hz, 1H), 8.38 (d, J=0.8 Hz, 1H), 8.26 (dd, J=8.0, 2.0 Hz, 1H), 7.49 (d, J=8.8 Hz, 1H), 7.32-7.25 (m, 2H), 4.58 (s, 4H), 3.41 (s, 1H), 3.39 (s, 4H), 3.17-3.12 (m, 3H), 2.82-2.66 (m, 2H), 2.09-2.04 (m, 1H), 1.80-1.75 (m, 1H), 1.71-1.66 (m, 1H), 1.59-1.50 (m, 1H). LC-MS m/z: 494.0 [M+1]$^+$. HPLC purity (214 nm): >99.9%; $t_R$=7.835 min.

Example 1f: Preparation of Compound 6

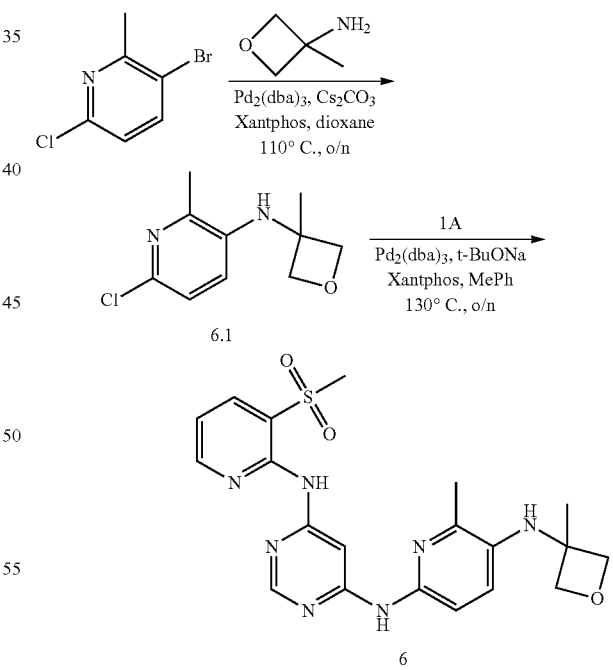

6-chloro-2-methyl-N-(3-methyloxetan-3-yl)81yridine-3-amine (6.1). A suspension of 3-bromo-6-chloro-2-methylpyridine (500 mg, 2.42 mmol), 3-methyloxetan-3-amine (253 mg, 2.91 mmol), Pd$_2$(dba)$_3$ (222 mg, 0.24 mmol), Xantphos (280 mg, 0.48 mmol) and Cs$_2$CO$_3$ (1578 mg, 4.84 mmol) in dry 1,4-dioxane (30 mL) was stirred at 110° C. overnight under nitrogen. After the reaction was completed, the mixture was concentrated and purified by column chromatography on silica gel (EtOAc/Hexane 60%) to give 6.1 (220 mg, 42.7% yield) as a yellow oil. LC-MS m/z: 213.1 [M+H]⁺. LCMS purity (214 nm): 98.77%; $t_R$=1.438 min.

N⁴-(6-methyl-5-((3-methyloxetan-3-yl)amino)82yridine-2-yl)-N⁶-(3-(methylsulfonyl)82yridine-2-yl)pyrimidine-4,6-diamine (6). A suspension of 6.1 (220 mg, 1.03 mmol), 1 A (329 mg, 1.24 mmol), Pd₂(dba)₃ (95 mg, 0.10 mmol), Xantphos (120 mg, 0.21 mmol) and t-BuONa (199 mg, 2.07 mmol) in dry toluene (30 mL) was stirred at 130° C. overnight under nitrogen. After the reaction was completed, the mixture was concentrated and purified by column chromatography on silica gel (MeOH/CH₂Cl₂ 15%). Then the mixture was further purification with reversed phase prep-HPLC to give 6 (80 mg, 17.5% yield) as a yellow solid. ¹H NMR (400 MHz, DMSO-d₆) δ9.69 (s, 1H), 9.37 (s, 1H), 8.75 (br, 1H), 8.60 (dd, J=5.2, 2.0 Hz, 1H), 8.29 (d, J=1.2 Hz, 1H), 8.25 (dd, J=8.0, 1.6 Hz, 1H), 7.27-7.24 (m, 2H), 6.45 (d, J=8.8 Hz, 1H), 5.28 (s, 1H), 4.65 (d, J=5.6 Hz, 2H), 4.48 (d, J=5.6 Hz, 2H), 3.38 (s, 3H), 2.36 (s, 3H), 1.55 (s, 3H). LC-MS m/z: 442.4 [M+H]⁺. HPLC purity (214 nm): >99.9%; $t_R$=6.984 min.

Example 1g: Preparation of Compound 7

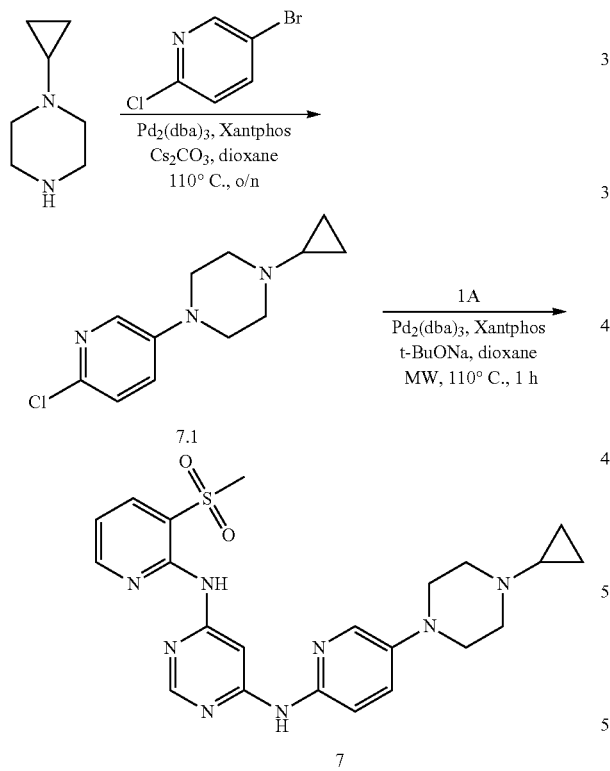

1-(6-chloropyridin-3-yl)-4-cyclopropylpiperazine (7.1). To a solution of 1-cyclopropylpiperazine (1.31 g, 10.38 mmol) in dioxane (30 mL) was added 5-bromo-2-chloropyridine (2.00 g, 10.38 mmol), Cs₂CO₃ (6.76 g, 20.76 mmol), Xantphos (301 mg, 0.52 mmol) and Pd₂(dba)₃ (238 mg, 0.26 mmol). Then the mixture was stirred at 110° C. overnight under nitrogen atmosphere. After consumption of the starting material (monitored by LCMS), the reaction mixture was cooled to room temperature. Then the reaction mixture was diluted with water (80 mL) and extracted with EtOAc (60 mL×3). The combined organic layers were washed with brine (50 mL), dried over anhydrous sodium sulfate and concentrated to dryness. The residue was purified by silica gel column chromatography (EtOAc/petrol ether=2/5) to give 7.1 (130 mg, 5% yield) as a yellow solid. LC-MS m/z: 238.4 [M+1]⁺. LCMS purity (214 nm): >99.9%; $t_R$=0.395 min.

N⁴-(5-(4-cyclopropylpipeiazin-1-yl) 83yridine-2-yl)-N⁶-(3-(methylsulfonyl)83yridine-2-yl)pyrimidine-4,6-diamine (7). To a solution of 7.1 (50 mg, 0.21 mmol) in dioxane (3 mL) was added 1A (56 mg, 0.21 mmol), t-BuONa (40 mg, 0.42 mmol), Xantphos (12 mg, 0.021 mmol) and Pd₂(dba)₃ (10 mg, 0.011 mmol). Then the mixture was irradiated with microwave for 1 h at 110° C. under nitrogen atmosphere. After consumption of the starting material (monitored by LCMS), the reaction mixture was cooled to room temperature. Then the reaction mixture was diluted with water (20 mL) and extracted with EtOAc (20 mL×3). The combined organic layers were washed with brine (20 mL), dried over anhydrous sodium sulfate and concentrated to dryness. The residue was purified by column chromatography on silica gel (CH₂Cl₂/MeOH=10/1) and reversed-phase Prep-HPLC to give 7 (18 mg, 18% yield) as a white solid. ¹H NMR (400 MHz, DMSO-d₆) δ 9.90 (s, 1H), 9.38 (s, 1H), 8.66 (dd, J=4.8, 2.0 Hz, 1H), 8.62 (br, 1H), 8.34 (d, J=0.8 Hz, 1H), 8.25 (dd, J=8.0, 1.6 Hz, 1H), 8.00 (d, J=2.8 Hz, 1H), 7.60 (d, J=8.8 Hz, 1H), 7.42 (dd, J=9.2, 3.2 Hz, 1H), 7.25 (dd, J=8.0, 4.8 Hz, 1H), 3.38 (s, 3H), 3.08 (t, 1=5.2 Hz, 4H), 2.69 (t, 1=5.2 Hz, 4H), 1.70-1.62 (m, 1H), 0.49-0.42 (m, 2H), 0.36-0.31 (m, 2H). LC-MS m/z: 467.2 [M+1]⁺. HPLC purity (214 nm): >99.9%; $t_R$=7.974 min.

Example 1h: Preparation of Compound 8

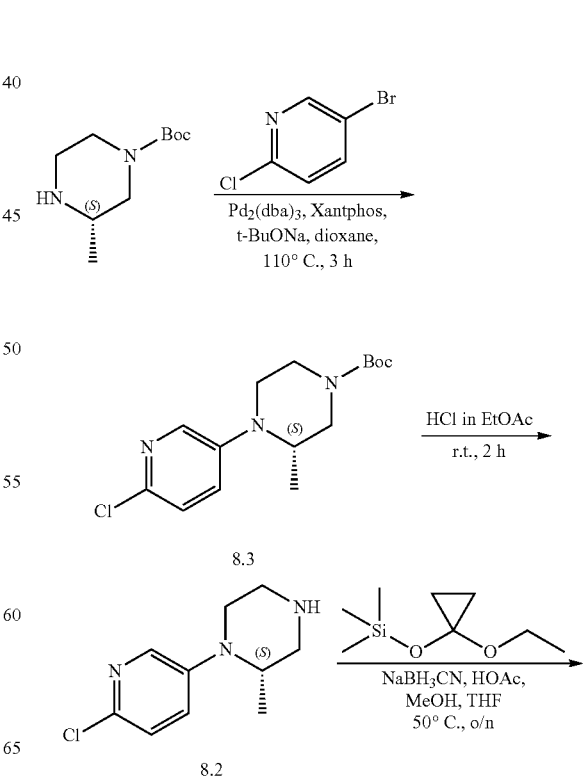

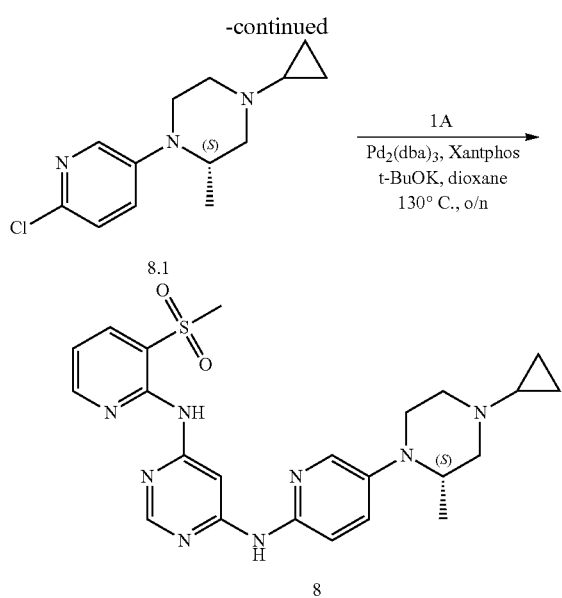

(S)-tert-butyl 4-(6-chloropyridin-3-yl)-3-methylpiperazine-1-carboxylate (83). To a solution of tert-butyl (S)-3-methylpiperazine-1-cathoxylate (20.0 g, 99.86 mmol) in dioxane (400 mL) was added 5-bromo-2-chloropyridine (19.22 g, 99.86 mmol), t-BuONa (19.19 g, 199.72 mmol), Pd$_2$(dba)$_3$ (2.29 g, 2.50 mmol) and Xantphos (1.44 g, 2.50 mmol). The mixture was stirred for 3 h at 100° C. under nitrogen. After consumption of the starting material (monitored by LCMS), the mixture was cooled to room temperature, diluted with water (200 mL) and extracted with EtOAc (90 mL×3). The combined organic layers were washed with brine (80 mL×2), dried over sodium sulfate and concentrated to dryness. The residue was purified by column chromatography on silica gel (petrol ether/EtOAc=5/1) to give 8.3 (23.00 g, 74% yield) as light-yellow oil. LC-MS m/z: 312.2 [M+1]$^+$. LCMS purity (214 nm): 94.60%; t$_R$=2.165 min.

(S)-1-(6-chloropyridin-3-yl)-2-methylpiperazine (8.2). To a solution of 83 (10.00 g, 32.07 mmol) in HCl in EtOAc (3 N, 120 mL) was stirred at room temperature overnight. After consumption of the starting material (monitored by LCMS), the solvent was removed in vacuo. The residue was diluted with saturated aqueous solution of NaHCO$_3$ (100 mL) and extracted with ethyl acetate (80 mL×3). The combined organic layers were washed with brine (60 mL×2), dried over sodium sulfate and concentrated to dryness to give 8.2 (6.70 g, crude) as a light brown solid used for next step directly. LC-MS m/z: 212.3 [M+1]$^+$. LCMS purity (254 nm): 97.60%; t$_R$=1.338 min.

(S)-1-(6-chloropyridin-3-yl)-4-cyclopropyl-2-methylpiperazine (8.1). To a solution of 8.2 (6.7 g, 31.65 mmol) in THF (70 mL) and MeOH (70 mL) was added (1-ethoxycyclopropoxy)trimethylsilane (16.55 g, 94.95 mmol), NaBH$_3$CN (5.97 g, 94.95 mmol) and HOAc (1.90 g, 31.65 mmol). The mixture was stirred at 50° C. overnight. After consumption of the starting material (monitored by LCMS), the mixture was diluted with water (90 mL) and extracted with EtOAc (80 mL×3). The combined organic layers were washed with brine (60 mL×2), dried over sodium sulfate and concentrated to dryness. The residue was purified by column chromatography on silica gel (petro ether/EtOAc=3/1) to give 8.1 (6.00 g, 75% yield for two steps) as light brown oil. LC-MS m/z: 252.4 [M+1]$^+$. LCMS purity (254 nm): 91.41%; t$_R$=2.008 min.

(S)—N$^4$-(5-(4-cyclopropyl-2-methylpiperazin-1-yl)85yridine-2-yl)-N$^6$-(3-(methylsulfonyl)85yridine-2-yl)pyrimidine-4,6-diamine (8). To a solution of 8.1 (3.50 g, 13.90 mmol) in dioxane (110 mL) was added 1A (3.69 g, 13.90 mmol), t-BuOK (3.12 g, 27.80 mmol), Pd$_2$(dba)$_3$ (637 mg, 0.70 mmol) and Xantphos (804 mg, 1.39 mmol). The mixture was stirred overnight at 130° C. under nitrogen atmosphere. After consumption of the starting material (monitored by LCMS), the mixture was cooled to room temperature, diluted with water (60 mL) and extracted with EtOAc (70 mL×3). The combined organic layers were washed with brine (50 mL×2), dried over sodium sulfate and concentrated to dryness. The residue was purified by column chromatography on silica gel (CH$_2$Cl$_2$/MeOH=10/1) and reversed phase prep-HPLC to give 8 (1.80 g, 27% yield) as a white solid. $^1$H NMR (400 MHz, DMSO-d$_6$) δ 9.90 (s, 1H), 9.39 (s, 1H), 8.66 (dd, J=4.8, 2.0 Hz, 1H), 8.62 (br, 1H), 8.35 (d, J=0.8 Hz, 1H), 8.25 (dd, J=8.0, 2.0 Hz, 1H), 7.97 (d, J=2.8 Hz, 1H), 7.61 (d, J=8.4 Hz, 1H), 7.41 (dd, J=9.2, 3.2 Hz, 1H), 7.25 (dd, J=7.6, 4.8 Hz, 1H), 3.82-3.71 (m, 1H), 3.38 (s, 3H), 3.20-3.10 (m, 1H), 2.95-2.78 (m, 2H), 2.70-2.58 (m, 2H), 2.49-2.42 (m, 1H), 1.70-1.58 (m, 1H), 0.90 (d, J=6.4 Hz, 3H), 0.51-0.41 (m, 2H), 0.41-0.32 (m, 1H), 0.32-0.19 (m, 1H). LC-MS m/z: 481.4 [M+1]$^+$. HPLC purity (254 nm): >99.9%; t$_R$=9.001 min.

Example 1i: Preparation of Compound 9

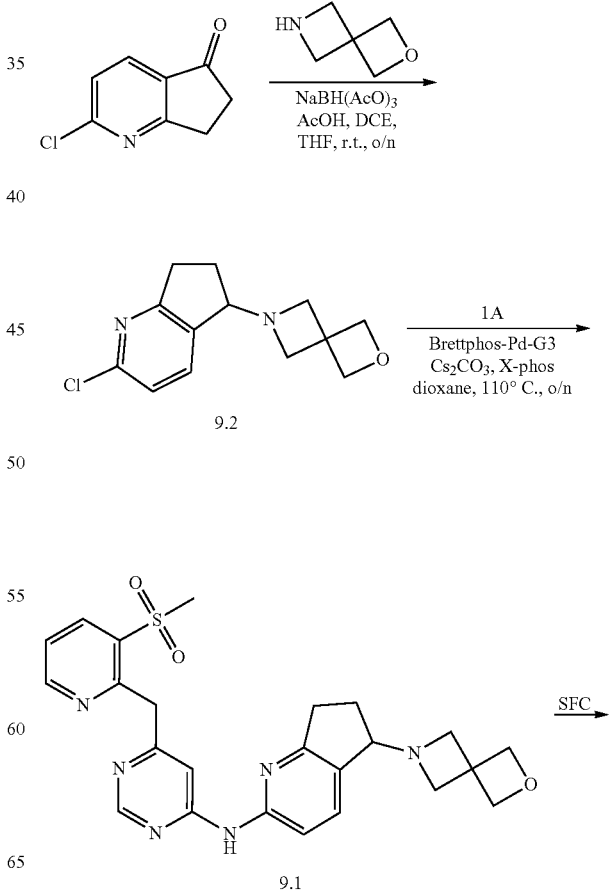

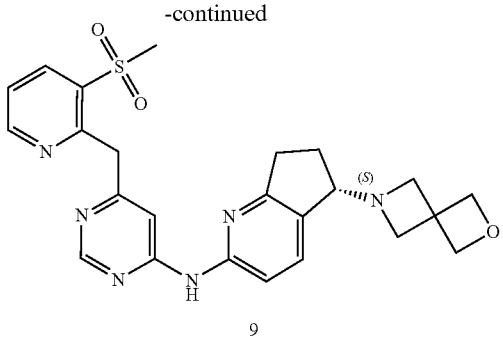

9

6-(2-chloro-6,7-dihydro-5H-cyclopenta[b]85yridine-5-yl)-2-oxa-6-azaspiro[3.3]heptane (9.2). To a solution of 2-chloro-6,7-dihydro-5H-cyclopenta[b]85yridine-5-one (3.10 g, 18.50 mmol) in THF (5 mL) and DCE (50 mL) was added 2-oxa-6-azaspiro[3.3]heptanes (2.75 g, 27.75 mmol), $NaBH(AcO)_3$ (11.76 g, 55.49 mmol) and HOAc (1.11 g, 18.50 mmol). The mixture was stirred at room temperature overnight. After consumption of the starting material (monitored by LCMS), the mixture was diluted with water (90 mL) and extracted with EtOAc (60 mL×3). The combined organic layers were washed with brine (50 mL×2), dried over sodium sulfate and concentrated to dryness. The residue was purified by column chromatography on silica gel (petro ether/THF=1/1) to give 9.2 (2.00 g, 43% yield) as light brown oil. LC-MS m/z: 251.2 $[M+1]^+$. LCMS purity (214 nm): 97.04%; $t_R$=1.462 min.

$N^4$-((5S)-5-(2-oxa-6-azaspiro[3.3]heptan-6-yl)-6,7-dihydro-5H-cyclopenta[b]86yridine-2-yl)-$N^6$-(3-(methylsulfonyl)86yridine-2-yl)pyrimidine-4,6-diamine (9). To a stirred solution of 9.2 (112 mg, 0.45 mmol) in dioxane (5 mL) was added 1A (118 mg, 0.45 mmol), $Cs_2CO_3$ (293 mg, 0.90 mmol), X-phos (21 mg, 0.045 mmol) and Brettphos Pd G3 (41 mg, 0.045 mmol). The mixture was stirred at 110° C. overnight under nitrogen. After consumption of the starting material (monitored by LCMS), the mixture was filtered and the filtrate was concentrated in vacuo. The residue was purified by column chromatography on silica gel ($CH_2Cl_2$/MeOH=8/1), reversed-phase Prep-HPLC to give 9.1, then further purified by SFC to give 9 (13 mg, 6% yield) as an off white solid. $^1$H NMR (400 MHz, DMSO-$d_6$) δ 10.13 (s, 1H), 9.46 (br, 1H), 9.06 (s, 1H), 8.63 (dd, J=4.8, 2.0 Hz, 1H), 8.39 (d, J=0.8 Hz, 1H), 8.26 (dd, J=7.6, 1.6 Hz, 1H), 7.59 (d, J=8.0 Hz, 1H), 7.32 (d, J=8.4 Hz, 1H), 7.27 (dd, J=7.6, 4.8 Hz, 1H), 4.59 (s, 4H), 3.72 (dd, J=6.8, 2.8 Hz, 1H), 3.39 (d, J=6.4 Hz, 5H), 3.28 (d, J=6.8 Hz, 2H), 3.02-2.91 (m, 1H), 2.82-2.70 (m, 1H), 2.12-2.01 (m, 1H), 1.85-1.76 (m, 1H). LC-MS m/z: 480.2 $[M+1]^+$. HPLC purity (214 nm): >99.9%; $t_R$=6.877 min.

Example 1j: Preparation of Compound 10

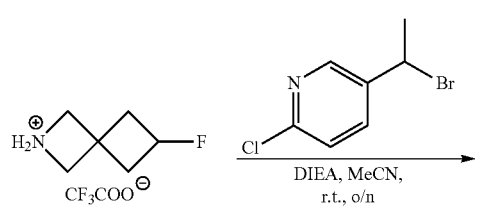

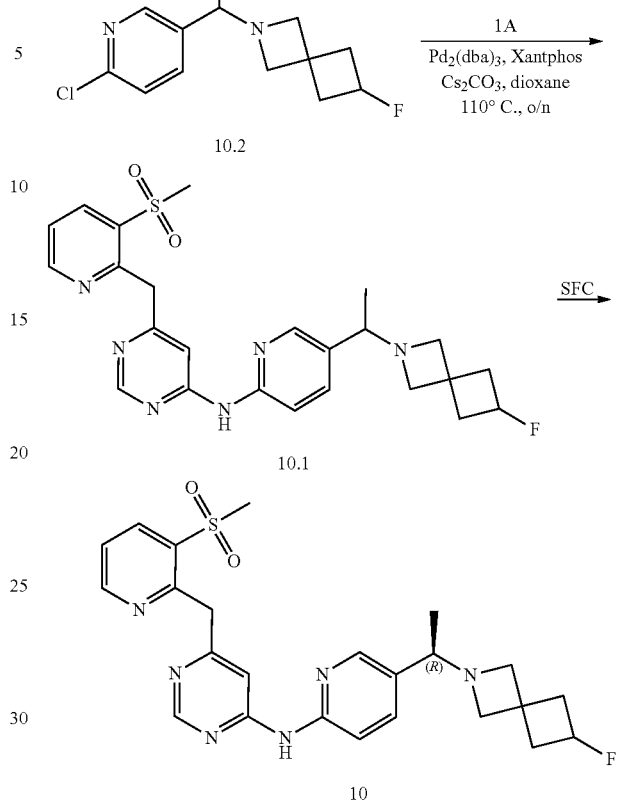

2-(1-(6-chloropyridin-3-yl)ethyl)-6-fluoro-2-azaspiro[3.3] heptane (10.2). To a solution of 6-fluoro-2-azaspiro[3.3]heptan-2-ium 2,2,2-trifluoroacetate (130 mg, 0.57 mmol) in MeCN (10 mL) was added 5-(1-bromoethyl)-2-chloropyridine (150 mg, 0.68 mmol) and 87yri (220 mg, 1.70 mmol). The mixture was stirred at room temperature overnight under nitrogen atmosphere. After consumption of the starting material (monitored by LCMS), the reaction mixture was diluted with water (60 mL) and extracted with EtOAc (30 mL×3). The combined organic layers were washed with brine (30 mL×2), dried over anhydrous sodium sulfate, filtrated and concentrated to dryness. The residue was purified by silica gel column chromatography (petrol ether/EtOAc=1/1) to give 10.2 (140 mg, 97% yield) as a colorless oil. LC-MS m/z: 255.0 $[M+1]^+$. LCMS purity (254 nm): >99.9%; $t_R$=1.523 min.

$N^4$-(5-((1R)-1-(6-fluoro-2-azaspiro[3.3]heptan-2-yl) ethyl) 87yridine-2-yl)-$N^6$-(3-(methylsulfonyl)87yridine-2-yl)pyrimidine-4,6-diamine (10). To a solution of 10.2 (140 mg, 0.55 mmol) in dioxane (10 mL) was added 1A (146 mg, 0.55 mmol), $Cs_2CO_3$ (358 mg, 1.10 mmol), Xantphos (32 mg, 0.055 mmol) and $Pd_2(dba)_3$ (25 mg, 0.027 mmol). Then the mixture was stirred at 110° C. overnight under nitrogen atmosphere. After consumption of the starting material (monitored by LCMS), the reaction mixture was cooled to room temperature. Then the reaction mixture was diluted with water (50 mL) and extracted with EtOAc (30 mL×3). The combined organic layers were washed with brine (50 mL), dried over anhydrous sodium sulfate and concentrated to dryness. The residue was purified by column chromatography on silica gel ($CH_2Cl_2$/MeOH=10/1), reversed-phase Prep-HPLC to give 10.1, then further purified by Prep-SFC to give 10 (14 mg, 5% yield) as an off white solid. ¹H NMR (400 MHz, DMSO-$d_6$) δ10.12 (s, 1H), 9.44 (s, 1H), 8.77 (s, 1H), 8.67 (dd, J=8.8, 1.6 Hz, 1H), 8.40 (d, J=0.8 Hz, 1H), 8.27 (dd, J=8.0, 2.0 Hz, 1H), 8.19 (d, J=1.6 Hz, 1H), 7.72-7.59 (m, 2H), 7.27 (dd, J=8.0, 5.2 Hz, 1H), 5.06-4.78 (m, 1H), 3.39 (s, 3H), 3.27-3.16 (m, 1H), 3.15-3.03 (m, 2H), 3.02-2.90 (m, 2H), 2.50-2.37 (m, 2H), 2.28-2.11 (m, 2H), 1.10 (d, J=6.4 Hz, 3H). LC-MS m/z: 484.0 [M+1]⁺. HPLC purity (214 nm): >99.9%; $t_R$=8.083 min.

Example 1k: Preparation of Compound 11

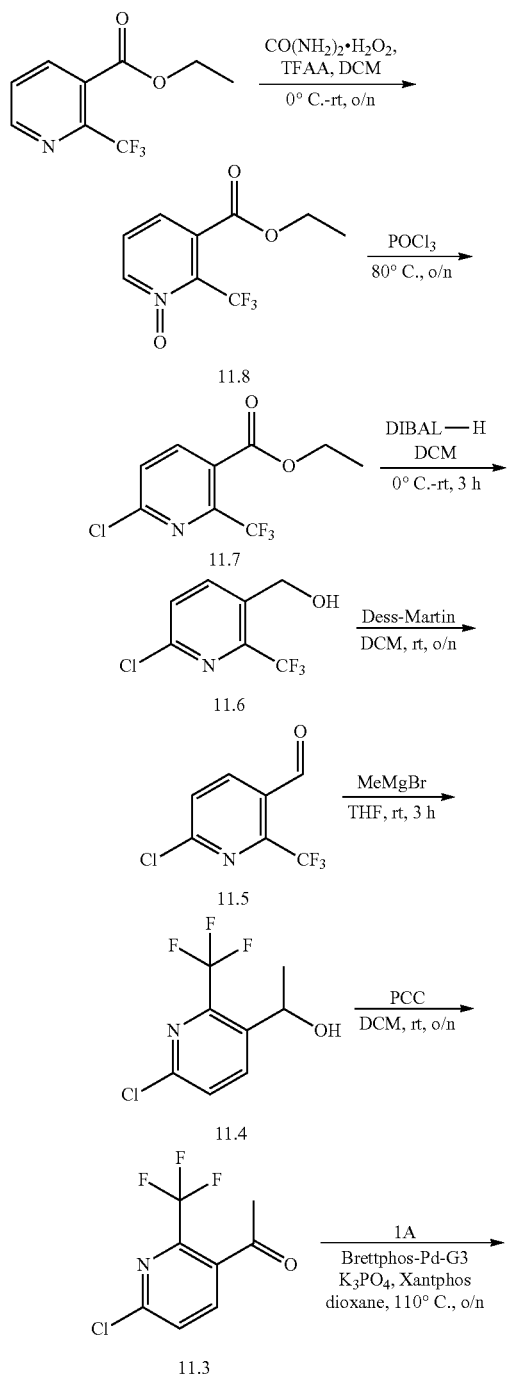

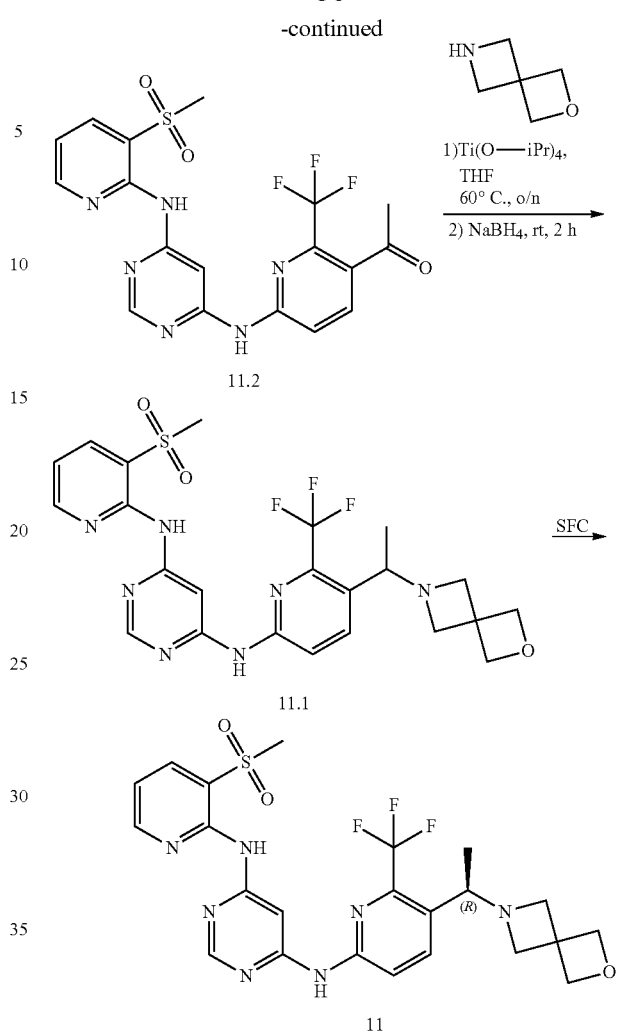

3-(ethoxycarbonyl)-2-(trifluoromethyl)pyridine 1-oxide (11.8). To a solution of ethyl 2-(trifluoromethyl)nicotinate (38 g, 173.4 mmol) in CH$_2$Cl$_2$ (1000 mL) was added CO(NH$_2$)$_2$·H$_2$O$_2$ (37.5 g, 398.8 mmol) at 0° C. The mixture was stirred at 0° C. for 1 hour. Then the solution of TFAA (72.8 g, 346.8 mmol) in CH$_2$Cl$_2$ (200 mL) was added drop wise into the reaction mixture at 0° C. The reaction mixture was warmed to room temperature and stirred at room temperature overnight. After the consumption of starting material (monitored by LCMS), the reaction mixture was washed with Na$_2$CO$_3$ solution (250 mL) and NaHSO$_3$ (250 mL×2). The organic phase was concentrated to give 3-(ethoxycarbonyl)-2-(trifluoromethyl)pyridine 1-oxide 11.8 (crude) as a colorless oil. LC-MS m/z: 236.1 [M+H]⁺. LCMS purity (254 nm): 95.74%; $t_R$=1.443 min.

Ethyl-6-chloro-2-(trifluoromethyl)nicotinate (11.7). A solution of 3-(ethoxycarbonyl)-2-(trifluoromethyl)pyridine 1-oxide 11.8 (crude, 388.03 mmol) in POCl$_3$ (150 mL) was heated to 80° C. and stirred at 80° C. overnight. After the consumption of starting material (monitored by LCMS), the mixture was cooled to 0° C. and quenched with Na$_2$CO$_3$ solution (500 mL) below 10° C. The mixture was extracted with MTBE (250 mL). The organic phase was concentrated and purified by silica gel column chromatography (0-25% EtOAc/Hexane) to give ethyl 6-chloro-2-(trifluoromethyl) nicotinate 11.7 (58 g, 59.08% yield two steps) as a colorless oil. LC-MS m/z: 254.1 [M+H]⁺. LCMS purity (214 nm): 88.85%; $t_R$=1.902 min.

(6-chloro-2-(trifluoromethyl)89yridine-3-yl)methanol (11.6). To a solution of ethyl 6-chloro-2-(trifluoromethyl)nicotinate 11.7 (19 g, 74.9 mmol) in $CH_2Cl_2$ (500 mL) was added drop wise DIBAL-H 1M in THF solution (150 mL, 149.8 mmol) at 0° C. The mixture was warmed to room temperature and stirred at room temperature for 3 hours. After the consumption of starting material (monitored by LCMS), the reaction mixture was quenched with water (30 mL) below 10° C. The mixture was filtered via diatomite and the filter cake was washed with $CH_2Cl_2$ (250 mL). The filtrate was concentrated to give (6-chloro-2-(trifluoromethyl)89yridine-3-yl)methanol 11.6 (crude) as a colorless oil. LC-MS m/z: 212.1 $[M+H]^+$. LCMS purity (214 nm): 92.14%; $t_R$=1.576 min.

6-chloro-2-(trifluoromethyl)nicotinaldehyde (11.5). To a solution of (6-chloro-2-(trifluoromethyl)89yridine-3-yl)methanol 11.6 (crude, 74.9 mmol) in $CH_2Cl_2$ (300 mL) was added Dess-Martin (38.9 g, 91.7 mmol). The mixture was stirred at room temperature overnight. After the consumption of starting material (monitored by LCMS), the reaction mixture was filtered via diatomite and the filter cake was washed with $CH_2Cl_2$ (200 mL). The filtrate was concentrated and purified by silica gel column chromatography (0-25% EtOAc/Hexane) to give 6-chloro-2-(trifluoromethyl)nicotinaldehyde 11.5 (9.5 g, 60.7% yield two steps) as a colorless oil. LC-MS m/z: none. LCMS purity (254 nm): 96.85%; $t_R$=1.758 min.

1-(6-chloro-2-(trifluoromethyl)89yridine-3-yl)ethanol (11.4). To a solution of 11.5 (330 mg, 1.57 mmol) in THF (20 mL) was added methylmagnesium bromide (1.0 M in THF, 2.4 mL, 2.36 mmol). The reaction was stirred at room temperature for 3 hours. After the reaction was completed, the mixture was poured into aq.$NH_4Cl$ (sat., 50 mL) and extracted with EtOAc (30 mL×3). The combined organic phases were washed with $H_2O$ (50 mL) and brine (50 mL). The organic phase was dried with anhydrous $Na_2SO_4$, concentrated and purified by silica gel column chromatography (EtOAc/Hexane 30%) to afford 11.4 (320 mg, 90.1% yield) as a yellow oil. LC-MS m/z: 226.1 $[M+H]^+$. LCMS purity (254 nm): >99%; $t_R$=1.669 min.

1-(6-chloro-2-(trifluoromethyl)89yridine-3-yl)89yridine (113). To a solution of 11.4 (100 mg, 0.44 mmol) in $CH_2Cl_2$ (20 mL) was added PCC (191 mg, 0.89 mmol). The reaction was stirred at room temperature overnight. After the reaction was completed, the mixture was concentrated and purified by silica gel column chromatography (EtOAc/Hexane 12%) to afford 11.3 (70 mg, 70.6% yield) as a yellow oil. LC-MS m/z: 224.1 $[M+H]^+$. LCMS purity (214 nm): 95.79%; $t_R$=1.729 min.

1-(6-((6-((3-(methylsulfonyl)90yridine-2-yl)amino)pyrimidin-4-yl)amino)-2-(trifluoromethyl)90yridine-3-yl)90yridine (11.2). A suspension of 11.3 (70 mg, 0.31 mmol), 1A (100 mg, 0.38 mmol), Brettphos-Pd-G3 (28 mg, 0.031 mmol), Xantphos (36 mg, 0.063 mmol) and $K_3PO_4$ (133 mg, 0.63 mmol) in dry 1,4-dioxane (30 mL) was stirred at 110° C. overnight under nitrogen. After the reaction was completed, the mixture was concentrated and purified by column chromatography on silica gel (EtOAc/Hexane 100%) to give 11.2 (100 mg, 70.6% yield) as a yellow solid. LC-MS m/z: 453.1 $[M+H]^+$. LCMS purity (254 nm): 89.51%; $t_R$=1.624 min.

$N^4$-(5-(1-(2-oxa-6-azaspiro[3.3]heptan-6-yl)ethyl)-6-(trifluoromethyl) 90yridine-2-yl)-$N^6$-(3-(methylsulfonyl)90yridine-2-yl)pyrimidine-4,6-diamine (11.1). To a stirred solution of 11.2 (100 mg, 0.22 mmol) in THF (20 mL) was added 2-oxa-6-azaspiro[3.3]heptane (44 mg, 0.44 mmol) and Titanium tetraisopropanolate (126 mg, 0.44 mmol). The mixture was stirred at 60° C. overnight. Then $NaBH_4$ (17 mg, 0.44 mmol) was added into the mixture. The mixture was stirred at room temperature for 2 hours. After reaction was completed, the mixture was quenched with 20 mL of water. The mixture was filtered via diatomite and the filter cake was washed with EtOAc (20 mL). The filtrate was concentrated and extracted with EtOAc (20 mL×3). The combined organic layers were washed with brine (20 mL), dried over anhydrous sodium sulfate, filtered and concentrated in vacuo. The residue was purified by reversed phase prep-HPLC to give 11.1 (33 mg, 27.9% yield) as a white solid. $^1$H NMR (400 MHz, DMSO-$d_6$) δ 10.50 (s, 1H), 9.53 (s, 1H), 8.86 (s, 1H), 8.55 (dd, J=4.8, 1.6 Hz, 1H), 8.45 (d, J=0.8 Hz, 1H), 8.27 (dd, J=8.0, 2.0 Hz, 1H), 8.09 (d, J=8.8 Hz, 1H), 7.84 (d, J=8.8 Hz, 1H), 7.30 (dd, J=8.0, 5.2 Hz, 1H), 4.59 (s, 4H), 3.56-3.54 (m, 1H), 3.40 (s, 3H), 3.23 (d, J=7.2 Hz, 2H), 3.18 (d, J=7.2 Hz, 2H), 1.10 (d, J=6.0 Hz, 3H). LC-MS m/z: 536.0 $[M+H]^+$. HPLC purity (214 nm): >99.9%; $t_R$=8.382 min.

1-$N^4$-(5-(1-(2-oxa-6-azaspiro[3.3]heptan-6-yl)ethyl)-6-(trifluoromethyl)90yridine-2-yl)-$N^6$-(3-(methylsulfonyl) 90yridine-2-yl)pyrimidine-4,6-diamine (11). 11.1 (80 mg) was purified by prep-SFC to give 11 (33.84 mg, 84.6% yield) as a white solid. $^1$H NMR (400 MHz, DMSO-$d_6$) δ 10.50 (s, 1H), 9.53 (s, 1H), 8.86 (s, 1H), 8.55 (dd, J=4.8, 1.6 Hz, 1H), 8.45 (d, 1=0.8 Hz, 1H), 8.27 (dd, J=8.0, 2.0 Hz, 1H), 8.09 (d, J=8.4 Hz, 1H), 7.84 (d, J=8.8 Hz, 1H), 7.30 (dd, J=7.6, 4.8 Hz, 1H), 4.59 (s, 4H), 3.56-3.54 (m, 1H), 3.40 (s, 3H), 3.23 (d, J=7.2 Hz, 2H), 3.18 (d, J=7.2 Hz, 2H), 1.10 (d, J=6.0 Hz, 3H). LC-MS m/z: 536.1 $[M+H]^+$. HPLC purity (214 nm): 97.67%; $t_R$=8.213 min.

Example 11: Preparation of Compound 12

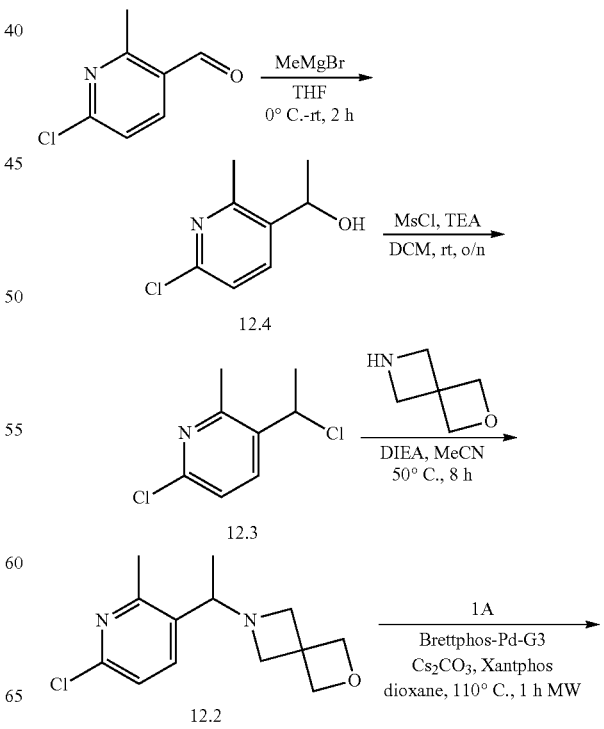

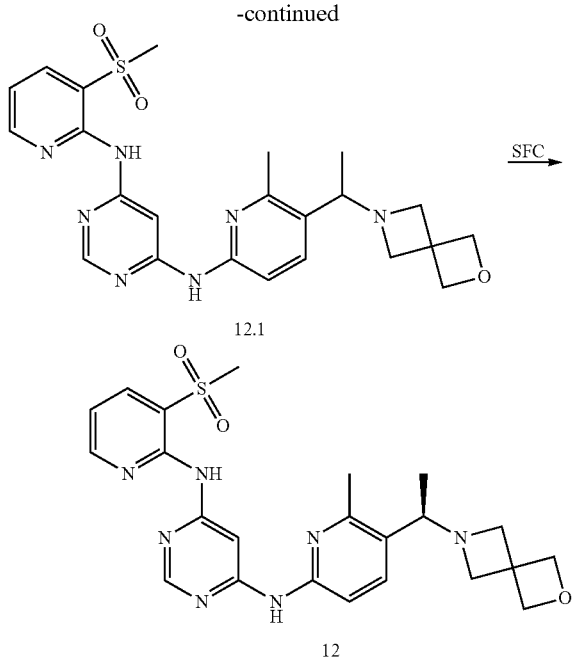

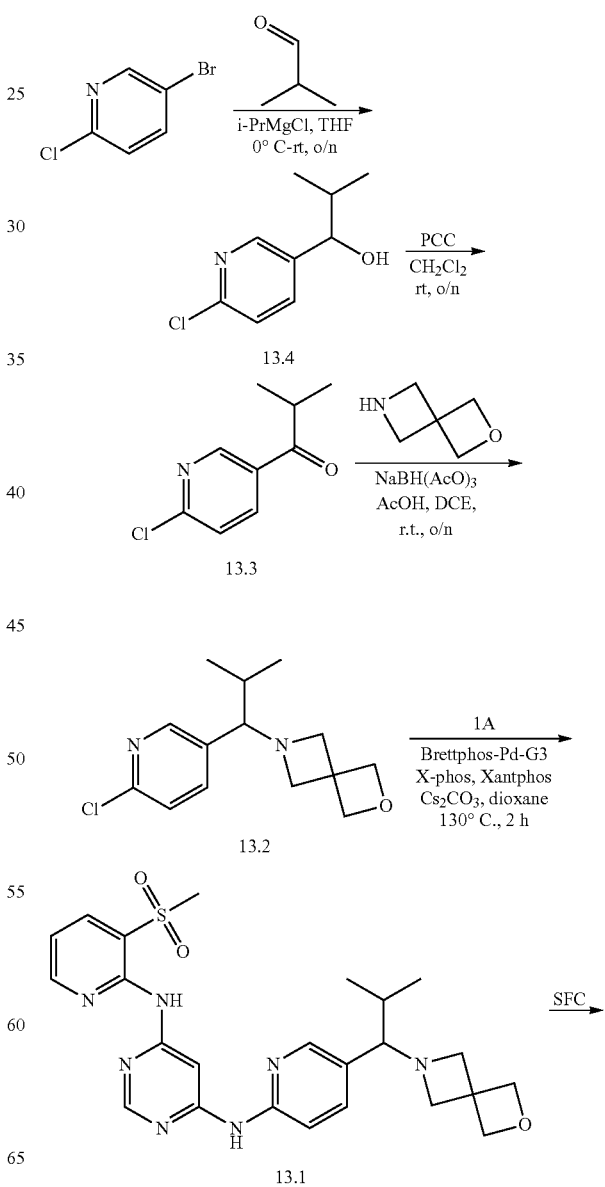

1-(6-chloro-2-methylpyridin-3-yl)ethanol (12.4). To a solution of 6-chloro-2-methylnicotinaldehyde (500 mg, 3.21 mmol) in THF (10 mL) was added MeMgBr (1M in THF, 6.4 mL, 6.43 mmol) at 0° C. Then the mixture was stirred at room temperature for 2 hours. After the reaction was completed, the mixture was quenched with $NH_4Cl$ solution (10 ml) and extracted by ethyl acetate (20 ml). Then the organic phase was dried by anhydrous sodium sulfate and evaporated in vacuo to give crude product. The crude product was purified by column chromatography on silica gel ($CH_2Cl_2$/MeOH=20/1) to give 12.4 (496 mg, 90% yield) as a colorless oil. LC-MS m/z: 172.0 $[M+H]^+$. LCMS purity (214 nm): >99.9%, $t_R$=1.177 min.

6-chloro-3-(1-chloroethyl)-2-methylpyridine (12.3). To a solution of 12.4 (300 mg, 1.75 mmol) in $CH_2Cl_2$ (10 mL) was added TEA (531 mg, 5.24 mmol) and MsCl (400 mg, 3.5 mmol). The mixture was stirred at room temperature overnight. After the reaction was completed, the mixture was poured into water (15 ml) and extracted by ethyl acetate (20 ml). Then the organic phase was dried by anhydrous sodium sulfate and evaporated in vacuo to give crude product. The crude product was purified by column chromatography on silica gel (Petroleum ether/Ethyl acetate=10/1) to give 12.3 (300 mg, 90% yield) as a colorless oil. LC-MS m/z: 190.2 $[M+H]^+$. LCMS purity (254 nm): 97.75%, $t_R$=1.628 min.

6-(1-(6-chloro-2-methylpyridin-3-yl)ethyl)-2-oxa-6-azaspiro[3.3] heptane (12.2). To a solution of 12.3 (200 mg, 1.05 mmol) in MeCN (10 mL) was added 2-oxa-6-azaspiro[3.3]heptane (209 mg, 2.10 mmol) and 92yri (408 mg, 3.16 mmol). The mixture was stirred at 50° C. for 8 hours. After the reaction was completed, the mixture was evaporated in vacuo to give crude product. The crude product was purified by column chromatography on silica gel ($CH_2Cl_2$/MeOH=20/1) to give 12.2 (200 mg, 75% yield) as a white solid. LC-MS m/z: 253.2 $[M+H]^+$. LCMS purity (214 nm): >99.9%, $t_R$=1.284 min.

$N^4$-(5-(1-(2-oxa-6-azaspiro[3.3]heptan-6-yl)ethyl)-6-methylpyridin-2-yl)-$N^6$-(3-(methylsulfonyl)92yridine-2-yl)pyrimidine-4,6-diamine (12). To a solution of 12.2 (100 mg, 0.40 mmol) and 1A (105 mg, 0.40 mmol) in dioxane (4 mL) was added Brettphos Pd G3 (36 mg, 0.04 mmol), Xantphos (23 mg, 0.04 mmol), $Cs_2CO_3$ (258 mg, 0.79 mmol). The mixture was stirred at 110° C. for 1 hour under nitrogen atmosphere in microwave. After the reaction was completed, the mixture was evaporated in vacuo to give crude product 12.1 which was purified with reversed phase prep-HPLC and Prep-SFC to give 12 (40.81 mg, 43% yield) as a white solid. $^1$H NMR (400 MHz, DMSO-$d_6$) δ 10.04 (s, 1H), 9.47 (s, 1H), 9.09 (s, 1H), 8.63 (d, J=3.6 Hz, 1H), 8.38 (s, 1H), 8.27 (d, J=7.2 Hz, 1H), 7.62 (d, J=8.4 Hz, 1H), 7.34-7.26 (m, 2H), 4.60 (s, 4H), 3.45-3.41 (m, 1H), 3.34 (s, 3H), 3.27-3.18 (m, 4H), 2.50 (s, 3H), 1.05 (d, J=6.4 Hz, 3H). LC-MS m/z: 482.3 $[M+H]^+$. HPLC purity (214 nm): >99.9%, $t_R$=7.123 min.

Example 1m: Preparation of Compound 13

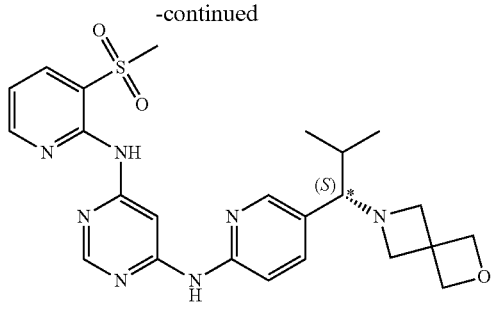

13

1-(6-chloropyridin-3-yl)-2-methylpropan-1-ol (13.4). To a solution of 5-bromo-2-chloropyridine (1.0 g, 5.20 mmol) in dry THF (30 mL) was added i-PrMgCl (2 M in THF, 10 mL, 20.79 mmol) at 0° C. The mixture was stirred at 0° C. until the reaction became turbid. Then isobutyraldehyde (1.87 g, 25.98 mmol) was added drop wise into the mixture below 5° C. The reaction mixture was slowly warmed to room temperature and stirred at room temperature overnight. After consumption of the starting material (monitored by LCMS), the reaction mixture was quenched with saturated $NH_4Cl$ solution (50 mL). The mixture was washed with EtOAc (50 mL). The organic layer was concentrated in vacuo and purified by silica gel column chromatography (Hexane to Hexane/EtOAc=3/1) to give 13.4 (850 mg, 88% yield) as a yellow solid. LC-MS m/z: 186.4 [M+H]$^+$. LCMS purity (254 nm): >99.9%; $t_R$=0.566 min.

1-(6-chloropyridin-3-yl)-2-methylpropan-1-one (13.3). To a solution of 13.4 (400 mg, 2.15 mmol) in $CH_2Cl_2$ (20 mL) was added PCC (929 mg, 4.31 mmol). The mixture was stirred at room temperature overnight. After consumption of the starting material (monitored by LCMS), the reaction mixture was concentrated in vacuo and purified by silica gel column chromatography (Hexane to Hexane/EtOAc=3/1) to give 13.3 (210 mg, 53% yield) as a colorless oil. LC-MS m/z: 184.1 [M+H]$^+$. LCMS purity (254 nm): >99.9%; $t_R$=0.823 min.

6-(1-(6-chloropyridin-3-yl)-2-methylpropyl)-2-oxa-6-azaspiro[3.3]heptane (13.2). A stirred solution of 13.3 (100 mg, 0.55 mmol) in DCE (5 mL) was added 2-oxa-6-azaspiro[3.3]heptane (54 mg, 0.55 mmol), AcOH (33 mg, 0.55 mmol) and NaBH(AcO)$_3$ (351 mg, 1.65 mmol). The mixture was stirred at room temperature overnight. After consumption of the starting material (monitored by LCMS), the mixture was diluted with water (30 mL) and extracted with $CH_2Cl_2$ (40 mL×3). The combined organic layers were washed with the brine (30 mL×3), dried over with sodium sulfate and concentrated to dryness. The residue was purified by column chromatography on silica gel ($CH_2Cl_2$/$CH_3OH$=10/1) to give 13.2 (82 mg, 56% yield) as light brown oil. LC-MS m/z: 267.2 [M+1]$^+$. LCMS purity (254 nm): 93.50%; tR=1.823 min.

(S)—N$^4$-(5-(2-methyl-1-(2-oxa-6-azaspiro[3.3]heptan-6-yl)propyl) pyridine-2-yl)-N$^6$-(3-(methylsulfonyl)93yridine-2-yl)pyrimidine-4,6-diamine (13). A stirred solution of 13.2 (80 mg, 0.30 mmol) in dioxane (6 mL) was added 1A (80 mg, 0.30 mmol), BrettPhos Pd G3 (27 mg, 0.03 mmol), X-phos (14 mg, 0.03 mmol), Xantphos (17 mg, 0.03 mmol), $Cs_2CO_3$ (196 mg, 0.60 mmol). The mixture was stirred at 130° C. for 2 h. After consumption of the starting material (monitored by LCMS), the mixture was concentrated in vacuo, the residue was purified by column chromatography on silica gel ($CH_2Cl_2$/$CH_3OH$=10/1) and reversed-phase Prep-HPLC to get 13.1 (48 mg, 32% yield). Then 13.1 (48 mg, 0.097 mmol) was further purified by Prep-SFC to give 13 (10 mg, 21% yield) as a white solid. $^1$H NMR (400 MHz, DMSO-d$_6$) δ 10.14 (s, 1H), 9.44 (s, 1H), 8.73 (s, 1H), 8.64 (dd, J=4.8, 2.0 Hz, 1H), 8.40 (d, J=0.8 Hz, 1H), 8.27 (dd, 1=8.0, 1.6 Hz, 1H), 8.08 (d, J=2.0 Hz, 1H), 7.69 (d, J=8.8 Hz, 1H), 7.52 (dd, J=8.8, 2.4 Hz, 1H), 7.27 (dd, J=8.0, 4.8 Hz, 1H), 4.62-4.57 (m, 4H), 3.39 (s, 3H), 3.23-3.15 (m, 4H), 3.03 (d, J=4.4 Hz, 1H), 1.89-1.81 (m, 1H), 0.72 (d, J=6.8 Hz, 3H), 0.66 (d, J=6.8 Hz, 3H). LC-MS m/z: 496.0 [M+1]$^+$. HPLC purity (214 nm): >99.9%; $t_R$=8.378 min.

Example 1n: Preparation of Compound 14 and Compound 14a

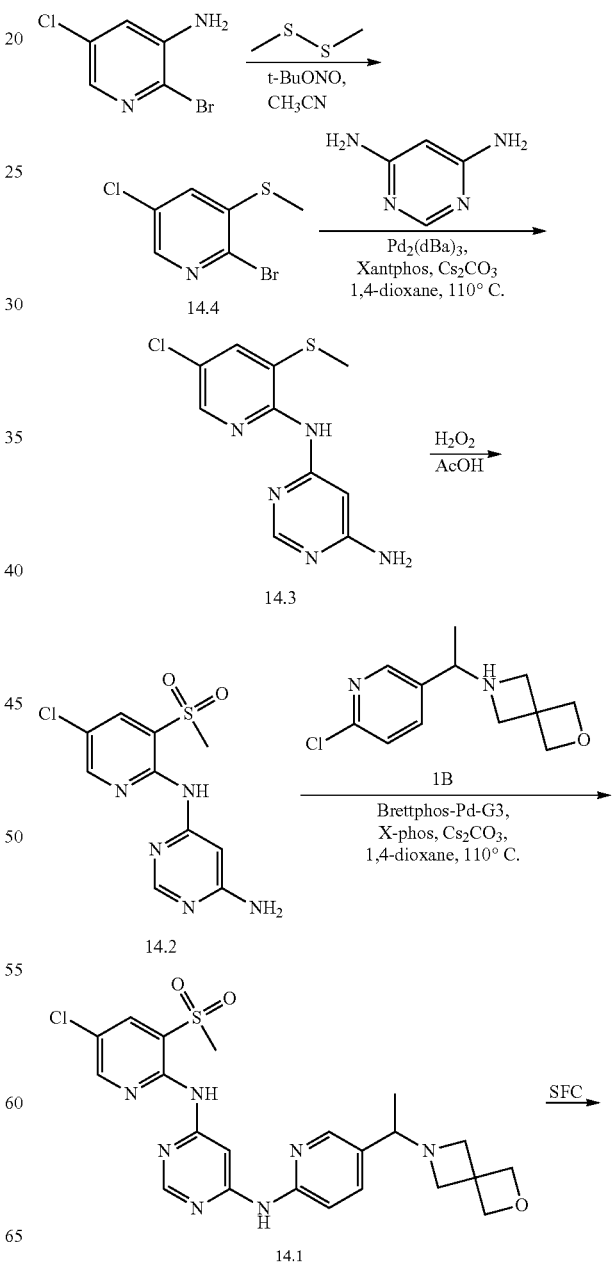

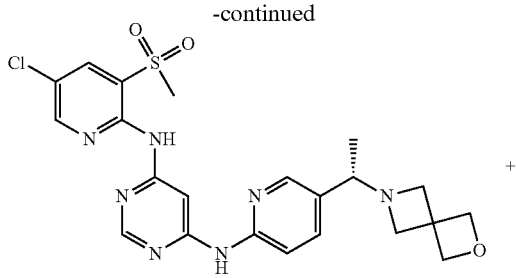

14

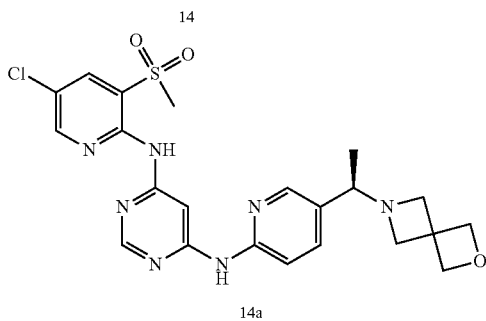

14a 2-bromo-5-chloro-3-(methylthio)pyridine (14.4). To a solution of 2-bromo-5-chloropyridin-3-amine (2.0 g, 9.64 mmol) in CH$_3$CN (50 mL) was added 1,2-dimethydisulfane (2.74 g, 29.10 mmol) and t-BuONO (3.0 g, 29.10 mmol) at room temperature, the reaction mixture was stirred at 80° C. overnight. After the reaction was completed, the mixture was concentrated, diluted by water (50 mL), extracted with CH$_2$Cl$_2$ (50 mL×2), washed with brine (50 mL), dried over anhydrous Na$_2$SO$_4$, concentrated and purified by column chromatography on silica gel (EtOAc:hexane=1:10) to give 14.4 (2.15 g, 93.5% yield) as a brown solid. LC-MS m/z: 237.6 [M+1]$^+$. LCMS purity (214 nm): 30.92%; t$_R$=1.671 min.

N$^4$-chloro-3-(methylthio)94yridine-2-yl)pyrimidine-4,6-diamine (14.3). A mixture of 14.4 (500 mg, 2.10 mmol), pyrimidine-4,6-diamine (279 mg, 2.53 mmol), Pd$_2$(dba)$_3$ (193 mg, 0.21 mmol), Xantphos (244 mg, 0.42 mmol) and Cs$_2$CO$_3$ (2.06 g, 6.33 mmol) in 1,4-dioxane (30 mL) was stirred at 110° C. overnight under argon atmosphere. After the reaction was completed, the mixture was diluted by water (30 mL) and extracted with CH$_2$Cl$_2$ (30 mL×3). The organic extract was washed with brine (50 mL), dried over anhydrous Na$_2$SO$_4$, concentrated and purified by column chromatography on silica gel (CH$_2$Cl$_2$:MeOH=10:1) to give 143 (325 mg, 57.9% yield) as a brown solid. LC-MS m/z: 267.8 [M+1]$^+$. LCMS purity (214 nm): >99.9%; t$_R$=1.363 min.

N$^4$-(5-chloro-3-(methylsulfonyl)pyridine-2-yl)pyrimidine-4,6-diamine (14.2). To a solution of 14.3 (620 mg, 2.32 mmol) in AcOH (5 mL) and H$_2$O (5 mL) was added 30% H$_2$O$_2$ (5.26 g, 46.44 mmol) at room temperature, the reaction mixture was stirred at 40° C. for 24 h. After the reaction was completed, the mixture was diluted by water (20 mL) and extracted with CH$_2$Cl$_2$ (20 mL×3). The organic extract was washed with brine (30 mL), dried over anhydrous Na$_2$SO$_4$, concentrated and purified by column chromatography on silica gel (CH$_2$Cl$_2$:MeOH=10:1) to give 14.2 (300 mg, 43.2% yield) as a yellow solid. LC-MS m/z: 300.0 [M+1]$^+$. LCMS purity (214 nm): 61.18%; t$_R$=1.231 min.

(S)—N$^4$-(5-(1-(2-oxa-6-azaspiro[3.3]heptan-6-yl)ethyl) 95yridine-2-yl)-N$^6$-(5-chloro-3-(methylsulfonyl)95yridine-2-yl)pyrimidine-4,6-diamine (14) and I—N$^4$-(5-(1-(2-oxa-6-azaspiro[3.3]heptan-6-yl)ethyl) 95yridine-2-yl)-N$^6$-(5-chloro-3-(methylsulfonyl)95yridine-2-yl)pyrimidine-4,6-diamine (14a). A mixture of 14.2 (120 mg, 0.40 mmol), 1B (105 mg, 0.44 mmol), Brettphos-Pd-G3 (73 mg, 0.08 mmol), X-phos (76 mg, 0.16 mmol) and Cs$_2$CO$_3$ (392 mg, 1.20 mmol) in 1,4-dioxane (20 mL) was stirred at 110° C. overnight under argon atmosphere. After the reaction was completed, the mixture was diluted by water (30 mL) and extracted with CH$_2$Cl$_2$ (20 mL×3). The organic extract was washed with brine (50 mL), dried over anhydrous Na$_2$SO$_4$, concentrated and purified by column chromatography on silica gel (CH$_2$Cl$_2$:MeOH=10:1) and then reversed phase prep-HPLC to give 14.1 (35 mg, 20.9% yield) as white solid, which was further purified by SFC to give 14 (6.73 mg, 4.1% yield) and 14a (7.78 mg, 4.6% yield) as white solid. Compound 14: $^1$H NMR (400 MHz, DMSO-d$_6$) δ 10.15 (s, 1H), 9.47 (s, 1H), 8.78 (s, 1H), 8.74 (d, J=2.4 Hz, 1H), 8.40 (d, J=0.8 Hz, 1H), 8.32 (d, J=2.4 Hz, 1H), 8.24 (d, J=1.6 Hz, 1H), 7.64-7.59 (m, 2H), 4.59 (t, J=7.2 Hz, 4H), 3.47 (s, 3H), 3.26 (d, J=7.2 Hz, 2H), 3.22-3.20 (m, 1H), 3.13 (d, J=6.8 Hz, 2H), 1.12 (d, J=6.4 Hz, 3H). LC-MS m/z: 502.3 [M+1]$^+$. HPLC purity (214 nm): >99.9%; t$_R$=7.665 min. Compound 14a: $^1$H NMR (400 MHz, DMSO-d$_6$) δ 10.15 (s, 1H), 9.47 (s, 1H), 8.78 (s, 1H), 8.74 (d, J=2.4 Hz, 1H), 8.40 (d, J=1.2 Hz, 1H), 8.32 (d, J=2.4 Hz, 1H), 8.25 (d, J=1.6 Hz, 1H), 7.64-7.59 (m, 2H), 4.59 (t, 1=6.8 Hz, 4H), 3.47 (s, 3H), 3.27-3.21 (d, J=7.2 Hz, 2H), 3.22-3.20 (m, 1H), 3.13 (d, J=7.2 Hz, 2H), 1.12 (d, J=6.4 Hz, 3H). LC-MS m/z: 502.3 [M+1]$^+$. HPLC purity (214 nm): >99.9%; t$_R$=7.664 min.

Example 1o: Preparation of Compound 15

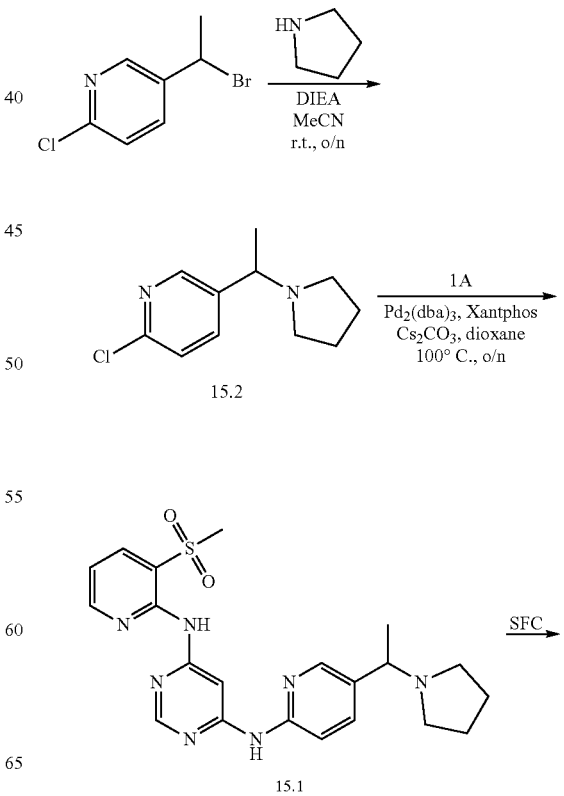

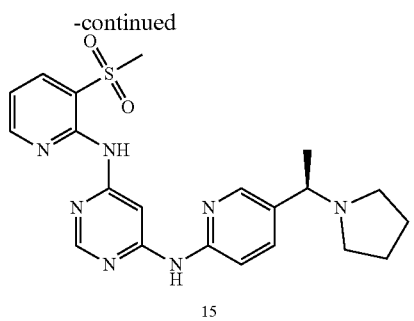

15

2-chloro-5-(1-(96yridine9696e-1-yl)ethyl)pyridine (15.2). To a stirred solution of 5-(1-bromoethyl)-2-chloropyridine (200 mg, 0.91 mmol) in MeCN (10 mL) was added 96yri (469 mg, 3.63 mmol) and pyrrolidine (64 mg, 0.91 mmol). The mixture was stirred at room temperature overnight. After consumption of the starting material (monitored by LCMS), the mixture was poured into ice water (20 mL) and extracted with EtOAc (20 mL×3). The combined organic layer was washed with brine (20 mL×3), dried over $Na_2SO_4$, filtered and concentrated in vacuo. The residue was purified by column chromatography on silica gel (petrol ether/EtOAc=1/3) to give 15.2 (140 mg, 73.2% yield) as light-yellow oil. LC-MS m/z: 211.4 [M+1]$^+$. LCMS purity (254 nm): 85.66%; $t_R$=1.706 min.

$N^4$-(3-(methylsulfonyl)96yridine-2-yl)-$N^6$-(5-(1-(96yridine9696e-1-yl) ethyl)96yridine-2-yl)pyrimidine-4,6-diamine (15.1). To a stirred solution of 15.2 (80 mg, 0.38 mmol) in dioxane (5 mL) was added 1A (101 mg, 0.38 mmol), $Cs_2CO_3$ (247 mg, 0.76 mmol), Xantphos (21 mg, 0.038 mmol) and Brettphos Pd G3 (34 mg, 0.038 mmol). The mixture was stirred overnight at 100° C. under nitrogen. After consumption of the starting material (monitored by LCMS), the mixture was cooled to room temperature, diluted with water (30 mL) and extracted with EtOAc (30 mL×3). The combined organic layers were washed with brine (30 mL×2), dried over sodium sulfate and concentrated to dryness. The residue was purified by column chromatography on silica gel ($CH_2Cl_2$/MeOH=20/1) and reversed-phase Prep-HPLC to give 15.1 (68 mg, 40.8% yield) as a white solid. $^1$H NMR (400 MHz, DMSO-$d_6$) δ 10.12 (s, 1H), 9.43 (s, 1H), 8.77 (s, 1H), 8.66 (dd, J=4.8, 1.6 Hz, 1H), 8.40 (d, J=0.8 Hz, 1H), 8.27 (dd, 1=8.0, 2.0 Hz, 1H), 8.22 (dd, J=1.6, 1.6 Hz, 1H), 7.72-7.62 (m, 2H), 7.27 (dd, J=8.0, 4.8 Hz, 1H), 3.38 (s, 3H), 3.27-3.19 (m, 1H), 2.49-2.42 (m, 2H), 2.35-2.23 (m, 2H), 1.74-1.60 (m, 4H), 1.36-1.27 (m, 3H). LC-MS m/z: 440.3 [M+1]$^+$. HPLC purity (214 nm): 99.14%; $t_R$=8.257 min.

I-$N^4$-(3-(methylsulfonyl)97yridine-2-yl)-$N^6$-(5-(1-(97yridine9797e-1-yl)ethyl)97yridine-2-yl)pyrimidine-4,6-diamine (15). 15.1 (55, 0.12 mmol) was purified by Prep-SFC to give 15 (20 mg, 36% yield) as a white solid. $^1$H NMR (400 MHz, DMSO-$d_6$) δ 10.15 (br, 1H), 9.44 (s, 1H), 8.77 (s, 1H), 8.66 (dd, J=4.8, 1.6 Hz, 1H), 8.40 (s, 1H), 8.27 (dd, J=8.0, 2.0 Hz, 1H), 8.24 (s, 1H), 7.69 (s, 2H), 7.27 (dd, J=8.0, 4.8 Hz, 1H), 3.39 (s, 3H), 3.28-3.12 (m, 1H), 2.49-2.41 (m, 2H), 2.40-2.18 (m, 2H), 1.77-1.58 (m, 4H), 1.44-1.30 (m, 3H). LC-MS m/z: 440.0 [M+1]$^+$. HPLC purity (214 nm): >99.9%; $t_R$=7.575 min.

Example 1p: Preparation of Compound 16

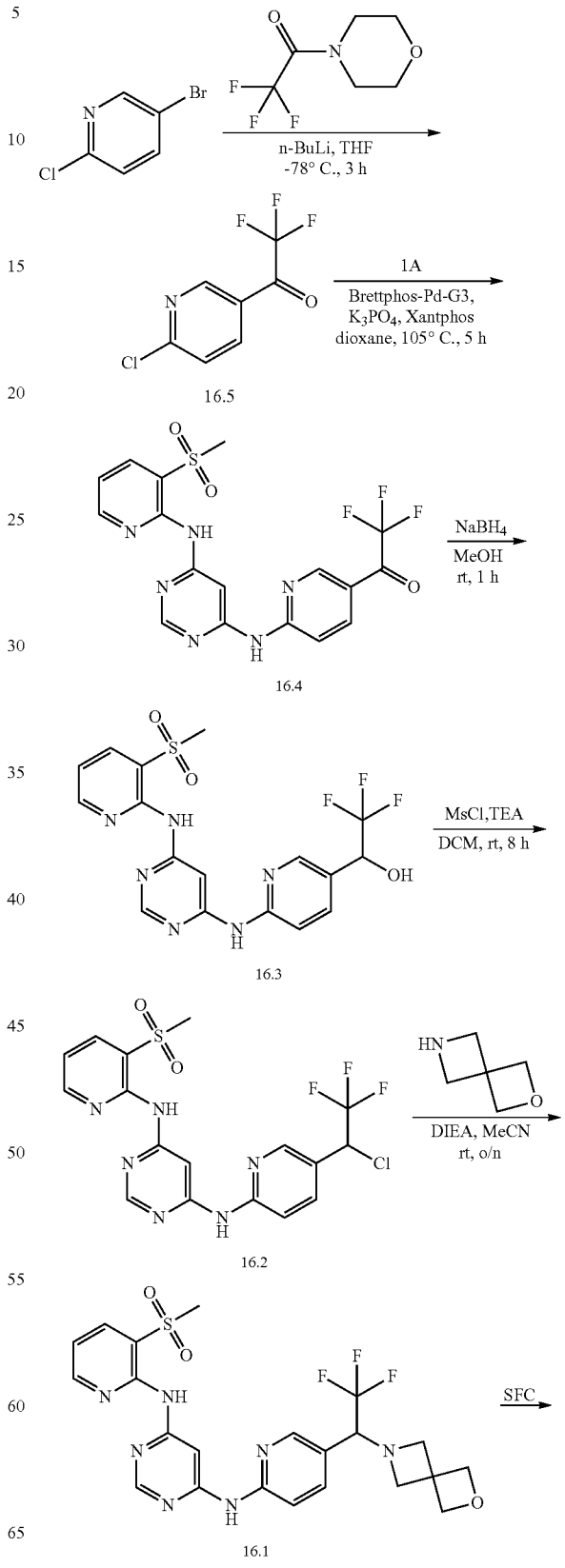

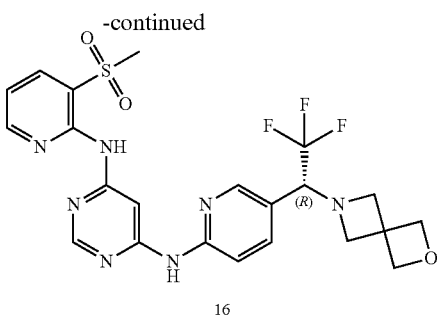

16

1-(6-chloropyridin-3-yl)-2,2,2-trifluoroethanone (16.5). To a solution of 5-bromo-2-chloropyridine (2 g, 10.39 mmol) in THF (20 mL) was added n-BuLi (2.5 M in hexane, 5 mL, 12.47 mmol) at −78° C. The mixture was stirred at −78° C. for 1 hour and then was added 2,2,2-trifluoro-1-morpholinoethanone (1.9 g, 10.39 mmol). After the reaction was completed, the mixture was quenched with NH$_4$Cl solution (40 ml) and extracted with ethyl acetate (20 ml). The organic phase was dried by anhydrous sodium sulfate and evaporated in vacuo to give crude product. The crude product was purified by column chromatography on silica gel (Petroleum ether/Ethyl acetate=10/1) to give 16.5 (700 mg, 32% yield) as a yellow solid. LC-MS m/z: 228.2 [M+H$_2$O+H]$^+$. LCMS purity (214 nm): 82.79%, $t_R$=1.258 min.

2,2,2-trifluoro-1-(6-((6-((3-(methylsulfonyl)98yridine-2-yl)amino) pyrimidin-4-yl)amino)98yridine-3-yl)98yridine (16.4). To a solution of 16.5 (200 mg, 0.95 mmol) and 1A (253 mg, 0.95 mmol) in dioxane (10 mL) was added Brettphos-Pd-G3 (86 mg, 0.095 mmol), Xantphos (55 mg, 0.095 mmol), K$_3$PO$_4$ (405 mg, 1.91 mmol). The mixture was stirred at 105° C. for 5 hours under nitrogen atmosphere. After the reaction was completed, the mixture was evaporated in vacuo to give crude product. The crude product was purified by column chromatography on silica gel (CH$_2$Cl$_2$/MeOH=20/1) to give 16.4 (120 mg, 29% yield) as a yellow solid. LC-MS m/z: 456.9[M+H$_2$O+H]$^+$. LCMS purity (254 nm): 94.55%, $t_R$=1.376 min.

2,2,2-trifluoro-1-(6-((6-((3-(methylsulfonyl)98yridine-2-yl)amino) pyrimidin-4-yl)amino)98yridine-3-yl)ethanol (163). To a solution of 16.4 (120 mg, 0.27 mmol) in MeOH (10 mL) was added NaBH$_4$ (15 mg, 0.41 mmol). The mixture was stirred at room temperature for 1 hour. After the reaction was completed, the mixture was evaporated in vacuo to give crude product. The crude product was purified by column chromatography on silica gel (CH$_2$Cl$_2$/MeOH=20/1) to give 163 (100 mg, 83% yield) as a yellow solid. LC-MS m/z: 440.9[M+H]$^+$. LCMS purity (214 nm): >99.9%, $t_R$=1.451 min.

N$^4$-(5-(1-chloro-2,2,2-trifluoroethyl)98yridine-2-yl)-N$^6$-(3-(methylsulfonyl)98yridine-2-yl)pyrimidine-4,6-diamine (16.2). To a solution of 163 (100 mg, 0.23 mmol) in DCM (10 mL) was added TEA (69 mg, 0.68 mmol) and MsCl (31 mg, 0.27 mmol). The mixture was stirred at room temperature for 8 hours. After the reaction was completed, the mixture was evaporated in vacuo to give crude product. The crude product was purified by column chromatography on silica gel (CH$_2$Cl$_2$/MeOH=20/1) to give 16.2 (100 mg, 96% yield) as a white solid. LC-MS m/z: 458.8 [M+H]$^+$. LCMS purity (254 nm): 54.57%, $t_R$=1.706 min.

1-N$^4$-(3-(methylsulfonyl)98yridine-2-yl)-N$^6$-(5-(2,2,2-trifluoro-1-(2-oxa-6-azaspiro[3.3]heptan-6-yl)ethyl)98yridine-2-yl)pyrimidine-4,6-diamine (16). To a solution of 16.2 (100 mg, 0.22 mmol) and 2-oxa-6-azaspiro[3.3]heptane (43 mg, 0.44 mmol) in MeCN (8 mL) was added 98yri (84 mg, 0.65 mmol). The mixture was stirred at room temperature for overnight. After the reaction was completed, the mixture was evaporated in vacuo to give crude 16.1, further purification with reversed phase prep-HPLC and prep-SFC to give 16 (21.06 mg, 37% yield) as a white solid. $^1$H NMR (400 MHz, DMSO-d$_6$) δ 10.33 (s, 1H), 9.48 (br, 1H), 8.78 (s, 1H), 8.66 (dd, J=4.8, 1.6 Hz, 1H), 8.44 (d, J=1.2 Hz, 1H), 8.30-8.26 (m, 2H), 7.80 (d, J=8.8 Hz, 1H), 7.71 (dd, J=8.8, 2.0 Hz, 1H), 7.29 (dd, J=8.0, 4.8 Hz, 1H), 4.61 (s, 4H), 4.18-4.15 (m, 1H), 3.42-3.34 (m, 7H). LC-MS m/z: 522.2 [M+H]$^+$. HPLC purity (214 nm): >99.9%, $t_R$=7.799 min.

Example 1q: Preparation of Compound 18

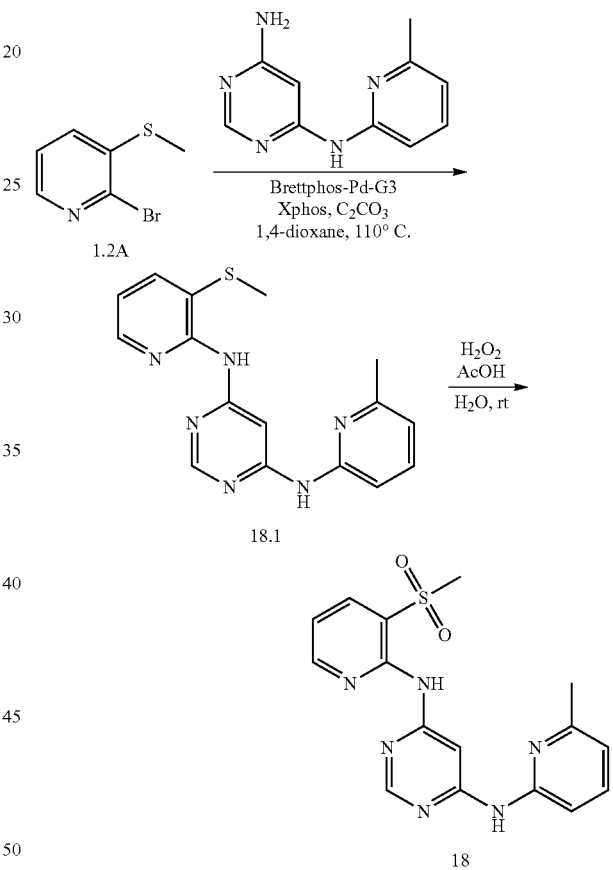

N$^4$-(6-methylpyridin-2-yl)-N$^6$-(3-(methylthio)99yridine-2-yl) pyrimidine-4,6-diamine (18.1). 2-bromo-3-(methylthio)pyridine (1.2A) was prepared as described in Example 1a. A mixture of 1.2A (290 mg, 1.42 mmol), N$^4$-(6-methylpyridin-2-yl)pyrimidine-4,6-diamine (285 mg, 1.42 mmol), Brettphos-Pd-G$_3$ (127 mg, 0.14 mmol), Xphos (133 mg, 0.28 mmol) and Cs$_2$CO$_3$ (1.39 g, 4.26 mmol) in 1,4-dioxane (30 mL) was stirred at 110° C. overnight under argon atmosphere. After the reaction was completed, the mixture was concentrated and purified by column chromatography on silica gel (EtOAc:hexane=7:3) to give 18.1 (380 mg, 82.5% yield) as a yellow liquid. LC-MS m/z: 325.3 [M+1]$^+$; purity (214 nm) 93.6%, $t_R$=1.618 min.

N$^4$-(6-methylpyridin-2-yl)-N$^6$-(3-(methylsulfonyl)99yridine-2-yl) pyrimidine-4,6-diamine (18). A mixture of 18.1

(330 mg, 1.02 mmol) and 30% H₂O₂ (3.5 mL) in AcOH (5 mL) and H₂O (5 mL) was stirred at 60° C. for 2 h under argon atmosphere. After the reaction was completed, the mixture was diluted by H₂O (50 mL) and extracted with EtOAc (30 mL×3). The combined organic layers were washed with brine (50 mL), dried over Na₂SO₄, concentrated and purified by reversed phase prep-HPLC to give 18 (101 mg, 27.9% yield) as a white solid. ¹H NMR (400 MHz, DMSO-d₆) δ 10.08 (s, 1H), 9.47 (s, 1H), 9.12 (s, 1H), 8.64 (dd, J=4.8, 2.0 Hz, 1H), 8.39 (s, 1H), 8.27 (dd, J=8.0, 2.0 Hz, 1H), 7.60 (t, J=8.0 Hz, 1H), 7.34 (d, J=8.0 Hz, 1H), 7.28 (dd, J=7.6, 4.8 Hz, 1H), 6.85 (d, J=7.2 Hz, 1H), 3.39 (s, 3H), 2.48 (s, 3H). LC-MS m/z: 357.1 [M+H]⁺. HPLC purity (214 nm): 99.3%; $t_R$=8.083 min.

Example 1r: Preparation of Compound 19

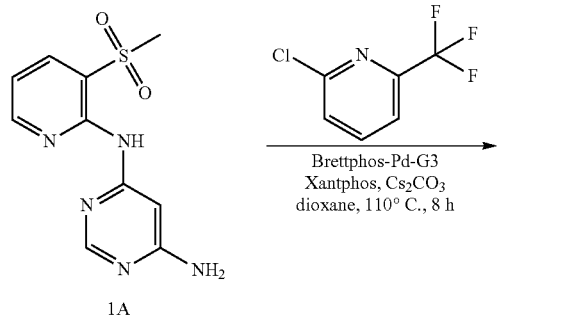

Synthesis of N⁴-(3-(methylsulfonyl)100yridine-2-yl)-N⁶-(6-(trifluoromethyl) 100yridine-2-yl)pyrimidine-4,6-diamine (19). N⁴-(3-(methylsulfonyl) 100yridine-2-yl)pyrimidine-4,6-diamine (1A) was prepared as described in Example 1a. To a solution of 1A (100 mg, 0.38 mmol) and 2-chloro-6-(trifluoromethyl)pyridine (68 mg, 0.38 mmol) in dioxane (10 mL) was added Brettphos-Pd-G3 (34 mg, 0.038 mmol), Xantphos (22 mg, 0.038 mmol) and Cs₂CO₃ (246 mg, 0.75 mmol). The mixture was stirred at 110° C. for 8 hours under nitrogen atmosphere. After the reaction was completed, the mixture was evaporated in vacuo to give crude product, further purification with reversed phase prep-HPLC to give 19 (9.94 mg, 6.4% yield) as a white solid. ¹H NMR (400 MHz, DMSO-d₆) δ 10.59 (s, 1H), 9.56 (s, 1H), 8.96 (s, 1H), 8.57 (dd, J=4.8, 2.0 Hz, 1H), 8.47 (d, J=1.2, 1H), 8.28 (dd, J=8.0, 1.6 Hz, 1H), 7.99 (dd, J=8.0, 8.0 Hz, 1H), 7.86 (d, J=8.4, 1H), 7.46 (d, J=7.6 Hz, 1H), 7.30 (dd, J=8.0, 5.2 Hz, 1H), 3.40 (s, 3H). LC-MS m/z: 411.0 [M+H]⁺. HPLC purity (214 nm): 99.39%, $t_R$=8.964 min.

Example 1s: Preparation of Compound 20

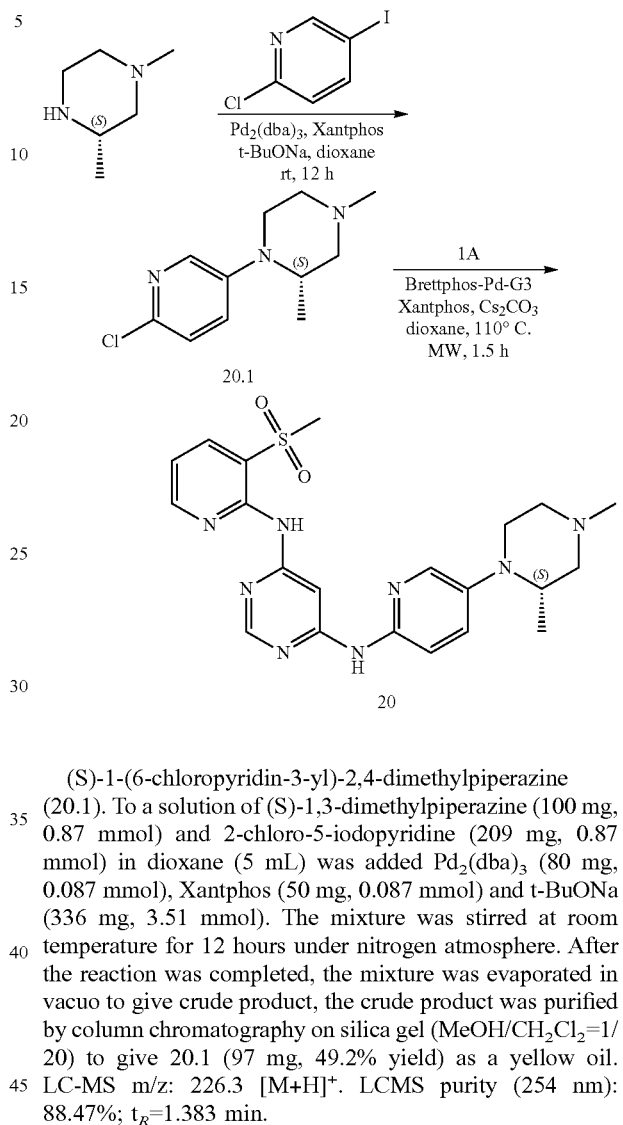

(S)-1-(6-chloropyridin-3-yl)-2,4-dimethylpiperazine (20.1). To a solution of (S)-1,3-dimethylpiperazine (100 mg, 0.87 mmol) and 2-chloro-5-iodopyridine (209 mg, 0.87 mmol) in dioxane (5 mL) was added Pd₂(dba)₃ (80 mg, 0.087 mmol), Xantphos (50 mg, 0.087 mmol) and t-BuONa (336 mg, 3.51 mmol). The mixture was stirred at room temperature for 12 hours under nitrogen atmosphere. After the reaction was completed, the mixture was evaporated in vacuo to give crude product, the crude product was purified by column chromatography on silica gel (MeOH/CH₂Cl₂=1/20) to give 20.1 (97 mg, 49.2% yield) as a yellow oil. LC-MS m/z: 226.3 [M+H]⁺. LCMS purity (254 nm): 88.47%; $t_R$=1.383 min.

(S)—N⁴-(5-(2,4-dimethylpiperazin-1-yl)101yridine-2-yl)-N⁶-(3-(methylsulfonyl)101yridine-2-yl)pyrimidine-4,6-diamine (20). To a solution of 20.1 (97 mg, 0.43 mmol) and 1A (114 mg, 0.43 mmol) in dioxane (3 mL) was added Brettphos-Pd-G3 (40 mg, 0.043 mmol), Xantphos (25 mg, 0.043 mmol) and Cs₂CO₃ (281 mg, 0.86 mmol). The mixture was stirred in the microwave at 110° C. for 1.5 hours. After the reaction was completed, the mixture was evaporated in vacuo to give crude product; further purification with reversed phase prep-HPLC gives title product 20 (37.16 mg, 18.9% yield) as a white solid. ¹H NMR (400 MHz, DMSO-d₆) δ9.89 (s, 1H), 9.38 (s, 1H), 8.66 (dd, J=4.8, 1.6 Hz, 1H), 8.62 (s, 1H), 8.34 (d, J=1.2, 1H), 8.25 (dd, J=8, 2 Hz, 1H), 7.97 (d, J=2.8 Hz, 1H), 7.62 (d, J=9.2 Hz, 1H), 7.40 (dd, J=8.8, 2.8 Hz, 1H), 7.25 (dd, J=8.0, 5.2 Hz, 1H), 3.83-3.81 (m, 1H), 3.38 (s, 3H), 3.19-3.16 (m, 1H), 3.00-2.95 (m, 1H), 2.71-2.66 (m, 1H), 2.37-2.32 (m, 1H), 2.20 (s, 3H), 2.18-2.15 (m, 1H), 0.98 (d, J=6.4 Hz, 3H). LC-MS m/z: 455.2 [M+H]⁺. HPLC purity (214 nm): 97.04%, $t_R$=4.659 min.

Example 1t: Preparation of Compound 21

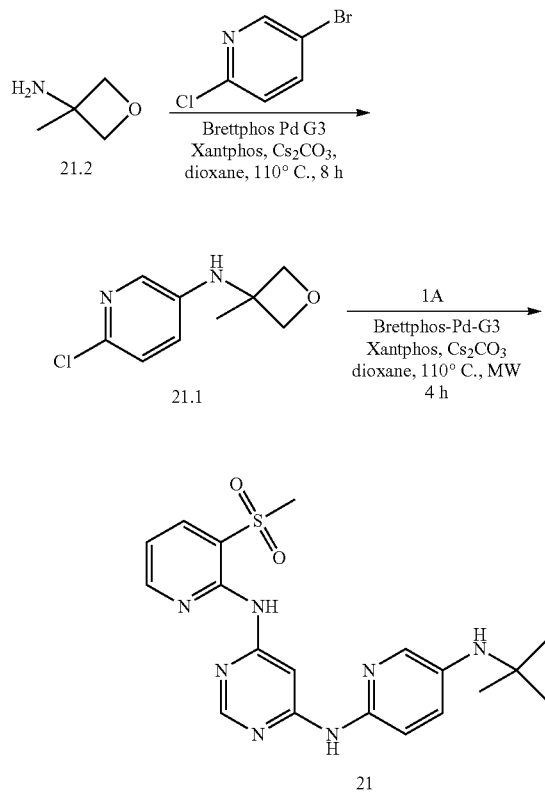

6-chloro-N-(3-methyloxetan-3-yl)101yridine-3-amine (21.1). To a solution of 21.2 (150 mg, 1.72 mmol) and 5-bromo-2-chloropyridine (331 mg, 1.72 mmol) in dioxane (10 mL) was added Brettphos-Pd-G3 (156 mg, 0.17 mmol), Xantphos (100 mg, 0.17 mmol) and $Cs_2CO_3$ (1.12 g, 3.44 mmol). The mixture was stirred at 110° C. for 8 hours under nitrogen atmosphere. After the reaction was completed, the mixture was evaporated in vacuo to give crude product, the crude product was purified by column chromatography on silica gel ($CH_2Cl_2$/MeOH=20/1) to give 21.1 (300 mg, 87.7% yield) as a brown oil. LC-MS m/z: 199.3 $[M+H]^+$. LCMS purity (214 nm): 96.19%; $t_R$=1.263 min.

$N^4$-(5-((3-methyloxetan-3-yl)amino)102yridine-2-yl)-$N^6$-(3-(methylsulfonyl)102yridine-2-yl)pyrimidine-4,6-diamine (21). To a solution of 21.1 (100 mg, 0.50 mmol) and 1A (134 mg, 0.50 mmol) in dioxane (4 mL) was added Brettphos-Pd-G3 (46 mg, 0.050 mmol), Xantphos (29 mg, 0.050 mmol) and $Cs_2CO_3$ (328 mg, 1.01 mmol). The mixture was stirred at 110° C. for 4 hours in microwave under nitrogen atmosphere. After the reaction was completed, the mixture was evaporated in vacuo to give crude product; further purification with reversed phase prep-HPLC to give 21 (14.00 mg, 6.5% yield) as a light yellow solid. $^1$H NMR (400 MHz, DMSO-$d_6$) δ 9.72 (s, 1H), 9.35 (s, 1H), 8.59 (dd, J=4.8, 1.6 Hz, 1H), 8.42 (br, 1H), 8.30 (d, J=1.2 Hz, 1H), 8.25 (dd, J=8.0, 2.0 Hz, 1H), 7.53 (d, J=3.2 Hz, 1H), 7.25 (dd, J=8.0, 4.8 Hz, 1H), 6.85 (dd, J=8.8, 2.8 Hz, 1H), 6.02 (s, 1H), 4.62 (d, J=5.6 Hz, 2H), 4.48 (d, 1=6.0 Hz, 2H), 3.37 (s, 3H), 1.56 (s, 3H). LC-MS m/z: 428.2 $[M+H]^+$. HPLC purity (214 nm): 95.62%, $t_R$=5.705 min.

Example 1u: Preparation of Compound 22

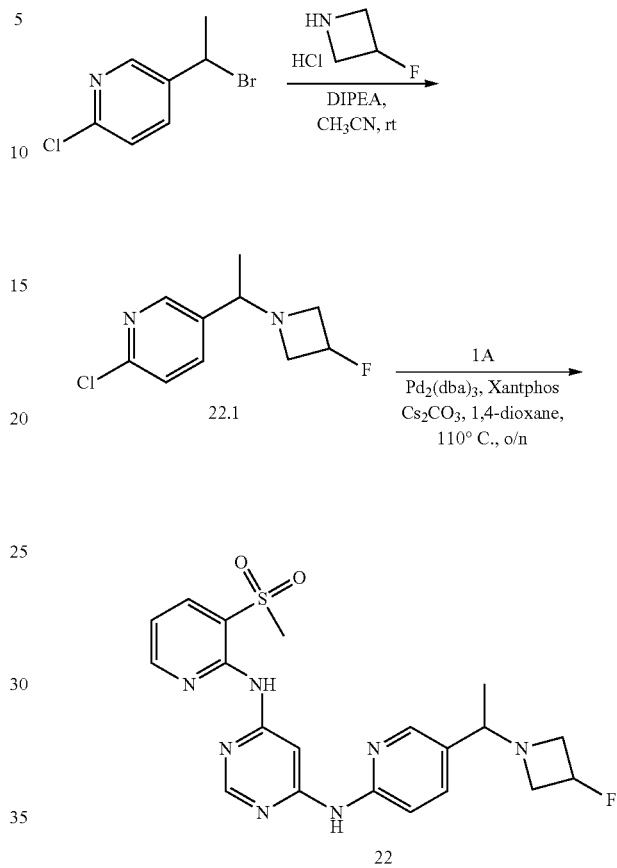

2-chloro-5-(1-(3-fluoroazetidin-1-yl)ethyl)pyridine (22.1). A mixture of 5-(1-bromoethyl)-2-chloropyridine (3.30 g, 14.97 mmol), 3-fluoroazetidine hydrochloride (2.08 g, 18.0 mmol) and 102yri (10.0 mL) in $CH_3CN$ (50 mL) was stirred at room temperature overnight. After the reaction was completed, the mixture was concentrated and purified by column chromatography on silica gel (EtOAc:hexane=1:3) to give 22.1 (1.76 g, 54.8% yield) as colorless oil. LC-MS m/z: 215.4 $[M+1]^+$. LCMS purity (214 nm): 91.48%; $t_R$=1.674 min.

$N^4$-(5-(1-(3-fluoroazetidin-1-yl)ethyl)102yridine-2-yl)-$N^6$-(3-(methylsulfonyl)102yridine-2-yl)pyrimidine-4,6-diamine (22). A mixture of 1A (150 mg, 0.57 mmol), 22.1 (120 mg, 0.57 mmol), $Pd_2(dba)_3$ (52 mg, 0.057 mmol), Xantphos (65 mg, 0.113 mmol) and $Cs_2CO_3$ (553 mg, 1.70 mmol) in 1,4-dioxane (30 mL) was stirred at 110° C. overnight under argon atmosphere. After the reaction was completed, the mixture was concentrated, purified by column chromatography on silica gel ($CH_2Cl_2$:MeOH=10:1) and then reversed phase prep-HPLC to give 22 (68 mg, 26.9% yield) as a white solid. $^1$H NMR (400 MHz, DMSO-$d_6$) δ 10.14 (s, 1H), 9.43 (s, 1H), 8.78 (s, 1H), 8.67 (dd, J=4.8, 1.6 Hz, 1H), 8.40 (s, 1H), 8.27 (dd, J=8.0, 2.0 Hz, 1H), 8.23 (d, J=1.6 Hz, 1H), 7.70-7.64 (m, 2H), 7.27 (dd, J=8.0, 4.8 Hz, 1H), 5.23-5.03 (m, 1H), 3.64-3.57 (m, 1H), 3.39-3.28 (m, 5H), 3.12-2.98 (m, 2H), 1.16 (d, J=6.4 Hz, 3H). LC-MS m/z: 444.2 $[M+1]^+$. HPLC purity (214 nm): >99.9%; $t_R$=7.834 min.

Example 1v: Preparation of Compound 23

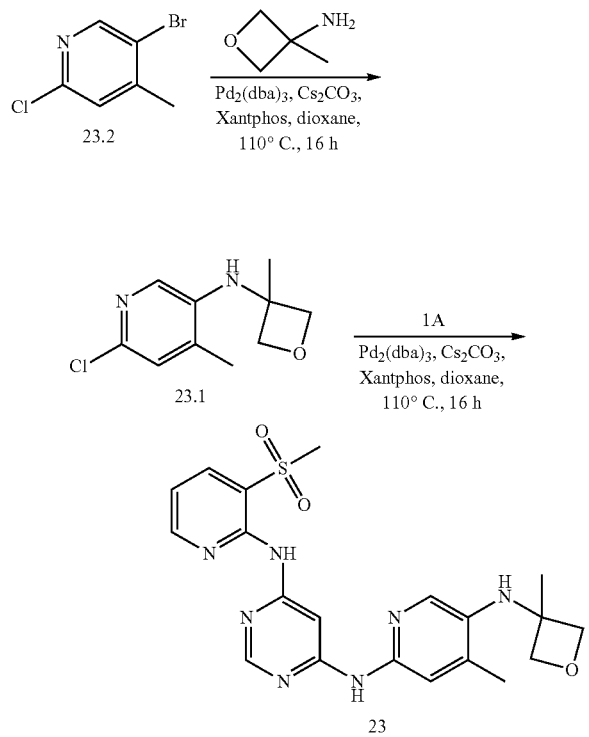

Example 1w: Preparation of Compound 24

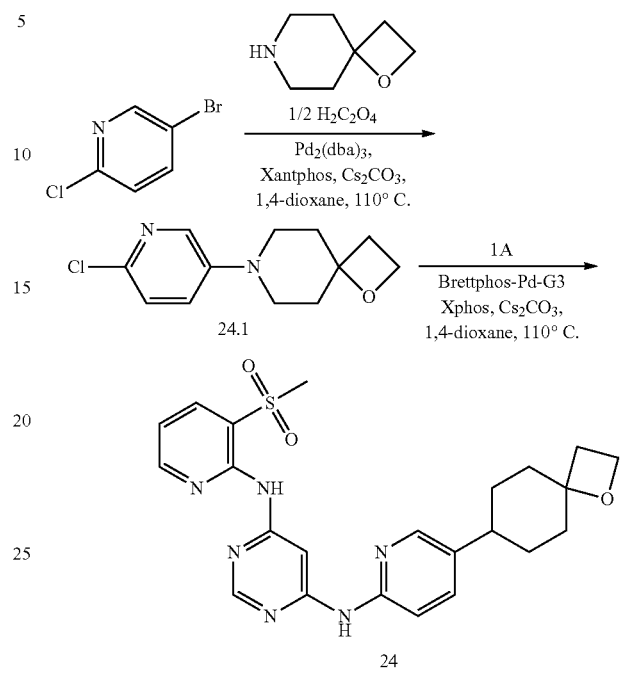

6-chloro-4-methyl-N-(3-methyloxetan-3-yl)103yridine-3-amine (23.1). A mixture of 23.2 (500 mg, 2.42 mmol), 3-methyloxetan-3-amine (253 mg, 2.91 mmol), Pd$_2$(dba)$_3$ (222 mg, 0.24 mmol), Xantphos (280 mg, 0.48 mmol) and Cs$_2$CO$_3$ (1.6 g, 4.84 mmol) in 1,4-dioxane (10 mL) was stirred at 110° C. for 16 h under Ar. Atmosphere. After the reaction was completed, the mixture was quenched by water (50 mL) and extracted with EtOAc (20 mL×2). The organic layer was washed with brine (50 mL), dried over Na$_2$SO$_4$, concentrated and purified by column chromatography on silica gel (hexane:EtOAc=4:1) to give 23.1 (300 mg, 58% yield) as a yellow solid. LC-MS m/z: 213.1 [M+1]$^+$. LCMS purity (214 nm): 78.10%; $t_R$=1.476 min.

N$^4$-(4-methyl-5-((3-methyloxetan-3-yl)amino)103yridine-2-yl)-N$^6$-(3-(methylsulfonyl)103yridine-2-yl)pyrimidine-4,6-diamine (23). A mixture of 23.1 (270 mg, 1.27 mmol), 1A (337 mg, 1.27 mmol), Pd$_2$(dba)$_3$ (116 mg, 0.13 mmol), Xantphos (147 mg, 0.25 mmol) and t-BuONa (244 mg, 2.54 mmol) in 1,4-dioxane (5 mL) was stirred at 110° C. for 16 h under Ar. Atmosphere. After the reaction was completed, the mixture was quenched by water (50 mL) and extracted with EtOAc (50 mL×2). The organic layer was washed with brine (50 mL), dried over Na$_2$SO$_4$, concentrated and purified by reversed phase prep-HPLC gives 23 (30.04 mg, 5.4% yield) as a yellow solid. $^1$H NMR (400 MHz, DMSO-d$_6$) δ9.65 (br, 1H), 9.34 (br, 1H), 8.59 (dd, J=4.8, 1.6 Hz, 1H), 8.47 (s, 1H), 8.31 (d, J=0.8 Hz, 1H), 8.24 (dd, J=8.0, 1.6 Hz, 1H), 7.42 (s, 1H), 7.25 (dd, J=7.6, 4.8 Hz, 1H), 7.06 (s, 1H), 5.26 (s, 1H), 4.69 (d, J=5.6 Hz, 2H), 4.51 (d, J=6.0 Hz, 2H), 3.37 (s, 3H), 2.14 (s, 3H), 1.61 (s, 3H). LC-MS m/z: 442.2 [M+1]$^+$. HPLC purity (254 nm): >99.9%; $t_R$=7.205 min.

3-(methylsulfonyl)104yridine-4-amine (24.1). A mixture of 5-bromo-2-chloropyridine (558 mg, 2.90 mmol), 1-oxa-7-azaspiro[3.5]nonane hemioxalate (250 mg, 1.45 mmol), Pd$_2$(dba)$_3$ (266 mg, 0.29 mmol), Xantphos (335 mg, 0.58 mmol) and Cs$_2$CO$_3$ (2.83 g, 8.7 mmol) in 1,4-dioxane (50 mL) was stirred at 110° C. overnight under argon atmosphere. After the reaction was completed, it was diluted by water (50 mL) and extracted with EtOAc (50 mL×3). The organic extract was washed by brine (100 mL), dried over anhydrous Na$_2$SO$_4$, concentrated and purified by column chromatography on silica gel (EtOAc:hexane=1:1) to give 24.1 (250 mg, 72.3% yield) as red solid. LC-MS: m/z=239.2 [M+1]$^+$. LCMS purity: 99.34% (254 nm), $t_R$=1.398 min.

N$^4$-(5-(1-oxa-7-azaspiro[3.5]nonan-7-yl)104yridine-2-yl)-N$^6$-(3-(methylsulfonyl)104yridine-2-yl)pyrimidine-4,6-diamine (24). A mixture of 24.1 (230 mg, 0.96 mmol), 1A (257 mg, 0.96 mmol), Brettphos Pd G3 (136 mg, 0.15 mmol), X-phos (143 mg, 0.30 mmol) and Cs$_2$CO$_3$ (975 mg, 3.0 mmol) in 1,4-dioxane (30 mL) was stirred at 110° C. overnight under argon atmosphere. After the reaction was completed, it was diluted by water (50 mL) and extracted with EtOAc (50 mL×3). The organic extract was washed by brine (100 mL), dried over anhydrous Na$_2$SO$_4$, concentrated and purified by column chromatography on silica gel (EtOAc:hexane=1:1) and then reversed phase prep-HPLC to give 24 (94.2 mg, 20.9% yield) as yellow solid. $^1$H NMR (400 MHz, DMSO-d$_6$) δ9.88 (s, 1H), 9.38 (s, 1H), 8.66 (dd, J=4.8, 2.0 Hz, 1H), 8.61 (s, 1H), 8.34 (d, J=0.8 Hz 1H), 8.25 (dd, J=8.0, 2.0 Hz, 1H), 8.02 (d, J=3.2 Hz, 1H), 7.59 (d, J=8.8 Hz, 1H), 7.43 (dd, J=9.2, 3.2 Hz, 1H), 7.25 (dd, J=8.0, 4.8 Hz, 1H), 4.42 (t, J=8.0 Hz, 2H), 3.38 (s, 3H), 3.25-3.19 (m, 2H), 3.06-3.00 (m, 2H), 2.39 (t, J=8.0 Hz, 2H), 1.95-1.84 (m, 4H). LC-MS m/z=468.3 [M+1]$^+$. HPLC purity: >99.9% (214 nm), $t_R$=7.512 min.

Example 1x: Preparation of Compound 25

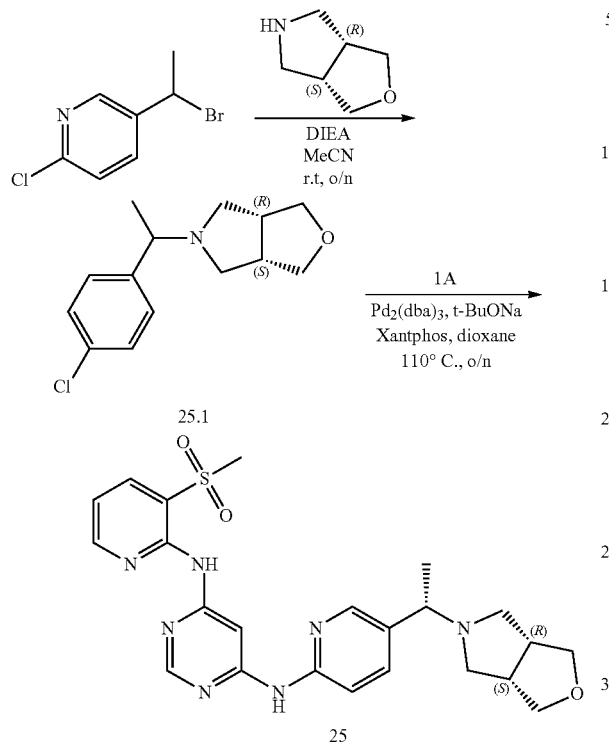

(3aR,6aS)-5-(1-(4-chlorophenyl)ethyl)hexahydro-1H-furo [3,4-c]pyrrole (25.1). To a solution of 5-(1-bromoethyl)-2-chloropyridine (200 mg, 0.91 mmol) in MeCN (20 mL) was added (3aR,6aS)-hexahydro-1H-furo[3,4-c]pyrrole (123 mg, 1.09 mmol) and 105yri (235 mg, 1.82 mmol). The reaction was stirred at room temperature overnight. After the reaction was completed, the mixture was evaporated in vacuo to give crude product. Further purification with silica gel column chromatography ($CH_2Cl_2$:MeOH=20:1) gives title product 25.1 (170 mg, 74.2% yield) as a yellow oil. LC-MS m/z: 253.4 [M+1]$^+$. LCMS purity (254 nm): 79.05%; $t_R$=0.354 min.

$N^4$-(3-(methylsulfonyl)105yridine-2-yl)-$N^6$-(5-(1-((3aR,6aS)-tetrahydro-1H-furo[3,4-c]pyrrol-5 (3H)-yl)ethyl) 105yridine-2-yl)pyrimidine-4,6-diamine (25). To a solution of 25.1 (170 mg, 0.68 mmol) in dioxane (25 mL) was added 1A (180 mg, 0.68 mmol), t-BuONa (131 mg, 1.36 mmol), $Pd_2(dba)_3$ (62 mg, 0.068 mmol) and Xantphos (39 mg, 0.068 mmol). The reaction was heated to 110° C. and stirred at 110° C. overnight under nitrogen atmosphere. After the reaction was completed, the mixture was filtered via diatomite. The filtrate was evaporated in vacuo to give crude product. Further purification with silica gel column chromatography ($CH_2Cl_2$:MeOH=10:1) gives crude product. The crude product was purified by reversed phase prep-HPLC and prep-SFC to give 25 (19.01 mg, 27.2% yield) as a white solid. $^1$H NMR (400 MHz, DMSO-$d_6$) δ 10.13 (s, 1H), 9.43 (s, 1H), 8.77 (s, 1H), 8.66 (dd, J=4.8, 0.8 Hz, 1H), 8.40 (d, J=0.8, 1H), 8.27 (dd, J=8.0, 2.0 Hz, 1H), 8.22 (s, 1H), 7.70-7.65 (m, 2H), 7.27 (dd, J=8.0, 4.8 Hz, 1H), 3.73-3.66 (m, 2H), 3.42-3.35 (m, 5H), 3.25-3.21 (m, 1H), 2.68-2.65 (m, 2H), 2.60-2.57 (m, 1H), 2.46-2.42 (m, 1H), 2.37-2.33 (m, 1H), 2.12-2.09 (m, 1H), 1.31 (d, J=6.4 Hz, 3H). LC-MS m/z: 482.0 [M+H]$^+$. HPLC purity (214 nm): 95.00%, $t_R$=7.655 min.

Example 1y: Preparation of Compound 26

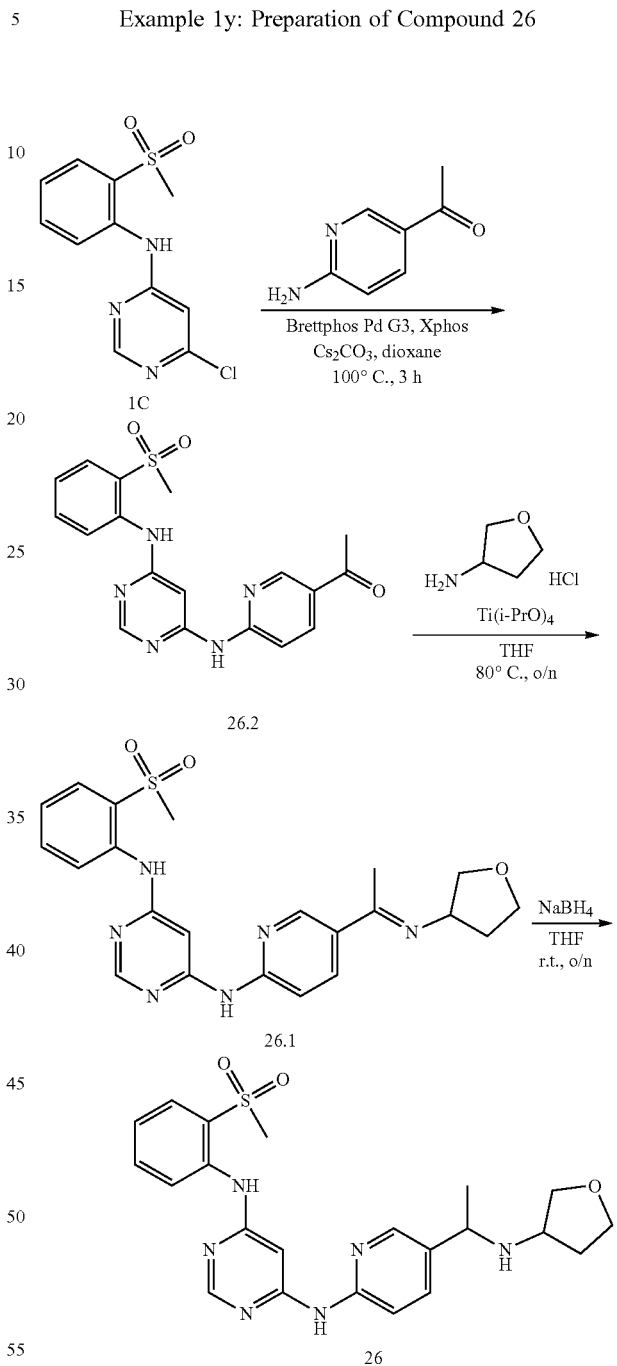

1-(6-((6-((2-(methylsulfonyl)phenyl)amino)pyrimidin-4-yl)amino) 106yridine-3-yl)106yridine (26.2). 6-chloro-N-(2-(methylsulfonyl)phenyl)pyrimidin-4-amine (1C) was prepared as described in Example 1 aa. To a stirred solution of 1C (400 mg, 1.41 mmol) in dioxane (10 mL) was added 1-(6-aminopyridin-3-yl)106yridine (191 mg, 1.41 mmol), $Cs_2CO_3$ (919 mg, 2.82 mmol), X-phos (67 mg, 0.14 mmol) and Brettphos Pd G3 (127 mg, 0.14 mmol). The mixture was stirred at 100° C. for 3 h under nitrogen. After consumption of the starting material (monitored by LCMS), the mixture was filtered and the filtrate was concentrated in vacuo. The residue was purified by column chromatography on silica gel (CH$_2$Cl$_2$/MeOH=9/1) to get 26.2 (350 mg, 65% yield) as a grey solid. LC-MS m/z: 384.1 [M+1]$^+$. LCMS purity (254 nm): 85.90%; t$_R$=1.604 min N$^4$-(2-(methylsulfonyl)phenyl)-N$^6$-(5-(1-(tetrahydrofuran-3-ylimino) ethyl)106yridine-2-yl)pyrimidine-4,6-diamine (26.1). To a solution of 26.2 (300 mg, 0.78 mmol) in THF (10 mL) was added tetrahydrofuran-3-amine hydrochloride (193 mg, 1.56 mmol) and Ti(Oi-Pr)$_4$ (667 mg, 2.35 mmol). The mixture was stirred at 80° C. overnight under nitrogen. After consumption of the starting material (monitored by LCMS), the mixture was used for next step directly. LC-MS m/z: 453.3 [M+H]$^+$. LCMS purity (254 nm): 72.01%; t$_R$=1.720 min and 1.753 min.

N$^4$-(2-(methylsulfonyl)phenyl)-N$^6$-(5-(1-(tetrahydrofuran-3-ylamino) ethyl)106yridine-2-yl)pyrimidine-4,6-diamine (26). To a solution of 26.1 (353 mg, 0.78 mmol) THF (10 mL) was added NaBH$_4$ (52 mg, 1.32 mmol). Then the reaction mixture was stirred at room temperature overnight. After consumption of the starting material (monitored by LCMS), the mixture was diluted with water (10 mL) and filtered. The filtrate was extracted with CH$_2$Cl$_2$/MeOH=10/1 (20 mL×3). The combined organic layers were washed with brine (30 mL×2), dried over Na$_2$SO$_4$, filtered and concentrated in vacuo. The residue was purified by column chromatography on silica gel (CH$_2$Cl$_2$/MeOH=8/1) and reversed phase prep-HPLC to give 26 (73.52 mg, 21% yield) as an off-white solid. $^1$H NMR (400 MHz, DMSO-d$_6$) δ9.92 (s, 1H), 8.79 (s, 1H), 8.31 (s, 1H), 8.18 (d, J=2.0 Hz, 1H), 8.02 (d, J=8.0 Hz, 1H), 7.91 (dd, J=8.2, 1.4 Hz, 1H), 7.78-7.63 (m, 2H), 7.52-7.42 (m, 2H), 7.40-7.32 (m, 1H), 3.78-3.65 (m, 2H), 3.65-3.50 (m, 2H), 3.47-3.41 (m, 0.5H), 3.22 (s, 3H), 3.21-3.18 (m, 0.5H), 3.08-2.97 (m, 1H), 2.35-2.20 (m, 1H), 1.94-1.75 (m, 1H), 1.73-1.64 (m, 0.5H), 1.55-1.44 (m, 0.5H), 1.30-1.20 (m, 3H). LC-MS m/z: 455.2 [M+H]$^+$. HPLC purity (214 nm): >99.9%; t$_R$=6.936 min.

Example 1z: Preparation of Compound 27

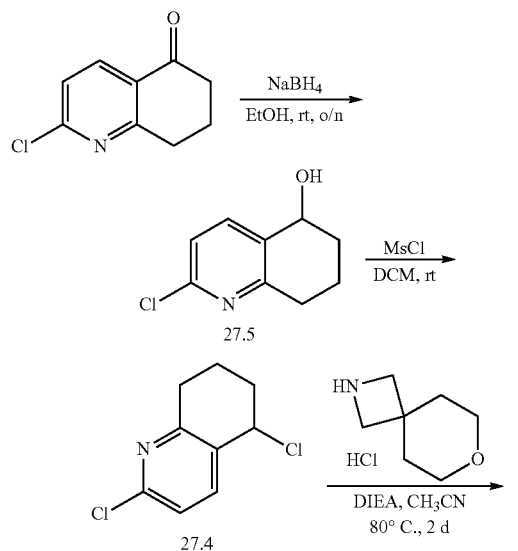

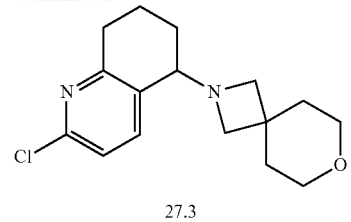

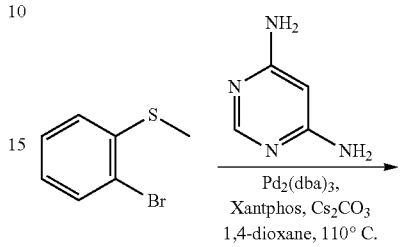

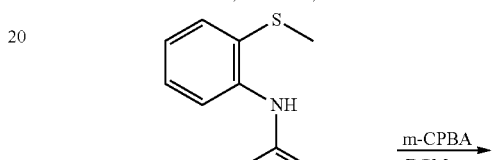

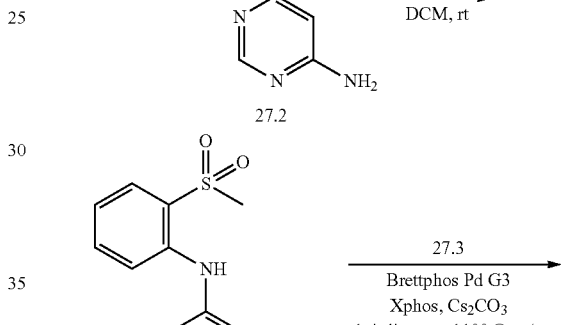

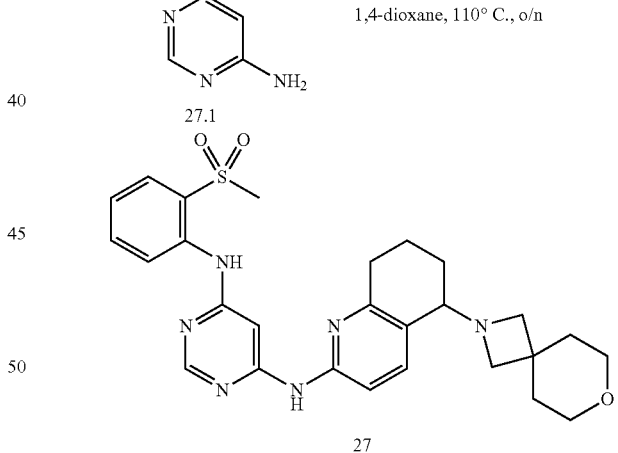

2-chloro-5,6,7,8-tetrahydroquinolin-5-ol (27.5). To a solution of 2-chloro-7,8-dihydroquinolin-5 (6H)-one (500 mg, 2.76 mmol) in EtOH (30 mL) was added NaBH$_4$ (157 mg, 4.14 mmol) with an ice bath, the reaction mixture was allowed to warm to room temperature and stirred overnight. After consumption of the starting material, the reaction mixture was concentrated remove the solvent, dissolved in EtOAc (100 mL), washed with brine (50 mL×3), dried over Na$_2$SO$_4$, filtered and concentrated to give crude 27.5 (480 mg, 95% yield) as yellow solid. LC-MS m/z: 184.3 [M+1]$^+$. LCMS purity (214 nm): >99.9%; t$_R$=1.349 min.

2,5-dichloro-5,6,7,8-tetrahydroquinoline (27.4). To a solution of 27.5 (100 mg, 0.54 mmol) in CH$_2$Cl$_2$ (20 mL)

was added Et₃N (167 mg, 1.65 mmol) and MsCl (94 mg, 0.88 mmol), then the reaction mixture was stirred at room temperature overnight. After consumption of the starting material, the reaction mixture was concentrated, dissolved in EtOAc (50 mL), washed with brine (50 mL×3), dried over Na₂SO₄, concentrated to give crude 27.4 (110 mg) as white solid, which was used to next step without purification. LC-MS m/z: 202.4 [M+1]⁺. LCMS purity (254 nm): 76.05%; $t_R$=2.044 min.

2-(2-chloro-5,6,7,8-tetrahydroquinolin-5-yl)-7-oxa-2-azaspiro[3.5]nonane (27.3). To a solution of 27.4 (1.0 g, 5.0 mmol) in CH₃CN (50 mL) was added 7-oxa-2-azaspiro[3.5]nonane hydrochloride (820 mg, 5.0 mmol) and 108yri (5 mL), then the mixture was stirred at 80° C. for 2 days. After the reaction was completed, the mixture was concentrated and purified by column chromatography on silica gel (eluting with 0.5% Et₃N in EtOAc) to give 27.3 (1.33 g, 91% yield) as yellow gel. LC-MS m/z: 293.2 [M+H]⁺. LCMS purity (214 nm): 98.09%; $t_R$=0.705 min.

N⁴-(2-(methylthio)phenyl)pyrimidine-4,6-diamine (27.2). A mixture of (2-bromophenyl)(methyl)sulfane (4.06 g, 20.0 mmol), pyrimidine-4,6-diamine (2.20 g, 20.0 mmol), Pd₂(dba)₃ (916 mg, 1.0 mmol), Xantphos (1.16 mg, 2.0 mmol) and Cs₂CO₃ (14.95 g, 46 mmol) in 1, 4-dioxane (150 mL) was stirred at 110° C. overnight under argon atmosphere. After the reaction was completed, the reaction mixture was filtered. The filtrate was concentrated and purified by column chromatography on silica gel (EtOAc) to give 27.2 (1.74 g, 37.5% yield) as yellow solid. LC-MS m/z: 233.3 [M+H]⁺. LCMS purity (214 nm): 98.14%. $t_R$=1.489 min.

N⁴-(2-(methylsulfonyl)phenyl)pyrimidine-4,6-diamine (27.1). A mixture of 27.2 (1.60 mg, 6.90 mmol) and m-CPBA (1.79 g, 10.35 mmol) in CH₂Cl₂ (100 mL) was stirred at room temperature overnight. To the mixture was added another portion m-CPBA (1.79 g, 10.35 mmol) with a water bath, the mixture was stirred for 4 h. After the reaction was completed, the reaction mixture was diluted by water (100 mL), basified by aqueous K₂CO₃ and extracted with CH₂Cl₂ (50 mL×2). The organic extract was washed by brine (100 mL), dried over anhydrous Na₂SO₄, filtered and concentrated to give crude 27.1 (850 mg, 46.7% yield) as brown solid. LC-MS m/z: 265.4 [M+H]⁺. LCMS purity (214 nm): 45.23%. $t_R$=1.294 min.

N⁴-(5-(7-oxa-2-azaspiro[3.5]nonan-2-yl)-5,6,7,8-tetrahydroquinolin-2-yl)-N⁶-(2-(methylsulfonyl)phenyl)pyrimidine-4,6-diamine (27). A mixture of 27.1 (132 mg, 0.50 mmol), 27.3 (146 mg, 0.50 mmol), Brettphos-Pd-G3 (68 mg, 0.075 mmol), Xphos (72 mg, 0.15 mmol) and Cs₂CO₃ (490 mg, 1.50 mmol) in 1, 4-dioxane (25 mL) was stirred at 110° C. overnight under argon atmosphere. After the reaction was completed, it was diluted by water (50 mL) and extracted with EtOAc (50 mL×2). The organic extract was washed by brine (50 mL), dried over Na₂SO₄, concentrated and purified by reversed phase prep-HPLC to give 27 (15 mg, 5.8% yield) as white solid. ¹H NMR (400 MHz, DMSO-d₆) δ9.90 (s, 1H), 8.74 (s, 1H), 8.31 (s, 1H), 7.97-7.91 (m, 2H), 7.77-7.73 (m, 1H), 7.57 (s, 1H), 7.49 (d, J=8.4 Hz, 1H), 7.38 (t, J=7.6 Hz, 1H), 7.24 (d, J=8.4 Hz, 1H), 3.47 (t, 1=4.8 Hz, 4H), 3.25 (t, 1=3.2 Hz, 1H), 3.22 (s, 3H), 3.06 (d, J=6.4 Hz, 2H), 2.81 (d, J=6.4 Hz, 2H), 2.74-2.63 (m, 2H), 2.08-2.04 (m, 1H), 1.82-1.79 (m, 1H), 1.62-1.52 (m, 6H). LC-MS m/z: 521.3 [M+H]⁺. HPLC purity (214 nm): >99.9%; $t_R$=8.481 min.

Example 1aa: Preparation of Compound 28

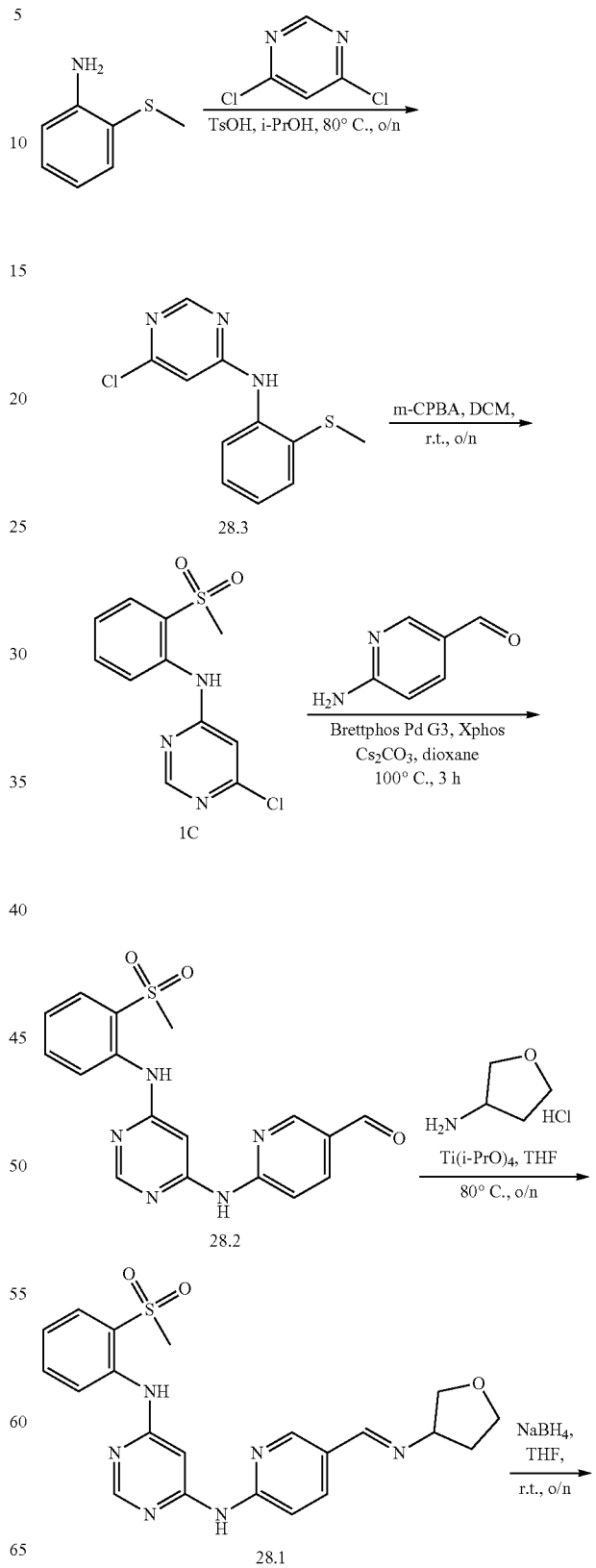

111

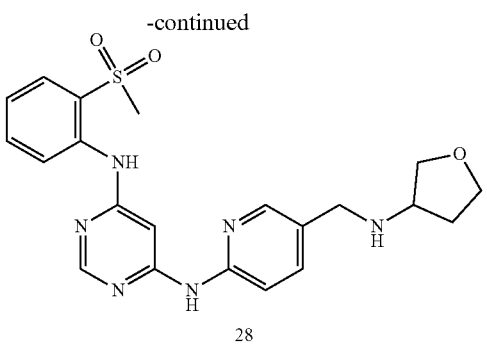

28

6-chloro-N-(2-(methylthio)phenyl)pyrimidin-4-amine (283). To a stirred solution of 2-(methylthio)aniline (1.00 g, 7.18 mmol) in i-PrOH (30 mL) was added 4,6-dichloropyrimidine (1.61 g, 10.77 mmol) and TsOH (247 mg, 1.44 mmol). The mixture was stirred at 80° C. overnight under nitrogen. After consumption of the starting material (monitored by LCMS), the mixture was poured into saturated aqueous solution of NaHCO$_3$ (60 mL) and extracted with EtOAc (50 mL×3). The combined organic layers were washed with brine (40 mL×2), dried over Na$_2$SO$_4$, filtered and concentrated in vacuo. The residue was purified by column chromatography on silica gel (petrol ether/EtOAc=1/1) to give 283 (1.45 g, 80% yield) as a yellow solid. LC-MS m/z: 252.2 [M+1]$^+$. LCMS purity (254 nm): 97.30%; $t_R$=1.907 min.

6-chloro-N-(2-(methylsulfonyl)phenyl)pyrimidin-4-amine (1C). To a stirred solution of 283 (1.45 g, 5.76 mmol) in CH$_2$Cl$_2$ (20 mL) was added m-CPBA (2.98 g, 17.28 mmol). The mixture was stirred at room temperature overnight. After consumption of the starting material (monitored by LCMS), the mixture was poured into water (50 mL) and extracted with EtOAc (60 mL×3). The combined organic layers were washed with brine (50 mL×2), dried over Na$_2$SO$_4$, filtered and concentrated in vacuo. The residue was purified by column chromatography on silica gel (petrol ether/EtOAc=1/1) to give 1C (800 mg, 49% yield) as a yellow solid. LC-MS m/z: 284.1 [M+1]$^+$. LCMS purity (254 nm): 83.78%; $t_R$=1.561 min.

6-((6-((2-(methylsulfonyl)phenyl)amino)pyrimidin-4-yl)amino) nicotinaldehyde (28.2). To a stirred solution of 1C (300 mg, 1.06 mmol) in dioxane (10 mL) was added 6-aminonicotinaldehyde (129 mg, 1.06 mmol), Cs$_2$CO$_3$ (689 mg, 2.11 mmol), X-phos (52 mg, 0.11 mmol) and Brettphos Pd G3 (100 mg, 0.11 mmol). The mixture was stirred at 100° C. 3 h under nitrogen. After consumption of the starting material (monitored by LCMS), the mixture was filtered and the filtrate was concentrated in vacuo. The residue was purified by column chromatography on silica gel (CH$_2$Cl$_2$/MeOH=9/1) to get 28.2 (350 mg, 90% yield) as a light green solid. LC-MS m/z: 370.3 [M+1]$^+$. LCMS purity (254 nm): 85.99%; $t_R$=1.581 min.

N$^4$-(2-(methylsulfonyl)phenyl)-N$^6$-(5-((tetrahydrofuran-3-ylimino) methyl)110yridine-2-yl)pyrimidine-4,6-diamine (28.1). To a solution of 28.2 (300 mg, 0.81 mmol) in THF (8 mL) was added tetrahydrofuran-3-amine hydrochloride (201 mg, 1.6 mmol) and Ti(Oi-Pr)$_4$ (692 mg, 2.44 mmol). The mixture was stirred at 80° C. overnight under nitrogen. After consumption of the starting material (monitored by LCMS, the mixture was used for next step directly. LC-MS m/z: 439.3 [M+H]$^+$. LCMS purity (254 nm): 76.91%; $t_R$=1.577 min.

112

N$^4$-(2-(methylsulfonyl)phenyl)-N$^6$-(5-((tetrahydrofuran-3-ylamino) methyl)110yridine-2-yl)pyrimidine-4,6-diamine (28). To a solution of 28.1 (355 mg, 0.81 mmol) in THF (8 mL) was added NaBH$_4$ (52 mg, 1.37 mmol). Then the reaction mixture was stirred at room temperature overnight. After consumption of the starting material (monitored by LCMS), the mixture was diluted with water (20 mL) and filtered. The filtrate was extracted with CH$_2$Cl$_2$/MeOH=10/1 (30 mL×3). The combined organic layers were washed with brine (30 mL×2), dried over Na$_2$SO$_4$, filtered and concentrated in vacuo. The residue was purified by column chromatography on silica gel (CH$_2$Cl$_2$/MeOH=9/1) and reversed phase prep-HPLC to give 28 (44.48 mg, 13% yield) as an off-white solid. $^1$H NMR (400 MHz, DMSO-d$_6$) δ9.92 (s, 1H), 8.78 (br, 1H), 8.31 (d, J=0.8 Hz, 1H), 8.19 (d, J=2.0 Hz, 1H), 8.00 (d, J=7.6 Hz, 1H), 7.91 (dd, J=7.8, 1.4 Hz, 1H), 7.77-7.69 (m, 1H), 7.67 (dd, J=8.6, 2.2 Hz, 1H), 7.48 (d, J=8.8 Hz, 1H), 7.44 (s, 1H), 7.39-7.33 (m, 1H), 3.79-3.56 (m, 5H), 3.44-3.39 (m, 1H), 3.28-3.24 (m, 1H), 3.22 (s, 3H), 2.37-2.18 (m, 1H), 1.99-1.86 (m, 1H), 1.73-1.61 (m, 1H). LC-MS m/z: 441.1 [M+H]$^+$. HPLC purity (214 nm): 95.00%; $t_R$=6.592 min.

Example 1ab: Preparation of Compound 29

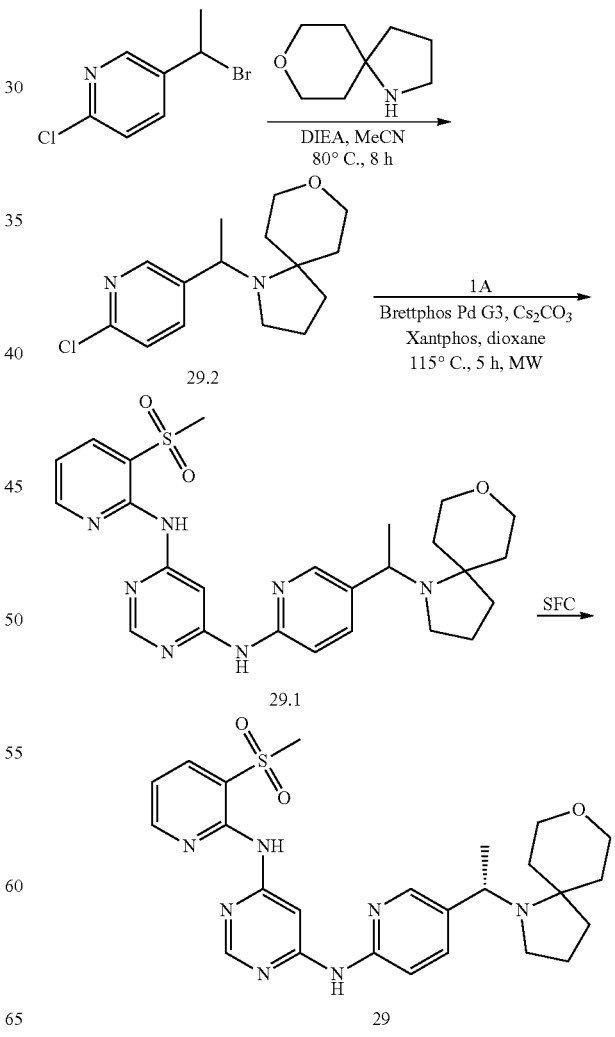

1-(1-(6-chloropyridin-3-yl)ethyl)-8-oxa-1-azaspiro[4.5]decane (29.2). To a solution of 5-(1-bromoethyl)-2-chloropyridine (150 mg, 0.68 mmol) in MeCN (8 mL) was added 111 yri (264 mg, 2.04 mmol) and 6-oxa-2-azaspiro[3.5]nonane (115 mg, 0.82 mmol). The mixture was stirred at 80° C. for 8 hours. After the reaction was completed, the mixture evaporated in vacuo to give crude product. The crude product was purified by column chromatography on silica gel ($CH_2Cl_2$/MeOH=20/1) to give 29.2 (100 mg, 52% yield) as a white solid. LC-MS m/z: 281.2 [M+H]$^+$. LCMS purity (214 nm): 92.51%, $t_R$=1.738 min.

(S)—N$^4$-(5-(1-(8-oxa-1-azaspiro[4.5]decan-1-yl)ethyl)111yridine-2-yl)-N$^6$-(3-(methylsulfonyl)111yridine-2-yl)pyrimidine-4,6-diamine (29). To a solution of 29.2 (60 mg, 0.21 mmol) and 1A (57 mg, 0.21 mmol) in dioxane (4 mL) was added Brettphos-Pd-G3 (19 mg, 0.021 mmol), Xantphos (12 mg, 0.021 mmol) and $Cs_2CO_3$ (139 mg, 0.43 mmol). The mixture was stirred at 115° C. for 5 hours in microwave under nitrogen atmosphere. After the reaction was completed, the mixture was evaporated in vacuo to give crude 29.1, further purification with reversed phase prep-HPLC and Prep-SFC to give 29 (8.68 mg, 16% yield) as a white solid. $^1$H NMR (400 MHz, DMSO-d$_6$) δ 10.08 (s, 1H), 9.43 (s, 1H), 8.72 (s, 1H), 8.65 (dd, J=4.4, 1.6 Hz, 1H), 8.39 (d, J=0.8 Hz, 1H), 8.27-8.25 (m, 2H), 7.72-7.64 (m, 2H), 7.27 (dd, J=8.0, 4.8 Hz, 1H), 4.18-4.13 (m, 1H), 3.88-3.83 (m, 1H), 3.80-3.76 (m, 1H), 3.39 (s, 3H), 3.37-3.36 (m, 1H), 3.31-3.30 (m, 1H), 2.88-2.82 (m, 1H), 2.71-2.66 (m, 1H), 1.82-1.64 (m, 6H), 1.38-1.35 (m, 4H), 1.10-1.06 (m, 1H). LC-MS m/z: 510.0 [M+H]$^+$. HPLC purity (254 nm): 97.18%, $t_R$=9.605 min.

Example 1ac: Preparation of Compound 30

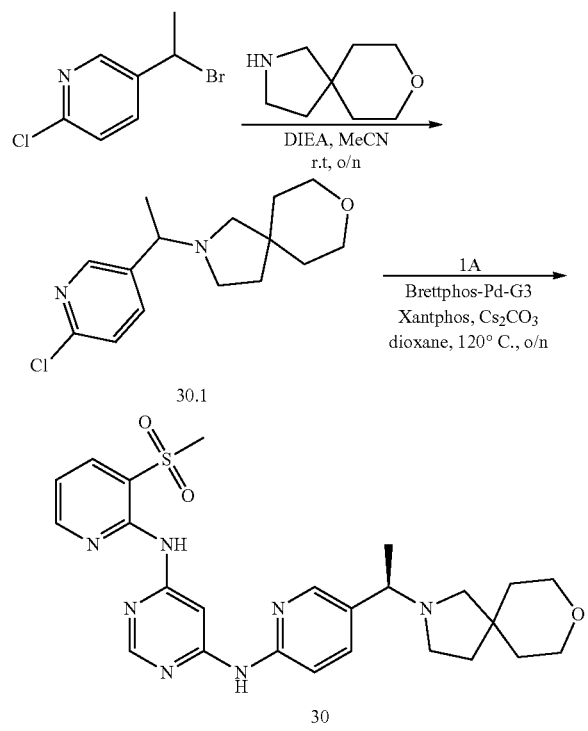

30

2-(1-(6-chloropyridin-3-yl)ethyl)-8-oxa-2-azaspiro[4.5]decane (30.1). To a solution of 5-(1-bromoethyl)-2-chloropyridine (250 mg, 1.13 mmol) in MeCN (20 mL) was added 8-oxa-2-azaspiro[4.5]decane (189 mg, 1.34 mmol) and 112yri (292 mg, 2.26 mmol). The reaction was stirred at room temperature overnight. After the reaction was completed, the mixture was evaporated in vacuo to give crude product. Further purification with silica gel column chromatography ($CH_2Cl_2$:MeOH=20:1) gives title product 30.1 (260 mg, 81.9% yield) as a yellow oil. LC-MS m/z: 281.4 [M+1]$^+$. LCMS purity (254 nm): 84%; $t_R$=0.370 min.

I-N$^4$-(5-(1-(8-oxa-2-azaspiro[4.5]decan-2-yl)ethyl)112yridine-2-yl)-N$^6$-(3-(methylsulfonyl)112yridine-2-yl)pyrimidine-4,6-diamine (30). To a solution of 30.1 (260 mg, 0.93 mmol) in dioxane (25 mL) was added N$^6$-(3-(methylsulfonyl)112yridine-2-yl)pyrimidine-4,6-diamine (247 mg, 0.71 mmol), $Cs_2CO_3$ (606 mg, 1.86 mmol) and Brettphos-Pd-G3 (83 mg, 0.093 mmol), Xantphos (48 mg, 0.083 mmol). The reaction was heated to 120° C. and stirred at 120° C. overnight under nitrogen atmosphere. After the reaction was completed, the mixture was filtered via diatomite. The filtrate was evaporated in vacuo to give crude product. Further purification with silica gel column chromatography ($CH_2Cl_2$:MeOH=10:1) gives crude product. The crude product was purified by reversed phase prep-HPLC and prep-SFC to give 30 (19.75 mg, 38.7% yield) as a white solid. $^1$H NMR (400 MHz, DMSO-d$_6$) δ 10.14 (s, 1H), 9.44 (s, 1H), 8.77 (s, 1H), 8.66 (dd, J=4.8, 1.6 Hz, 1H), 8.40 (s, 1H), 8.27 (dd, J=8.0, 2.0 Hz, 1H), 8.22 (s, 1H), 7.70-7.65 (m, 2H), 7.27 (dd, J=8.0, 4.8 Hz, 1H), 3.53-3.47 (m, 4H), 3.39 (s, 3H), 3.24-3.22 (m, 1H), 2.67-2.62 (m, 1H), 2.37-2.25 (m, 3H), 1.62-1.58 (m, 2H), 1.50-1.39 (m, 4H), 1.28 (d, J=11.6 Hz, 3H). LC-MS m/z: 510.0 [M+H]$^+$. HPLC purity (214 nm): >99.9%, $t_R$=8.629 min.

Example 1ad: Preparation of Compound 31

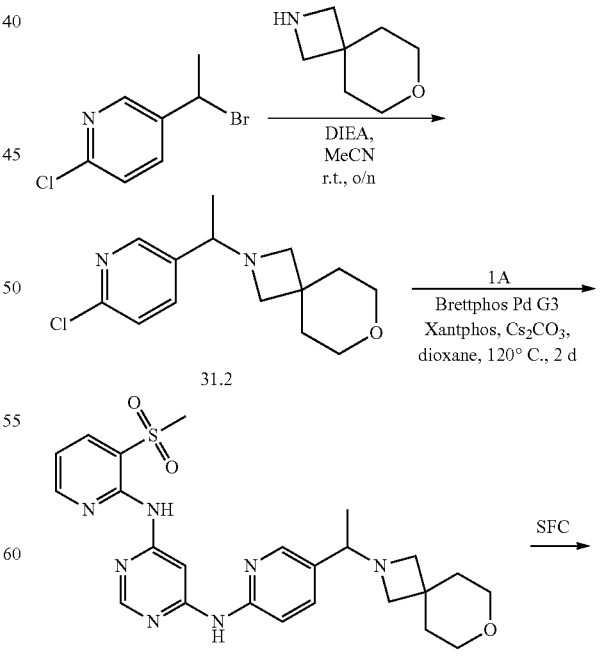

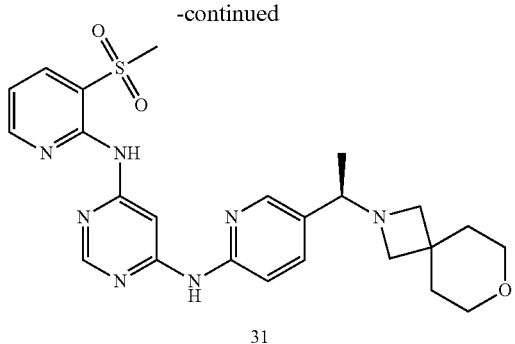

31

2-(1-(6-chloropyridin-3-yl)ethyl)-7-oxa-2-azaspiro[3.5]nonane (31.2). To a stirred solution of 5-(1-bromoethyl)-2-chloropyridine (200 mg, 0.91 mmol) in MeCN (10 mL) was added 113yri (469 mg, 3.63 mmol) and 7-oxa-2-azaspiro[3.5]nonane (115 mg, 0.91 mmol). The mixture was stirred at room temperature overnight. After consumption of the starting material (monitored by LCMS), the mixture was poured into ice water (20 mL) and extracted with EtOAc (20 mL×3). The combined organic layers were washed with brine (20 mL×3), dried over $Na_2SO_4$, filtered and concentrated in vacuo. The residue was purified by column chromatography on silica gel (petrol ether/EtOAc=1/3) to give 31.2 (200 mg, 82.6% yield) as light-yellow oil. LC-MS m/z: 267.4 [M+1]$^+$. LCMS purity (254 nm): 76.92%; $t_R$=1.629 min.

$N^4$-(5-(1-(7-oxa-2-azaspiro[3.5]nonan-2-yl)ethyl)113yridine-2-yl)-$N^6$-(3-(methylsulfonyl)113yridine-2-yl)pyrimidine-4,6-diamine (31.1). To a stirred solution of 31.2 (170 mg, 0.64 mmol) in dioxane (10 mL) was added 1A (169 mg, 0.64 mmol), $Cs_2CO_3$ (415 mg, 1.27 mmol), Xantphos (37 mg, 0.064 mmol) and Brettphos Pd G3 (58 mg, 0.064 mmol). The mixture was stirred at 120° C. for 2 d under nitrogen. After consumption of the starting material (monitored by LCMS), the mixture was cooled to room temperature, diluted with water (30 mL) and extracted with EtOAc (30 mL×3). The combined organic layers were washed with brine (30 mL×2), dried over sodium sulfate and concentrated to dryness. The residue was purified by column chromatography on silica gel ($CH_2Cl_2$/MeOH=20/1) and reversed-phase Prep-HPLC to give 31.1 (37 mg, 11.7% yield) as a white solid. $^1$H NMR (400 MHz, DMSO-$d_6$) δ 10.11 (s, 1H), 9.44 (br, 1H), 8.76 (s, 1H), 8.66 (dd, J=4.8, 2.0 Hz, 1H), 8.40 (d, J=1.2 Hz, 1H), 8.27 (dd, J=8.0, 2.0 Hz, 1H), 8.24-8.20 (m, 1H), 7.71-7.61 (m, 2H), 7.27 (dd, J=8.0, 4.8 Hz, 1H), 3.46 (t, J=5.2 Hz, 4H), 3.39 (s, 3H), 3.32-3.26 (m, 1H), 2.93 (d, J=6.4 Hz, 2H), 2.83 (d, J=6.4 Hz, 2H), 1.63 (t, J=5.6 Hz, 4H), 1.18-1.09 (m, 3H). LC-MS m/z: 496.2 [M+1]$^+$. HPLC purity (214 nm): >99.9%; $t_R$=7.486 min.

I-$N^4$-(5-(1-(7-oxa-2-azaspiro[3.5]nonan-2-yl) ethyl)pyridine-2-yl)-$N^6$-(3-(methylsulfonyl)114yridine-2-yl)pyrimidine-4,6-diamine (31). 31.1 (25, 0.05 mmol) was purified by Prep-SFC to give 31 (8 mg, 32% yield) as a white solid. $^1$H NMR (400 MHz, DMSO-$d_6$) δ 10.12 (s, 1H), 9.43 (s, 1H), 8.76 (s, 1H), 8.66 (dd, J=4.8, 1.6 Hz, 1H), 8.40 (d, 1=1.2 Hz, 1H), 8.27 (dd, J=8.0, 2.0 Hz, 1H), 8.23-8.19 (m, 1H), 7.72-7.60 (m, 2H), 7.27 (dd, 1=8.0, 4.8 Hz, 1H), 3.46 (t, J=5.2 Hz, 4H), 3.39 (s, 3H), 3.32-3.28 (m, 1H), 2.93 (d, J=6.4 Hz, 2H), 2.83 (d, J=6.8 Hz, 2H), 1.63 (t, J=5.2 Hz, 4H), 1.19-1.07 (m, 3H). LC-MS m/z: 496.3 [M+1]$^+$. HPLC purity (214 nm): 97.09%; $t_R$=7.597 min.

Example 1ae: Preparation of Compound 32 and Compound 32a

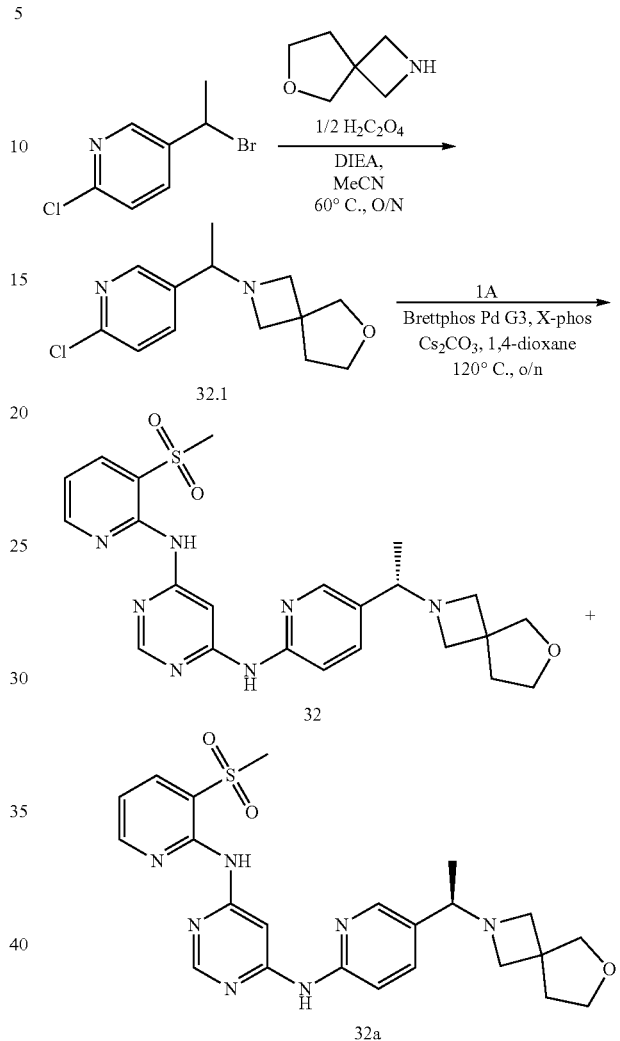

2-(1-(6-chloropyridin-3-yl)ethyl)-6-oxa-2-azaspiro[3.4]octane (32.1). A mixture of 5-(1-bromoethyl)-2-chloropyridine (400 mg, 1.81 mmol), 6-Oxa-2-azaspiro[3.4]octane oxalate (2:1) (286 mg, 0.90 mmol) and 114yri (467 mg, 3.62 mmol) in $CH_3CN$ (215 mL) was stirred at 60° C. overnight under argon atmosphere. After consumption of the starting material, the reaction mixture was cooled to room temperature, concentrated and purified by column chromatography on silica gel (0.5% $Et_3N$ in EtOAc) to give 32.1 (150 mg, 32.8% yield) as a pale-yellow oil. LC-MS m/z: 253.0 [M+1]$^+$. LCMS purity (214 nm): 80.63%; $t_R$=1.315 min.

(S)—$N^4$-(5-(1-(6-oxa-2-azaspiro[3.4]octan-2-yl)ethyl)114yridine-2-yl)-$N^6$-(3-(methylsulfonyl)114yridine-2-yl)pyrimidine-4,6-diamine (32) & I-$N^4$-(5-(1-(6-oxa-2-azaspiro[3.4]octan-2-yl)ethyl)114yridine-2-yl)-$N^6$-(3-(methylsulfonyl)114yridine-2-yl)pyrimidine-4,6-diamine (32a). A mixture of 32.1 (150 mg, 0.59 mmol), 1A (157 mg, 0.59 mmol), Brettphos-Pd-$G_3$ (54 mg, 0.060 mmol), X-phos (28 mg, 0.059 mmol) and $Cs_2CO_3$ (385 mg, 1.18 mmol) in 1,4-dioxane (20 mL) was stirred at 120° C. overnight under argon atmosphere. After consumption of the staring material, the reaction mixture was cooled to room temperature, diluted with water (50 mL) and extracted with EtOAc (50 mL×2). The organic extract was washed with brine (50 mL), dried over anhydrous Na$_2$SO$_4$, concentrated and purified by reversed phase prep-HPLC to give 32.1 (28.89 mg, 10.1% yield) as white solid and further purified by SFC to give 32 (5.49 mg, 1.9% yield) and 32a (5.34 mg, 1.9% yield) as white solid.

Compound 32: $^1$H NMR (400 MHz, DMSO-d$_6$) δ 10.13 (s, 1H), 9.44 (s, 1H), 8.77 (s, 1H), 8.67 (dd, J=4.8, 1.6 Hz, 1H), 8.40 (s, 1H), 8.27 (dd, J=8.0, 2.0 Hz, 1H), 8.22 (s, 1H), 7.67-7.66 (m, 2H), 7.27 (dd, J=8.0, 4.8 Hz, 1H), 3.68 (s, 2H), 3.62 (t, J=7.2 Hz, 2H), 3.39 (s, 3H), 3.29-3.26 (m, 1H), 3.11 (t, 1=7.2 Hz, 2H), 2.99 (t, 1=6.8 Hz, 2H), 1.98 (t, J=7.2 Hz, 2H), 1.13 (d, J=6.4 Hz, 3H). LC-MS m/z: 482.3 [M+1]$^+$. HPLC purity (214 nm): >99.9%; $t_R$=7.156 min. Compound 32a: $^1$H NMR (400 MHz, DMSO-d$_6$) δ 10.13 (s, 1H), 9.44 (s, 1H), 8.77 (s, 1H), 8.67 (dd, J=4.8, 1.6 Hz, 1H), 8.40 (s, 1H), 8.27 (dd, J=8.0, 1.6 Hz, 1H), 8.22 (s, 1H), 7.70-7.64 (m, 2H), 7.27 (dd, J=8.0, 4.8 Hz, 1H), 3.68 (s, 2H), 3.62 (t, J=7.2 Hz, 2H), 3.39 (s, 3H), 3.30-3.26 (m, 1H), 3.13-3.09 (m, 2H), 2.99 (t, 1=6.8 Hz, 2H), 1.98 (t, 1=7.2 Hz, 2H), 1.13 (d, J=6.4 Hz, 3H). LC-MS m/z: 482.3 [M+1]$^+$. HPLC purity (214 nm): >99.9%; $t_R$=7.159 min.

Example 1af: Preparation of Compound 33

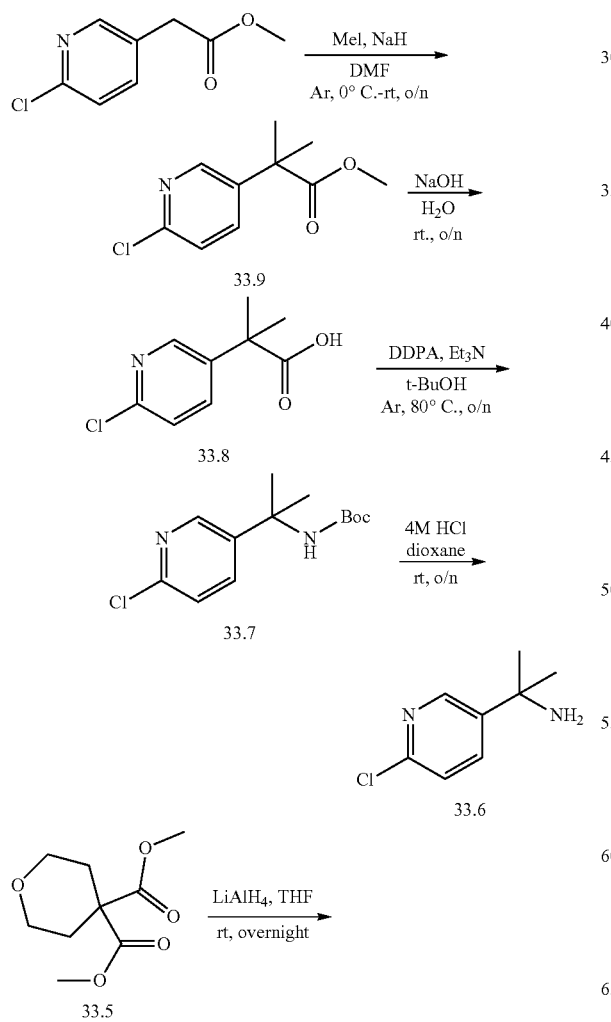

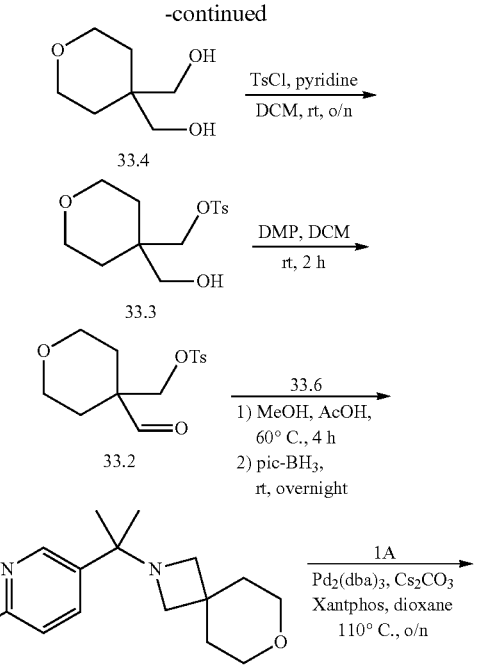

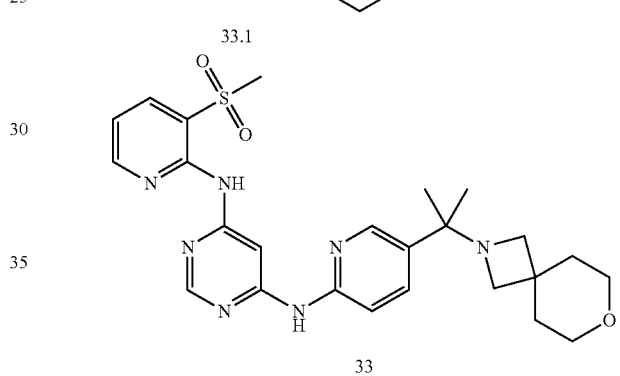

Methyl 2-(6-chloropyridin-3-yl)-2-methylpropanoate (33.9). To a solution of 60% NaH (4.14 g, 103.50 mmol) in dry DMF (150 mL) was added methyl 2-(6-chloropyridin-3-yl)acetate (7.68 g, 41.40 mmol) slowly at 0'C and the mixture was allowed to warm to room temperature slowly and stirred at room temperature overnight under argon. After the reaction was completed, it was quenched by water (100 mL) slowly at 0'C and the mixture was extracted with EtOAc (100 mL×2). The combined organic layers were washed with brine (200 mL×4), dried over anhydrous Na$_2$SO$_4$ and concentrated to give crude 33.9 (8.0 g, 90.5% yield) as brown oil. LC-MS m/z: 214.2 [M+H]$^+$. LCMS purity (254 nm): 84.16%; $t_R$=0.813 min 2-(6-chloropyridin-3-yl)-2-methylpropanoic acid (33.8). A mixture of 33.9 (8.0 g, 37.40 mmol) and NaOH (7.48 g, 187.0 mmol) in H$_2$O (100 mL) was stirred at room temperature overnight. After the reaction was completed, the mixture was washed by EtOAc (100 mL). The water layer was acidified by 2N HCl to adjust pH to 2-3 and extracted with EtOAc (100 mL×3). The combined organic layers were washed with brine (200 mL), dried over anhydrous Na$_2$SO$_4$ and concentrated to give crude 33.8 (7.40 g, 99% yield) as yellow oil. LC-MS m/z: 200.2 [M+H]$^+$. LCMS purity (254 nm): 98.67%; $t_R$=0.383 min.

tert-butyl (2-(6-chloropyridin-3-yl)propan-2-yl)carbamate (33.7). To a solution of 33.8 (8.32 g, 41.68 mmol) and Et$_3$N (17.4 mL, 125.10 mmol) in t-BuOH (100 mL) was added DPPA (13.5 mL, 62.60 mmol), the resulting mixture was stirred at 80'C overnight under argon. After cooling to room temperature, the mixture was concentrated to give a residue. The residue was purified by column chromatography on silica gel (eluting with 10% EtOAc in hexane) to give 33.7 (6.18 g, 54.8% yield) as a white solid. LC-MS m/z: 271.3 [M+H]$^+$. LCMS purity (254 nm): 93.53%; t$_R$=0.866 min.

2-(6-chloropyridin-3-yl)propan-2-amine (33.6). A mixture of 33.7 (6.18 g, 22.8 mmol) in a solution of 4 M HCl (g) in 1, 4-dioxane (50 mL) was stirred at room temperature overnight. After the reaction was completed, water (50 mL) and aqueous K$_2$CO$_3$ was added to adjust pH to 9-10, and extracted with DCM (50 mL×3). The combined organic layers were washed with brine (50 mL), dried over anhydrous Na$_2$SO$_4$ and concentrated to give crude 33.6 (3.83 g, 98.3% yield) as yellow oil. LC-MS m/z: 171.3 [M+H]$^+$. LCMS purity (254 nm): 97.27%; t$_R$=1.300 min (tetrahydro-2H-pyran-4,4-diyl)dimethanol (33.4). To a solution of 33.5 (5 g, 24.73 mmol) in THF (50 mL) was added LiAlH$_4$ (4.69 g, 123.64 mmol). Then the reaction mixture was stirred at room temperature overnight. Then the reaction mixture was quenched with water (5 mL) and 15% NaOH (5 mL), added Mg$_2$SO$_4$ and filtered. The filtrate was concentrated and the residue was purified by column chromatography on silica gel (EtOAc/Hexane=1/1) to give 33.4 (3.30 g, 91.3% yield) as a colorless oil. LC-MS m/z: 147.2 [M+1]$^+$. LCMS purity (214 nm): no UV absorption.

(4-(hydroxymethyl)tetrahydro-2H-pyran-4-yl)methyl 4-methylbenzenesulfonate (33.3). To a solution of 33.4 (1 g, 6.84 mmol) in DCM (30 mL) was added pyridine (1.08 g, 13.68 mmol) and TsCl (1.56 g, 8.21 mmol), the resulting mixture was stirred at room temperature overnight. Then the reaction mixture was poured into water (30 mL) and extracted with EtOAc (30 mL×3). The organic layers were washed with brine, dried over Na$_2$SO$_4$ and filtered. The filtrate was concentrated and the residue was purified by column chromatography on silica gel (EtOAc/Hexane=¹) give 33.3 (600 mg, 29.2% yield) as a yellow solid. LC-MS m/z: 301.1 [M+H]$^+$. LCMS purity (254 nm): 95.71%; t$_R$=1.546 min.

(4-formyltetrahydro-2H-pyran-4-yl)methyl 4-methylbenzenesulfonate (33.2). A mixture of 33.3 (600 mg, 2.00 mmol), Dess-Martin periodinane (1.69 g, 4.00 mmol), and DCM (10 mL) was stirred at room temperature for 2 h. Then, it was poured into water (10 mL) and extracted with DCM (10 mL×3), washed with brine and dried over Na$_2$SO$_4$ and filtered. The filtrate was concentrated and the residue was purified by column chromatography on silica gel (EtOAc/Hexane=1/5) to give 33.2 (300 mg, 50.3% yield) as a yellow solid. LC-MS m/z: 299.1 [M+1]$^+$. LCMS purity (214 nm): 90.01%; t$_R$=1.691 min.

2-(2-(6-chloropyridin-3-yl)propan-2-yl)-7-oxa-2-azaspiro[3.5]nonane (33.1). To a mixture of 33.2 (260 mg, 0.87 mmol), 33.6 (149 mg, 0.87 mmol) in MeOH (5 mL) was added one drop of AcOH. The resulting mixture was stirred at 60° C. for 4 h. Then, Pic-BH$_3$ (186 mg, 1.74 mmol) was added to the reaction mixture and then the reaction was stirred at room temperature overnight. After the reaction was 118yridine 118, it was poured into water (20 mL) and neutralized with 2 N NaOH to pH 7-8, and extracted with EtOAc (20 mL×3), washed with brine and dried over Na$_2$SO$_4$ and filtered. The filtrate was concentrated and the residue was purified by column chromatography on silica gel (EtOAc/Hexane=1/1) give 33.1 (110 mg, 45.1% yield) as a yellow solid. LC-MS m/z: 281.2 [M+1]$^+$. LCMS purity (214 nm): 97.18%; t$_R$=1.167 min.

N$^4$-(5-(2-(7-oxa-2-azaspiro[3.5]nonan-2-yl)propan-2-yl)118yridine-2-yl)-N$^6$-(3-(methylsulfonyl)118yridine-2-yl)pyrimidine-4,6-diamine (33). A mixture of 33.1 (90 mg, 0.32 mmol), 1A (85 mg, 0.32 mmol), Pd$_2$(dba)$_3$ (27 mg, 0.03 mmol), XantPhos (35 mg, 0.06 mmol), Cs$_2$CO$_3$ (209 mg, 0.64 mmol) and dioxane (3 mL) was stirred at 110° C. overnight under nitrogen. Then, it was poured into water (10 mL) and extracted with EtOAc (10 mL×3), washed with brine and dried over Na$_2$SO$_4$ and filtered. The filtrate was concentrated, the residue was purified by column chromatography on silica gel (EtOAc/Hexane=1/1) and reversed phase prep-HPLC to give 33 (25.43 mg, 15.6% yield) as a white solid. $^1$H NMR (400 MHz, DMSO-d$_6$) δ 10.07 (s, 1H), 9.40 (s, 1H), 8.69 (s, 1H), 8.63 (dd, J=4.4, 1.6 Hz, 1H), 8.37 (d, J=0.8 Hz, 1H), 8.34 (d, J=2.0 Hz, 1H), 8.24 (dd, J=7.6, 1.6 Hz, 1H), 7.78 (dd, J=8.4, 2.0 Hz, 1H), 7.67 (d, J=8.8 Hz, 1H), 7.25 (dd, J=7.6, 4.8 Hz, 1H), 3.44 (t, 1=4.8 Hz, 4H), 3.36 (s, 3H), 2.87 (s, 4H), 1.57 (t, 1=5.2 Hz, 4H), 1.25 (s, 6H). LC-MS m/z: 510.0 [M+H]$^+$. HPLC purity (214 nm): >99.9%; t$_R$=8.419 min.

Example 1ag: Preparation of Compound 34

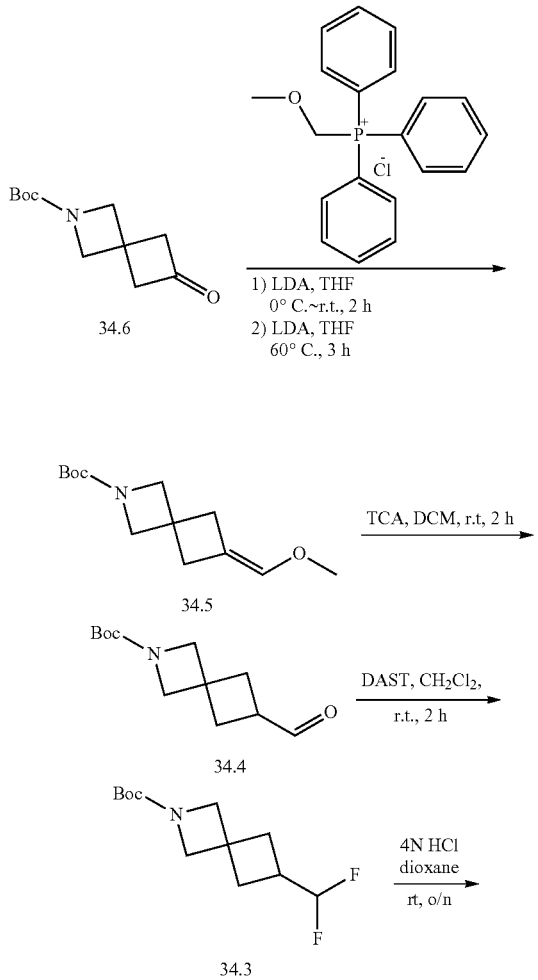

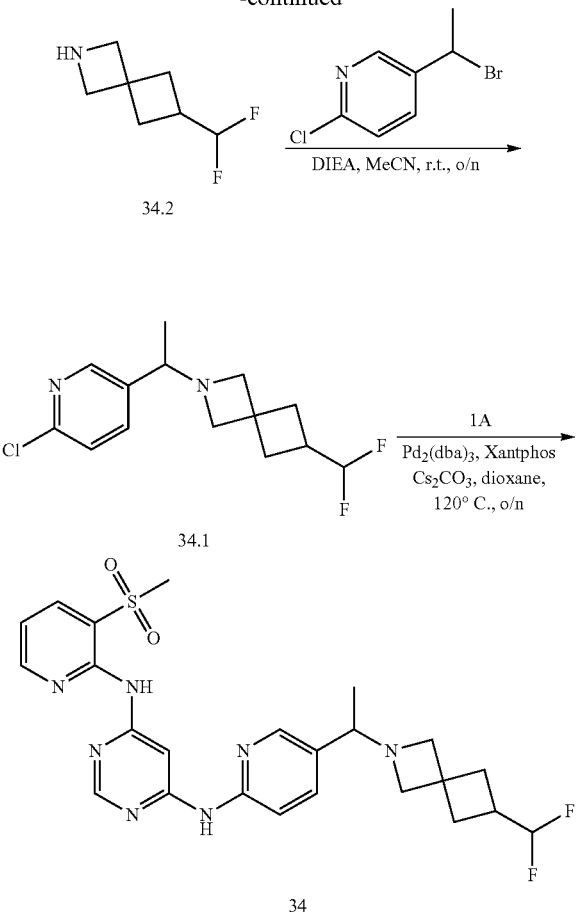

tert-butyl 6-(methoxymethylene)-2-azaspiro[3.3]heptane-2-carboxylate (34.5). To a stirred solution of (methoxymethyl)triphenylphosphonium chloride (2.92 g, 8.52 mmol) in THF (30 mL) was dropwise added LDA (2.0 N, 2.6 mL, 5.12 mmol) at 0° C. under nitrogen. Then the reaction was warmed to room temperature and stirred at room temperature for 2 h. 34.6 (900 mg, 4.26 mmol) dissolved in THF (10 mL) was dropwise added. After the addition, the reaction solution was stirred at 60° C. under nitrogen for 3 h. After consumption of the starting material (monitored by LCMS), the mixture was diluted with water (50 mL) and extracted with EtOAc (60 mL×3). The combined organic layers were washed with brine (40 mL×2), dried over sodium sulfate and concentrated to dryness. The residue was purified by column chromatography on silica gel (petrol ether/THF=10/1) to give 34.5 (320 mg, 31% yield) as light yellow oil. LC-MS m/z: 184.4 [M-55]$^+$. LCMS purity (214 nm): 97.15%; $t_R$=1.955 min.

tert-butyl 6-formyl-2-azaspiro[3.3]heptane-2-carboxylate (34.4). Into a 100 mL one-necked roundbottom flask, a mixture of 34.5 (300 mg, 1.25 mmol) and 2,2,2-trichloroacetic acid (614 mg, 3.76 mmol) in $CH_2Cl_2$ (20 mL) was stirred at room temperature for 2 h. After consumption of the starting material (monitored by LCMS), the mixture was diluted with water (50 mL) and extracted with $CH_2Cl_2$ (50 mL×3). The combined organic layers were washed with brine (40 mL×2), dried over sodium sulfate and concentrated to dryness to give 34.4 (280 mg, 99% yield) as colorless oil. LC-MS m/z: 170.4 [M-55]$^+$. No UV spectrum absorption.

tert-butyl 6-(difluoromethyl)-2-azaspiro[3.3]heptane-2-carboxylate (34.3). Into a 100 mL one-necked roundbottom flask, a mixture of 34.4 (280 mg, 1.24 mmol) and DAST (401 mg, 2.49 mmol) in $CH_2Cl_2$ (20 mL) was stirred at room temperature for 2 h. After consumption of the starting material (monitored by LCMS), the mixture was diluted with saturated aqueous solution of $NaHCO_3$ (30 mL) and extracted with $CH_2Cl_2$ (50 mL×3). The combined organic layers were washed with brine (40 mL×2), dried over sodium sulfate and concentrated to dryness to give 34.3 (260 mg, 85% yield) as a light brown solid. LC-MS m/z: 192.3 [M-55]$^+$. No UV spectrum absorption.

6-(difluoromethyl)-2-azaspiro[3.3]heptane (34.2). Into a 100 mL one-necked roundbottom flask, a mixture of 34.3 (150 mg, 0.61 mmol) in HCl in dioxane (4 N, 5 mL) was stirred at room temperature overnight. After consumption of the starting material (monitored by LCMS), the solvent was removed in vacuo. The residue was diluted with saturated aqueous solution of $NaHCO_3$ (20 mL) and extracted with ethyl acetate (30 mL×3). The combined organic layers were washed with brine (30 mL×2), dried over sodium sulfate and concentrated to dryness to give 34.2 (80 mg, 90% yield) as light brown oil. LC-MS m/z: 148.4 [M+1]$^+$. No UV spectrum absorption.

2-(1-(6-chloropyridin-3-yl)ethyl)-6-(difluoromethyl)-2-azaspiro[3.3] heptane (34.1). A solution of 34.2 (100 mg, 0.68 mmol) in MeCN (2 mL) was added 120yri (263 mg, 2.04 mmol), then 5-(1-bromoethyl)-2-chloropyridine (150 mg, 0.68 mmol) was drop-wise added. The mixture was stirred at room temperature overnight under nitrogen. After consumption of the starting material (monitored by LCMS), the mixture was filtered and the filtrate was concentrated at reduced pressure. The residue was dissolved in EtOAc (30 mL) and washed with water (30 mL×2) then brine (30 mL×2). The organic layer was dried over anhydrous sodium sulfate and concentrated in vacuo to give the crude product. The target product was purified by column chromatography on silica gel ($CH_2Cl_2/CH_3OH$=10:1) to give 34.1 (60 mg, 31% yield) as a yellow solid. LC-MS m/z: 287.4 [M+1]$^+$. LCMS purity (214 nm): 93.51%; $t_R$=1.826 min.

$N^4$-(5-(1-(6-(difluoromethyl)-2-azaspiro[3.3]heptan-2-yl)ethyl) 120yridine-2-yl)-$N^6$-(3-(methylsulfonyl)120yridine-2-yl)pyrimidine-4,6-diamine (34). A solution of 34.1 (40 mg, 0.14 mmol), 1A (37 mg, 0.14 mmol), $Pd_2(dba)_3$ (9 mg, 0.01 mmol), Xantphos (6 mg, 0.01 mmol) and $Cs_2CO_3$ (91 mg, 0.28 mmol) in dioxane (1 mL) was stirred at 120° C. overnight under nitrogen. After consumption of the starting material (monitored by LCMS), the mixture was filtered and the filtrate was concentrated at reduced pressure. The residue was dissolved in EtOAc (30 mL) and washed with water (20 mL×2) then brine (20 mL×2). The organic layer was dried over anhydrous sodium sulfate and concentrated in vacuo to give the crude product. The product was purified by column chromatography on silica gel ($CH_3OH/CH_2Cl_2$=1/10) and reversed phase prep-HPLC to give 34 (9 mg, 12% yield) as a white solid. $^1$H NMR (400 MHz, DMSO-$d_6$) δ 10.11 (s, 1H), 9.43 (s, 1H), 8.77 (s, 1H), 8.67 (dd, J=4.8 Hz, 1.6 Hz, 1H), 8.40 (d, J=1.2 Hz, 1H), 8.26 (dd, J=8.0 Hz, 2.0 Hz, 1H), 8.21-8.17 (m, 1H), 7.68-7.60 (m, 2H), 7.27 (dd, J=8.0 Hz, 5.2 Hz, 1H), 6.15-5.83 (m, 1H), 3.39 (s, 3H), 3.23-3.16 (m, 1H), 3.12 (d, J=7.2 Hz, 1H), 3.06-2.98 (m, 2H), 2.91 (d, J=7.2 Hz, 1H), 2.60-2.53 (m, 1H), 2.18-2.11 (m, 2H), 2.06-2.00 (m, 2H), 1.11 (d, J=6.4 Hz, 3H). LC-MS m/z: 516.2 [M+1]$^+$. HPLC purity (254 nm): 99.14%; $t_R$=9.156 min.

Example 1ah: Preparation of Compound 35

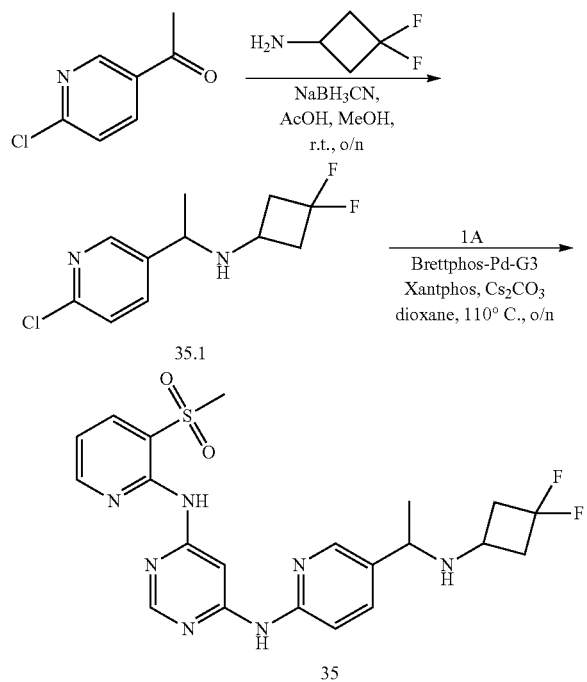

N-(1-(6-chloropyridin-3-yl)ethyl)-3,3-difluorocyclobutanamine (35.1). To a solution of 1-(6-chloropyridin-3-yl)ethan-1-one (150 mg, 0.96 mmol) in MeOH (10 mL) was added 3,3-difluorocyclobutanamine (206 mg, 1.93 mmol) and AcOH (12 mg, 0.19 mmol). The mixture was stirred at room temperature for 1 h under nitrogen atmosphere. Then NaBH$_3$CN (121 mg, 1.93 mmol) was added. The mixture was stirred at room temperature overnight. After consumption of the starting material (monitored by LCMS), the reaction mixture was concentrated in vacuo. Then the residue was diluted with water (50 mL) and extracted with EtOAc (30 mL×3). The combined organic layers were washed with brine (30 mL), dried over anhydrous sodium sulfate, filtrated and concentrated to dryness. The residue was purified by reversed-phase column chromatography (MeOH/H$_2$O=1/1) to give 35.1 (75 mg, 32% yield) as a white solid. LC-MS m/z: 247.2 [M+1]. LCMS purity (214 nm): 98.57%; $t_R$=1.481 min.

N$^4$-(5-(1-(3,3-difluorocyclobutylamino)ethyl)122yridine-2-yl)-N$^6$-(3-(methylsulfonyl)122yridine-2-yl)pyrimidine-4,6-diamine (35). To a solution of 35.1 (75 mg, 0.30 mmol) in dioxane (10 mL) was added 1A (81 mg, 0.30 mmol), Cs$_2$CO$_3$ (198 mg, 0.61 mmol), Xantphos (17 mg, 0.030 mmol) and Brettphos Pd G3 (14 mg, 0.015 mmol). Then the mixture was stirred at 110° C. overnight under nitrogen atmosphere. After consumption of the starting material (monitored by LCMS), the reaction mixture was cooled to room temperature. Then the reaction mixture was diluted with water (50 mL) and extracted with EtOAc (30 mL×3). The combined organic layers were washed with brine (50 mL), dried over anhydrous sodium sulfate and concentrated to dryness. The residue was purified by Prep-TLC (CH$_2$Cl$_2$/MeOH=10/1) and reversed-phase Prep-HPLC to give 35 (34 mg, 24% yield) as a white solid. $^1$H NMR (400 MHz, DMSO-d$_6$) δ 10.11 (s, 1H), 9.43 (br, 1H), 8.77 (s, 1H), 8.65 (dd, J=4.8, 2.0 Hz, 1H), 8.40 (d, J=1.2 Hz, 1H), 8.27 (dd, J=8.0, 2.0 Hz, 1H), 8.24-8.20 (m, 1H), 7.72-7.65 (m, 2H), 7.27 (dd, J=8.0, 4.8 Hz, 1H), 3.74-3.61 (m, 1H), 3.39 (s, 3H), 2.99-2.82 (m, 1H), 2.77-2.61 (m, 2H), 2.57-2.51 (m, 1H), 2.42-2.15 (m, 2H), 1.27 (d, J=6.8 Hz, 3H). LC-MS m/z: 476.2 [M+H]. HPLC purity (254 nm): >99.9%; $t_R$=8.049 min.

Example 1ai: Preparation of Compound 36

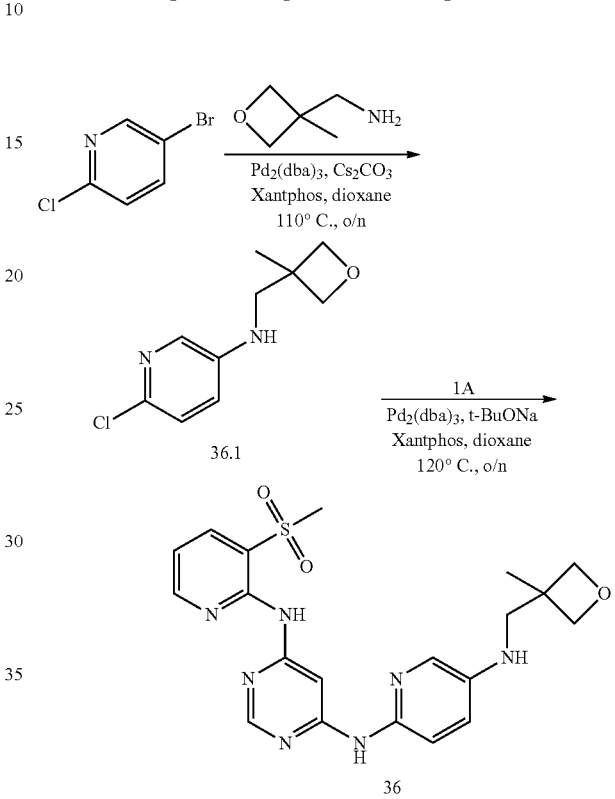

6-chloro-N-((3-methyloxetan-3-yl)methyl)122yridine-3-amine (36.1). To a solution of 5-bromo-2-chloropyridine (250 mg, 1.30 mmol) in dioxane (20 mL) was added (3-methyloxetan-3-yl)methanamine (158 mg, 1.56 mmol), Cs$_2$CO$_3$ (847 mg, 2.60 mmol), Pd$_2$(dba)$_3$ (119 mg, 0.13 mmol) and Xantphos (75 mg, 0.13 mmol). The reaction was heated to 110° C. and stirred at 110° C. overnight under nitrogen atmosphere. After the reaction was completed, the mixture was filtered via diatomite. The filtrate was evaporated in vacuo to give crude product. Further purification with silica gel column chromatography (EtOAc:Hexane=9:1) gives title product 36.1 (160 mg, 57.9% yield) as a yellow solid. LC-MS m/z: 213.3 [M+1]$^+$. LCMS purity (254 nm): >99.9%; $t_R$=0.532 min.

N$^4$-(5-(((3-methyloxetan-3-yl)methyl)amino)123yridine-2-yl)-N$^6$-(3-(methylsulfonyl)123yridine-2-yl)pyrimidine-4,6-diamine (36). To a solution of 36.1 (160 mg, 0.75 mmol) in dioxane (20 mL) was added 1A (200 mg, 0.75 mmol), Cs$_2$CO$_3$ (490 mg, 1.50 mmol) and Pd$_2$(dba)$_3$ (69 mg, 0.075 mmol), Xantphos (44 mg, 0.075 mmol). The reaction was heated to 120° C. and stirred at 120° C. overnight under nitrogen atmosphere. After the reaction was completed, the mixture was filtered via diatomite. The filtrate was evaporated in vacuo to give crude product. Purification with silica gel column chromatography (CH$_2$Cl$_2$:MeOH=10/1) gives crude product and purified by reversed phase prep-HPLC gives 36 (61.41 mg, 18.5% yield) as a yellow solid. $^1$H NMR (400 MHz, DMSO-$d_6$) δ9.69 (s, 1H), 9.34 (s, 1H), 8.60 (dd, J=4.8, 2.0 Hz, 1H), 8.45 (br, 1H), 8.30 (d, J=1.2 Hz, 1H), 8.25 (dd, J=8.0, 2.0 Hz, 1H), 7.79 (d, J=2.8 Hz, 1H), 7.49 (d, J=8.0 Hz, 1H), 7.24 (dd, J=8.0, 5.2 Hz, 1H), 7.10 (dd, J=9.2, 3.2 Hz, 1H), 5.57 (t, J=6.0 Hz, 1H), 4.43 (d, J=5.6 Hz, 2H), 4.26 (d, J=5.6 Hz, 2H), 3.38 (s, 3H), 3.24 (d, J=6.0 Hz, 2H), 1.34 (s, 3H). LC-MS m/z: 442.2 [M+H]$^+$. HPLC purity (214 nm): 98.68%, $t_R$=7.157 min.

Example 1ai: Preparation of Compound 37

(53.26 mg, 11.8% yield) as a white solid. $^1$H NMR (400 MHz, DMSO-$d_6$) δ9.71 (s, 1H), 9.33 (s, 1H), 8.59 (dd, J=4.8, 1.6 Hz, 1H), 8.45 (s, 1H), 8.29 (d, J=0.8 Hz, 1H), 8.23 (dd, J=8.0, 2.0 Hz, 1H), 7.65 (d, J=2.8 Hz, 1H), 7.51 (d, J=8.4 Hz, 1H), 7.22 (dd, J=8.0, 4.8 Hz, 1H), 7.00 (dd, J=8.8, 2.8 Hz, 1H), 6.03 (d, J=6.8 Hz, 1H), 3.81-3.77 (m, 1H), 3.31 (s, 3H), 3.08-3.01 (m, 2H), 2.46-2.39 (m, 2H). LC-MS m/z: 448.3 [M+H]$^+$. HPLC purity (254 nm): 98.05%; $t_R$=8.244 min.

Example 1ak: Preparation of Compound 38

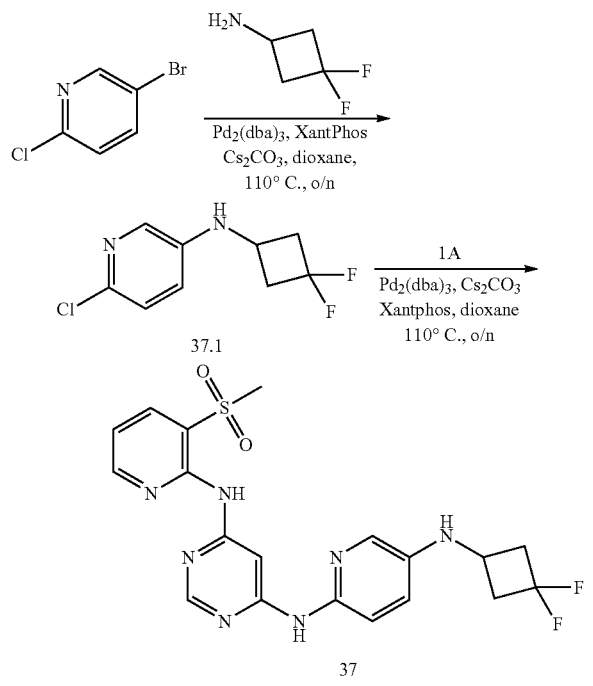

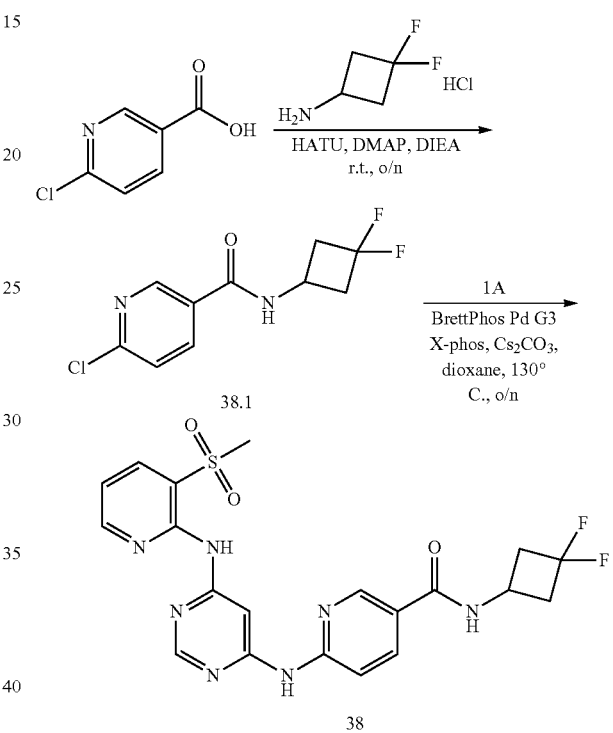

6-chloro-N-(3,3-difluorocyclobutyl)123yridine-3-amine (37.1). A mixture of 5-bromo-2-chloropyridine (1.00 g, 5.20 mmol), 3,3-difluorocyclobutanamine (557 mg, 5.20 mmol), Pd$_2$(dba)$_3$ (476 mg, 0.52 mmol), XantPhos (601 mg, 1.04 mmol), Cs$_2$CO$_3$ (3.39 g, 10.40 mmol) and dioxane (50 mL) was stirred at 110° C. overnight under nitrogen. Then the reaction mixture was poured into water (100 mL) and extracted with EtOAc (100 mL×3). The combined organic layers were washed with brine, dried over Na$_2$SO$_4$ and filtered. The filtrate was concentrated and the residue was purified by column chromatography on silica gel (EtOAc/Hexane=1/1) to give 37.1 (400 mg, 35.2% yield) as a yellow solid. LC-MS m/z: 219.1 [M+1]$^+$. LCMS purity (214 nm): 34.11%; $t_R$=1.676 min.

N$^4$-(5-(3,3-difluorocyclobutylamino)124yridine-2-yl)-N$^6$-(3-(methylsulfonyl)124yridine-2-yl)pyrimidine-4,6-diamine (37). A mixture of 37.1 (220 mg, 1.01 mmol), 1A (267 mg, 1.01 mmol), Pd$_2$(dba)$_3$ (92 mg, 0.10 mmol), XantPhos (116 mg, 0.20 mmol), Cs$_2$CO$_3$ (656 mg, 2.01 mmol) and dioxane (10 mL) was stirred at 110° C. overnight under nitrogen. Then the mixture was poured into water (10 mL) and extracted with EtOAc (10 mL×3). The combined organic layers were washed with brine, dried over Na$_2$SO$_4$ and filtered. The filtrate was concentrated, the residue was purified by column chromatography on silica gel (CH$_2$Cl$_2$/MeOH=10/1) and reversed phase prep-HPLC to give 37

6-chloro-N-(3,3-difluorocyclobutyl)nicotinamide (38.1). To a solution of 6-chloronicotinic acid (250 mg, 1.59 mmol) in DMF (6 ml) was added 3,3-difluorocyclobutanamine hydrochloride (228 mg, 1.59 mmol), HATU (905 mg, 2.38 mmol) and 124yri (615 mg, 4.76 mmol). The mixture was stirred at room temperature overnight. After consumption of the starting material (monitored by LCMS), the mixture was diluted with brine (20 ml) and extracted with EtOAc (30 mL×2), the combined organic layers were washed with brine (30 mL×2), dried over anhydrous sodium sulfate, filtered and concentrated in vacuo. The residue was purified by column chromatography on silica gel (Hexane/EtOAc=4/1) to get 38.1 (230 mg, 59% yield) as a brown solid. LC-MS m/z: 247.2 [M+H]$^+$. LCMS purity (254 nm): 96.79%; $t_R$=1.371 min.

N-(3,3-difluorocyclobutyl)-6-(6-(3-(methylsulfonyl)pyridine-2-ylamino)pyrimidin-4-ylamino)nicotinamide (38). To a stirred solution of 38.1 (170 mg, 0.69 mmol) in dioxane (6 mL) was added 1A (183 mg, 0.69 mmol), Cs$_2$CO$_3$ (449 mg, 1.38 mmol), X-phos (33 mg, 0.069 mmol) and Brettphos-Pd-G3 (62 mg, 0.069 mmol). The mixture was stirred at 130° C. overnight under nitrogen. After consumption of the starting material (monitored by LCMS), the mixture was filtered and the filtrate was concentrated in vacuo. The residue was purified by column chromatography on silica gel (CH$_2$Cl$_2$/MeOH=10/1) and reversed-phase Prep-HPLC to give 38 (42 mg, 13% yield) as an off-white solid. $^1$H NMR (400 MHz, DMSO-d$_6$) δ 10.52 (s, 1H), 9.51 (s, 1H), 8.83-8.79 (m, 3H), 8.67 (dd, J=4.8, 1.6 Hz, 1H), 8.48 (d, J=0.8 Hz, 1H), 8.28 (dd, J=8.0, 2.0 Hz, 1H), 8.14 (dd, J=8.8, 2.8 Hz, 1H), 7.85 (d, J=8.8 Hz, 1H), 7.30 (dd, J=8.0, 5.2 Hz, 1H), 4.34-4.20 (m, 1H), 3.40 (s, 3H), 3.04-2.90 (m, 2H), 2.83-2.69 (m, 2H). LC-MS m/z: 476.3[M+H]$^+$. HPLC purity (214 nm): >99.9%; t$_R$=7.685 min.

Example 1al: Preparation of Compound 39

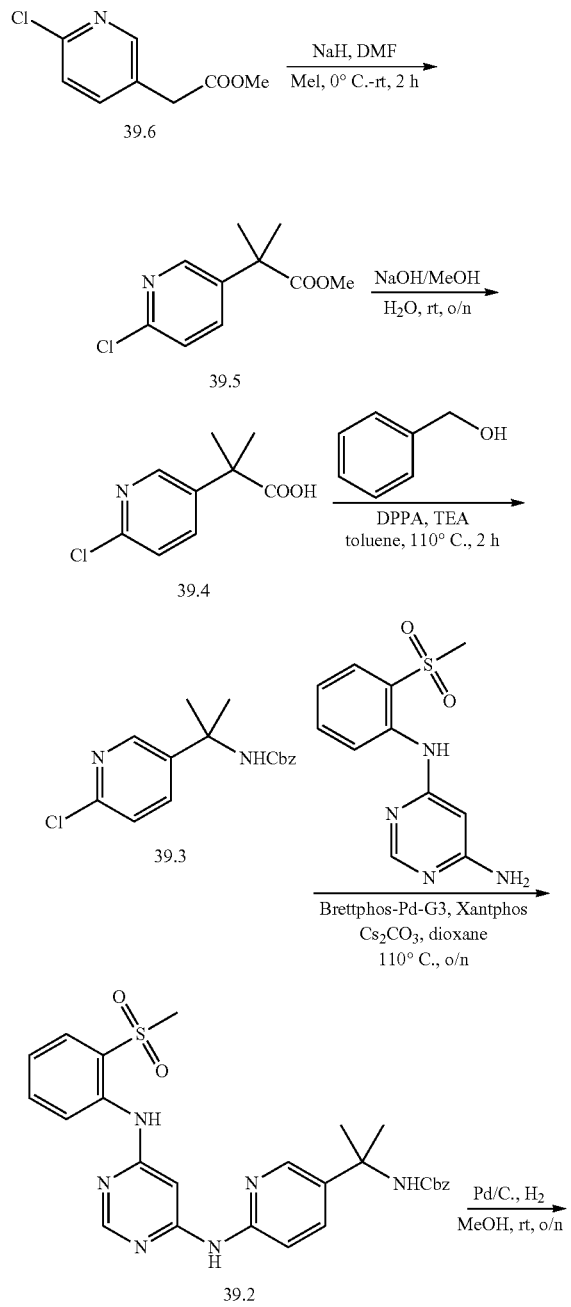

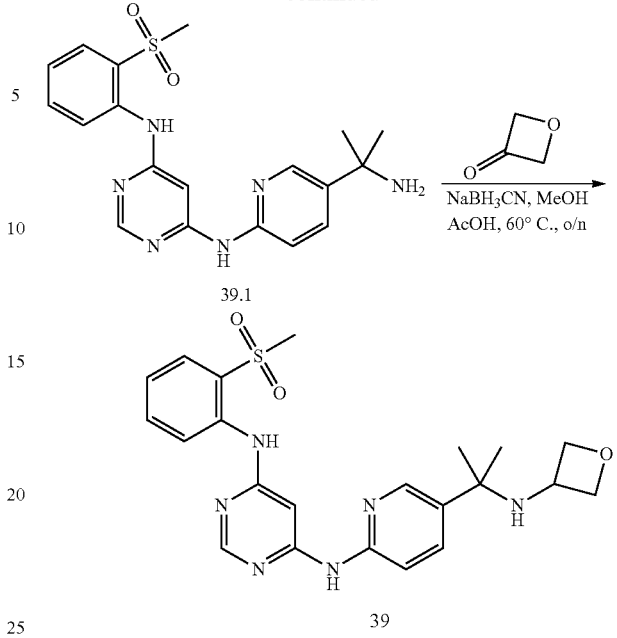

Methyl 2-(6-chloropyridin-3-yl)-2-methylpropanoate (39.5). A solution of 39.6 (400 mg, 2.16 mmol) in DMF (10 mL) was added 60% NaH (259 mg, 6.47 mmol) at 0° C., the mixture was stirred at 0° C. for 30 min. Then iodomethane (673 mg, 4.74 mmol) was added into the mixture at 0° C. The mixture was stirred at room temperature for 2 hours. After reaction was completed, the mixture was poured into water (50 mL) and extracted with EtOAc (30 mL×3). The combined organic layers were washed with brine (40 mL), dried over anhydrous sodium sulfate, filtered and concentrated in vacuo. The residue was purified by column chromatography on silica gel (Hexane/EtOAc=3:1) to get 39.6 (260 mg, 56.5% yield) as a yellow solid. LC-MS m/z: 214.2 [M+H]$^+$. LCMS purity (214 nm): 97.99%; t$_R$=0.802 min.

2-(6-chloropyridin-3-yl)-2-methylpropanoic acid (39.4). A mixture of 39.5 (260 mg, 1.22 mmol), NaOH (97 mg, 2.43 mmol), MeOH (15 mL) and H$_2$O (15 mL) was stirred at room temperature overnight. Then the reaction mixture was diluted with water (20 mL) and acidified with 2 N HCl to pH 5-6. The mixture was extracted with EtOAc (20 mL×3). The combined organic layers were washed with brine (40 mL) and dried over Na$_2$SO$_4$ and filtered. The filtrate was concentrated to give 39.4 (180 mg, 74.1% yield) as a yellow oil. LC-MS m/z: 200.2 [M+H]$^+$. LCMS purity (254 nm): 97.60%; t$_R$=0.393 min.

benzyl (2-(6-chloropyridin-3-yl)propan-2-yl)carbamate (39.3). A mixture of 39.4 (650 mg, 3.26 mmol), phenylmethanol (704 mg, 6.51 mmol), DPPA (1348 mg, 4.90 mmol), TEA (988 mg, 9.77 mmol) and toluene (20 mL) was stirred at 110° C. for 2 h. Then it was poured into water (50 mL) and extracted with EtOAc (30 mL×3). The combined organic layers were washed with brine (40 mL) and dried over Na$_2$SO$_4$ and filtered. The filtrate was concentrated and the residue was purified by column chromatography on silica gel (EtOAc/Hexane=1/5) to give 39.3 (500 mg, 50.4% yield) as a yellow solid. LC-MS m/z: 305.2 [M+H]$^+$. LCMS purity (254 nm): 87.77%; t$_R$=2.036 min.

benzyl(2-(6-(((6-((2-(methylsulfonyl)phenyl)amino)pyrimidin-4-yl)amino)126yridine-3-yl)propan-2-yl)carbamate (39.2). A suspension of 39.3 (300 mg, 0.98 mmol), N$^4$-(2-

(methylsulfonyl)phenyl)pyrimidine-4,6-diamine (312 mg, 1.18 mmol), Brettphos-Pd-G3 (91 mg, 0.10 mmol), Xantphos (116 mg, 0.20 mmol) and Cs$_2$CO$_3$ (641 mg, 1.97 mmol) in dry 1,4-dioxane (30 mL) was stirred at 110° C. overnight under nitrogen. After the reaction was completed, the mixture was concentrated and purified by column chromatography on silica gel (EtOAc/Hexane 80%) to give 39.2 (330 mg, 62.8% yield) as a yellow solid. LC-MS m/z: 533.2 [M+1]$^+$. LCMS purity (254 nm): 87.32%; $t_R$=2.032 min.

N$^4$-(5-(2-aminopropan-2-yl)126yridine-2-yl)-N$^6$-(2-(methylsulfonyl) phenyl)pyrimidine-4,6-diamine (39.1). A mixture of 39.2 (330 mg, 0.62 mmol) and Pd/C (10% wt, 30 mg) in MeOH (30 mL) was stirred at room temperature overnight under hydrogen atmosphere. After reaction was completed, the mixture was filtered and the filtrate was concentrated in vacuo. The residue was purified by column chromatography on silica gel (MeOH/CH$_2$Cl$_2$ 10%) to get 39.1 (150 mg, 60.8% yield) as a white solid. LC-MS m/z: 399.3 [M+H]$^+$. LCMS purity (254 nm): 98.07%; $t_R$=1.480 min.

N$^4$-(2-(methylsulfonyl)phenyl)-N$^6$-(5-(2-(oxetan-3-ylamino)propan-2-yl)127yridine-2-yl)pyrimidine-4,6-diamine (39). A mixture of 39.1 (150 mg, 0.38 mmol), oxetan-3-one (54 mg, 0.75 mmol), NaBH$_3$CN (71 mg, 1.13 mmol), AcOH (0.1 mL), and MeOH (10 mL) was stirred at 60° C. overnight. Then, the reaction mixture was poured into water (20 mL) and adjusted pH to 7~8 with 2 M NaOH solution. The mixture was extracted with EtOAc (20 mL×3). The combined organic layers were washed with brine, dried over Na$_2$SO$_4$ and filtered. The filtrate was concentrated and the residue was purified by reversed phase prep-HPLC to give 39 (29 mg, 16.9% yield) as a white solid. $^1$H NMR (400 MHz, DMSO-d$_6$) δ9.91 (s, 1H), 8.78 (s, 1H), 8.31 (d, J=0.8 Hz, 1H), 8.27 (d, J=2.0 Hz, 1H), 8.02 (d, J=7.6 Hz, 1H), 7.91 (dd, J=8.0, 1.6 Hz, 1H), 7.77-7.71 (m, 2H), 7.46-7.44 (m, 2H), 7.38-7.34 (m, 1H), 4.44 (dd, 1=7.2, 6.0 Hz, 2H), 4.29 (dd, J=6.8, 6.8 Hz, 2H), 3.74-3.64 (m, 1H), 3.23 (s, 3H), 3.00 (d, J=9.2 Hz, 1H), 1.31 (s, 6H). LC-MS m/z: 455.2 [M+H]$^+$. HPLC purity (214 nm): 97.84%; $t_R$=7.060 min.

Example 1am: Preparation of Compound 40

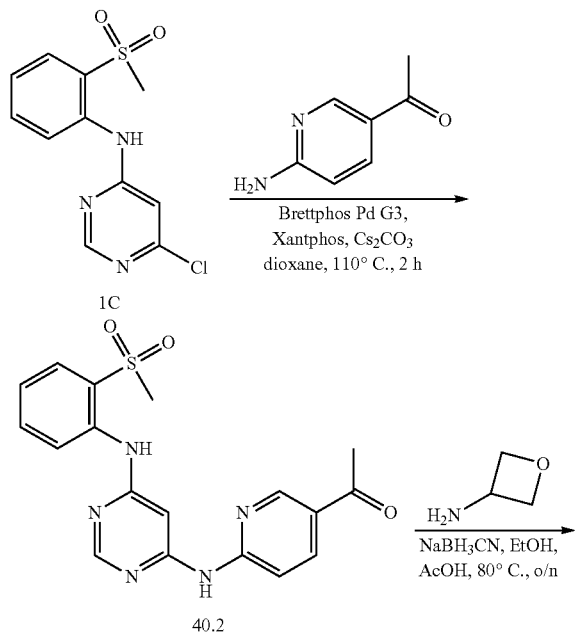

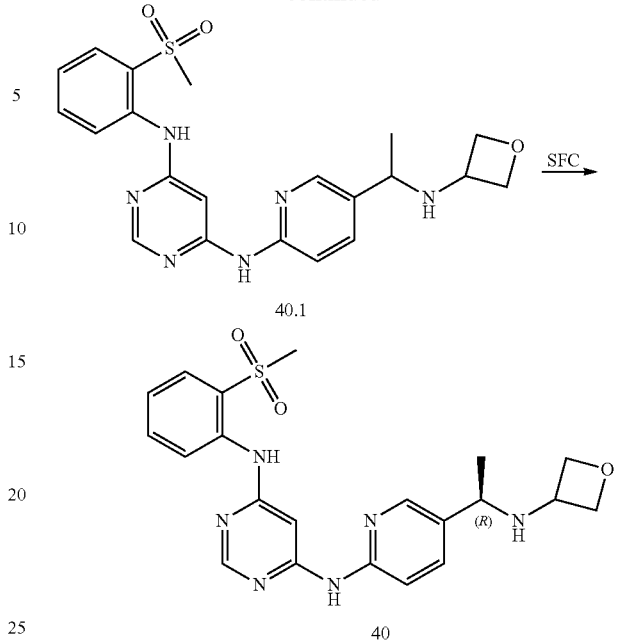

1-(6-(6-(2-(methylsulfonyl)phenylamino)pyrimidin-4-ylamino) pyridine-3-yl)128yridine (40.2). 6-chloro-N-(2-(methylsulfonyl)phenyl)pyrimidin-4-amine (1C) was prepared as described in Example 1 aa. To a solution of 1C (400 mg, 1.41 mmol) in dioxane (15 mL) was added 1-(6-aminopyridin-3-yl) 128yridine (288 mg, 2.11 mmol), Cs$_2$CO$_3$ (919 mg, 2.82 mmol), Xantphos (81 mg, 0.14 mmol) and Brettphos Pd G3 (63 mg, 0.070 mmol). Then the mixture was stirred at 110° C. for 2 h under nitrogen atmosphere. After consumption of the starting material (monitored by LCMS), the reaction mixture was cooled to room temperature. Then the reaction mixture was diluted with water (60 mL) and extracted with EtOAc (40 mL×3). The combined organic layers were washed with brine (40 mL×2), dried over anhydrous sodium sulfate and concentrated to dryness. The residue was purified by silica gel column chromatography (petrol ether/EtOAc=¼) to give 40.2 (415 mg, 77% yield) as a yellow solid. LC-MS m/z: 384.2 [M+1]$^+$. LCMS purity (254 nm): 91.05%; $t_R$=0.470 min.

I-N$^4$-(2-(methylsulfonyl)phenyl)-N$^6$-(5-(1-(oxetan-3-ylamino)ethyl)128yridine-2-yl)pyrimidine-4,6-diamine (40). To a solution of 40.2 (255 mg, 0.66 mmol) in EtOH (10 mL) was added oxetan-3-amine (146 mg, 2.00 mmol) and AcOH (12 mg, 0.20 mmol). The mixture was stirred at room temperature for 1 h under nitrogen atmosphere. Then NaBH$_3$CN (84 mg, 1.33 mmol) was added. The mixture was stirred at 80° C. overnight. After consumption of the starting material (monitored by LCMS), the reaction mixture was concentrated in vacuo. The residue was diluted with water (50 mL) and extracted with EtOAc (50 mL×3). The combined organic layers were washed with brine (50 mL), dried over anhydrous sodium sulfate, filtrated and concentrated to dryness. The residue was purified by column chromatography on silica gel (CH$_2$Cl$_2$/MeOH=10/1) to give 40.1, reversed-phase Prep-HPLC and Prep-SFC to give 40 (34 mg, 11.6% yield) as an off white solid. $^1$H NMR (400 MHz, DMSO-d$_6$) δ9.92 (s, 1H), 8.79 (s, 1H), 8.32 (d, J=0.4 Hz, 1H), 8.15 (d, J=1.6 Hz, 1H), 8.01 (d, J=7.6 Hz, 1H), 7.91 (dd, J=8.4, 1.6 Hz, 1H), 7.77-7.70 (m, 1H), 7.67 (dd, J=8.8, 2.0 Hz, 1H), 7.51-7.41 (m, 2H), 7.39-7.31 (m, 1H), 4.57 (t, J=6.4 Hz, 1H), 4.41-4.25 (m, 2H), 4.12 (t, 1=6.4 Hz, 1H), 3.83-3.55 (m, 2H), 3.22 (s, 3H), 1.25 (d, J=6.4 Hz, 3H). LC-MS m/z: 441.2 [M+1]$^+$. HPLC purity (214 nm): 98.85%; $t_R$=6.651 min.

Example 1an: Preparation of Compound 41

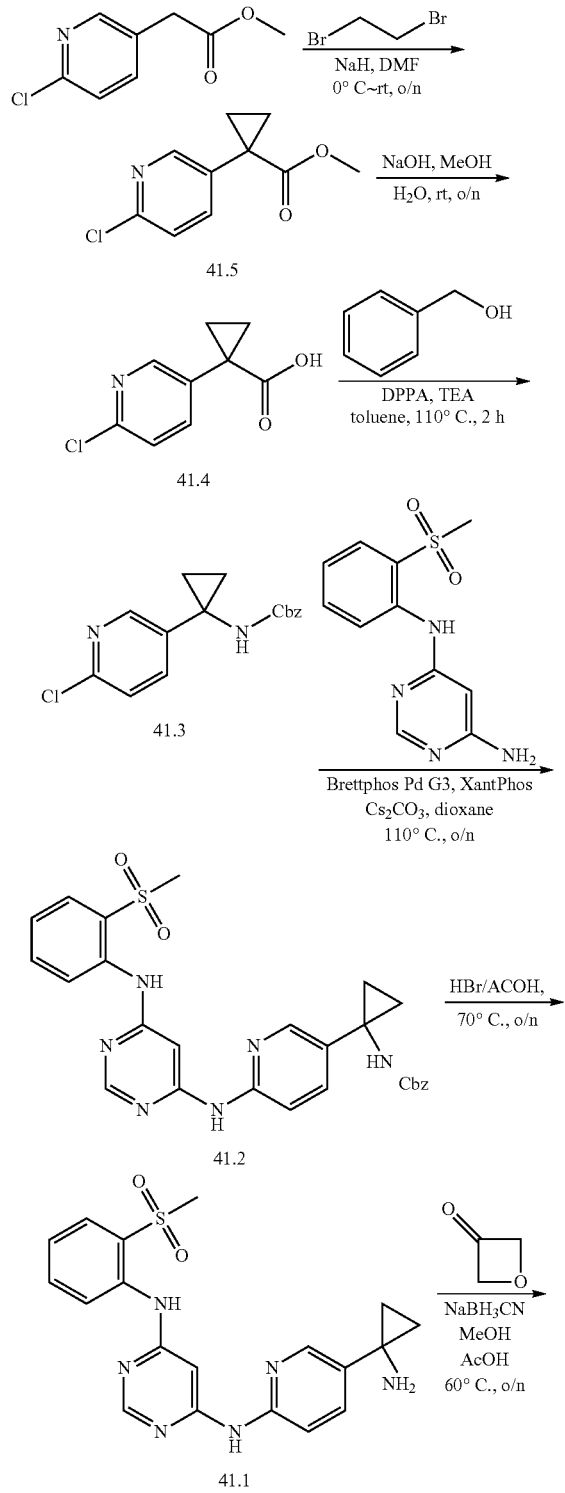

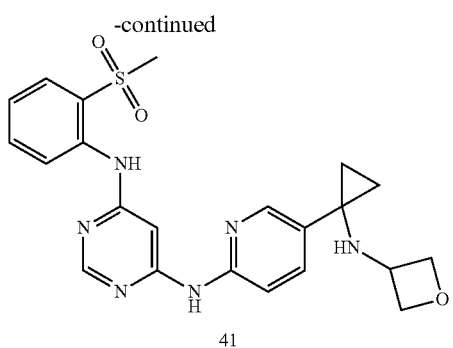

Synthesis of 1-(6-chloropyridin-3-yl)cyclopropanecarboxylate (41.5). To a solution of methyl 2-(6-chloropyridin-3-yl)acetate (1 g, 5.39 mmol) in THF (30 mL) was added NaH (60% wt, 862 mg, 21.55 mmol) and the resulting mixture was stirred at room temperature for 0.5 h. Then 1,2-dibromoethane (1.01 g, 5.39 mmol) was added to the reaction mixture and the resulting mixture was stirred at room temperature overnight. Then the reaction was quenched with saturated NH$_4$Cl (50 mL) and extracted with EtOAc (30 mL×3). The combined organic layers were washed with brine, dried over Na$_2$SO$_4$ and filtered. The filtrate was concentrated and the residue was purified by column chromatography on silica gel (EtOAc/Hexane=10/1) to give 41.5 (500 mg, 43.9% yield) as a yellow solid. LC-MS m/z: 212.1 [M+1]$^+$. LCMS purity (254 nm): 90.53%; $t_R$=1.623 min.

Synthesis of 1-(6-chloropyridin-3-yl)cyclopropanecarboxylic acid (41.4). A mixture of 41.5 (500 mg, 2.36 mmol), NaOH (189 mg, 4.73 mmol), MeOH (5 mL) and H$_2$O (5 mL) was stirred at room temperature overnight. Then the reaction mixture was diluted with water (20 mL) and acidified with 2 N HCl to pH 5-6. The mixture was extracted with EtOAc (20 mL×3). The organic layers were washed with brine, dried over Na$_2$SO$_4$ and filtered. The filtrate was concentrated to give 41.4 (450 mg, 96.4% yield) as a yellow oil. LC-MS m/z: 198.1 [M+H]$^+$. LCMS purity (214 nm): 99.77%; $t_R$=1.407 min.

Synthesis of benzyl 1-(6-chloropyridin-3-yl)cyclopropylcarbamate (41.3). A mixture of 41.4 (450 mg, 2.28 mmol), phenylmethanol (492 mg, 4.55 mmol), DPPA (940 mg, 3.42 mmol), TEA (691 mg, 6.83 mmol) and toluene (20 mL) was stirred at 110° C. for 2 h. Then the reaction mixture was poured into water (50 mL) and extracted with EtOAc (30 mL×3). The combined layers were washed with brine, dried over Na$_2$SO$_4$ and filtered. The filtrate was concentrated and the residue was purified by column chromatography on silica gel (EtOAc/Hexane=1/5) to give 41.3 (300 mg, 44.5% yield) as a yellow solid. LC-MS m/z: 303.1 [M+1]$^+$. LCMS purity (214 nm): 98.53%; $t_R$=1.752 min.

Synthesis of benzyl 1-(6-(6-(2-(methylsulfonyl)phenylamino)pyrimidin-4-ylamino) 130yridine-3-yl)cyclopropylcarbamate (41.2). A mixture of 41.3 (300 mg, 0.99 mmol), N$^4$-(2-(methylsulfonyl)phenyl)pyrimidine-4,6-diamine (262 mg, 0.99 mmol), Brettphos Pd G3 (90 mg, 0.099 mmol), XantPhos (115 mg, 0.20 mmol), Cs$_2$CO$_3$ (646 mg, 1.99 mmol) and dioxane (10 mL) was stirred at 110° C. overnight under nitrogen. Then the reaction mixture was poured into water (10 mL) and extracted with EtOAc (10 mL×3). The combined organic layers were washed with brine, dried over Na$_2$SO$_4$ and filtered. The filtrate was concentrated and the residue was purified by column chromatography on silica gel (EtOAc/Hexane=1/1) to give 41.2

(350 mg, 66.6% yield) as a yellow solid. LC-MS m/z: 531.2 [M+1]⁺. LCMS purity (214 nm): 70.21%; $t_R$=1.609 min.

Synthesis of N⁴-(5-(1-aminocyclopropyl)130yridine-2-yl)-N⁶-(2-(methylsulfonyl) phenyl)pyrimidine-4,6-diamine (41.1). A solution of 41.2 (200 mg, 0.38 mmol) in 33% HBr in AcOH (3 mL) was was stirred at 70° C. overnight. Then the reaction mixture was poured into water (20 mL) and neutralized with 2 M NaOH to pH 7-8. The mixture was extracted with EtOAc (20 mL×3). The combined organic layers were washed with brine, dried over Na₂SO₄ and filtered. The filtrate was concentrated and the residue was purified by column chromatography on silica gel (EtOAc/Hexane=1/1) to give 41.1 (110 mg, 73.6% yield) as a yellow solid. LC-MS m/z: 397.2 [M+H]⁺. LCMS purity (214 nm): 73.40%; $t_R$=1.322 min.

Synthesis of N⁴-(2-(methylsulfonyl)phenyl)-N⁶-(5-(1-(oxetan-3-ylamino) cyclopropyl)130yridine-2-yl)pyrimidine-4,6-diamine (41). A mixture of 41.1 (110 mg, 0.28 mmol), oxetan-3-one (40 mg, 0.55 mmol), NaBH₃CN (44 mg, 0.69 mmol), AcOH (0.2 mL) and MeOH (5 mL) was stirred at 60° C. overnight. Then the reaction mixture was poured into water (20 mL) and neutralized with 2 M NaOH to pH 7~8. The mixture was extracted with EtOAc (20 mL×3). The combined organic layers were washed with brine and dried over Na₂SO₄ and filtered. The filtrate was concentrated and the residue was purified by column chromatography on silica gel (EtOAc/Hexane=1/1) and reversed phase prep-HPLC to give 41 (55 mg, 43.8% yield) as a white solid. ¹H NMR (400 MHz, DMSO-d₆) δ 9.92 (s, 1H), 8.79 (s, 1H), 8.31 (d, 1=0.8 Hz, 1H), 8.20 (d, J=2.0 Hz, 1H), 8.01 (d, J=7.6 Hz, 1H), 7.91 (dd, J=8.0, 1.6 Hz, 1H), 7.76-7.71 (m, 1H), 7.65 (dd, J=8.4, 2.4 Hz, 1H), 7.46-7.42 (m, 2H), 7.38-7.34 (m, 1H), 4.43-4.39 (m, 2H), 4.11 (dd, J=6.4, 6.4 Hz, 2H), 3.97-3.91 (m, 1H), 3.58 (d, J=9.6 Hz, 1H), 3.22 (s, 3H), 0.86-0.83 (m, 2H), 0.80-0.77 (m, 2H). LC-MS m/z: 453.3 [M+H]⁺. HPLC purity (214 nm): >99.9%; $t_R$=7.364 min.

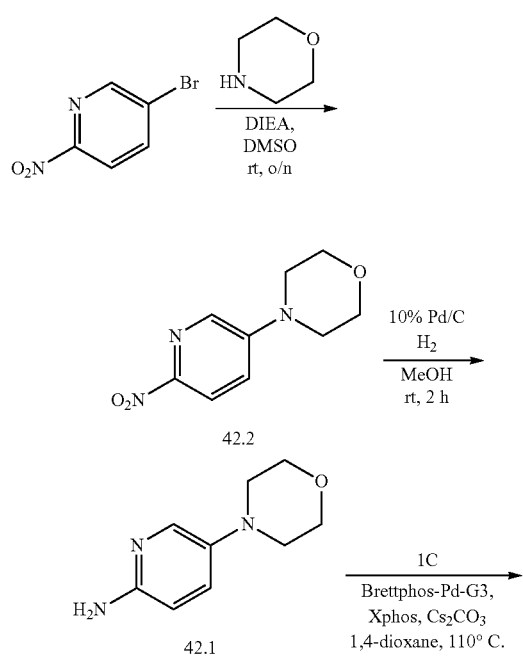

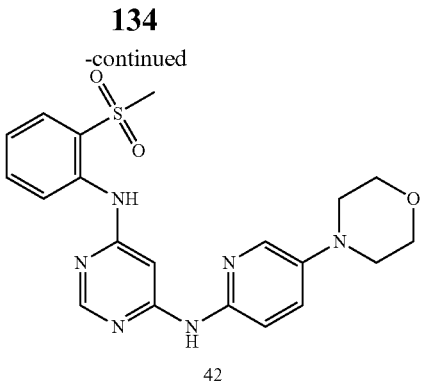

42

4-(6-nitropyridin-3-yl)morpholine (42.2). To a solution of 5-bromo-2-nitropyridine (500 mg, 2.46 mmol) in DMSO (20 mL) was added morpholine (322 mg, 3.69 mmol) and 131 yri (635 mg, 4.92 mmol), the reaction was stirred at 100° C. overnight. After consumption of the starting material, the mixture was diluted by water (100 mL) and extracted with EtOAc (70 mL×2). The organic extract was washed with brine (150 mL×4), dried over Na₂SO₄ and concentrated to give crude 42.2 (505 mg, 98% yield) as brown solid. LC-MS m/z: 210.4 [M+1]⁺; LCMS purity (214 nm): 71.43%; $t_R$=1.402 min.

5-morpholinopyridin-2-amine (42.1). To a solution of 42.2 (50 mg, 0.24 mmol) in MeOH (20 mL) was added 10% Pd/C (10 mg) and the reaction mixture was stirred at room temperature under hydrogen atmosphere for 2 hours. The reaction mixture was filtered and the filtrate was concentrated to give crude 42.1 (35 mg, 81.4% yield) as orange oil. LC-MS m/z: 180.4 [M+1]⁺; LCMS purity (214 nm): 55.49%; $t_R$=1.353 min.

N⁴-(2-(methylsulfonyl)phenyl)-N⁶-(5-morpholinopyridin-2-yl) pyrimidine-4,6-diamine (42). A mixture of 42.1 (130 mg, 0.73 mmol), 1C (205 mg, 0.73 mmol), Brettphos-Pd-G3 (132 mg, 0.145 mmol), Xphos (138 mg, 0.290 mmol) and Cs₂CO₃ (710 mg, 2.178 mmol) in 1,4-dioxane (30 mL) was stirred at 110° C. under argon atmosphere overnight. After consumption of the starting material, it was filtered to remove the solid, diluted by water (50 mL) and extracted with EtOAc (50 mL×2). The organic extract was washed by brine (50 mL), dried over anhydrous Na₂SO₄, concentrated and purified by reversed phase Prep-HPLC to give 42 (65.56 mg, 21.2% yield) as light grey solid. ¹H NMR (400 MHz, DMSO-d₆) δ 9.74 (s, 1H), 8.71 (s, 1H), 8.29 (s, 1H), 8.03 (d, J=7.6 Hz, 1H), 7.95 (d, J=3.2 Hz, 1H), 7.90 (dd, J=8.0, 1.6 Hz, 1H), 7.75-7.01 (m, 1H), 7.48-7.41 (m, 2H), 7.36-7.32 (m, 1H), 7.30 (s, 1H), 3.75 (t, J=5.2 Hz, 4H), 3.22 (s, 3H), 3.08 (t, J=5.2 Hz, 1H). LC-MS m/z: 427.1 [M+1]⁺. HPLC purity (214 nm): 98.40%; $t_R$=7.375 min.

Example 1ap: Preparation of Compound 43

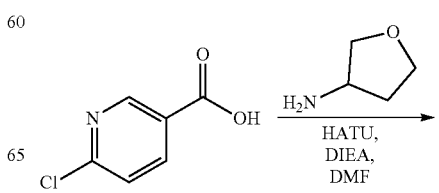

Example 1aq: Preparation of Compound 44

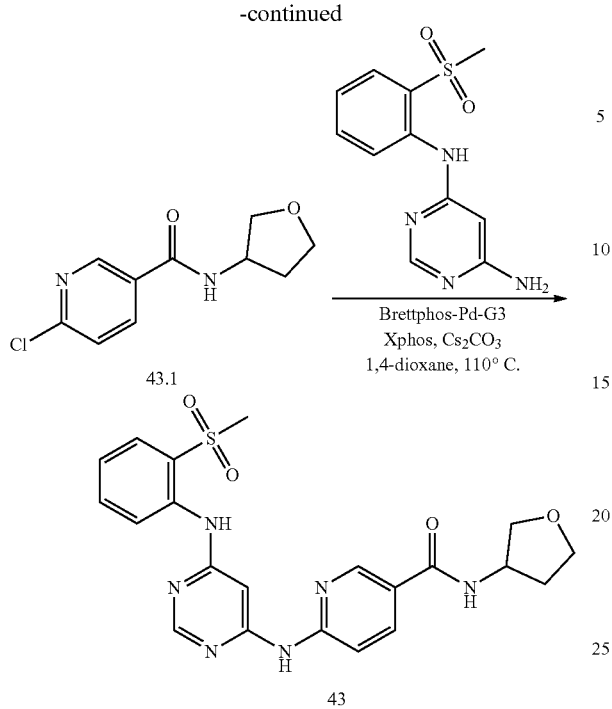

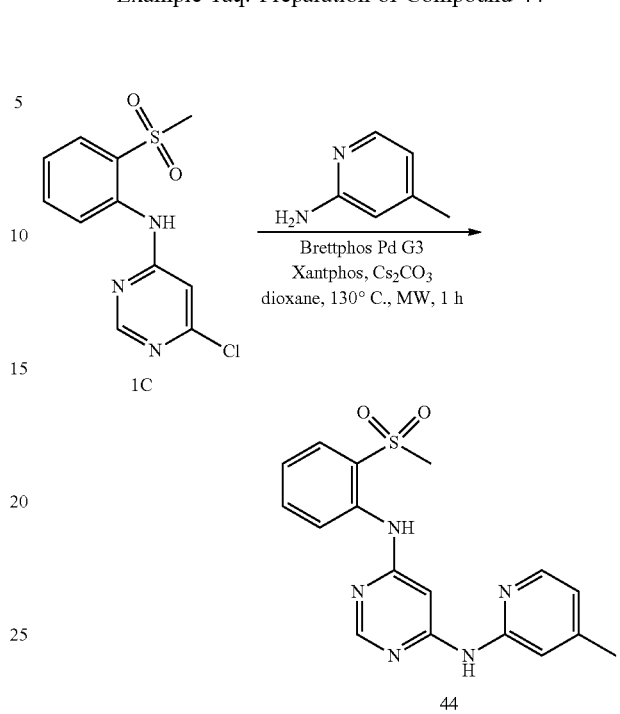

6-chloro-N-(tetrahydrofuran-3-yl)nicotinamide (43.1). To a mixture of 6-chloronicotinic acid (500 mg, 3.17 mmol) in DMF (50 mL) was added tetrahydrofuran-3-amine (276 mg, 3.17 mmol), HATU (1801 mg, 4.74 mmol) and 132yri (1223 mg, 9.48 mmol), the reaction mixture was stirred at room temperature overnight. After the reaction was completed, it was diluted by water (50 mL) and extracted with EtOAc (50 mL×3). The organic extract was washed by brine (100 mL×4), dried over anhydrous $Na_2SO_4$, concentrated and purified by column chromatography on silica gel (EtOAc: hexane=6:4) to give 43.1. (400 mg, 55.6% yield). LC-MS: m/z=227.2 [M+1]$^+$. LCMS purity (214 nm): 48.84%; $t_R$=1.067 min.

6-(6-(2-(methylsulfonyl)phenylamino)pyrimidin-4-ylamino)-N-(tetrahydrofuran-3-yl)nicotinamide (43). A mixture of M-(2-(methylsulfonyl)phenyl)pyrimidine-4,6-diamine (233 mg, 0.88 mmol), 43.1 (200 mg, 0.88 mmol), Brettphos Pd G3 (120 mg, 0.13 mmol), X-phos (124 mg, 0.26 mmol) and $Cs_2CO_3$ (858 g, 2.64 mmol) in 1,4-dioxane (30 mL) was stirred at 110° C. overnight under argon atmosphere. After the reaction was completed, it was diluted by water (50 mL) and extracted with EtOAc (50 mL×3). The organic extract was washed by brine (100 mL), dried over anhydrous $Na_2SO_4$, concentrated and purified by column chromatography on silica gel ($CH_2Cl_2$:MeOH=20:1) and then reversed phase prep-HPLC to give 43 (7.4 mg, 1.9% yield) as a white solid. $^1$H NMR (400 MHz, DMSO-d$_6$) δ 10.29 (s, 1H), 8.88 (s, 1H), 8.76 (d, J=2.0 Hz, 1H), 8.52 (d, J=6.4 Hz 1H), 8.37 (d, J=0.8 Hz, 1H), 8.12 (dd, J=8.8, 2.8 Hz, 1H), 8.01 (d, J=8.0 Hz, 1H), 7.92 (d, J=8.0, 1.6 Hz, 1H), 7.77-7.73 (m, 1H), 7.63 (d, J=8.4 Hz, 1H), 7.46 (s, 1H), 7.41-7.37 (m, 1H), 4.48-4.43 (m, 1H), 3.89-3.83 (m, 2H), 3.74-3.69 (m, 1H), 3.58 (dd, J=8.8, 4.4 Hz, 1H), 3.23 (s, 3H), 2.20-2.11 (m, 1H), 1.95-1.88 (m, 1H). LC-MS m/z=455.2 [M+1]$^+$. HPLC purity: >99.9% (214 nm), $t_R$=6.657 min.

$N^4$-(4-methylpyridin-2-yl)-$N^6$-(2-(methylsulfonyl)phenyl) pyrimidine-4,6-diamine (44). To a solution of 1C (100 mg, 0.35 mmol) in dioxane (5 mL) was added 4-methylpyridin-2-amine (38 mg, 0.35 mmol), $Cs_2CO_3$ (230 mg, 0.70 mmol), Brettphos Pd G3 (16 mg, 0.018 mmol) and Xantphos (20 mg, 0.035 mmol). The mixture was irradiated with microwave for 1 h at 130° C. under nitrogen atmosphere. After consumption of the starting material (monitored by LCMS), the mixture was cooled to room temperature, diluted with water (30 mL) and extracted with EtOAc (20 mL×3). The combined organic layers were washed with brine (30 mL×2), dried over sodium sulfate and concentrated to dryness. The residue was purified by column chromatography on silica gel ($CH_2Cl_2$/MeOH=10/1) and reversed phase prep-HPLC to give 44 (55 mg, 44% yield) as a white solid. $^1$H NMR (400 MHz, DMSO-d$_6$) δ 9.88 (s, 1H), 8.80 (s, 1H), 8.32 (d, J=0.8 Hz, 1H), 8.13 (d, J=5.2 Hz, 1H), 8.00 (d, J=7.6 Hz, 1H), 7.91 (dd, J=8.0, 1.2 Hz, 1H), 7.77-7.69 (m, 1H), 7.49 (s, 1H), 7.41-7.29 (m, 2H), 6.80 (d, J=5.2 Hz, 1H), 3.22 (s, 3H), 2.28 (s, 3H). LC-MS m/z: 356.2 [M+1]$^+$. HPLC purity (254 nm): >99.9%; $t_R$=8.171 min.

Example 1ar: Preparation of Compound 45

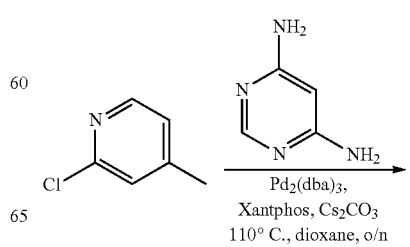

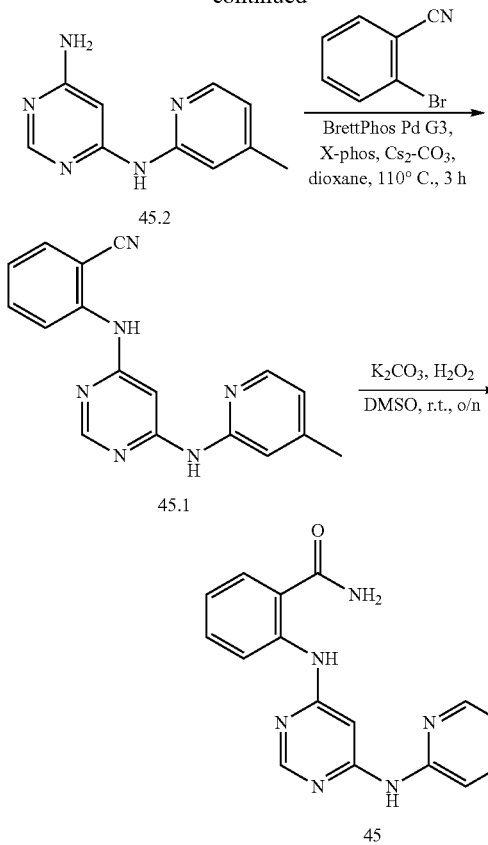

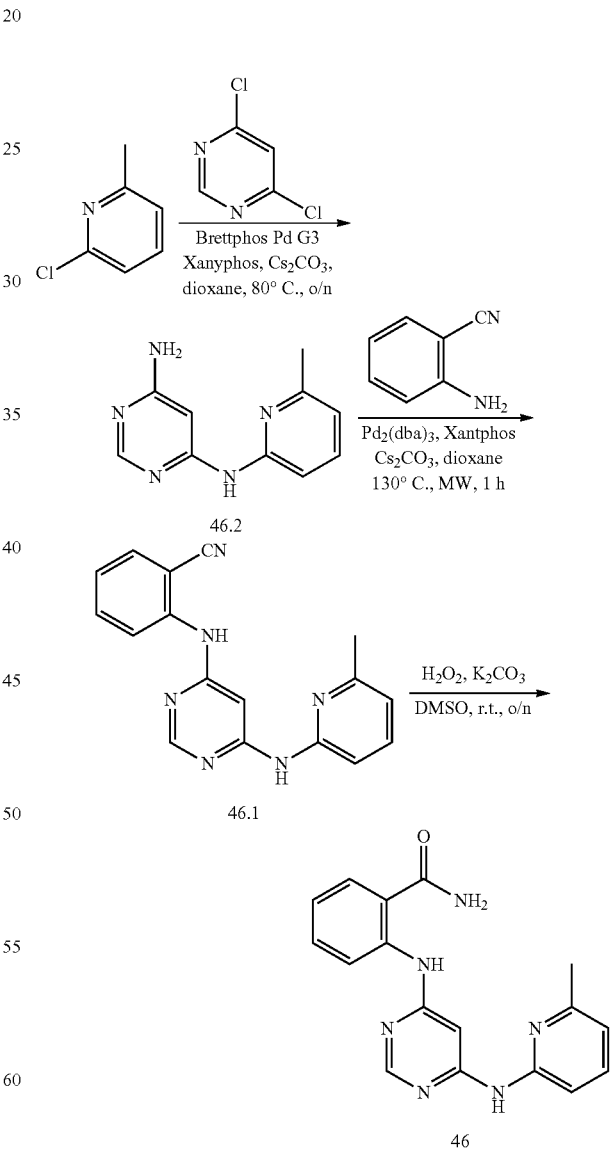

N4-(4-methylpyridin-2-yl)pyrimidine-4,6-diamine (45.2). A mixture of 2-chloro-4-methylpyridine (2.0 g, 15.68 mmol), pyrimidine-4,6-diamine (2.59 g, 23.52 mmol), Cs$_2$CO$_3$ (10.26 g, 31.50 mmol), Xantphos (914 mg, 1.58 mmol) and Pd$_2$(dba)$_3$ (723 mg, 0.79 mmol) in dioxane (60 mL) was stirred at 110° C. overnight under nitrogen. After the reaction was completed and cooled down to room temperature, the mixture was filtered and the filtrate was concentrated in vacuo. The residue was purified by column chromatography on silica gel (CH$_2$Cl$_2$/MeOH (TEA=15/1/ 0.01) to get 45.2 (1.10 g, 35% yield) as a light green solid. LC-MS m/z: 202.3 [M+1]$^+$. LCMS purity (254 nm): 98.67%; $t_R$=1.320 min.

2-((6-((4-methylpyridin-2-yl)amino)pyrimidin-4-yl) amino) benzonitrile (45.1). A mixture of 45.2 (300 mg, 1.49 mmol), 2-bromobenzonitrile (271 mg, 1.49 mmol), BrettPhos-Pd-G3 (136 mg, 0.15 mmol), X-phos (72 mg, 0.15 mmol) and Cs$_2$CO$_3$ (971 mg, 2.98 mmol) in dioxane (10 mL) was stirred at 110° C.; for 3 h under nitrogen. After consumption of the starting material (monitored by LCMS), the mixture was filtered and concentrated at reduced pressure. The residue was dissolved in EtOAc (60 mL) and washed with water (30 mL×2) then brine (30 mL×2). The organic layer was dried over anhydrous sodium sulfate, filtered, then the filtrate concentrated in vacuo to give the crude product, the target product was purified by column chromatography on silica gel (CH$_2$Cl$_2$/CH$_3$OH=10/1) give 45.1 (90 mg, 20% yield) as a yellow solid. LC-MS m/z: 303.3 [M+1]$^+$. LCMS purity (254 nm): 89.14%; $t_R$=0.755 min.

2-((6-((4-methylpyridin-2-yl)amino)pyrimidin-4-yl) amino) benzamide (45). To a stirred solution of 45.1 (90 mg, 0.30 mmol) in DMSO (3 mL) was added K$_2$CO$_3$ (124 mg, 0.90 mmol) and H$_2$O$_2$ (30% wt, 102 mg, 0.90 mmol). The mixture was stirred at room temperature overnight. After consumption of the starting material (monitored by LCMS), the mixture was diluted with water (10 mL) and extracted with EtOAc (10 mL×3). The combined organic layers were washed with brine (10 mL×3), dried over sodium sulfate, filtered, then the filtrate was concentrated to dryness. The final product was purified by reversed-phase prep-HPLC to give 45 (50 mg, 52% yield) as a white solid. $^1$H NMR (400 MHz, DMSO-d$_6$) δ 11.08 (s, 1H), 9.84 (s, 1H), 8.43 (d, J=7.6 Hz, 1H), 8.38 (s, 1H), 8.24 (br, 1H), 8.15 (d, J=5.2 Hz, 1H), 7.76 (dd, 1=8.0 Hz, 1.6 Hz, 1H), 7.69 (br, 1H), 7.52-7.46 (m, 1H), 7.45 (s, 1H), 7.33 (s, 1H), 7.05-7.00 (m, 1H), 6.80 (d, J=4.4 Hz, 1H), 2.28 (s, 3H). LC-MS m/z: 321.3 [M+1]$^+$. HPLC purity (214 nm): >99.9%; $t_R$=7.364 min.

Example 1as: Preparation of Compound 46

6-chloro-N-(6-methylpyridin-2-yl)pyrimidin-4-amine (46.2). To a stirred solution of 6-methylpyridin-2-amine (1.00 g, 9.25 mmol) in dioxane (20 mL) was added 4,6- dichloropyrimidine (1.38 g, 9.25 mmol), Pd$_2$(dba)$_3$ (842 mg, 0.92 mmol), Xantphos (532 mg, 0.92 mmol), Cs$_2$CO$_3$ (6.03 g, 18.49 mmol). The mixture was stirred at 80° C. overnight under nitrogen. After consumption of the starting material (monitored by LCMS), the mixture was cooled down to room temperature, poured into water (50 mL) and extracted with EtOAc (50 mL×3). The combined organic layers were washed with brine (40 mL×2), dried over anhydrous sodium sulfate, filtered and concentrated in vacuo. The residue was purified by column chromatography on silica gel (petrol ether/EtOAc=1/1) to give 46.2 (0.60 g, 29% yield) as a yellow solid. LC-MS m/z: 221.3 [M+H]$^+$. LCMS purity (214 nm): 53.54%; t$_R$=1.703 min.

2-(6-(6-methylpyridin-2-ylamino)pyrimidin-4-ylamino) benzonitrile (46.1). To a stirred solution of 46.2 (300 mg, 1.36 mmol) in dioxane (10 mL) was added 2-aminobenzonitrile (161 mg, 1.36 mmol), Brettphos-Pd-G3 (127 mg, 0.14 mmol), Xantphos (81 mg, 0.14 mmol) and Cs$_2$CO$_3$ (886 mg, 2.72 mmol). The mixture was irradiated with microwave for 3 h at 130° C. under nitrogen. After consumption of the starting material (monitored by LCMS), the mixture was cooled down to room temperature, poured into water (30 mL) and extracted with EtOAc (30 mL×3). The combined organic layers were washed with brine, dried over anhydrous sodium sulfate, filtered and concentrated in vacuo. The residue was purified by column chromatography on silica gel (petrol ether/EtOAc=1/3) and reversed-phase Prep-HPLC to give 46.1 (170 mg, 41% yield) as a white solid. LC-MS m/z: 303.4 [M+H]$^+$. LCMS purity (254 nm): 81.02%; t$_R$=1.821 min.

2-(6-(5-methylpyridin-2-ylamino)pyrimidin-4-ylamino) benzamide (46). To a stirred solution of 46.1 (170 mg, 0.56 mmol) in DMSO (5 mL) was added K$_2$CO$_3$ (233 mg, 1.69 mmol), H$_2$O$_2$ (30% w/w, 191 mg, 1.69 mmol). The mixture was stirred at room temperature overnight under nitrogen. After consumption of the starting material (monitored by LCMS), the mixture was poured into ice water (20 mL) and extracted with EtOAc (20 mL×3). The combined organic layers were washed with brine (20 mL×3), dried over anhydrous sodium sulfate, filtered and concentrated in vacuo. The residue was purified by column chromatography on silica gel (CH$_2$Cl$_2$/MeOH=10/1) and reversed-phase Prep-HPLC to give 46 (44 mg, 24% yield) as a white solid. $^1$H NMR (400 MHz, DMSO-d$_6$) δ 11.00 (br, 1H), 9.87 (br, 1H), 8.36 (s, 1H), 8.29 (d, J=8.4 Hz, 1H), 8.23 (s, 1H), 7.83-7.65 (m, 3H), 7.58 (dd, J=7.8, 7.8 Hz, 1H), 7.51 (dd, J=7.6, 7.6 Hz, 1H), 7.29 (d, J=8.0 Hz, 1H), 7.05 (dd, J=7.6, 7.6 Hz, 1H), 6.80 (d, J=7.6 Hz, 1H), 2.41 (s, 3H). LC-MS m/z: 321.3 [M+H]$^+$. HPLC purity (254 nm): 97.09%; t$_R$=7.374 min.

Example 1at: Preparation of Compound 47

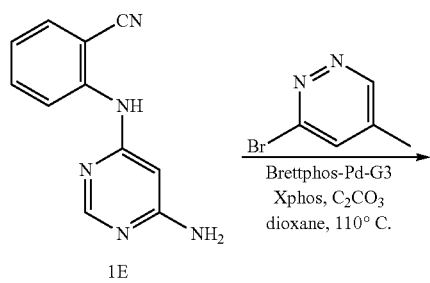

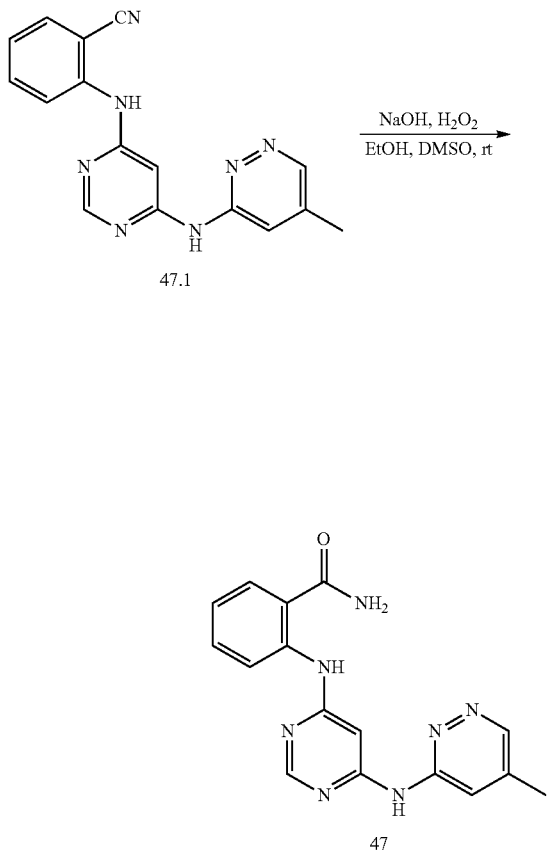

2-((6-((5-methylpyridazin-3-yl)amino)pyrimidin-4-yl) amino) benzonitrile (47.1). 2-((6-aminopyrimidin-4-yl) amino)benzonitrile (1E) was prepared as described in Example 1au. A mixture of 1E (150 mg, 0.71 mmol), 3-bromo-5-methylpyridazine (135 mg, 0.78 mmol), Brettphos-Pd-G3 (64 mg, 0.071 mmol), Xphos (68 mg, 0.142 mmol) and Cs$_2$CO$_3$ (692 mg, 2.13 mmol) in 1,4-dioxane (40 mL) was stirred at 110° C. overnight under argon atmosphere. After the reaction was completed, the mixture was filtered by suction. The filtrate was concentrated and purified by column chromatography on silica gel (EtOAc) to give 47.1 (70 mg, 32.6% yield) as yellow solid. LC-MS m/z: 304.4 [M+H]$^+$. LCMS purity (254 nm): 70.04%; t$_R$=1.558 min.

2-((6-((5-methylpyridazin-3-yl)amino)pyrimidin-4-yl) amino) benzamide (47). To a solution of 47.1 (70 mg, 0.23 mmol) in DMSO (15 mL), EtOH (7.5 mL) and water (1.0 mL) was added NaOH (9 mg, 0.23 mmol) and 30% H$_2$O$_2$ (131 mg, 1.16 mmol), then it was stirred at room temperature for 3 h. After the reaction was completed, it was diluted by water (30 mL) and extracted with EtOAc (30 mL×2). The organic extract was washed by water (50 mL×4) and brine (60 mL) successively, dried over Na$_2$SO$_4$, concentrated and purified by reversed phase prep-HPLC to give 47 (15 mg, 20.3% yield) as light-yellow solid. $^1$H NMR (400 MHz, DMSO-d$_6$) δ 11.14 (s, 1H), 10.18 (s, 1H), 8.72 (d, J=1.6 Hz, 1H), 8.44-8.42 (m, 2H), 8.23 (s, 1H), 7.77 (d, J=7.6 Hz, 1H), 7.73 (s, 1H), 7.69 (s, 1H), 7.49 (t, J=7.6 Hz, 1H), 7.36 (s, 1H), 7.05 (t, 1=7.6 Hz, 1H), 2.30 (s, 3H). LC-MS m/z: 322.2 [M+H]$^+$. HPLC purity (214 nm): >99.9%; t$_R$=6.223 min.

Example 1au: Preparation of Compound 48

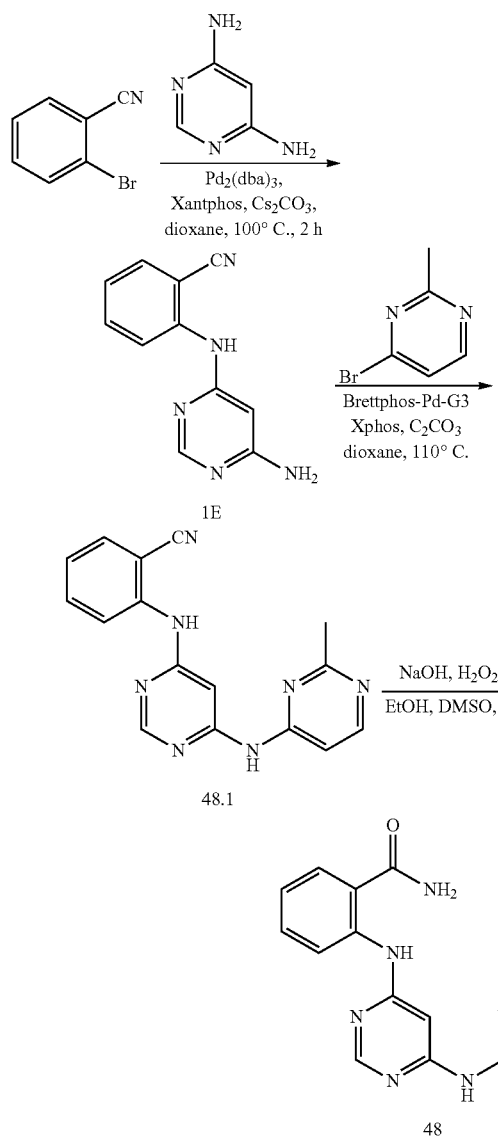

2-((6-aminopyrimidin-4-yl)amino)benzonitrile (1E). To a solution of 2-bromobenzonitrile (6.00 g, 32.96 mmol) in dioxane (100 mL) was added pyrimidine-4,6-diamine (3.63 g, 32.96 mmol), $Cs_2CO_3$ (21.48 g, 65.93 mmol), $Pd_2(dba)_3$ (1.51 g, 1.65 mmol) and Xantphos (1.91 g, 3.30 mmol). The mixture was heated to 100° C. and stirred at 100° C. for 2 h under nitrogen atmosphere. After consumption of the starting material (monitored by LCMS), the reaction was cooled to room temperature. The mixture was filtered via diatomite and the filter cake was washed with MeOH. The filtrate was concentrated and purified by silica gel column chromatography (petrol ether/EtOAc=2/1) to give 1E (1.20 g, 17% yield) as of a red solid. LC-MS m/z: 212.2 [M+H]+. LCMS purity (214 nm): 78.98%; $t_R$=1.283 min.

2-((6-((2-methylpyrimidin-4-yl)amino)pyrimidin-4-yl) amino) benzonitrile (48.1). A mixture of 1E (150 mg, 0.71 mmol), 4-bromo-2-methylpyrimidine (135 mg, 0.78 mmol), Brettphos-Pd-G3 (64 mg, 0.071 mmol), Xphos (68 mg, 0.142 mmol) and $Cs_2CO_3$ (692 mg, 2.13 mmol) in 1,4-dioxane (40 mL) was stirred at 110° C. overnight under argon atmosphere. After the reaction was completed, the mixture was filtered by suction. The filtrate was concentrated and purified by column chromatography on silica gel (EtOAc:hexane=7:3) to give 48.1 (115 mg, 53.5% yield) as yellow solid. LC-MS m/z: 304.2 [M+H]+. LCMS purity (214 nm): 83.62%; $t_R$=1.541 min.

2-((6-((2-methylpyrimidin-4-yl)amino)pyrimidin-4-yl) amino) benzamide (48). To a solution of 48.1 (115 mg, 0.38 mmol) in DMSO (15 mL), EtOH (7.5 mL) and water (1.5 mL) was added NaOH (15 mg, 0.38 mmol) and 30% $H_2O_2$ (215 mg, 1.90 mmol), then it was stirred at room temperature for 3 h. After the reaction was completed, it was diluted by water (40 mL) and extracted with EtOAc (40 mL×2). The organic extract was washed by water (60 mL×4) and brine (60 mL) successively, dried over $Na_2SO_4$, concentrated and purified by reversed phase prep-HPLC to give 48 (25 mg, 20.5% yield) as white solid. $^1$H NMR (400 MHz, DMSO-$d_6$) δ 11.10 (s, 1H), 10.31 (s, 1H), 8.43 (s, 1H), 8.37 (d, J=6.0 Hz, 1H), 8.29 (d, J=8.0 Hz, 1H), 8.23 (s, 1H), 7.78 (dd, J=8.0, 1.6 Hz, 1H), 7.74 (s, 1H), 7.57 (s, 1H), 7.54-7.50 (m, 1H), 7.39 (d, 1=6.0 Hz, 1H), 7.10-7.06 (m, 1H), 2.51 (s, 3H). LC-MS m/z: 322.3 [M+H]+. HPLC purity (214 nm): 99.09%; $t_R$=6.119 min.

Example 1ay: Preparation of Compound 49

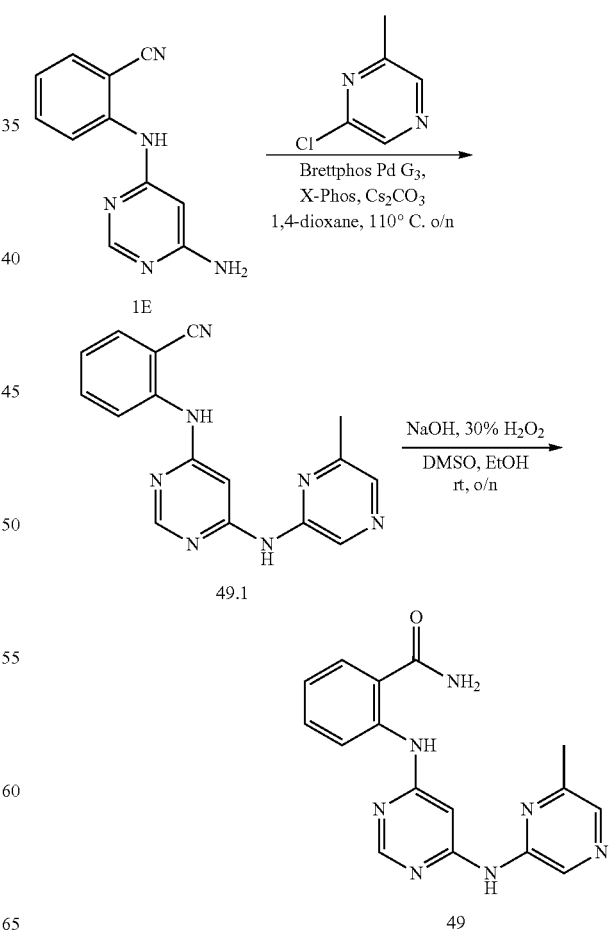

2-(6-(6-methylpyrazin-2-ylamino)pyrimidin-4-ylamino) benzonitrile (49.1). A mixture of 1E (100 mg, 0.47 mmol), 2-chloro-6-methylpyrazine (60 mg, 0.47 mmol), Brettphos Pd G3 (43 mg, 0.047 mmol), X-phos (22 mg, 0.047 mmol) and Cs$_2$CO$_3$ (306 mg, 0.94 mmol) in 1,4-dioxane (10 mL) was stirred at 110° C. overnight under argon atmosphere. After the reaction was finished, it was concentrated and purified by column chromatography on silica gel (CH$_2$Cl$_2$: MeOH=19:1) to give the compound 49.1 (80 mg 56% yield) as a yellow solid. LC-MS m/z: 304.2[M+1]$^+$. LCMS purity (214 nm):87.4%; $t_R$=1.352 min.

2-(6-(6-methylpyrazin-2-ylamino)pyrimidin-4-ylamino) benzamide (49). To a solution of 49.1 (100 mg, 0.33 mmol) in DMSO (10 mL), EtOH (2 mL) and H$_2$O (0.2 mL) was added NaOH (20 mg, 0.49 mmol) and 30% H$_2$O$_2$ (187 mg, 1.65 mmol) was stirred at room temperature overnight under argon atmosphere. After the reaction was finished, it was diluted by water (30 mL) and extracted with EtOAc (30 mL×2). The organic extract was washed by brine (50 mL), dried over anhydrous Na$_2$SO$_4$, concentrated and purified by reversed phase Prep-HPLC to give 49 (35.81 mg, 33.8% yield) as a white solid. $^1$H NMR (400 MHz, DMSO-d$_6$) δ 11.05 (s, 1H), 10.22 (s, 1H), 8.69 (s, 1H), 8.41 (s, 1H), 8.28 (d, J=8.0 Hz, 1H), 8.23 (s, 1H), 8.06 (s, 1H), 7.78 (d, J=7.6 Hz, 1H), 7.73 (s, 1H), 7.54-7.50 (m, 2H), 7.07 (t, J=7.6 Hz, 1H), 2.42 (s, 3H). LC-MS m/z: 322.3 [M+1]$^+$. HPLC purity (214 nm): >99.9%; $t_R$=6.518 min.

Example 1aw: Preparation of Compound 50

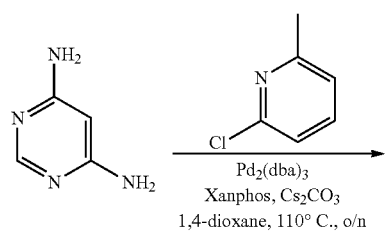

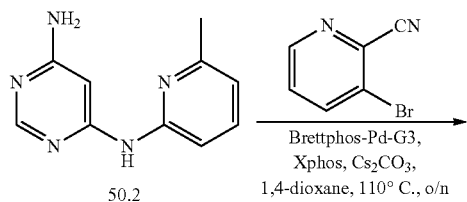

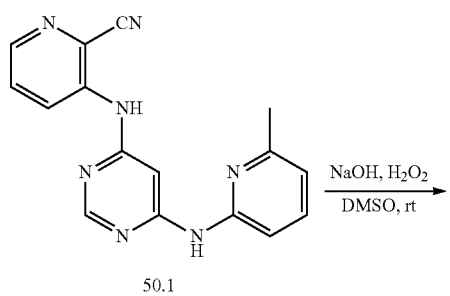

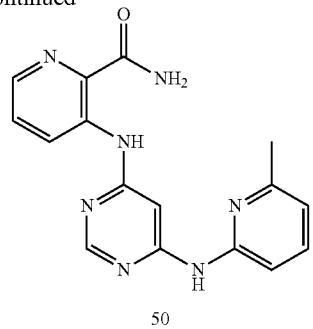

50

N$^4$-(6-methylpyridin-2-yl)pyrimidine-4,6-diamine (50.2). A mixture of 2-chloro-6-methylpyridine (1.27 g, 10.0 mmol), pyrimidine-4, 6-diamine (1.10 g, 10.0 mmol), Pd$_2$(dba)$_3$ (0.915 g, 1.0 mmol), Xantphos (1.15 g, 2.0 mmol) and Cs$_2$CO$_3$ (9.75 g, 30 mmol) in 1,4-dioxane (70 mL) was stirred at 110° C. under argon atmosphere overnight. After consumption of the starting material, the mixture was filtered to remove the solid, diluted by water (100 mL) and extracted with EtOAc (100 mL×2). The organic extract was washed by brine (100 mL), dried over anhydrous Na$_2$SO$_4$, concentrated and purified by column chromatography on silica gel (CH$_2$Cl$_2$:MeOH=15:1) to give 50.2 (720 mg, 35.8% yield) as green solid. LC-MS m/z: 202.3 [M+1]$^+$; LCMS purity (214 nm): 90.90%; $t_R$=1.331 min.

3-((6-(((6-methylpyridin-2-yl)amino)pyrimidin-4-yl) amino) picolinonitrile (50.1). A mixture of 50.2 (50 mg, 0.25 mmol), 3-bromopicolinonitrile (46 mg, 0.25 mmol), Brett-phos-Pd-G3 (23 mg, 0.025 mmol), Xphos (24 mg, 0.05 mmol) and Cs$_2$CO$_3$ (245 mg, 0.75 mmol) in 1,4-dioxane (20 mL) was stirred at 110° C. under argon atmosphere overnight. After consumption of the starting material, the mixture was filtered to remove the solid, diluted by water (50 mL) and extracted with EtOAc (50 mL×2). The organic extract was washed by brine (50 mL), dried over anhydrous Na$_2$SO$_4$ and concentrated to give crude 50.1 (60 mg, 80% yield) as orange solid. LC-MS m/z: 304.3 [M+1]$^+$; LCMS purity (214 nm): 24.37%; $t_R$=1.608 min.

3-((6-((6-methylpyridin-2-yl)amino)pyrimidin-4-yl) amino) picolinamide (50). To a solution of 50.1 (36 mg, 0.12 mmol) and NaOH (4.75 mg, 0.12 mmol) in DMSO (6 mL) and EtOH (3 mL) was added 30% H$_2$O$_2$ (68 mg 0.6 mmol), and the reaction mixture was stirred at room temperature overnight. After consumption of the starting material, the mixture was diluted by water (50 mL) and extracted with EtOAc (50 mL×2). The organic extract was washed by brine (50 mL), dried over anhydrous Na$_2$SO$_4$, concentrated and purified by reversed phase Prep-HPLC to give 50 (3.18 mg, 8.4% yield) as white solid. $^1$H NMR (400 MHz, DMSO-d$_6$) δ 11.89 (s, 1H), 9.96 (s, 1H), 9.08 (dd, J=8.4, 1.2 Hz, 1H), 8.49 (s, 1H), 8.44 (s, 1H), 8.21 (dd, J=4.4, 1.2 Hz, 1H), 9.78 (s, 1H), 7.62-7.57 (m, 3H), 7.34 (d, J=8.4 Hz, 1H), 6.83 (d, J=7.2 Hz, 1H), 2.44 (s, 3H). LC-MS m/z: 322.3 [M+1]$^+$. HPLC purity (214 nm): 94.19%; $t_R$=8.143 min.

Example 1ax: Preparation of Compound 51

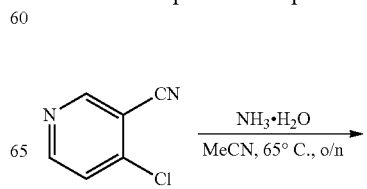

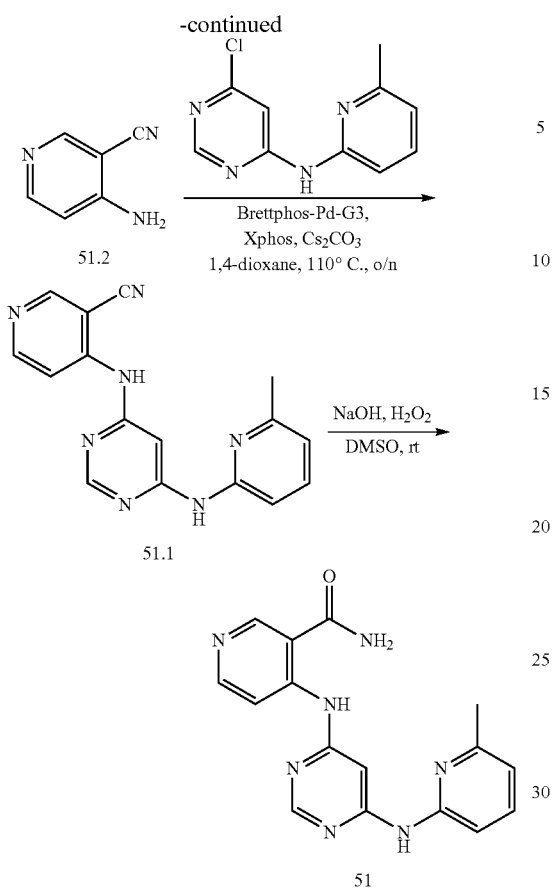

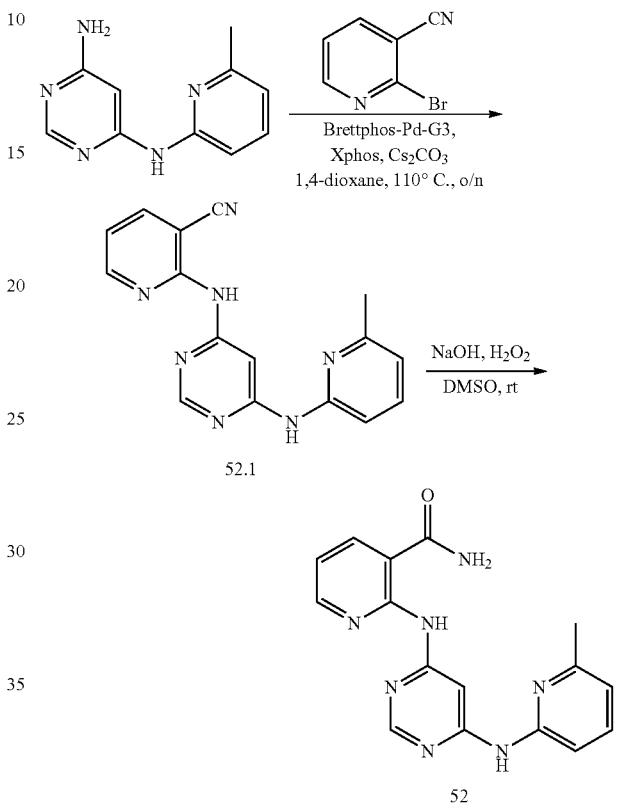

4-aminonicotinonitrile (51.2). A solution of 4-chloronicotinonitrile (138 mg, 1.0 mmol) in MeCN (10 mL) and NH$_3$·H$_2$O (5 mL) in a sealed tube was stirred at 65° C. overnight. After cooling to room temperature, the mixture was evaporated under reduced pressure to give crude 52.1 (105 mg, 88.2% yield) as grey oil. LC-MS m/z: 120.2 [M+1]$^+$; LCMS purity (214 nm): 72.58%; $t_R$=0.851 min.

4-((6-((6-methylpyridin-2-yl)amino)pyrimidin-4-yl) amino) nicotinonitrile (51.1). A mixture of 51.2 (100 mg, 0.84 mmol), 6-chloro-N-(6-methylpyridin-2-yl)pyrimidin-4-amine (185 mg, 0.84 mmol), Brettphos-Pd-G3 (77 mg, 0.084 mmol), Xphos (80 mg, 0.0168 mmol) and Cs$_2$CO$_3$ (821 mg, 2.52 mmol) in 1,4-dioxane (20 mL) was stirred at 110° C. under argon atmosphere overnight. It was filtered to remove the solid, diluted by water (50 mL) and extracted with EtOAc (50 mL×2). The organic extract was washed by brine (50 mL), dried over anhydrous Na$_2$SO$_4$ and concentrated to give crude compound 51.1 (100 mg, 39.2% yield) as green solid. LC-MS m/z: 304.2 [M+1]$^+$; LCMS purity (254 nm): 16.98%; $t_R$=1.669 min.

4-((6-((6-methylpyridin-2-yl)amino)pyrimidin-4-yl) amino) nicotinamide (51). To a solution of 51.1 (58 mg, 0.19 mmol) and NaOH (7.65 mg, 0.19 mmol) in DMSO (4 mL) and EtOH (2 mL) was added 30% H$_2$O$_2$ (108 mg 0.96 mmol), the reaction was stirred at room temperature overnight. After consumption of the starting material, the mixture was diluted by water (50 mL) and extracted with EtOAc (50 mL×2). The organic extract was washed by brine (50 mL), dried over anhydrous Na$_2$SO$_4$, concentrated and purified by reversed phase Prep-HPLC to give 51 (14.72 mg, 24.1% yield) as white solid. $^1$H NMR (400 MHz, DMSO-d$_6$) δ 11.65 (s, 1H), 10.06 (s, 1H), 8.88 (s, 1H), 8.52-8.48 (m, 3H), 8.45 (s, 1H), 7.93 (s, 1H), 7.68 (s, 1H), 7.61 (t, J=4.0 Hz, 1H), 7.35 (d, J=8.4 Hz, 1H), 6.85 (d, J=7.6 Hz, 1H), 2.44 (s, 3H). LC-MS m/z: 322.3 [M+1]$^+$. HPLC purity (214 nm): >99.9%; $t_R$=8.639 min.

Example 1ay: Preparation of Compound 52

2-((6-((6-methylpyridin-2-yl)amino)pyrimidin-4-yl) amino) nicotinonitrile (52.1). A mixture of N$^4$-(6-methylpyridin-2-yl)pyrimidine-4,6-diamine (201 mg, 1.0 mmol), 2-bromopicolinonitrile (275 mg, 1.5 mmol), Brettphos-Pd-G3 (91 mg, 0.1 mmol), Xphos (95 mg, 0.2 mmol) and Cs$_2$CO$_3$ (980 mg, 3.0 mmol) in 1,4-dioxane (30 mL) was stirred at 110° C. under argon atmosphere overnight. After consumption of the starting material, the mixture was filtered to remove the solid, diluted by water (50 mL) and extracted with EtOAc (50 mL×2). The organic extract was washed by brine (50 mL), dried over anhydrous Na$_2$SO$_4$, concentrated and purified by column chromatography on silica gel (EtOAc:hexane=7:13) to give 52.1 (150 mg, 49.5% yield) as yellow solid. LC-MS m/z: 304.2 [M+1]$^+$; LCMS purity (214 nm): 97.65%; $t_R$=1.664 min.

2-((6-((6-methylpyridin-2-yl)amino)pyrimidin-4-yl) amino) nicotinamide (52). To a solution of 52.1 (152 mg, 0.5 mmol) and NaOH (20 mg, 0.5 mmol) in DMSO (6 mL) and EtOH (3 mL) was added 30% H$_2$O$_2$ (56 mg 2.5 mmol), and the reaction was stirred at room temperature overnight. After consumption of the starting material, the mixture was diluted by water (50 mL) and extracted with EtOAc (50 mL×2). The organic extract was washed by brine (50 mL), dried over anhydrous Na$_2$SO$_4$, concentrated and purified by reversed phase Prep-HPLC to give 52 (63.99 mg, 39.9% yield) as white solid. $^1$H NMR (400 MHz, DMSO-d$_6$) δ

11.59 (s, 1H), 9.96 (s, 1H), 9.17 (s, 1H), 8.47 (dd, J=4.8, 1.6 Hz, 1H), 8.39 (s, 1H), 8.35 (s, 1H), 8.24 (dd, J=8.0, 1.6 Hz, 1H), 7.89 (s, 1H), 7.59 (t, J=8.0 Hz, 1H), 7.33 (d, J=8.0 Hz, 1H), 7.08 (dd, J=7.6, 4.8 Hz, 1H), 6.83 (d, J=7.6 Hz, 1H), 2.48 (s, 3H). LC-MS m/z: 322.3 [M+1]$^+$. HPLC purity (214 nm): >99.9%; $t_R$=7.158 min.

Example 1az: Preparation of Compound 53

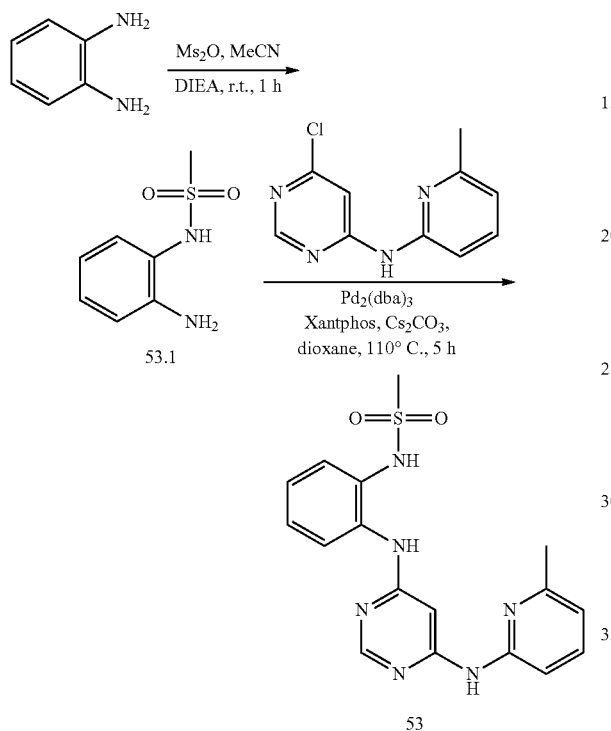

N-(2-aminophenyl)methanesulfonamide (53.1). To a solution of benzene-1,2-diamine (216 mg, 2.00 mmol) in MeCN (10 mL) was added 142yri (774 mg, 5.99 mmol) and Ms$_2$O (522 mg, 3.00 mmol). The mixture was stirred at room temperature for 1 h under nitrogen atmosphere. After consumption of the starting material (monitored by LCMS), the reaction mixture was diluted with water (20 mL) and adjusted pH to 8-9 with saturated sodium bicarbonate aqueous solution. The mixture was extracted with EtOAc (40 mL×3). The combined organic layers were washed with brine (40 mL), dried over anhydrous sodium sulfate, filtrated and concentrated to dryness. The residue was purified by silica gel column chromatography (petrol ether/EtOAc=1/1) to give 53.1 (165 mg, 44% yield) as a yellow solid. LC-MS m/z: 187.2 [M+1]$^+$. LCMS purity (214 nm): 93.87%; $t_R$=0.449 min.

N-(2-(6-(6-methylpyridin-2-ylamino)pyrimidin-4-ylamino)phenyl) methanesulfonamide (53). To a solution of 53.1 (165 mg, 0.89 mmol) in dioxane (15 mL) was added 6-chloro-N-(6-methylpyridin-2-yl)pyrimidin-4-amine (195 mg, 0.89 mmol), Cs$_2$CO$_3$ (577 mg, 1.77 mmol), Xantphos (51 mg, 0.089 mmol) and Brettphos Pd G3 (40 mg, 0.044 mmol). Then the mixture was stirred at 110° C. for 5 h under nitrogen atmosphere. After consumption of the starting material (monitored by LCMS), the reaction mixture was cooled to room temperature. Then the reaction mixture was diluted with water (40 mL) and extracted with EtOAc (30 mL×3). The combined organic layers were washed with brine (50 mL), dried over anhydrous sodium sulfate and concentrated to dryness. The residue was purified by Prep-TLC (CH$_2$Cl$_2$/MeOH=10/1) and reversed-phase Prep-HPLC to give 53 (36 mg, 11.0% yield) as a light-yellow solid. $^1$H NMR (400 MHz, DMSO-d$_6$) δ 9.79 (s, 1H), 9.04 (br, 1H), 8.54 (s, 1H), 8.26 (s, 1H), 7.60 (d, J=7.6 Hz, 1H), 7.55 (dd, J=8.0, 8.0 Hz, 1H), 7.49 (s, 1H), 7.41 (d, J=7.6 Hz, 1H), 7.35-7.23 (m, 2H), 7.20 (dd, J=7.6, 7.6 Hz, 1H), 6.77 (d, J=7.2 Hz, 1H), 2.89 (s, 3H), 2.33 (s, 3H). LC-MS m/z: 369.2 [M-1]$^+$. HPLC purity (254 nm): 98.94%; $t_R$=5.795 min.

Example 1ba: Preparation of Compound 54

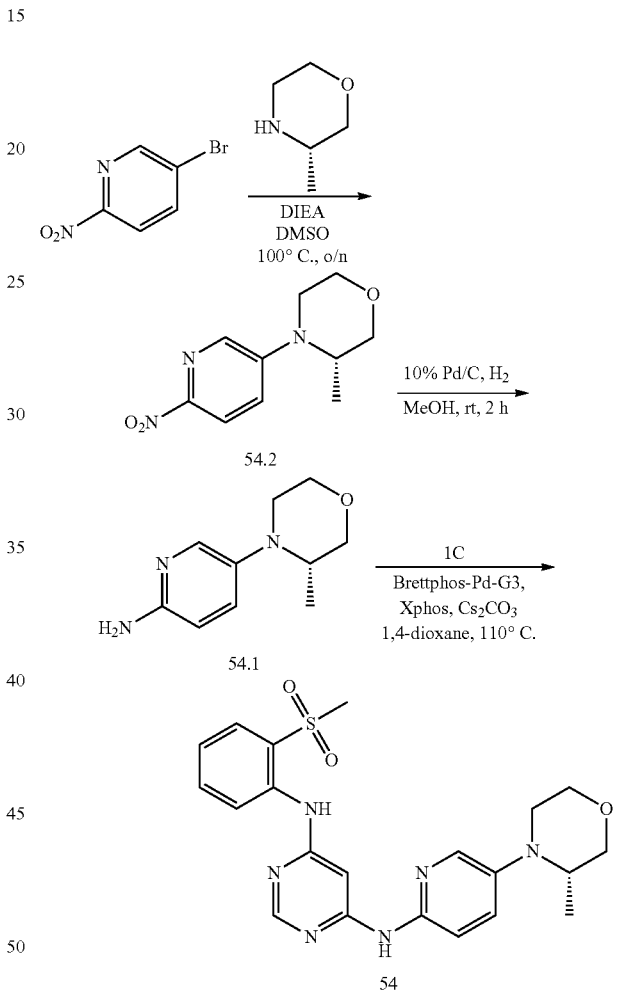

(S)-3-methyl-4-(6-nitropyridin-3-yl)morpholine (54.2). To a solution of 5-bromo-2-nitropyridine (1.0 g, 4.93 mmol) in DMSO (40 mL) was added (S)-3-methylmorpholine (746 mg, 7.92 mmol) and 143yri (1.27 g, 9.84 mmol), the reaction mixture was stirred at 100° C. overnight. After consumption of the starting material, the reaction mixture was diluted by water (100 mL) and extracted with EtOAc (70 mL×2). The organic extract was washed by brine (150 mL×4), dried over anhydrous Na$_2$SO$_4$, concentrated and purified by column chromatography on silica gel (CH$_2$Cl$_2$:MeOH=10:1) to give 54.2 (240 mg, 21.8% yield) as brown oil. LC-MS m/z: 224.4 [M+1]$^+$; LCMS purity (214 nm): 78.20%; $t_R$=1.836 min.

(S)-5-(3-methylmorpholino)143yridine-2-amine (54.1). To a solution of 54.2 (120 mg, 0.54 mmol) in MeOH (30 mL) was added 10% Pd/C (40 mg), the reaction was stirred at room temperature under hydrogen atmosphere for 2 hours. The reaction mixture was filtered and the filtrate was evaporated under reduced pressure to give crude 54.1 (97 mg, 93.3% yield). LC-MS m/z: 194.4 [M+1]⁺; LCMS purity (214 nm): 44.23%; $t_R$=1.302 min.

(S)—N⁴-(5-(3-methylmorpholino)144yridine-2-yl)-N⁶-(2-(methylsulfonyl) phenyl)pyrimidine-4,6-diamine (54). A mixture of 54.1 (110 mg, 0.57 mmol), 1C (162 mg, 0.57 mmol), Brettphos-Pd-G3 (104 mg, 0.114 mmol), Xphos (109 mg, 0.23 mmol) and Cs₂CO₃ (557 mg, 1.71 mmol) in 1,4-dioxane (30 mL) was stirred at 110° C. under argon atmosphere overnight. After consumption of the starting material, the mixture was filtered to remove the solid, diluted by water (50 mL) and extracted with EtOAc (50 mL×2). The organic extract was washed by brine (50 mL), dried over anhydrous Na₂SO₄, concentrated and purified by reversed phase Prep-HPLC to give 54 (15.79 mg, 6.3% yield) as off white solid. ¹H NMR (400 MHz, DMSO-d₆) δ9.00 (s, 1H), 8.53 (s, 1H), 8.22 (d, J=2.4 Hz, 1H), 8.19 (d, J=0.8 Hz, 1H), 7.92-7.88 (m, 2H), 7.73-7.68 (m, 2H), 7.36-7.32 (m, 1H), 6.77 (d, J=9.2 Hz, 1H), 6.10 (d, J=0.8 Hz, 1H), 4.26-4.24 (m, 1H), 3.92 (dd, J=11.2, 3.6 Hz, 1H), 3.76-3.70 (m, 2H), 3.63 (dd, J=11.2, 2.8 Hz, 1H), 3.51-3.45 (m, 1H), 3.19 (s, 3H), 3.06-2.98 (m, 1H). LC-MS m/z: 441.3 [M+1]⁺. HPLC purity (254 nm): 99.38%; $t_R$=7.630 min.

Example 1bb: Preparation of Compound 55

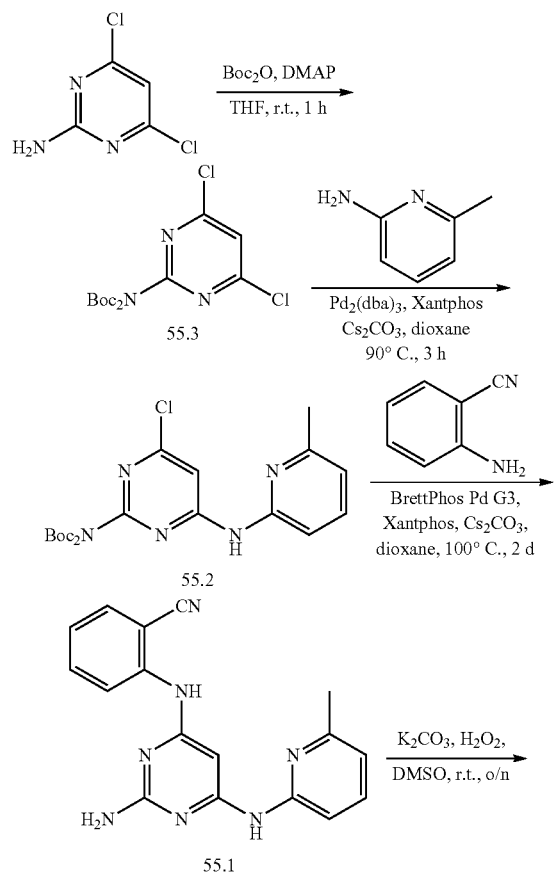

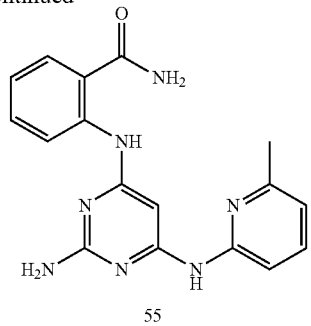

55 di-tert-butyl (4,6-dichloropyrimidin-2-yl)carbamate (55.3). To a stirred solution of 4,6-dichloropyrimidin-2-amine (2.00 g, 12.20 mmol) and DMAP (1.79 g, 14.63 mmol) in THF (40 mL) was added Boc₂O (5.32 g, 24.39 mmol). The mixture was stirred at room temperature for 1 h. After consumption of the starting material (monitored by LCMS), the mixture was diluted with water (50 mL) and extracted with ethyl acetate (50 mL×3). The combined organic layers were washed with brine (40 mL×2), dried over sodium sulfate and concentrated to dryness. The residue was purified by column chromatography on silica gel (petrol ether/EtOAc=10/1) to give 55.3 (1.70 g, 38.3% yield) as an off white solid. LC-MS m/z: 208.1 [M-156+1]⁺. LCMS purity (254 nm): 99.32%; $t_R$=2.174 min.

di-tert-butyl (4-chloro-6-((6-methylpyridin-2-yl)amino)pyrimidin-2-yl)carbamate (55.2). To a stirred solution of 55.3 (800 mg, 2.20 mmol) in dioxane (40 mL) was added 6-methylpyridin-2-amine (238 mg, 2.20 mmol), Cs₂CO₃ (1.43 g, 4.39 mmol), Xantphos (127 mg, 0.22 mmol) and Pd₂(dba)₃ (201 mg, 0.22 mmol). The mixture was stirred at 90° C. for 3 h under nitrogen. After consumption of the starting material (monitored by LCMS), the mixture was diluted with water (50 mL) and extracted with EtOAc (40 mL×3). The combined organic layers were washed with brine (50 mL×2), dried over sodium sulfate and concentrated to dryness. The residue was purified by column chromatography on silica gel (petrol ether/EtOAc=5/1) to give 55.2 (800 mg, 83.6% yield) as an off white solid. LC-MS m/z: 436.2 [M+1]⁺. LCMS purity (254 nm): 98.58%; $t_R$=2.503 min.

2-((2-amino-6-((6-methylpyridin-2-yl)amino)pyrimidin-4-yl) amino)benzonitrile (55.1). To a stirred solution of 55.2 (500 mg, 1.15 mmol) in dioxane (30 mL) was added 2-aminobenzonitrile (136 mg, 1.15 mmol), Cs₂CO₃ (747 mg, 2.29 mmol), Xantphos (69 mg, 0.12 mmol) and Brettphos Pd G3 (109 mg, 0.12 mmol). The mixture was stirred at 100° C. for 2 d under nitrogen. After consumption of the starting material (monitored by LCMS), the mixture was cooled down to room temperature, diluted with water (40 mL) and extracted with EtOAc (40 mL×3). The combined organic layers were washed with brine (30 mL×2), dried over sodium sulfate and concentrated to dryness. The residue was purified by column chromatography on silica gel (CH₂Cl₂/MeOH=10/1) to give 55.1 (200 mg, 54.9% yield) as a light brown solid. LC-MS m/z: 318.3 [M+1]⁺. LCMS purity (254 nm): 44.16%; $t_R$=1.830 min.

2-((2-amino-6-((6-methylpyridin-2-yl)amino)pyrimidin-4-yl) amino)benzamide (55). To a stirred solution of 55.1 (100 mg, 0.32 mmol) in DMSO (4 mL) was added K₂CO₃ (131 mg, 0.94 mmol) and H₂O₂ (30% wt, 107 mg, 0.94 mmol). The mixture was stirred at room temperature overnight. After LCMS showed that the reaction was completed (monitored by LCMS), the mixture was diluted with water (20 mL) and extracted with ethyl acetate (20 mL×3). The combined organic layers were washed with water (20 mL×3) then brine (20 mL×3), dried over anhydrous sodium sulfate and concentrated to dryness. The residue was purified by reversed-phase Prep-HPLC to get 55 (11 mg, 10.4% yield) as a light yellow solid. $^1$H NMR (400 MHz, DMSO-$d_6$) δ 10.69 (s, 1H), 9.35 (s, 1H), 8.40-8.31 (m, 1H), 8.16 (br, 1H), 7.72 (dd, J=8.0, 1.6 Hz, 1H), 7.66-7.56 (m, 2H), 7.54-7.47 (m, 1H), 7.45-7.39 (m, 1H), 6.99-6.91 (m, 1H), 6.74 (d, J=7.2 Hz, 1H), 6.68 (s, 1H), 6.10 (s, 2H), 2.37 (s, 3H). LC-MS m/z: 336.3 [M+1]$^+$. HPLC purity (254 nm): 97.69%; $t_R$=8.525 min.

Example 1bc: Preparation of Compound 56

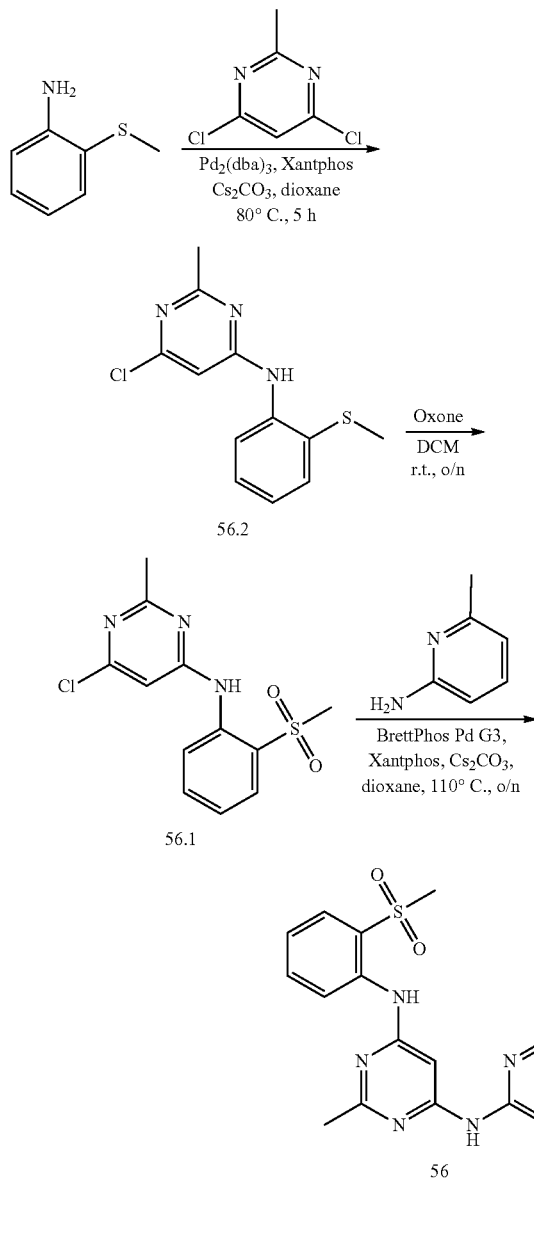

6-chloro-2-methyl-N-(2-(methylthio)phenyl)pyrimidin-4-amine (56.2). To a stirred solution of 2-(methylthio)aniline (5.00 g, 35.91 mmol) in dioxane (50 mL) was added 4,6-dichloro-2-methylpyrimidine (5.85 g, 35.91 mmol), Cs$_2$CO$_3$ (23.40 g, 71.82 mmol), Xantphos (521 mg, 0.90 mmol) and Pd$_2$(dba)$_3$ (824 mg, 0.90 mmol). The mixture was stirred at 80° C. for 5 h under nitrogen. After consumption of the starting material (monitored by LCMS), the mixture was filtered and the filtrate was concentrated in vacuo. The residue was purified by column chromatography on silica gel (Hexane/EtOAc=5/1) to get 56.2 (2.00 g, 21% yield) as an off-white solid. LC-MS m/z: 266.1 [M+H]$^+$. LCMS purity (254 nm): 97.51%; $t_R$=1.833 min.

6-chloro-2-methyl-N-(2-(methylsulfonyl)phenyl) pyrimidin-4-amine (56.1). To a stirred solution of 56.2 (300 mg, 1.13 mmol) in CH$_2$Cl$_2$ (8 mL) was added Oxone (1.39 g, 2.26 mmol). The mixture was stirred at room temperature overnight. After consumption of the starting material (monitored by LCMS), the mixture was filtered and the filtrate was concentrated in vacuo to get 56.1 (320 mg, 95% yield) as an off-white solid. LC-MS m/z: 298.1 [M+H]$^+$. LCMS purity (254 nm): 91.94%; $t_R$=1.655 min.

2-methyl-$N^4$-(6-methylpyridin-2-yl)-$N^6$-(2-(methyl sulfonyl) phenyl) pyrimidine-4,6-diamine (56). To a stirred solution of 56.1 (300 mg, 1.01 mmol) in dioxane (8 mL) was added 6-methylpyridin-2-amine (109 mg, 1.01 mmol), Cs$_2$CO$_3$ (656 mg, 2.02 mmol), X-phos (48 mg, 0.10 mmol) and Brettphos Pd G3 (91 mg, 0.10 mmol). The mixture was stirred at 110° C. overnight under nitrogen. After consumption of the starting material (monitored by LCMS), the mixture was filtered and the filtrate was concentrated in vacuo. The residue was purified by column chromatography on silica gel (Hexane/EtOAc=2/3) and reversed phase prep-HPLC to get 56 (196 mg, 53% yield) as a white solid. $^1$H NMR (400 MHz, DMSO-$d_6$) δ9.88 (s, 1H), 8.64 (s, 1H), 7.99 (d, J=8.0 Hz, 1H), 7.92 (dd, J=8.0, 1.6 Hz, 1H), 7.80-7.72 (m, 1H), 7.62 (s, 1H), 7.55 (dd, J=8.0, 8.0 Hz, 1H), 7.39-7.32 (m, 1H), 7.22 (d, J=8.0 Hz, 1H), 6.77 (d, J=7.6 Hz, 1H), 3.23 (s, 3H), 2.38 (s, 3H), 2.34 (s, 3H). LC-MS m/z: 370.1 [M+H]$^+$. HPLC purity (254 nm): 99.70%; $t_R$=8.599 min.

Example 1bd: Preparation of Compound 57

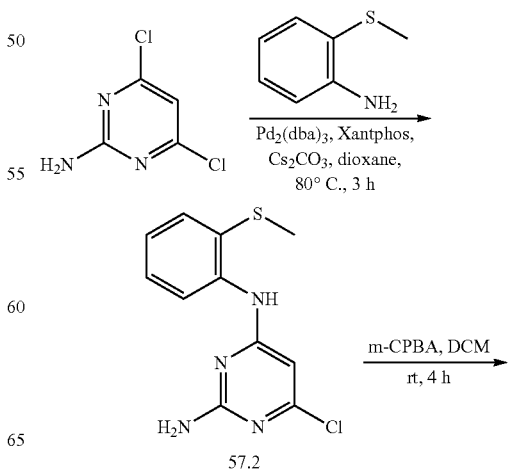

153

-continued

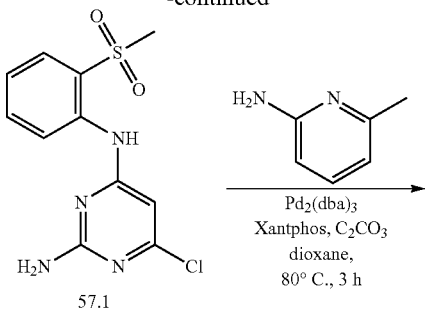

57.1

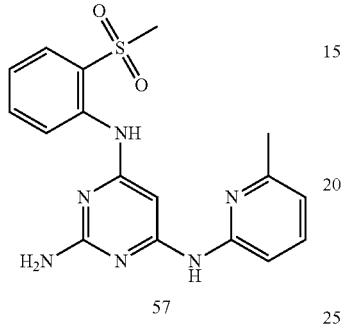

57

6-chloro-N⁴-(2-(methylthio)phenyl)pyrimidine-2,4-diamine (57.2). A suspension of 4,6-dichloropyrimidin-2-amine (800 mg, 4.88 mmol), 2-(methylthio)aniline (814 mg, 5.85 mmol), $Pd_2$(bda)$_3$ (458 mg, 0.50 mmol), Xantphos (579 mg, 1.00 mmol) and $Cs_2CO_3$ (3180 mg, 9.76 mmol) in dry 1,4-dioxane (50 mL) was stirred at 80° C. for 3 hours under nitrogen. After the reaction was completed, the mixture was concentrated and purified by column chromatography on silica gel (EtOAc/Hexane 30%) to give 57.2 (190 mg, 14.6% yield) as a white solid. LC-MS m/z: 267.4 [M+H]⁺. LCMS purity (214 nm): 52.21%; $t_R$=0.713 min.

6-chloro-N⁴-(2-(methylsulfonyl)phenyl)pyrimidine-2,4-diamine (57.1). A solution of 57.2 (190 mg, 0.71 mmol) in $CH_2Cl_2$ (10 mL) was added m-CPBA (579 mg, 2.85 mmol). The mixture was stirred at room temperature for 4 hours. After reaction was completed, the mixture was dilute with water (20 mL), extracted with $CH_2Cl_2$ (20 mL×3). The combined organic layers were washed with brine (40 mL), dried over anhydrous sodium sulfate, filtered and concentrated in vacuo. The residue was purified by column chromatography on silica gel (EtOAc/Hexane 60%) to get 57.1 (110 mg, 51.7% yield) as a colorless oil. LC-MS m/z: 299.1 [M+H]⁺. LCMS purity (254 nm): 77.02%; $t_R$=0.618 min.

N⁴-(6-methylpyridin-2-yl)-N⁶-(2-(methylsulfonyl)phenyl)pyrimidine-2,4,6-triamine (57). A suspension of 57.1 (140 mg, 0.47 mmol), 6-methylpyridin-2-amine (62 mg, 0.57 mmol), $Pd_2$(bda)$_3$ (46 mg, 0.05 mmol), Xantphos (58 mg, 0.10 mmol) and $Cs_2CO_3$ (306 mg, 0.94 mmol) in dry 1,4-dioxane (20 mL) was stirred at 80° C. for 3 hours under nitrogen. After the reaction was completed, the mixture was concentrated and purified by column chromatography on silica gel (EtOAc/Hexane 80%) to give crude product, and purified by reversed phase prep-HPLC to give 57 (6 mg, 3.4% yield) as a white solid. ¹H NMR (400 MHz, DMSO-d$_6$) δ9.45 (br, 1H), 8.35 (br, 1H), 8.09 (d, J=6.8 Hz, 1H), 7.86 (d, J=7.6 Hz, 1H), 7.71-7.61 (m, 2H), 7.54-7.51 (m, 1H), 7.29-7.24 (m, 1H), 6.76-6.74 (m, 2H), 6.19-6.17 (m, 2H), 3.22 (s, 3H), 2.36 (s, 3H). LC-MS m/z: 371.1 [M+H]⁺. HPLC purity (214 nm): 99.28%; $t_R$=7.784 min.

154

Example 1be: Preparation of Compound 58

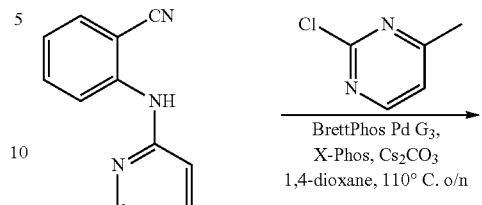

1E

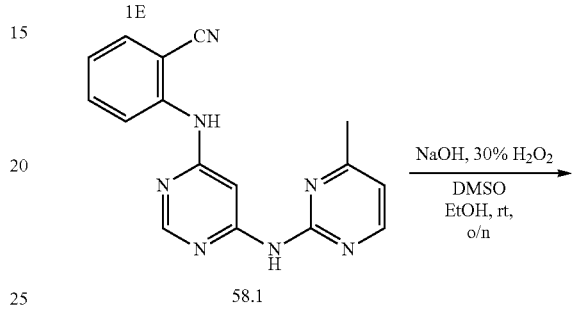

58.1

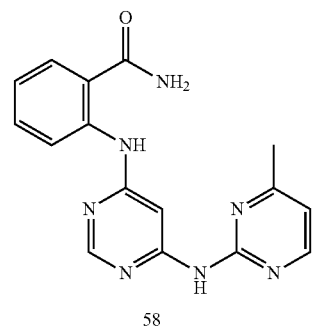

58

2-(6-(4-methylpyrimidin-2-ylamino)pyrimidin-4-ylamino) benzonitrile (58.1). A mixture of 1E (100 mg, 0.47 mmol), BrettPhos Pd G3 (43 mg, 0.047 mmol), 2-chloro-4-methylpyrimidine (60 mg, 0.47 mmol), X-phos (23 mg, 0.048 mmol) and $Cs_2CO_3$ (306 mg, 0.94 mmol) in 1,4-dioxane (20 mL) was stirred at 110° C. overnight under argon atmosphere. After the reaction was completed, it was concentrated and purified by column chromatography on silica gel ($CH_2Cl_2$:MeOH=19:1) to give the compound 58.1 (110 mg 76.6% 148yrid) as a yellow solid. LC-MS m/z: 304.2[M+1]⁺. LCMS purity (214 nm):48.81%; $t_R$=1.368 min.

2-(6-(4-methylpyrimidin-2-ylamino)pyrimidin-4-ylamino)benzamide (58). To a solution of 58.1 (100 mg, 0.33 mmol) in DMSO (5 mL), EtOH (1 mL) and $H_2O$ (0.1 mL) was added NaOH (20 mg, 0.49 mmol) and 30% $H_2O_2$ (186 mg, 1.64 mmol), then the reaction mixture was stirred at room temperature overnight under argon atmosphere. After the reaction was completed, it was diluted by water (30 mL) and extracted with EtOAc (30 mL×2). The organic extract was washed by brine (50 mL), dried over anhydrous $Na_2SO_4$, concentrated and purified by reversed phase Prep-HPLC to give 58 (11.15 mg, 10.5% yield) as a white solid. ¹H NMR (400 MHz, DMSO-d$_6$) δ 11.13 (s, 1H), 10.02 (s, 1H), 8.48 (d, J=5.2 Hz, 1H), 8.40-8.38 (m, 2H), 8.23 (s, 1H), 7.94 (s, 1H), 7.78 (dd, J=8.0, 1.2 Hz, 1H), 7.71 (s, 1H), 7.52 (t, J=7.2 Hz, 1H), 7.06 (t, 1=6.8 Hz, 1H), 6.95 (d, J=4.8 Hz, 1H), 2.42 (s, 3H). LC-MS m/z: 322.1[M+1]⁺. HPLC purity (214 nm):91.45%; $t_R$=6.772 min.

Example 1bf: Preparation of Compound 59

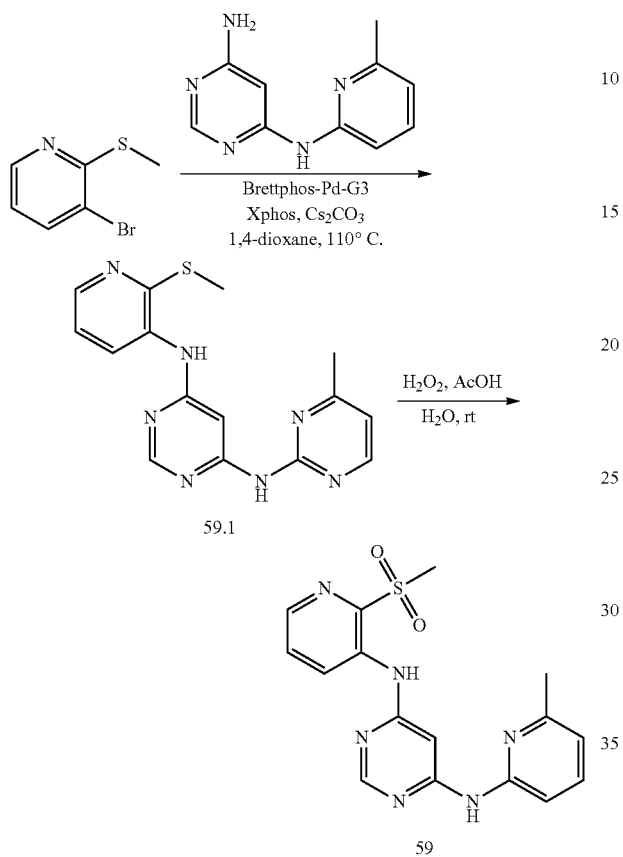

Hz, 1H), 8.40 (dd, J=4.4, 1.6 Hz, 1H), 8.37 (s, 1H), 7.73 (dd, J=8.8, 4.4 Hz, 1H), 7.61-7.57 (m, 2H), 7.35 (d, J=8.0, 1H), 6.83 (d, J=7.6 Hz, 1H), 3.43 (s, 3H), 2.41 (s, 3H). LC-MS m/z: 357.2 [M+H]⁺. HPLC purity (214 nm): >99.9%; $t_R$=7.758 min.

Example 1bg: Preparation of Compound 60

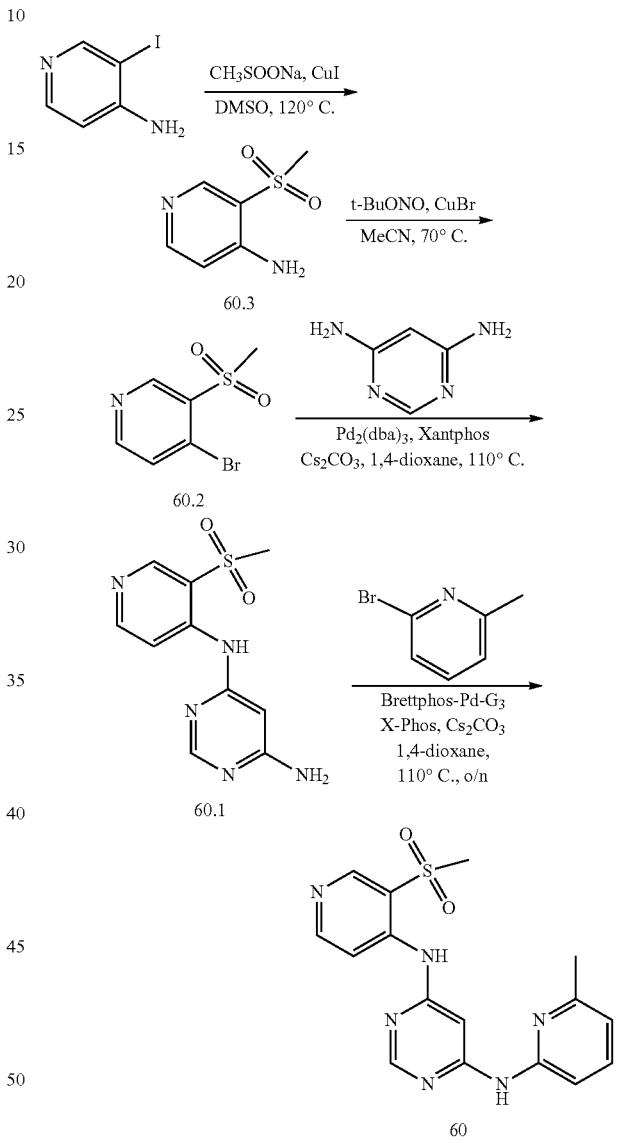

N⁴-(6-methylpyridin-2-yl)-N⁶-(2-(methylthio)149yridine-3-yl) pyrimidine-4,6-diamine (59.1). A mixture of 3-bromo-2-(methylthio)pyridine (300 mg, 1.47 mmol), N⁴-(6-methylpyridin-2-yl)pyrimidine-4,6-diamine (354 mg, 1.76 mmol), Brettphos-Pd-G3 (136 mg, 0.15 mmol), Xphos (138 mg, 0.29 mmol) and $Cs_2CO_3$ (1.44 g, 4.41 mmol) in 1,4-dioxane (20 mL) was stirred at 110° C. overnight under argon atmosphere. After the reaction was completed, the mixture was diluted by $H_2O$ (30 mL) and extracted with EtOAc (30 mL×3). The combined organic layers were washed by brine (50 mL), dried over $Na_2SO_4$, concentrated and purified by column chromatography on silica gel ($CH_2Cl_2$:MeOH=15:1) to give 59.1 (260 mg, 54.5% yield) as a yellow solid. LC-MS m/z: 325.4[M+1]⁺. Purity (in 214 nm) 91.0%; $t_R$=1.482 min.

N⁴-(6-methylpyridin-2-yl)-N⁶-(2-(methylsulfonyl)149yridine-3-yl) pyrimidine-4,6-diamine (59). A mixture of 59.1 (210 mg, 0.65 mmol) and 30% $H_2O_2$ (3.5 mL) in AcOH (5 mL) and $H_2O$ (5 mL) was stirred at 60° C. for 2 h under argon atmosphere. After the reaction was completed, the mixture was diluted by $H_2O$ (50 mL) and extracted with EtOAc (50 mL×3). The combined organic layers were washed with brine (100 mL), dried over $Na_2SO_4$, concentrated and purified by reversed phase prep-HPLC to give 59 (6 mg, 2.6% yield) as a white solid. ¹H NMR (400 MHz, DMSO-d₆) δ9.99 (s, 1H), 9.14 (s, 1H), 8.70 (dd, J=8.8, 1.2

3-(methylsulfonyl)150yridine-4-amine (60.3). A mixture of 3-iodo-4-aminopyridine (5.0 g, 22.73 mmol), $CH_3SOONa$ (2.30 g, 22.73 mmol) and CuI (4.32 g, 22.73 mmol) in DMSO (50 mL) was stirred at 120° C. overnight under argon atmosphere. After the reaction was completed, it was filtered and the filtrate was evaporated under reduced pressure to give crude 60.3 (3.70 g, 94.5% yield) as yellow solid. LC-MS m/z=173.2 [M+1]⁺. LCMS purity (254 nm): 61.94%; $t_R$=0.599 min.

4-bromo-3-(methylsulfonyl)pyridine (60.2). To a mixture of 603 (1.0 g, 5.81 mmol) and CuBr (1.25 mg, 8.76 mmol) in MeCN (30 mL) was added t-BuONO (1.2 mL, 11.60 mmol) slowly, the mixture was stirred at room temperature for 1 hour and then stirred at 70° C. overnight. The reaction mixture was filtered and the filtrate was concentrated and purified by column chromatography on silica gel (MeOH:CH$_2$Cl$_2$=1:9) to give 60.2 (700 mg, 51.1% yield) as brown solid. LC-MS m/z=236.2 [M+1]$^+$. LCMS purity: 69.20% (214 nm), $t_R$=1.205 min.

N$^4$-(3-(methylsulfonyl)151yridine-4-yl)pyrimidine-4,6-diamine (60.1). A mixture of 60.2 (300 mg, 1.27 mmol), 4,6-diaminopyrimidine (140 mg, 1.28 mmol), Pd$_2$(dba)$_3$ (50 mg, 0.054 mmol), Xantphos (62 mg, 0.108 mmol) and Cs$_2$CO$_3$ (832 mg, 2.56 mmol) in 1,4-dioxane (30 mL) was stirred at 110° C. overnight under argon atmosphere. After the reaction was completed, it was diluted by water (50 mL) and extracted with EtOAc (50 mL×3). The organic extract was washed by brine (100 mL), dried over anhydrous Na$_2$SO$_4$, concentrated and purified by column chromatography on silica gel (MeOH: CH$_2$Cl$_2$=1:9) to give 60.1 (200 mg, 59.3% yield) as yellow solid. LC-MS m/z=266.2[M+1]$^+$. LCMS purity: 60.87% (254 nm), $t_R$=1.107 min.

N$^4$-(6-methylpyridin-2-yl)-N$^6$-(3-(methylsulfonyl)151yridine-4-yl) pyrimidine-4,6-diamine (60). A mixture of 60.1 (180 mg, 0.68 mmol), 2-bromo-6-methylpyridine (117 mg, 0.68 mmol), Brettphos-Pd-G3 (93 mg, 0.102 mmol), X-phos (97 mg, 0.204 mmol) and Cs$_2$CO$_3$ (663 mg, 2.04 mmol) in 1,4-dioxane (25 mL) was stirred at 110° C. overnight under argon atmosphere. After the reaction was completed, the mixture was diluted by water (50 mL) and extracted with EtOAc (50 mL×3). The organic extract was washed by brine (100 mL), dried over anhydrous Na$_2$SO$_4$, concentrated and purified by reversed phase prep-HPLC to give 60 (7.18 mg, 3.0% yield) as white solid. $^1$H NMR (400 MHz, DMSO-d$_6$) δ 10.17 (s, 1H), 9.25 (s, 1H), 8.85 (s, 1H), 8.66 (d, J=6.0 Hz, 1H), 8.51 (s, 1H), 8.40 (d, J=6.0 Hz, 1H), 7.74 (s, 1H), 7.62 (t, J=8.0 Hz, 1H), 7.39 (d, J=8.0 Hz, 1H), 6.86 (d, J=7.2 Hz, 1H), 3.44 (s, 3H), 2.44 (s, 3H). LC-MS m/z=357.3 [M+1]$^+$. HPLC purity: 96.69% (254 nm), $t_R$=7.662 min.

Example 1bh: Preparation of Compound 61

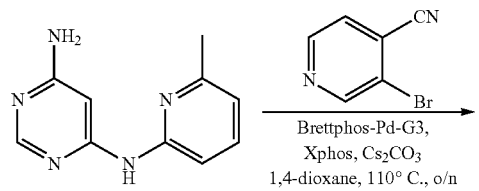

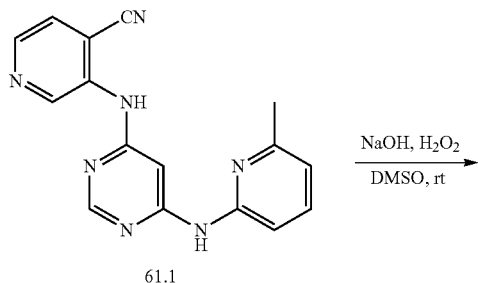

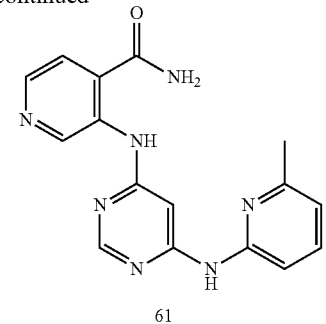

61

3-((6-(((6-methylpyridin-2-yl)amino)pyrimidin-4-yl)amino) isonicotinonitrile (61.1). A mixture of N$^4$-(6-methylpyridin-2-yl)pyrimidine-4,6-diamine (201 mg, 1.0 mmol), 3-bromoisonicotinonitrile (275 mg, 1.50 mmol), Brettphos-Pd-G3 (91 mg, 0.10 mmol), Xphos (95 mg, 0.20 mmol) and Cs$_2$CO$_3$ (980 mg, 3.0 mmol) in 1, 4-dioxane (30 mL) was stirred at 110° C. overnight under argon atmosphere. After consumption of the starting material, the mixture was filtered to remove the solid, diluted by water (50 mL) and extracted with EtOAc (50 mL×2). The organic extract was washed by brine (50 mL), dried over anhydrous Na$_2$SO$_4$ and concentrated to give crude 61.1 (250 mg, 82.4% yield) as orange solid. LC-MS m/z: 304.2 [M+1]$^+$; LCMS purity (214 nm): 41.65%; $t_R$=1.533 min.

3-((6-(((6-methylpyridin-2-yl)amino)pyrimidin-4-yl)amino) isonicotinamide (61). To a solution of 61.1 (150 mg, 0.5 mmol) and NaOH (20 mg, 0.5 mmol) in DMSO (6 mL) and EtOH (3 mL) was added 30% H$_2$O$_2$ (56 mg 2.5 mmol), and the reaction was allowed to stir at room temperature overnight. After consumption of the starting material, the mixture was diluted by water (50 mL) and extracted with EtOAc (50 mL×2). The organic extract was washed by brine (50 mL), dried over anhydrous Na$_2$SO$_4$, concentrated and purified by reversed phase Prep-HPLC to give 61 (38.63 mg, 24% yield) as light-yellow solid. $^1$H NMR (400 MHz, DMSO-d$_6$) δ 10.45 (s, 1H), 9.92 (s, 1H), 9.52 (s, 1H), 8.41 (s, 1H), 8.37 (s, 1H), 8.32 (d, J=4.8 Hz, 1H), 7.99 (s, 1H), 7.65 (d, J=4.8 Hz, 1H), 7.61-7.57 (m, 2H), 7.33 (d, J=8.4 Hz, 1H), 6.82 (d, J=7.2 Hz, 1H), 2.42 (s, 3H). LC-MS m/z: 322.3 [M+1]$^+$, LCMS purity (214 nm): 99.20%; $t_R$=6.193 min.

Example 1bi: Preparation of Compound 62

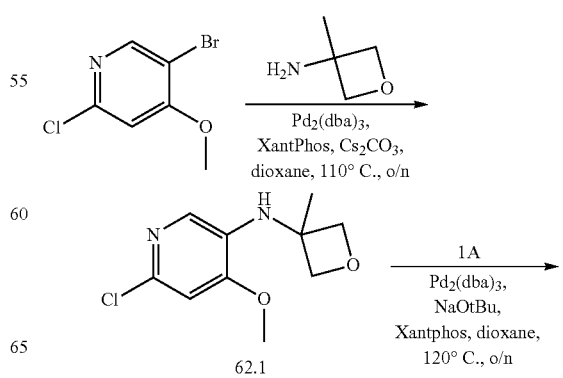

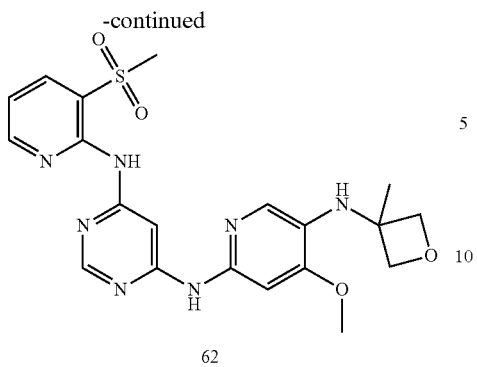

62

6-chloro-4-methoxy-N-(3-methyloxetan-3-yl)152yridine-3-amine (62.1). A mixture of 5-bromo-2-chloro-4-methoxypyridine (400 mg, 1.80 mmol), 3-methyloxetan-3-amine (157 mg, 1.80 mmol), Pd$_2$(dba)$_3$ (165 mg, 0.18 mmol), XantPhos (208 mg, 0.36 mmol), Cs$_2$CO$_3$ (1.17 g, 3.60 mmol) and dioxane (10 mL) was stirred at 110° C. overnight under nitrogen. Then the reaction mixture was poured into water (100 mL) and extracted with EtOAc (100 mL×3). The combined organic layers were washed with brine, dried over Na$_2$SO$_4$ and filtered. The filtrate was concentrated and the residue was purified by column chromatography on silica gel (EtOAc/Hexane=1/1) to give 62.1 (200 mg, 48.6% yield) as a yellow solid. LC-MS m/z: 229.2 [M+1]$^+$. LCMS purity (214 nm): 96.16%; t$_R$=0.470 min.

N$^4$-(5-(3,3-difluorocyclobutylamino)153yridine-2-yl)-N$^6$-(3-methylsulfonyl)yridin-2-yl)pyrimidine-4,6-diamine (62). A mixture of 62.1 (200 mg, 0.87 mmol), N$^4$-(3-(methylsulfonyl)153yridine-2-yl)pyrimidine-4,6-diamine (1A, 232 mg, 0.87 mmol), Pd$_2$(dba)$_3$ (80 mg, 0.09 mmol), XantPhos (101 mg, 0.17 mmol), tBuONa (168 mg, 1.75 mmol) and dioxane (10 mL) was stirred at 120° C. overnight under nitrogen. Then the reaction mixture was poured into water (10 mL) and extracted with EtOAc (10 mL×3). The combined organic layer were washed with brine and dried over Na$_2$SO$_4$ and filtered. The filtrate was concentrated, the residue was purified by column chromatography on silica gel (DCM/MeOH=10/1) and reversed phase prep-HPLC to give 62 (58.1 mg, 14.8% yield) as an off-white solid. $^1$H NMR (400 MHz, DMSO-d$_6$) δ9.69 (s, 1H), 9.37 (s, 1H), 8.60 (dd, J=4.8, 2.0 Hz, 2H), 8.33 (d, J=0.8 Hz, 1H), 8.25 (dd, J=8.0, 2.0 Hz, 1H), 7.32 (s, 1H), 7.25 (dd, J=8.0, 4.8 Hz, 1H), 7.07 (s, 1H), 5.18 (s, 1H), 4.66 (d, J=6.0 Hz, 2H), 4.45 (d, J=6.0 Hz, 2H), 3.85 (s, 3H), 3.37 (s, 3H), 1.55 (s, 3H). LC-MS m/z: 458.3 [M+H]$^+$. LCMS purity (214 nm): >99.9%; t$_R$=1.596 min. HPLC purity (214 nm): >99.9%; t$_R$=7.152 min.

Example 1bj: Preparation of Compound 63

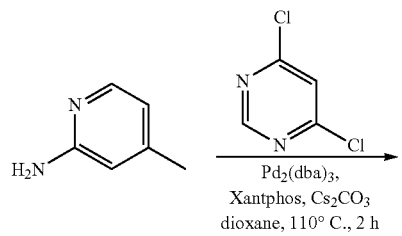

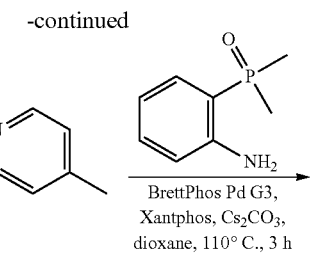

63.1

6-chloro-N-(4-methylpyridin-2-yl)pyrimidin-4-amine (63.1). To a solution of 4-methylpyridin-2-amine (1.00 g, 9.25 mmol) in dioxane (30 mL) was added 4,6-dichloropyrimidine (1.38 g, 9.25 mmol), Cs$_2$CO$_3$ (6.03 g, 18.49 mmol), Pd$_2$(dba)$_3$ (0.42 g, 0.46 mmol) and Xantphos (0.54 g, 0.92 mmol). The mixture was heated to 110° C. and stirred at 110° C. for 2 h under nitrogen atmosphere. After consumption of the starting material (monitored by LCMS), the reaction was cooled to room temperature. The mixture was filtered via diatomite and the filter cake was washed with MeOH. The filtrate was concentrated and purified by silica gel column chromatography (petrol ether/EtOAc=3/1) to give 63.1 (1.50 g, 74% yield) as of a light-yellow solid. LC-MS m/z: 221.2 [M+H]$^+$. LCMS purity (214 nm): 94.61%; t$_R$=0.752 min.

N$^4$-(2-(dimethylphosphoryl)phenyl)-N$^6$-(4-methylpyridin-2-yl) pyrimidine-4,6-diamine (63). To a solution of (2-aminophenyl)dimethylphosphine oxide (100 mg, 0.59 mmol) in dioxane (15 mL) was added 63.1 (196 mg, 0.89 mmol), Cs$_2$CO$_3$ (385 mg, 1.18 mmol), Xantphos (34 mg, 0.059 mmol) and Brettphos-Pd-G3 (27 mg, 0.03 mmol). Then the mixture was stirred at 110° C. for 3 h under nitrogen atmosphere. After consumption of the starting material (monitored by LCMS), the reaction mixture was cooled to room temperature. The reaction mixture was diluted with water (30 mL) and extracted with EtOAc (20 mL×3). The combined organic layers were washed with brine (30 mL), dried over anhydrous sodium sulfate and concentrated to dryness. The residue was purified by silica gel column chromatography (CH$_2$Cl$_2$/MeOH=10/1) and reversed-phase Pre-HPLC to give 63 (27 mg, 13% yield) as a white solid. $^1$H NMR (400 MHz, DMSO-d$_6$) δ 10.81 (s, 1H), 9.82 (s, 1H), 8.41 (dd, J=8.0, 4.0 Hz, 1H), 8.36 (s, 1H), 8.12 (d, J=5.2 Hz, 1H), 7.63-7.46 (m, 2H), 7.36 (s, 1H), 7.31 (s, 1H), 7.09 (dd, J=7.6, 7.6 Hz, 1H), 6.79 (d, J=4.4 Hz, 1H), 2.27 (s, 3H), 1.80 (s, 3H), 1.77 (s, 3H). LC-MS m/z: 354.3 [M+H]$^+$. HPLC purity (214 nm): 95.40%; t$_R$=6.916 min.

Example 1bk: Preparation of Compound 64

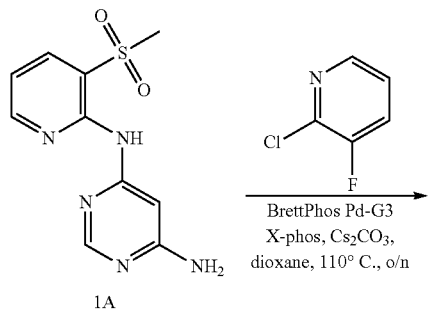

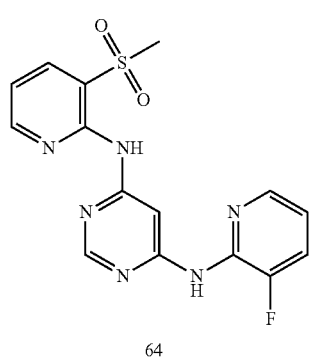

N⁴-(3-fluoropyridin-2-yl)-N⁶-(3-(methylsulfonyl)154yridine-2-yl) pyrimidine-4,6-diamine (64). To a stirred solution of 1A (133 mg, 0.50 mmol) in dioxane (10 mL) was added 2-chloro-3-fluoropyridine (65 mg, 0.50 mmol), Brettphos-Pd-G3 (45 mg, 0.05 mmol), X-phos (24 mg, 0.05 mmol) and Cs₂CO₃ (326 mg, 1.00 mmol). The mixture was stirred at 110° C. overnight. After consumption of the starting material (monitored by LCMS), the mixture was filtered and the filtrate was concentrated at reduced pressure. The residue was dissolved in EtOAc (20 mL) and washed with water (20 mL×2) then brine (20 mL×2). The organic layer was dried over anhydrous sodium sulfate and concentrated in vacuo to give the crude product. The final product was purified by column chromatography on silica gel (CH₂Cl₂/CH₃OH=10/1) and reversed phase prep-HPLC to give 64 (48 mg, 27% yield) as a white solid. ¹H NMR (400 MHz, DMSO-d₆) δ9.76 (s, 1H), 9.49 (s, 1H), 8.75 (s, 1H), 8.63 (dd, J=4.8, 1.2 Hz, 1H), 8.38 (s, 1H), 8.28-8.22 (m, 2H), 7.77-7.70 (m, 1H), 7.28-7.23 (m, 1H), 7.21-7.15 (m, 1H), 3.39 (s, 3H). LC-MS m/z: 361.0 [M+1]⁺. HPLC purity (214 nm): >99.9%; t$_R$=7.468 min.

Example 1bl: Preparation of Compound 65

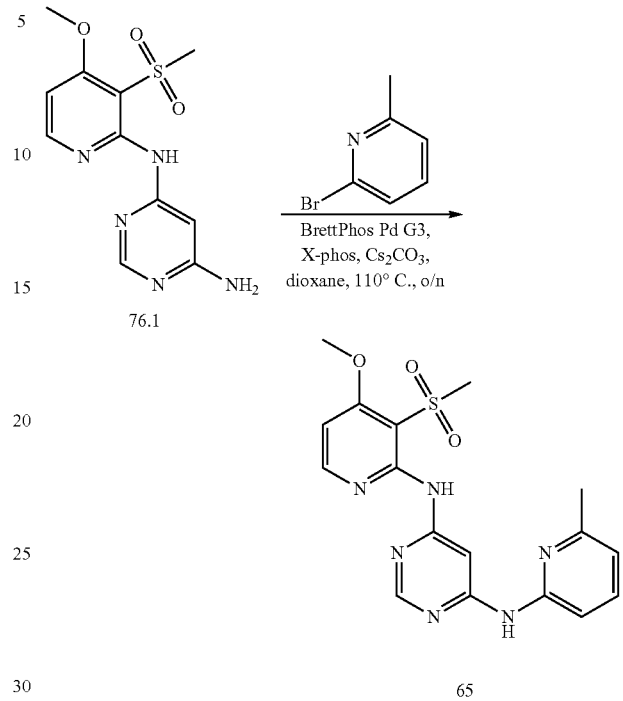

N⁴-(4-methoxy-3-(methylsulfonyl)155yridine-2-yl)-N⁶-(6-methylpyridin-2-yl)pyrimidine-4,6-diamine (65). N⁴-(4-methoxy-3-(methylsulfonyl)155yridine-2-yl)pyrimidine-4,6-diamine (76.1) was prepared as described in Example 1bw. A solution of 76.1 (50 mg, 0.17 mmol), 2-bromo-6-methylpyridine (29 mg, 0.17 mmol), BrettPhos Pd G3 (18 mg, 0.02 mmol), X-phos (10 mg, 0.02 mmol) and Cs₂CO₃ (111 mg, 0.34 mmol) in dioxane (2 mL) was stirred at 110° C. overnight under nitrogen. After consumption of the starting material (monitored by LCMS), the mixture was filtered and the filtrate was concentrated at reduced pressure. The residue was dissolved in EtOAc (30 mL) and washed with water (30 mL×2) then brine (30 mL×2). The organic layer was dried over anhydrous sodium sulfate and in vacuo to give the crude product. The target product was purified by column chromatography on silica gel (CH₂Cl₂/CH₃OH=10/1) and reversed phase prep-HPLC to give 65 (22 mg, 34% yield) as a white solid. ¹H NMR (400 MHz, DMSO-d₆) δ 10.41 (s, 1H), 10.03 (s, 1H), 9.11 (s, 1H), 8.44 (d, J=6.0 Hz, 1H), 8.36 (d, J=0.8 Hz, 1H), 7.60 (dd, J=8.0, 8.0 Hz, 1H), 7.35 (d, J=8.0 Hz, 1H), 6.99 (d, J=6.0 Hz, 1H), 6.84 (d, J=7.6 Hz, 1H), 4.03 (s, 3H), 3.47 (s, 3H), 2.47 (s, 3H). LC-MS m/z: 387.0 [M+1]⁺. HPLC purity (214 nm): 97.81%; t$_R$=8.150 min.

Example 1bm: Preparation of Compound 66

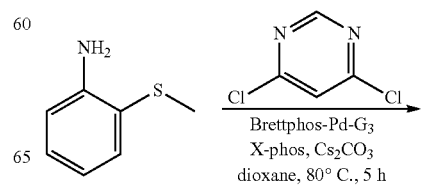

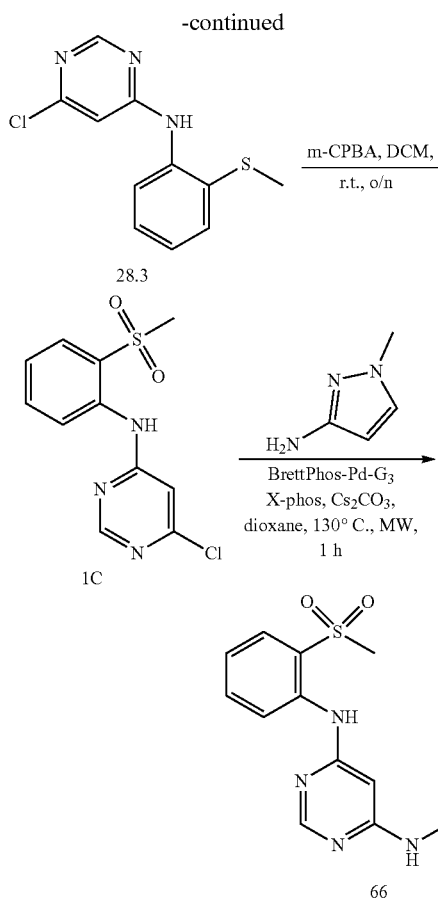

6-chloro-N-(2-(methylthio)phenyl)pyrimidin-4-amine (283). To a stirred solution of 2-(methylthio)aniline (1.00 g, 7.18 mmol) in dioxane (20 mL) was added 4,6-dichloropyrimidine (1.07 g, 7.18 mmol), Brettphos-Pd-G3 (653 mg, 0.72 mmol), X-phos (343 mg, 0.72 mmol), $Cs_2CO_3$ (4.68 g, 14.37 mmol). The mixture was stirred at 80° C. for 5 h under nitrogen. After consumption of the starting material (monitored by LCMS), the mixture was cooled down to room temperature, poured into water (50 mL) and extracted with EtOAc (50 mL×3). The combined organic layers were washed with brine, dried over $Na_2SO_4$, filtered and concentrated in vacuo. The residue was purified by column chromatography on silica gel (petrol ether/EtOAc=10/1) to give 28.3 (1.45 g, 80% yield) as a yellow solid. LC-MS m/z: 252.3 $[M+H]^+$. LCMS purity (214 nm): 42.31%; $t_R$=1.908 min.

6-chloro-N-(2-(methylsulfonyl)phenyl)pyrimidin-4-amine (1C). 6-chloro-N-(2-(methylsulfonyl)phenyl)pyrimidin-4-amine (1C) was prepared from 28.3 as described in Example 1aa. 1C (600 mg, 37% yield). LC-MS m/z: 284.1 $[M+H]^+$. LCMS purity (254 nm): 50.74%; $t_R$=1.632 min.

$N^4$-(1-methyl-1H-pyrazol-3-yl)-$N^6$-(2-(methylsulfonyl)phenyl) pyrimidine-4,6-diamine (66). To a stirred solution of 1C (100 mg, 0.35 mmol) in dioxane (5 mL) was added 1-methyl-1H-pyrazol-3-amine (34 mg, 0.35 mmol), Brettphos-Pd-G3 (32 mg, 0.035 mmol), X-phos (17 mg, 0.035 mmol), $Cs_2CO_3$ (230 mg, 0.70 mmol). The mixture was stirred in a microwave reactor at 130° C. for 1 h under nitrogen. After consumption of the starting material (monitored by LCMS), the mixture was cooled down to room temperature, poured into water (10 mL) and extracted with EtOAc (20 mL×3). The combined organic layers were washed with brine, dried over $Na_2SO_4$, filtered and concentrated in vacuo. The residue was purified by column chromatography on silica gel (petrol ether/EtOAc=1/1) and reversed phase Prep-HPLC to give 66 (55 mg, 45% yield) as a white solid. $^1$H NMR (400 MHz, DMSO-$d_6$) δ9.58 (s, 1H), 8.64 (s, 1H), 8.23 (d, J=0.8 Hz, 1H), 7.97 (dd, J=8.4, 0.8 Hz, 1H), 7.89 (dd, J=8.0, 1.2 Hz, 1H), 7.76-7.69 (m, 1H), 7.56 (d, J=2.0 Hz, 1H), 7.36-7.30 (m, 1H), 6.86 (br, 1H), 6.18 (br, 1H), 3.75 (s, 3H), 3.21 (s, 3H). LC-MS m/z: 345.3 $[M+H]^+$. HPLC purity (214 nm): >99.9%; $t_R$=6.588 min.

Example 1bn: Preparation of Compound 67

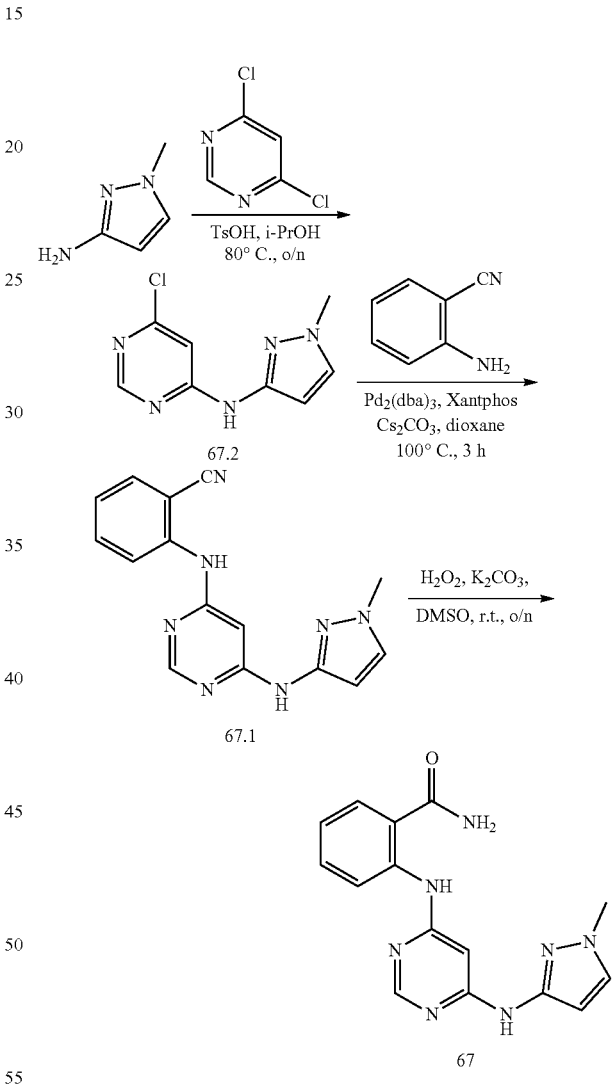

6-chloro-N-(1-methyl-1H-pyrazol-3-yl)pyrimidin-4-amine (67.2). To a stirred solution of 1-methyl-1H-pyrazol-3-amine (500 mg, 5.15 mmol) in i-PrOH (20 mL) was added TsOH (177 mg, 1.03 mmol) and 4,6-dichloropyrimidine (767 mg, 5.15 mmol). The mixture was stirred at 80° C. overnight. After consumption of the starting material (monitored by LCMS), the mixture was poured into ice/water (50 mL) and extracted with EtOAc (60 mL×3). The combined organic layers were washed with brine (40 mL×2), dried over anhydrous sodium sulfate, filtered and concentrated in vacuo. The residue was purified by column chromatography on silica gel (petrol ether/EtOAc=1/1) to give 67.2 (600 mg, 55.6% yield) as an off-white solid. LC-MS m/z: 210.2 [M+H]⁺. LCMS purity (214 nm): 87.48%; $t_R$=0.554 min.

2-((6-((1-methyl-1H-pyrazol-3-yl)amino)pyrimidin-4-yl)amino)benzonitrile (67.1). To a stirred solution of 67.2 (300 mg, 1.43 mmol) in dioxane (10 mL) was added 2-aminobenzonitrile (169 mg, 1.43 mmol), $Cs_2CO_3$ (933 mg, 2.83 mmol), Xantphos (81 mg, 0.14 mmol), and $Pd_2(dba)_3$ (128 mg, 0.14 mmol). The mixture was stirred at 100° C. for 3 h under nitrogen. After consumption of the starting material (monitored by LCMS), the mixture was diluted with water (20 mL) and extracted with EtOAc (30 mL×3). The combined organic layers were washed with brine (30 mL×2), dried over anhydrous sodium sulfate, and concentrated to dryness. The residue was purified by column chromatography on silica gel (petrol ether/EtOAc=1/1) and reversed-phase Prep-HPLC to give 67.1 (300 mg, 72.0% yield) as a light yellow solid. LC-MS m/z: 292.4 [M+1]⁺. LCMS purity (254 nm): 83.16%; $t_R$=1.501 min.

2-((6-((1-methyl-1H-pyrazol-3-yl)amino)pyrimidin-4-yl)amino)benzamide (67). To a stirred solution of 67.1 (300 mg, 1.03 mmol) in DMSO (10 mL) was added $K_2CO_3$ (427 mg, 3.09 mmol) and $H_2O_2$ (30% w/w, 350 mg, 3.09 mmol). The mixture was stirred at room temperature overnight. After consumption of the starting material (monitored by LCMS), the mixture was diluted with water (20 mL) and extracted with EtOAc (30 mL×3). The combined organic layers were washed with brine (20 mL×2), dried over anhydrous sodium sulfate, and concentrated to dryness. The residue was purified by reversed-phase Prep-HPLC to give 67 (107 mg, 33.6% yield) as a light-yellow solid. ¹H NMR (400 MHz, DMSO-d₆) δ 10.93 (s, 1H), 9.53 (s, 1H), 8.35 (d, J=8.0 Hz, 1H), 8.27 (d, J=0.4 Hz, 1H), 8.21 (s, 1H), 7.75 (dd, J=7.8, 1.4 Hz, 1H), 7.68 (s, 1H), 7.55 (d, J=2.4 Hz, 1H), 7.52-7.43 (m, 1H), 7.06-0.93 (m, 1H), 6.87 (br, 1H), 6.14 (br, 1H), 3.76 (s, 3H). LC-MS m/z: 310.3 [M+1]⁺. HPLC purity (254 nm): 90.97%; $t_R$=5.990 min.

Example 1bo: Preparation of Compound 68

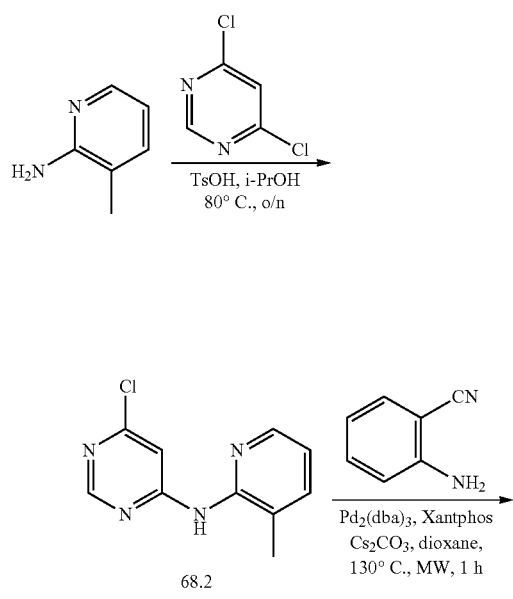

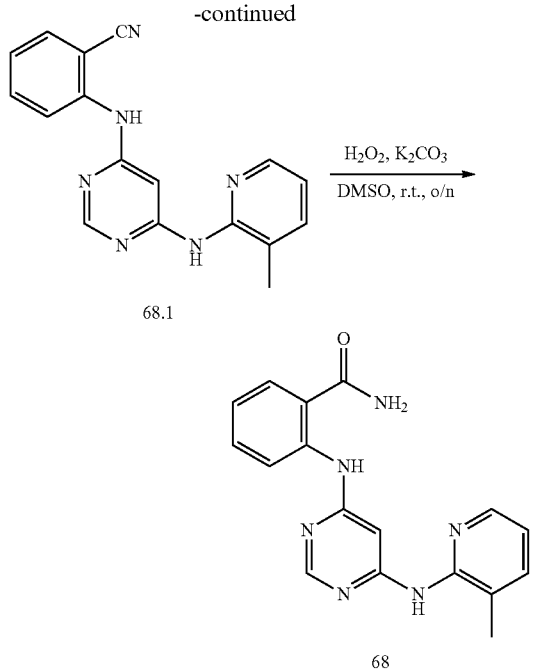

6-chloro-N-(3-methylpyridin-2-yl)pyrimidin-4-amine (68.2). To a stirred solution of 3-methylpyridin-2-amine 500 mg, 4.62 mmol) in i-PrOH (40 mL) was added TsOH*H₂O (439 mg, 2.31 mmol) and 4,6-dichloropyrimidine (1.03 g, 6.93 mmol). The mixture was stirred at 80° C. overnight. After consumption of the starting material (monitored by LCMS), the mixture was diluted with water (100 mL), adjusted to pH 7-8 with NH₃·H₂O, extracted with EtOAc (50 mL×3). The combined organic layers were washed with brine (50 mL×3), dried over sodium sulfate, filtered and concentrated in vacuo to give the crude product, the target product was purified by column chromatography on silica gel (EtOAc/petroleum ether=1/1) to give 68.2 (480 mg, 47% yield) as a yellow solid. LC-MS m/z: 221.1 [M+1]⁺. LCMS purity (214 nm): 94.65%; tR=0.710 min.

2-((6-((3-methylpyridin-2-yl)amino)pyrimidin-4-yl)amino) benzonitrile (68.1). A mixture of 68.2 (200 mg, 0.91 mmol), 2-aminobenzonitrile (107 mg, 0.91 mmol), Pd₂(dba)₃ (83 mg, 0.091 mmol), Xantphos (53 mg, 0.091 mmol) and Cs₂CO₃ (593 mg, 1.82 mmol) in dioxane (10 mL) was irradiated with microwave for 1 h at 130° C. under nitrogen. After consumption of the starting material (monitored by LCMS), the mixture was filtered and concentrated at reduced pressure. The residue was dissolved in EtOAc (60 mL) and washed with water (30 mL×2) then brine (30 mL×2). The organic layer was dried over anhydrous sodium sulfate, filtered, then the filtrate was concentrated in vacuo to give the crude product, the target product was purified by column chromatography on silica gel (CH₂Cl₂/CH₃OH=10/1) give 68.1 (90 mg, 33% yield) as a yellow solid. LC-MS m/z: 303.3 [M+1]⁺. LCMS purity (214 nm): 80.20%; $t_R$=0.737 min.

2-((6-((3-methylpyridin-2-yl)amino)pyrimidin-4-yl)amino) benzamide (68). To a stirred solution of 68.1 (90 mg, 0.30 mmol) in DMSO (3 mL) was added K₂CO₃ (124 mg, 0.90 mmol) and H₂O₂ (30% wt, 102 mg, 0.90 mmol). The mixture was stirred at room temperature overnight. After consumption of the starting material (monitored by LCMS), the mixture was diluted with water (10 mL) and extracted with EtOAc (10 mL×3). The combined organic layers were washed with brine (10 mL×3), dried over sodium sulfate, filtered and concentrated was to dryness. The final product was purified by reversed-phase Prep-HPLC to give 68 (40 mg, 42% yield) as a white solid. $^1$H NMR (400 MHz, DMSO-$d_6$) δ 11.04 (s, 1H), 8.66 (s, 1H), 8.41 (d, J=8.4 Hz, 1H), 8.35 (s, 1H), 8.22-8.20 (m, 2H), 7.76 (dd, J=7.6 Hz, 1.2 Hz, 1H), 7.68 (br, 1H), 7.60 (d, J=7.2 Hz, 1H), 7.51-7.46 (m, 1H), 7.38 (s, 1H), 7.05-6.96 (m, 2H), 2.30 (s, 3H). LC-MS m/z: 321.4 [M+1]$^+$. HPLC purity (214 nm): >99.9%; $t_R$=7.354 min.

Example 1bp: Preparation of Compound 69

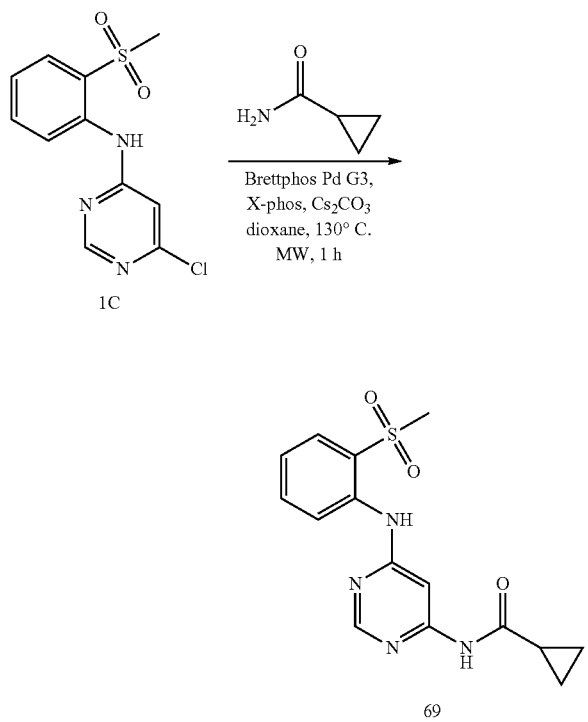 [SMILES: CS(=O)(=O)c1ccccc1Nc1cc(Cl)ncn1 ; NC(=O)C1CC1 ; CS(=O)(=O)c1ccccc1Nc1cc(NC(=O)C2CC2)ncn1]

N$^4$-(cyclopropylcarbonyl)-N$^6$-(2-(methylsulfonyl)phenyl)pyrimidine-4,6-diamine (69). To a stirred solution of 1C (240 mg, 0.85 mmol) in dioxane (10 mL) was added cyclopropanecathoxamide (72 mg, 0.85 mmol), Brettphos-Pd-G3 (77 mg, 0.085 mmol), X-phos (41 mg, 0.085 mmol), Cs$_2$CO$_3$ (551 mg, 1.69 mmol). The mixture was stirred in a microwave reactor at 130° C. for 1 h under nitrogen. After consumption of the starting material (monitored by LCMS), the mixture was cooled down to room temperature, poured into water (40 mL) and extracted with EtOAc (50 mL×3). The combined organic layers were washed with brine, dried over Na$_2$SO$_4$, filtered and concentrated in vacuo. The residue was purified by column chromatography on silica gel (petrol ether/EtOAc=1/3) and reversed phase Prep-HPLC to give 69 (67 mg, 24% yield) as a white solid. $^1$H NMR (400 MHz, DMSO-$d_6$) δ 10.93 (br, 1H), 8.98 (br, 1H), 8.36 (d, J=1.2 Hz, 1H), 7.94-7.88 (m, 2H), 7.76-7.70 (m, 1H), 7.57 (d, J=1.2 Hz, 1H), 7.44-7.38 (m, 1H), 3.20 (s, 3H), 2.06-1.98 (m, 1H), 0.86-0.80 (m, 4H). LC-MS m/z: 333.3 [M+H]$^+$. HPLC purity (214 nm): >99%; $t_R$=7.158 min.

Preparation of Compound 70

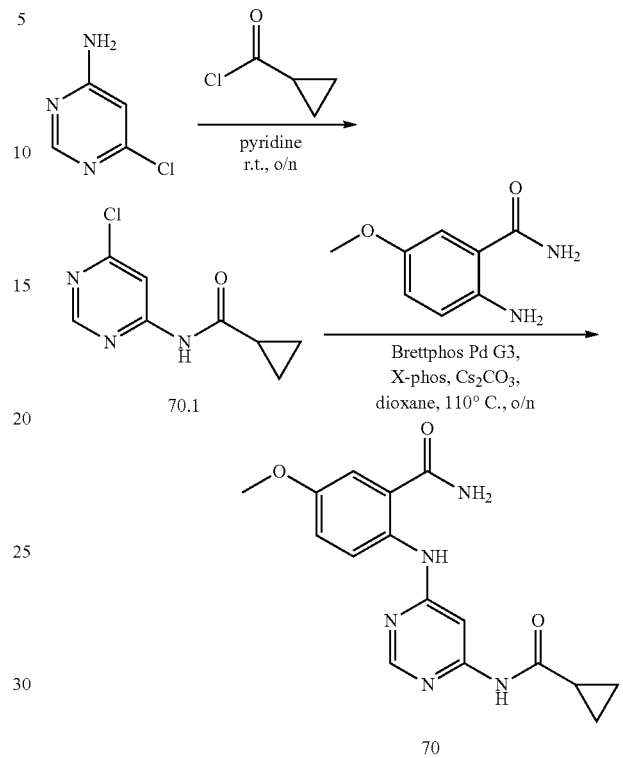

N-(6-chloropyrimidin-4-yl)cyclopropanecarboxamide (70.1). To a solution of 6-chloropyrimidin-4-amine (500 mg, 3.86 mmol) in pyridine (30 mL) was added dropwise cyclopropanecarbonyl chloride (807 mg, 7.72 mmol) at 0° C. The mixture was stirred at room temperature$_{overnight}$. After consumption of the starting material (monitored by LCMS), the mixture was diluted with water (100 mL) and extracted with EtOAc (50 mL×3). The combined organic layers were washed with brine (50 mL×3), dried over anhydrous sodium sulfate, filtered and the filtrate was concentrated to dryness. The final product was purified by column chromatography on silica gel (EtOAc/petroleum ether=1/1) to give 70.1 (600 mg, 79% yield) as a white solid. LC-MS m/z: 198.4 [M+1]$^+$. LCMS purity (214 nm): 78.30%; $t_R$=0.539 min.

2-((6-(cyclopropanecarboxamido)pyrimidin-4-yl) amino)-5-methoxy benzamide (70). A mixture of 70.1 (200 mg, 1.01 mmol), 2-amino-5-methoxybenzamide (168 mg, 1.01 mmol), BrettPhos Pd G3 (91 mg, 0.10 mmol), X-phos (48 mg, 0.10 mmol) and Cs$_2$CO$_3$ (659 mg, 2.02 mmol) in $_{dioxane}$ (10 mL). The mixture was stirred at 110° C. overnight under nitrogen. After consumption of the starting material (monitored by LCMS), the mixture was filtered and the filtrate was concentrated under reduced pressure. The residue was dissolved in EtOAc (60 mL). The organic layer was washed with brine (30 mL×2), dried over anhydrous sodium sulfate, filtered and the filtrate was concentrated in vacuo. The final product was purified by column chromatography on silica gel (CH$_2$Cl$_2$/CH$_3$OH=10/1) and reversed phase prep-HPLC to give 70 (19.63 mg, 6% yield) as a white solid. $^1$H NMR (400 MHz, DMSO-$d_6$) δ 10.83 (s, 1H), 10.46 (s, 1H), 8.33 (d, J=1.2 Hz, 1H), 8.12 (s, 1H), 8.06 (d, J=9.2 Hz, 1H), 7.66 (s, 1H), 7.38 (d, J=0.8 Hz, 1H), 7.25 (d, J=2.8 Hz, 1H), 7.08 (dd, J=8.8, 2.8 Hz, 1H), 3.76 (s, 3H), 2.00-

1.96 (m, 1H), 0.81-0.78 (m, 4H). LC-MS m/z: 328.3 [M+1]$^+$. HPLC purity (214 nm): >99.9%; $t_R$=6.345 min.

Example 1br: Preparation of Compound 71

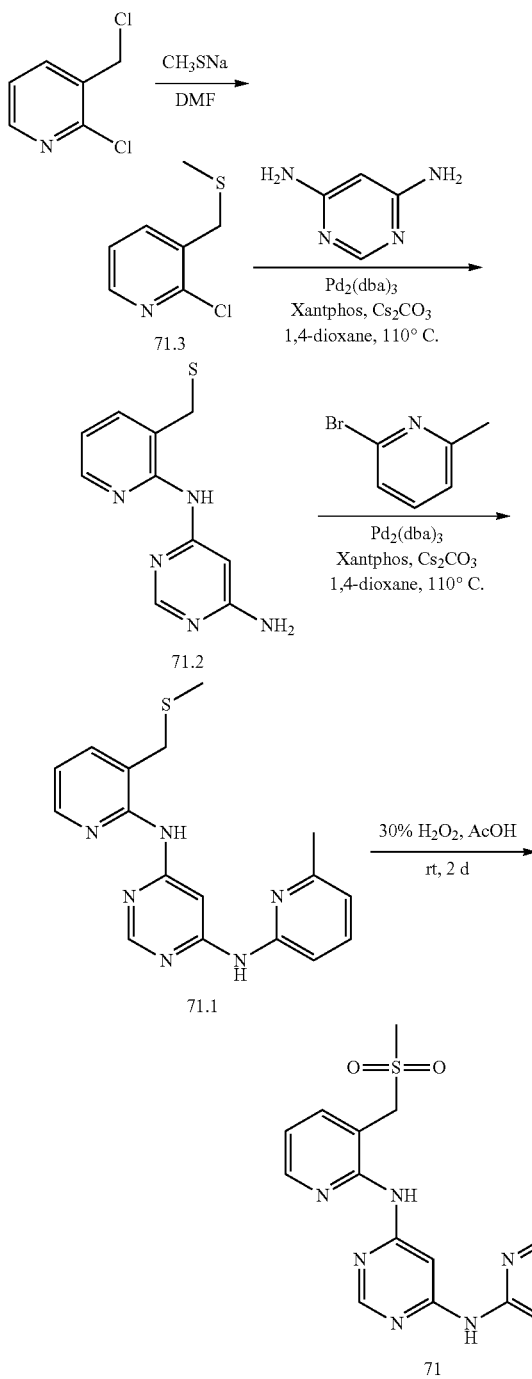

2-chloro-3-((methylthio)methyl)pyridine (713). A mixture of 2-chloro-3-(chloromethyl)pyridine (1.22 g, 7.50 mmol) and sodium methanethiolate (525 mg, 7.50 mmol) in DMF (30 mL) was stirred at room temperature overnight. After the reaction was completed, the mixture was diluted by water (50 mL) and extracted with EtOAc (50 mL×2). The organic extract was washed by water (100 mL×4) and brine (50 mL) successively, dried over anhydrous Na$_2$SO$_4$, filtered and concentrated to give crude 713 (1.05 g, 80.6% yield) as yellow oil. LC-MS m/z: 174.2 [M+H]$^+$. LCMS purity (214 nm): 74.31%; $t_R$=1.772 min.

N$^4$-(3-((methylthio)methyl)162yridine-2-yl)pyrimidine-4,6-diamine (71.2). A mixture of 713 (868 mg, 5.0 mmol), pyrimidine-4,6-diamine (1.10 g, 10.0 mmol), Pd$_2$(dba)$_3$ (458 mg, 0.5 mmol), Xantphos (579 mg, 1.0 mmol) and Cs$_2$CO$_3$ (4.88 g, 15.0 mmol) in 1,4-dioxane (50 mL) was stirred at 110° C. overnight under argon atmosphere. After the reaction was completed, the mixture was concentrated and purified by column chromatography on silica gel (CH$_2$Cl$_2$: MeOH=9:1) to give 71.2 (670 mg, 54.2% yield) as yellow solid. LC-MS m/z: 248.2 [M+H]$^+$. LCMS purity (214 nm): 80.14%; $t_R$=0.562 min.

N$^4$-(6-methylpyridin-2-yl)-N$^6$-(3-((methylthio)methyl) 162yridine-2-yl) pyrimidine-4,6-diamine (71.1). A mixture of 71.2 (247 mg, 1.0 mmol), 2-bromo-6-methylpyridine (172 mg, 1.0 mmol), Pd$_2$(dba)$_3$ (92 mg, 0.10 mmol), Xantphos (116 mg, 0.20 mmol) and Cs$_2$CO$_3$ (975 mg, 3.0 mmol) in 1,4-dioxane (50 mL) was stirred at 110° C. overnight under argon atmosphere. After the reaction was completed, the mixture was concentrated and purified by column chromatography on silica gel (CH$_2$Cl$_2$:MeOH=19:1) to give 71.1 (285 mg, 84.2% yield) as light-yellow solid. LC-MS m/z: 339.3 [M+H]$^+$. LCMS purity (214 nm): 61.80%; $t_R$=1.975 min.

N$^4$-(6-methylpyridin-2-yl)-N$^6$-(3-((methylsulfonyl) methyl) 162yridine-2-yl)pyrimidine-4,6-diamine (71). To a solution of 71.1 (285 mg, 0.84 mmol) in AcOH (10 mL) and water (5 mL) was added 30% H$_2$O$_2$ (2 mL), the reaction mixture was stirred at room temperature for 2 days. After the reaction was completed, it was diluted by water (30 mL), basified by aqueous K$_2$CO$_3$ and extracted with EtOAc (30 mL×2). The organic extract was washed by brine (35 mL), dried over anhydrous Na$_2$SO$_4$, concentrated and purified by reversed phase Prep-HPLC to give 71 (70 mg, 22.4% yield) as white solid. $^1$H NMR (400 MHz, DMSO-d$_6$) δ9.86 (s, 1H), 8.95 (s, 1H), 8.61 (s, 1H), 8.40 (dd, J=4.8, 1.6 Hz, 1H), 8.33 (d, J=0.8 Hz, 1H), 7.80 (dd, J=8.0, 2.0 Hz, 1H), 7.57 (t, J=8.0 Hz, 1H), 7.32 (d, J=8.0 Hz, 1H), 7.16 (dd, J=7.2, 4.4 Hz, 1H), 6.80 (d, J=7.2 Hz, 1H), 4.80 (s, 2H), 3.06 (s, 3H), 2.39 (s, 3H). LC-MS m/z: 371.2 [M+H]$^+$. HPLC purity (254 nm): 99.85%; $t_R$=7.118 min.

Example 1bs: Preparation of Compound 72

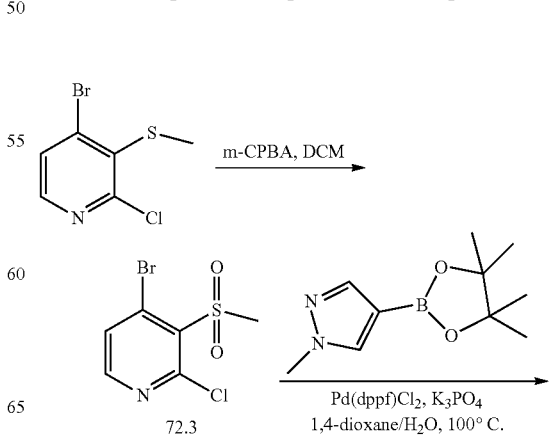

-continued

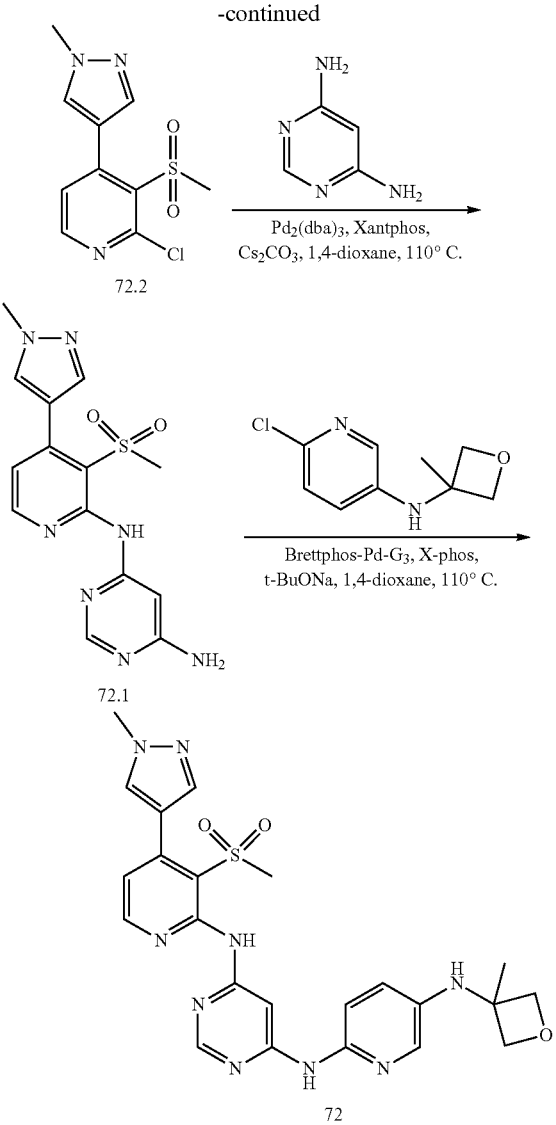

4-bromo-2-chloro-3-(methylsulfonyl)pyridine (723). To a solution of 4-bromo-2-chloro-3-(methylthio)pyridine (500 mg, 2.10 mmol) in $CH_2Cl_2$ (30 mL) was added m-CPBA (367 mg, 2.12 mmol), and the mixture was stirred at room temperature overnight. The reaction mixture was filtered and the filtrate was concentrated and then purified by column chromatography on silica gel (EtOAc:hexane=1:1) to give 72.3 (375 mg, 65.8% yield) as white solid. LC-MS: m/z=270.0 [M+1]$^+$. LCMS purity: 93.24% (254 nm), $t_R$=1.469 min.

2-chloro-4-(1-methyl-1H-pyrazol-4-yl)-3-(methylsulfonyl)pyridine (72.2). To a solution of 723 (275 mg, 1.02 mmol) in 1,4-dioxane (30 mL) and $H_2O$ (6 mL) was added 1-methyl-4-(4,4,5,5-tetramethyl-1,3,2-dioxaborolan-2-yl)-1H-pyrazole (213 mg, 1.02 mmol), Pd(dppf)$C_{12}$ (146 mg, 0.2 mmol) and $K_3PO_4$ (649 mg, 3.0 mmol), the reaction mixture was stirred at 100° C. overnight under argon atmosphere. After the reaction was completed, it was diluted by water (50 mL) and extracted with EtOAc (50 mL×3). The organic extract was washed by brine (100 mL), dried over anhydrous $Na_2SO_4$, concentrated and purified by column chromatography on silica gel ($CH_2Cl_2$:MeOH=19:1) to give 72.2 (160 mg, 58.0% yield) as yellow solid. LC-MS: m/z 271.9[M+1]$^+$. LCMS purity (254 nm): 57.94%; $t_R$=1.107 min.

$N^4$-(4-(1-methyl-1H-pyrazol-4-yl)-3-(methylsulfonyl) 164yridine-2-yl) pyrimidine-4,6-diamine (72.1). A mixture of 72.2 (90 mg, 0.33 mmol), pyrimidine-4,6-diamine (37 mg, 0.33 mmol), Pd$_2$(dba)$_3$ (59 mg, 0.064 mmol), Xantphos (75 mg, 0.13 mmol) and Cs$_2$CO$_3$ (370 mg, 0.64 mmol) in 1,4-dioxane (15 mL) was stirred at 110° C. overnight under argon atmosphere. After the reaction was completed, it was diluted by water (50 mL) and extracted with EtOAc (50 mL×3). The organic extract was washed by brine (100 mL), dried over anhydrous Na$_2$SO$_4$, concentrated and purified by column chromatography on silica gel (CH$_2$Cl$_2$:MeOH=9:1) to give 72.1 (60 mg, 52.6% yield) as green solid. LC-MS: m/z=345.8[M+1]$^+$. LCMS purity: 85.25% (214 nm), $t_R$=1.135 min.

$N^4$-(4-(1-methyl-1H-pyrazol-4-yl)-3-(methylsulfonyl) 164yridine-2-yl)-$N^6$-(5-(3-methyloxetan-3-ylamino)164yridine-2-yl)pyrimidine-4,6-diamine (72). A mixture of 72.1 (30 mg, 0.087 mmol), 6-chloro-N-(3-methyloxetan-3-yl) 164yridine-3-amine (17 mg, 0.087 mmol), Brettphos-Pd-G$_3$ (32 mg, 0.035 mmol), Xphos (33 mg, 0.070 mmol) and t-BuONa (24 mg, 0.26 mmol) in 1,4-dioxane (3 mL) was purged with argon and stirred at 110° C. for 2 h under microwave irradiation. After the reaction was completed, it was diluted by water (30 mL) and extracted with EtOAc (20 mL×3). The organic extract was washed by brine (50 mL), dried over anhydrous Na$_2$SO$_4$, concentrated and purified by column chromatography on silica gel (CH$_2$Cl$_2$:MeOH=9:1) and then reversed phase prep-HPLC to give 72 (5.3 mg, 12.0% yield) as white solid. $^1$H NMR (400 MHz, DMSO-d$_6$) δ 10.31 (s, 1H), 9.67 (s, 1H), 8.42 (d, J=4.8 Hz, 1H), 8.39 (s, 1H), 8.27 (d, J=0.8 Hz, 1H), 8.03 (s, 1H), 7.68 (s, 1H), 7.56-7.50 (m, 2H), 6.97 (d, 1=4.8 Hz, 1H), 6.82 (d, J=8.8, 2.8 Hz, 1H), 6.00 (s, 1H), 4.59 (d, J=6.0 Hz, 2H), 4.45 (d, J=6.0 Hz, 2H), 3.90 (s, 3H), 3.09 (s, 3H), 1.53 (s, 3H). LC-MS: m/z=508.0 [M+1]$^+$. HPLC purity: 96.27% (2154 nm), $t_R$=6.522 min.

Example 1bt: Preparation of Compound 73

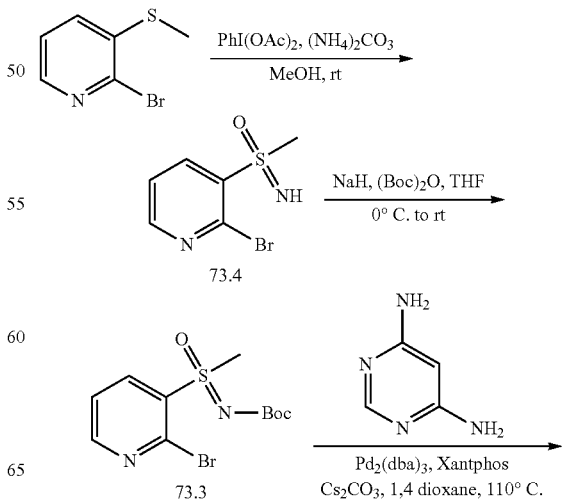

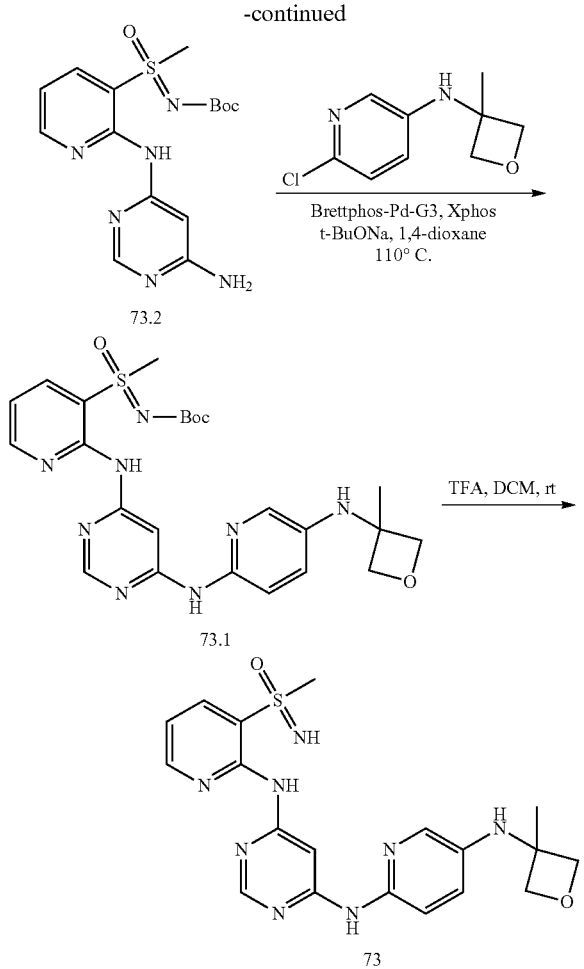

2-bromo-3-(S-methylsulfonimidoyl)pyridine (73.4). A mixture of 2-bromo-3-(methylthio)pyridine (1.0 g, 4.90 mmol), $(NH_4)_2CO_3$ (0.71 g, 7.35 mmol) and PhI(Oac)$_2$ (3.63 g, 11.27 mmol) in MeOH (30 mL) was stirred at room temperature overnight. After the reaction was completed, the mixture was concentrated and purified by column chromatography on silica gel (EtOAc:hexane=9:1) to give 73.4 (880 mg, 76.4% yield) as a yellow liquid. LC-MS m/z: 234.9 [M+1]$^+$; LCMS purity (254 nm) >99.9%, $t_R$=0.674 min.

N-Boc-2-bromo-3-(S-methylsulfonimidoyl)pyridine (73.3). A mixture of 73.4 (880 mg, 3.74 mmol) and 60% NaH (449 mg, 11.22 mmol) in THF (20 mL) was stirred was stirred at 0° C. for 0.5 h under argon atmosphere. To the reaction mixture was added (Boc)$_2$O (2.44 g, 11.22 mmol), then the reaction mixture was stirred at room temperature overnight under argon atmosphere. After the reaction was completed, it was quenched by water (20 mL) drop-wise and extracted with EtOAc (40 mL×3). The combined organic extracts were washed by brine (100 mL), dried over Na$_2$SO$_4$, concentrated and purified by column chromatography on silica gel (EtOAc:hexane=1:1) to give 73.3 (1.20 g, 95.6% yield) as a yellow liquid. LC-MS m/z: 279.0 [M-55]$^+$; LCMS purity (214 nm) >99.9%, $t_R$=1.379 min.

N$^4$-(3-(N-Boc-S-methylsulfonimidoyl)165yridine-2-yl) pyrimidine-4,6-diamine (73.2). A mixture of 73.3 (750 mg, 2.24 mmol), pyrimidine-4,6-diamine (246 mg, 2.24 mmol), Pd$_2$(dba)$_3$ (201 mg, 0.22 mmol), Xantphos (260 mg, 0.45 mmol) and Cs$_2$CO$_3$ (2.19 g, 6.72 mmol) in 1,4-dioxane (30 mL) was stirred at 110° C. overnight under argon atmosphere. After the reaction was completed, the mixtures was concentrated, diluted by H$_2$O (50 mL) and extracted with EtOAc (3×50 mL). The combined organic layers were washed by brine (100 mL), dried over Na$_2$SO$_4$, concentrated and purified by column chromatography on silica gel (CH$_2$Cl$_2$:MeOH=15:1) to give 73.2 (160 mg, 19.6% yield) as a yellow solid. LC-MS m/z: 365.2 [M+1]$^+$; LCMS purity (214 nm) 92.4%, $t_R$=1.309 min.

N$^4$-(3-(N-Boc-S-methylsulfonimidoyl)166yridine-2-yl)-N$^6$-(5-((3-methyloxetan-3-yl)amino)166yridine-2-yl)pyrimidine-4,6-diamine (73.1). A mixture of 73.2 (160 mg, 0.44 mmol), 6-chloro-N-(3-methyloxetan-3-yl) 166yridine-3-amine (96 mg, 0.48 mmol), BrettPhos-Pd-G3 (36 mg, 0.04 mmol), Xphos (43 mg, 0.09 mmol) and t-BuONa (127 mg, 1.32 mmol) in 1,4-dioxane (20 mL) was stirred at 110° C. overnight under argon atmosphere. After the reaction was completed, the mixture was diluted by H$_2$O (30 mL) and extracted with EtOAc (30 mL×3). The combined organic layers were washed with brine (50 mL), dried over Na$_2$SO$_4$, concentrated and purified by column chromatography on silica gel (EtOAc: MeOH=19:1) to give 73.1 (100 mg, 43.3% yield) as a yellow solid. LC-MS m/z: 527.3 [M+1]$^+$; LCMS purity (214 nm) 39.7%, $t_R$=1.641 min.

N$^4$-(5-((3-methyloxetan-3-yl)amino)166yridine-2-yl)-N$^6$-(3-(S-methylsulfonimidoyl)166yridine-2-yl)pyrimidine-4,6-diamine (73). To a solution of 73.1 (100 mg, 0.19 mmol) in CH$_2$Cl$_2$ (15 mL) was added TFA (5 mL) and the reaction mixture was stirred at room temperature for 2 h. After the reaction was completed, the mixtures was concentrated, basified by aqueous K$_2$CO$_3$ (30 mL) and extracted with EtOAc (20 mL×3). The combined organic layers were washed with brine (40 mL), dried over Na$_2$SO$_4$, concentrated and purified by reversed phase prep-HPLC to give 73 (10 mg, 12.3% yield) as a white solid. $^1$H NMR (400 MHz, DMSO-d$_6$) δ 10.64 (s, 1H), 9.67 (s, 1H), 8.51 (dd, J=4.8, 2.0 Hz, 1H), 8.42 (s, 1H), 8.28 (d, J=0.8 Hz, 1H), 8.22 (dd, J=8.0, 2.0 Hz, 1H), 7.54-7.52 (m, 2H), 7.20 (dd, J=8.0, 4.8 Hz, 1H), 6.85 (dd, J=8.8, 2.8 Hz, 1H), 6.01 (s, 1H), 5.15 (s, 1H), 4.62 (d, J=6.0 Hz, 2H), 4.48 (d, J=5.6 Hz, 2H), 3.17 (s, 3H), 1.55 (s, 3H). LC-MS m/z: 427.2 [M+1]$^+$. HPLC purity (214 nm): 95.5%; $t_R$=4.927 min.

Example 1bu: Preparation of Compound 74

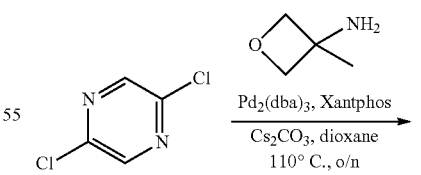

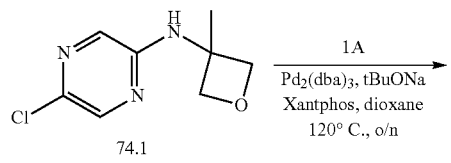

74.1

-continued

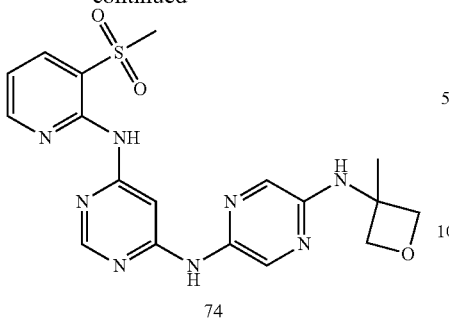

74

-continued

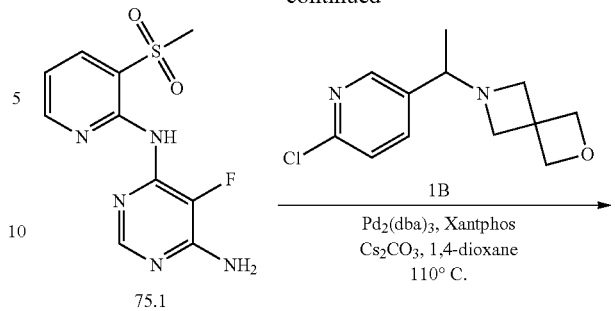

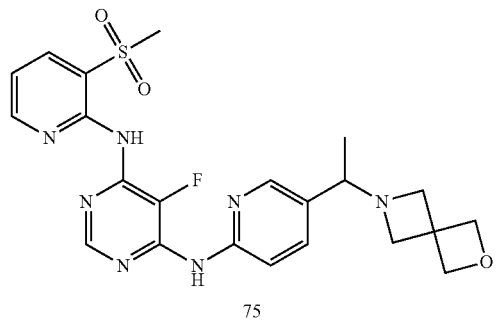

75 ethyl 5-chloro-N-(3-methyloxetan-3-yl)pyrazin-2-amine (74.1). A solution of 2,5-dichloropyrazine (900 mg, 6.04 mmol), 3-methyloxetan-3-amine (795 mg, 9.06 mmol), $Pd_2(dba)_3$ (553 mg, 0.60 mmol), Xantphos (699 mg, 1.21 mmol) and $Cs_2CO_3$ (3.94 g, 12.08 mmol) in dry 1,4-dioxane (50 mL) was stirred at 110° C. overnight under nitrogen. After the reaction was completed, the mixture was cooled to room temperature and filtered. The filtrate was concentrated in vacuo. The residue was purified by column chromatography on silica gel (MeOH/$CH_2Cl_2$=1/20) to give 74.1 (200 mg, 16.6% yield) as a brown solid. LC-MS m/z: 200.3 [M+1]$^+$. LCMS purity (214 nm): >99.9%; $t_R$=0.541 min.

$N^4$-(5-(3-methyloxetan-3-ylamino)pyrazin-2-yl)-$N^6$-(3-(methyl sulfonyl)167yridine-2-yl)pyrimidine-4,6-diamine (74). A solution of 74.1 (30 mg, 0.15 mmol), 1A (40 mg, 0.15 mmol), $Pd_2(dba)_3$ (14 mg, 0.015 mmol), Xantphos (17 mg, 0.030 mmol) and tBuONa (213 mg, 0.30 mmol) in dry 1,4-dioxane (10 mL) was stirred at 120° C. overnight under nitrogen. After the reaction was completed, the mixture was cooled to room temperature and filtered. The filtrate was concentrated in vacuo. The residue was purified by column chromatography on silica gel (MeOH/$CH_2Cl_2$=1/20) and reversed phase prep-HPLC to give 74 (13.56 mg, 21.1% yield) as a yellow solid. $^1$H NMR (400 MHz, DMSO-$d_6$) δ9.78 (s, 1H), 9.38 (s, 1H), 8.59 (dd, J=4.8, 2.0 Hz, 1H), 8.52 (br, 1H), 8.32 (d, J=0.8 Hz, 1H), 8.25 (dd, J=8.0, 1.6 Hz, 1H), 8.13 (br, 1H), 7.72 (d, J=1.6 Hz, 1H), 7.25 (dd, J=7.6, 4.8 Hz, 1H), 7.21 (s, 1H), 4.64 (d, J=6.0 Hz, 2H), 4.42 (d, J=6.0 Hz, 2H), 3.38 (s, 3H), 1.61 (s, 3H). LC-MS m/z: 429.2 [M+H]$^+$. HPLC purity (214 nm): 92.04%; $t_R$=6.931 min.

Example 1bv: Preparation of Compound 75

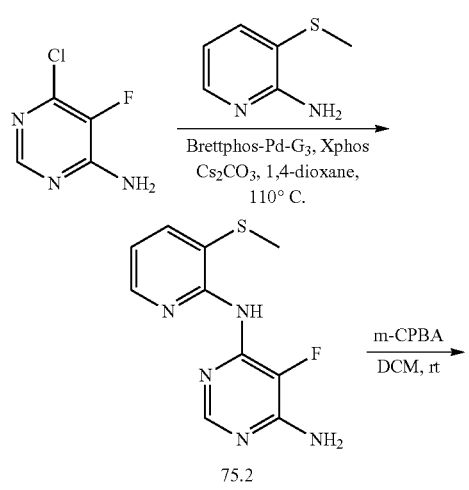

75.2

5-fluoro-$N^4$-(3-(methylthio)168yridine-2-yl)pyrimidine-4,6-diamine (75.2). A mixture of 6-chloro-5-fluoropyrimidin-4-amine (600 mg, 4.07 mmol), 3-(methylthio) 168yridine-2-amine (570 mg, 4.07 mmol), Brettphos-Pd-G3 (371 mg, 0.41 mmol), Xphos (391 mg, 0.82 mmol) and $Cs_2CO_3$ (3.99 g, 12.24 mmol) in 1,4-dioxane (30 mL) was stirred at 110° C. overnight under argon atmosphere. After the reaction was completed, the mixture was diluted by $H_2O$ (50 mL) and extracted with EtOAc (50 mL×2). The combined organic layers were washed with brine (60 mL), dried over $Na_2SO_4$, concentrated and purified by column chromatography on silica gel ($CH_2Cl_2$:MeOH=12:1) to give 75.2 (270 mg, 26.4% yield) as a yellow solid. LC-MS m/z: 252.3 [M+1]$^+$, purity (in 214 nm) >99.9%; $t_R$=1.265 min.

5-fluoro-$N^4$-(3-(methylsulfonyl)168yridine-2-yl)pyrimidine-4,6-diamine (75.1). A mixture of 75.2 (150 mg, 0.60 mmol) and m-CPBA (206 mg, 1.20 mmol) in $CH_2Cl_2$ (15 mL) was stirred at room temperature overnight. After the reaction was completed, the mixture was diluted by water (50 mL), basified by aqueous $K_2CO_3$ and extracted with $CH_2Cl_2$ (50 mL×2). The combined organic layers were washed with brine (50 mL), dried over $Na_2SO_4$ and concentrated to give 75.1 (70 mg, 41.4% yield) as a yellow solid. LC-MS m/z: 283.9 [M+1]$^+$. Purity (in 214 nm): 89.8%; $t_R$=1.004 min.

$N^4$-(5-(1-(2-oxa-6-azaspiro[3.3]heptan-6-yl)ethyl) 168yridine-2-yl)-5-fluoro-$N^6$-(3-(methylsulfonyl)168yridine-2-yl)pyrimidine-4,6-diamine (75). A mixture of 75.1 (60 mg, 0.21 mmol), 1B (50 mg, 0.21 mmol), $Pd_2(dba)_3$ (18 mg, 0.02 mmol), Xantphos (23 mg, 0.04 mmol) and $Cs_2CO_3$ (205 mg, 0.63 mmol) in 1,4-dioxane (20 mL) was stirred at 110° C. overnight under argon atmosphere. After the reaction was completed, the mixture was diluted by $H_2O$ (30 mL) and extracted with EtOAc (20 mL×3). The combined organic layers were washed by brine (40 mL), dried over $Na_2SO_4$, concentrated and purified by column chromatography on silica gel ($CH_2Cl_2$:MeOH=12:1) and then reversed phase prep-HPLC to give 75 (10 mg, 9.8% yield) as a light-yellow solid. $^1$H NMR (400 MHz, DMSO-$d_6$) δ9.81 (s, 1H), 8.86 (s, 1H), 8.55 (d, J=3.2 Hz, 1H), 8.26 (s, 1H), 8.22

(dd, J=8.0, 1.6 Hz, 1H), 8.18 (d, J=1.6 Hz, 1H), 7.97 (d, J=8.4 Hz, 1H), 7.67 (dd, J=8.8, 2.0 Hz, 1H), 7.30 (dd, J=7.6, 5.2 Hz, 1H), 4.57 (t, J=6.4 Hz, 4H), 3.36 (s, 3H), 3.25-3.13 (m, 5H), 1.10 (d, J=6.4 Hz, 3H). LC-MS m/z: 486.2 [M+1]$^+$. HPLC purity (214 nm): >99.9%; $t_R$=6.354 min.

Example 1bw: Preparation of Compound 76

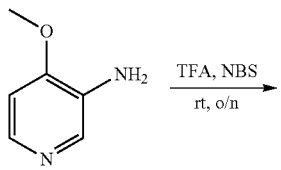

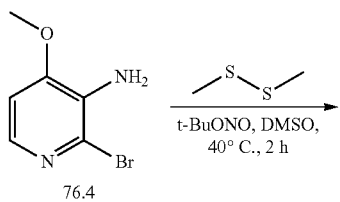

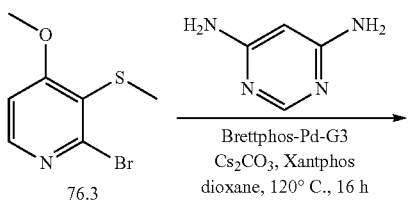

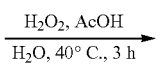

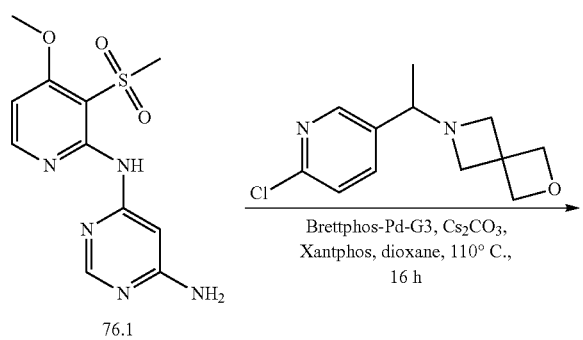

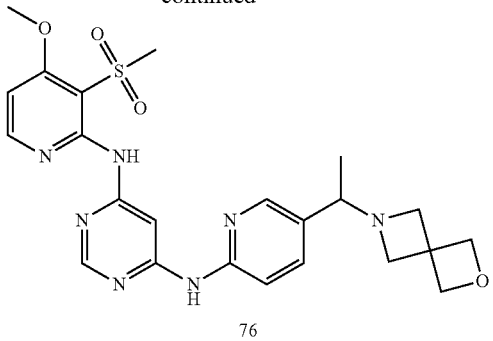

2-bromo-4-methoxypyridin-3-amine (76.4). To a solution of 4-methoxypyridin-3-amine (2 g, 16.13 mmol) in TFA (20 mL) was added NBS (3.4 g, 19.35 mmol) and the reaction mixture was stirred at room temperature overnight. After the reaction was completed, the mixture was quenched by water (80 mL) and extracted with EtOAc (50 mL×3). The organic extract was washed by sodium bicarbonate solution (60 mL×3), dried over Na$_2$SO$_4$, concentrated and purified by column chromatography on silica gel ((hexane:EtOAc=1:1) to give 76.4 (3 g, 92% yield) as a yellow solid. LC-MS m/z: 203.0 [M+1]$^+$. LCMS purity (214 nm): 98.87%; $t_R$=0.961 min.

2-bromo-4-methoxy-3-(methylthio)pyridine (763). A mixture of 76.4 (1.5 g, 7.39 mmol), 1,2-dimethyldisulfane (2.1 g, 22.17 mmol) in DMSO (20 mL) was added t-BuONO (2.3 g, 22.17 mmol). The mixture was stirred at 40° C. for 2 h. After the reaction was completed, the mixture was quenched with water (60 mL) and extracted with EtOAc (50 mL×3). The organic layer was washed with brine (50 mL), dried over Na$_2$SO$_4$, concentrated and purified by column chromatography on silica gel ((hexane:EtOAc=3:1) to give 76.3 (660 mg, 38% yield) as a yellow solid. LC-MS m/z: 233.9 [M+1]$^+$. LCMS purity (214 nm): 85.87%; $t_R$=1.580 min.

N$^4$-(4-methoxy-3-(methylthio)170yridine-2-yl)pyrimidine-4,6-diamine (76.2). A mixture of 763 (660 mg, 2.83 mmol), pyrimidine-4,6-diamine (312 mg, 2.83 mmol), Brettphos-Pd-G3 (256 mg, 0.28 mmol), Xphos (329 mg, 0.57 mmol) and Cs$_2$CO$_3$ (1.85 g, 5.66 mmol) in 1,4-dioxane (15 mL) was stirred at 120° C. for 16 h under Ar. Atmosphere. After the reaction was completed, the mixture was concentrated and purified by column chromatography on silica gel (hexane:EtOAc=2:1) to give 76.2 (600 mg, 80.8% yield) as a yellow solid. LC-MS m/z: 264.1 [M+1]$^+$. LCMS purity (254 nm): 83.51%; $t_R$=1.176 min.

N$^4$-(4-methoxy-3-(methylsulfonyl)170yridine-2-yl)pyrimidine-4,6-diamine (76.1). To a solution of 76.2 (600 mg, 2.28 mmol) in acetic acid (10 mL) was added H$_2$O$_2$ (3 mL, 33% in H$_2$O) and the reaction mixture was stirred at 40° C. for 3 h. After the reaction was completed, the mixture was quenched with water (80 mL) and extracted with EtOAc (50 mL×3). The combined organic layers were washed by sodium bicarbonate solution (60 mL×3), dried over Na$_2$SO$_4$, concentrated and purified by column chromatography on silica gel ((hexane:EtOAc=2:1) to give 76.1 (300 mg, 44.6% yield) as a yellow solid. LC-MS m/z: 296.1 [M+1]$^+$. LCMS purity (214 nm): 93.00%; $t_R$=1.126 min.

N$^4$-(5-(1-(2-oxa-6-azaspiro[3.3]heptan-6-yl)ethyl) 170yridine-2-yl)-N$^6$-(4-methoxy-3-(methylsulfonyl)170yridine-2-yl)pyrimidine-4,6-diamine (76). A mixture of 76.1 (100 mg, 0.34 mmol), 1B (81 mg, 0.34 mmol), Brettphos- Pd-G3 (31 mg, 0.03 mmol), Xphos (39 mg, 0.07 mmol) and Cs$_2$CO$_3$ (222 mg, 0.68 mmol) in 1,4-dioxane (3 mL) was stirred at 110° C. for 16 h under Ar. Atmosphere. After the reaction was completed, the mixture was quenched with water (20 mL) and extracted with EtOAc (10 mL×3). The combined organic layers were washed with brine (20 mL), dried over Na$_2$SO$_4$, concentrated and purified by reversed phase prep-HPLC to give 76 (51.77 mg, 30.6% yield) as a white solid. $^1$H NMR (400 MHz, DMSO-d$_6$) δ 10.36 (br, 1H), 10.03 (br, 1H), 8.75 (s, 1H), 8.44 (d, J=5.6 Hz, 1H), 8.34 (d, J=0.8 Hz, 1H), 8.16 (d, J=2.0 Hz, 1H), 7.66 (d, J=8.8 Hz, 1H), 7.59 (dd, J=8.8, 2.0 Hz, 1H), 6.95 (d, J=6.0 Hz, 1H), 4.56 (s, 4H), 4.01 (s, 3H), 3.44 (s, 3H), 3.23 (d, J=7.2 Hz, 2H), 3.20-3.15 (m, 1H), 3.10 (d, J=7.2 Hz, 2H), 1.08 (d, J=6.4 Hz, 3H). LC-MS m/z: 498.0 [M+1]$^+$. HPLC purity (214 nm): 97.83%; t$_R$=6.621 min.

Example 1bx: Preparation of Compound 77

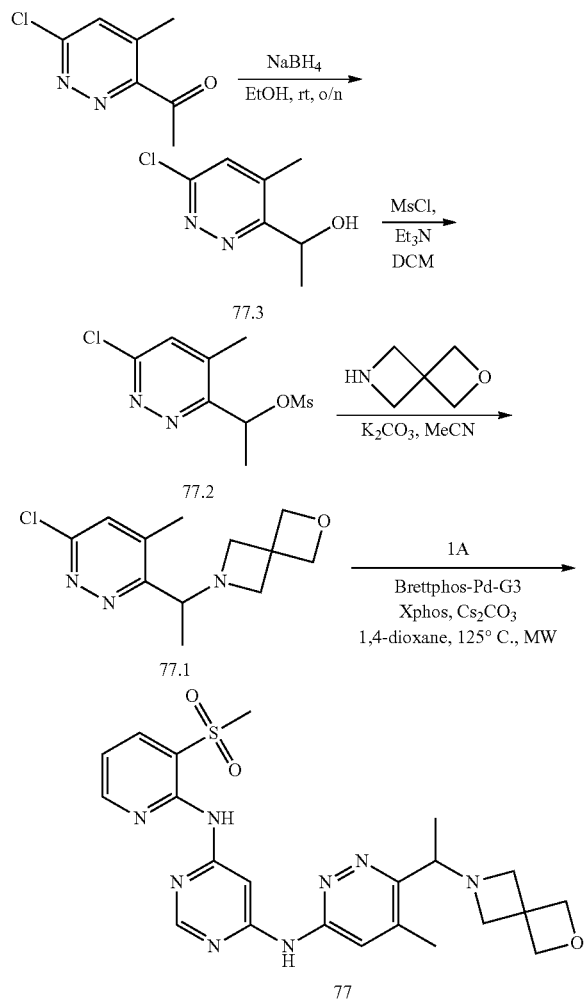

1-(6-chloro-4-methylpyridazin-3-yl)ethanol (773). To a solution of 1-(6-chloro-4-methylpyridazin-3-yl)ethan-1-one (500 mg, 2.93 mmol) in EtOH (20 mL) was added NaBH$_4$ (168 mg, 4.41 mmol), the reaction was stirred at room temperature for 15 min. After consumption of starting materials, the reaction mixture was diluted by water (100 mL) and extracted with EtOAc (50 mL×3). The organic extract was washed by brine (100 mL), dried over anhydrous Na$_2$SO$_4$ and concentrated to give 773 (480 mg, 95% yield) as light-yellow oil. LC-MS m/z: 173.2[M+1]$^+$; LCMS purity (214 nm): 76.47%; t$_R$=0.483 min.

1-(6-chloro-4-methylpyridazin-3-yl)ethyl methanesulfonate (77.2). To a solution of 77.3 (430 mg, 2.49 mmol) in CH$_2$Cl$_2$ (30 mL) was added MsCl (429 mg, 3.74 mmol) and Et$_3$N (755 mg, 7.47 mmol), the reaction was stirred at room temperature for 2 hours. After consumption of starting materials, the reaction mixture was diluted by water (100 mL) and extracted with EtOAc (50 mL×2). The organic extract was washed by brine (50 mL), dried over anhydrous Na$_2$SO$_4$ and concentrated to give crude 77.2 (490 mg, 78.4% yield) as light-yellow oil. LC-MS m/z: 251.2 [M+1]$^+$; LCMS purity (214 nm): 63.30%; t$_R$=1.468 min.

6-(1-(6-chloro-4-methylpyridazin-3-yl)ethyl)-2-oxa-6-azaspiro[3.3]heptane (77.1). To a solution of 77.2 (440 mg, 1.76 mmol) and 2-oxa-6-azaspiro[3.3]heptane (174 mg, 1.76 mmol) in MeCN (20 mL) was added 171 yri (454 mg, 3.52 mmol), the reaction was stirred at 65° C. overnight. After consumption of starting materials, the mixture was concentrated, diluted by water (100 mL) and extracted with EtOAc (50 mL×3). The organic extract was washed with brine (100 mL), dried over anhydrous Na$_2$SO$_4$, concentrated and purified by column chromatography on silica gel (0.5% Et$_3$N in EtOAc) to give 77.1 (120 mg, 27.0% yield) as colorless oil. LC-MS m/z: 254.2 [M+1]$^+$; LCMS purity (214 nm): 94.63%; t$_R$=1.308 min.

N$^4$-(6-(1-(2-oxa-6-azaspiro[3.3]heptan-6-yl)ethyl)-5-methylpyri 172yridi-3-yl)-N$^6$-(3-(methylsulfonyl)172yridine-2-yl)pyrimidine-4,6-diamine (77). A mixture of 77.1 (80 mg, 0.32 mmol), 1A (83 mg, 0.32 mmol), Brettphos-Pd-G3 (57 mg, 0.06 mmol), Xphos (60 mg, 0.13 mmol) and Cs$_2$CO$_3$ (309 mg, 0.95 mmol) in 1,4-dioxane (4 mL) was purged with argon and stirred at 125° C. for 2 hours under microwave irradiation. After the reaction was completed, the reaction mixture was filtered and the filtrate was concentrated and then purified by reversed phase Prep-HPLC to give 77 (19.88 mg, 13.1% yield) as white solid. $^1$H NMR (400 MHz, DMSO-d$_6$) δ 10.50 (s, 1H), 9.48 (s, 1H), 8.62 (dd, J=4.8, 2.0 Hz, 1H), 8.46 (d, J=3.6 Hz, 1H), 8.45 (s, 1H), 8.28 (dd, J=8.0, 2.0 Hz, 1H), 8.00 (s, 1H), 7.29 (dd, J=7.6, 4.8 Hz, 1H), 4.59 (s, 4H), 3.83 (s, 1H), 3.43 (s, 3H), 3.34 (s, 2H), 3.20 (s, 2H), 2.43 (s, 3H), 1.23 (d, J=6.4 Hz, 3H). LC-MS m/z: 483.0 [M+1]$^+$. HPLC purity (254 nm): 98.28%; t$_R$=6.644 min.

Example 1by: Preparation of Compound 78

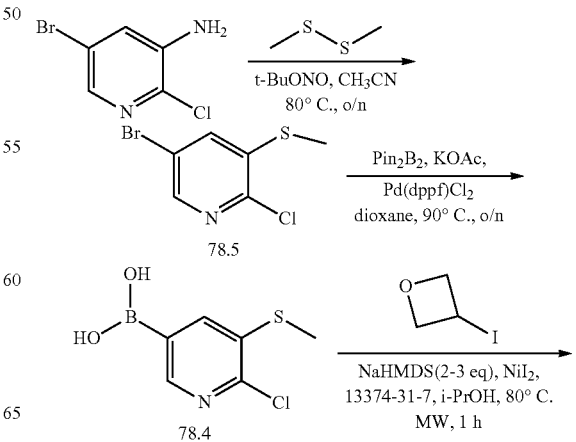

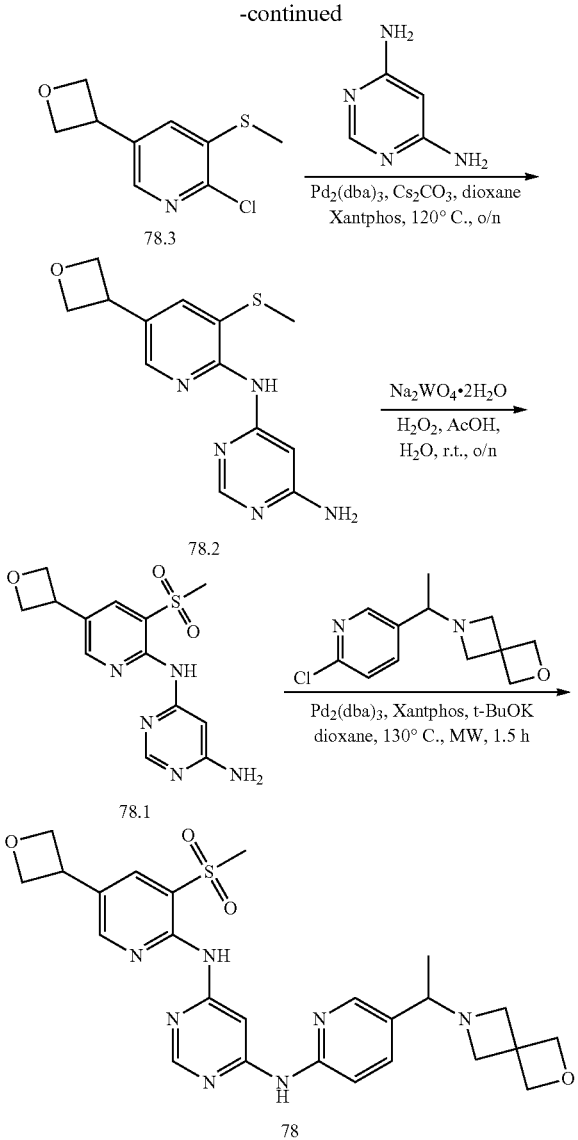

5-bromo-2-chloro-3-(methylthio)pyridine (78.5). To a stirred solution of 5-bromo-2-chloropyridin-3-amine (5.00 g, 24.10 mmol), MeSSMe (4.53 g, 48.20 mmol) in MeCN (150 mL) was drop-wise added t-BuONO (4.96 g, 48.20 mmol) at 0° C. The mixture was stirred at 80° C. overnight. After consumption of the starting material (monitored by LCMS), the mixture was concentrated at reduced pressure. The residue was dissolved in EtOAc (150 mL) and washed with water (100 mL×2) then brine (100 mL×2). The organic layer was dried over anhydrous sodium sulfate and concentrated in vacuo to give the crude product. The target product was purified by column chromatography on silica gel (EtOAc/Hexane=1/1) to give 78.5 (4.00 g, 70% yield) as a yellow solid. LC-MS m/z: 238.0 [M+1]$^+$. LCMS purity (214 nm): 72.13%; $t_R$=0.939 min.

(6-chloro-5-(methylthio)173yridine-3-yl)boronic acid (78.4). A stirred solution of 78.5 (3.00 g, 12.58 mmol), Pin$_2$B$_2$ (3.51 g, 13.84 mmol), Pd(dppf)Cl$_2$ (922 mg, 1.26 mmol) and KOAc (3.70 g, 37.74 mmol) in dioxane (100 mL). The mixture was stirred at 90° C.; overnight under nitrogen. After consumption of the starting material (monitored by LCMS), the solid was filtered out, and the filtrate was concentrated under vacuum. The target product was purified by reversed phase prep-HPLC to give 78.4 (700 mg, 27% yield) as a white solid. LC-MS m/z: 204.1 [M+1]$^+$. LCMS purity (214 nm): 91.28%; $t_R$=0.480 min.

2-chloro-3-(methylthio)-5-(oxetan-3-yl)pyridine (783). A stirred solution of 78.4 (300 mg, 1.47 mmol), 3-iodooxetane (271 mg, 1.47 mmol), NiI$_2$ (47 mg, 0.15 mmol), (1S,2R)-2-aminocyclohexanol hydrochloride (23 mg, 0.15 mmol) and NaHMDS (1 N, 3 mL, 3.00 mmol) in i-PrOH (10 mL) was irradiated with microwave for 1 hour at 80° C. under nitrogen. After consumption of the starting material (monitored by LCMS), the mixture was filtered and the filtrate was concentrated at reduced pressure. The residue was dissolved in EtOAc (30 mL) and washed with water (30 mL×2) then brine (30 mL×2). The organic layer was dried over anhydrous sodium sulfate and concentrated in vacuo to give the crude product. The target product was purified by column chromatography on silica gel (CH$_2$Cl$_2$/CH$_3$OH=10/1) to give 78.3 (100 mg, 31% yield) as a yellow solid. LC-MS m/z: 216.2 [M+1]$^+$. LCMS purity (254 nm): >99.9%; $t_R$=0.717 min.

N$^4$-(3-(methylthio)-5-(oxetan-3-yl)pyridine-2-yl)pyrimidine-4,6-diamine (78.2). To a stirred solution of 783 (400 mg, 1.85 mmol), pyrimidine-4,6-diamine (204 mg, 1.85 mmol), Pd$_2$(dba)$_3$ (174 mg, 0.19 mmol), Xantphos (110 mg, 0.19 mmol) and Cs$_2$CO$_3$ (1.21 g, 3.70 mmol) in dioxane (20 mL). The mixture was stirred at 120° C. overnight under nitrogen. After consumption of the starting material (monitored by LCMS), the mixture was filtered and the filtrate was concentrated at reduced pressure. The residue was dissolved in EtOAc (30 mL) and washed with water (20 mL×2) then brine (20 mL×2). The organic layer was dried over anhydrous sodium sulfate and concentrated in vacuo to give the crude product. The final product was purified by column chromatography on silica gel (CH$_3$OH/CH$_2$Cl$_{2=1/10}$) to give 78.2 (246 mg, 46% yield) as a yellow solid. LC-MS m/z: 290.2 [M+1]$^+$. LCMS purity (214 nm): >99.9%; $t_R$=0.569 min.

N$^4$-(3-(methylsulfonyl)-5-(oxetan-3-yl) 174yridine-2-yl) pyrimidine-4,6-diamine (78.1). To a stirred solution of 78.2 (246 mg, 0.85 mmol) in AcOH (5 mL) was added H$_2$O$_2$ (30% wt, 1.93 g, 17.00 mmol) and Na$_2$WO$_4$·2H$_2$O (281 mg, 0.85 mmol), the reaction was stirred at room temperature overnight. After consumption of the starting material (monitored by LCMS), the mixture was diluted with water (100 mL), then adjusted to pH 6~7 with NaHCO$_3$. The mixture solution was extracted with EtOAc (30 mL×3). The combined organic layers were washed with brine (30 mL×2), dried over sodium sulfate and concentrated to dryness. The residue was purified by column chromatography on silica gel (CH$_2$Cl$_2$/MeOH=10/1) to give 78.1 (90 mg, 33% yield) as a yellow solid. LC-MS m/z: 322.1 [M+1]$^+$. LCMS purity (254 nm): >99.9%; $t_R$=0.511 min.

N$^4$-(5-(1-(2-oxa-6-azaspiro[3.3]heptan-6-yl)ethyl) 175yridine-2-yl)-N$^6$-(3-(methylsulfonyl)-5-(oxetan-3-yl) 175yridine-2-yl)pyrimidine-4,6-diamine (78). To a stirred solution of 78.1 (50 mg, 0.16 mmol), 1B (37 mg, 0.16 mmol), Pd$_2$(dba)$_3$ (18 mg, 0.02 mmol), Xantphos (12 mg, 0.02 mmol) and t-BuOK (36 mg, 0.32 mmol) in dioxane (2 mL). The mixture was irradiated with microwave for 1.5 h at 130° C. under nitrogen. After consumption of the starting material (monitored by LCMS), the mixture was filtered and the filtrate was concentrated at reduced pressure. The residue was dissolved in EtOAc (30 mL) and washed with water (20 mL×2) then brine (20 mL×2). The organic layer was dried over sodium sulfate and concentrated in vacuo to give the crude product. The final product was purified by column chromatography on silica gel (CH$_2$Cl$_2$/CH$_3$OH=10/1) to give 78 (33 mg, 40% yield) as a white solid. $^1$H NMR (400 MHz, DMSO-d$_6$) δ 10.12 (s, 1H), 9.44 (s, 1H), 8.77 (br, 1H), 8.65 (d, J=2.4 Hz, 1H), 8.39 (d, J=1.2 Hz, 1H), 8.35 (d, J=2.4 Hz, 1H), 8.22-8.18 (m, 1H), 7.63 (s, 2H), 5.00-4.95 (m, 2H), 4.72-4.66 (m, 2H), 4.61-4.56 (m, 4H), 4.44-4.36 (m, 1H), 3.42 (s, 3H), 3.27-3.25 (m, 2H), 3.24-3.17 (m, 1H), 3.15-3.11 (m, 2H), 1.12 (d, J=6.4 Hz, 3H). LC-MS m/z: 524.0 [M+1]$^+$. HPLC purity (214 nm): >99.9%; t$_R$=7.030 min.

Example 1bz: Preparation of Compound 79

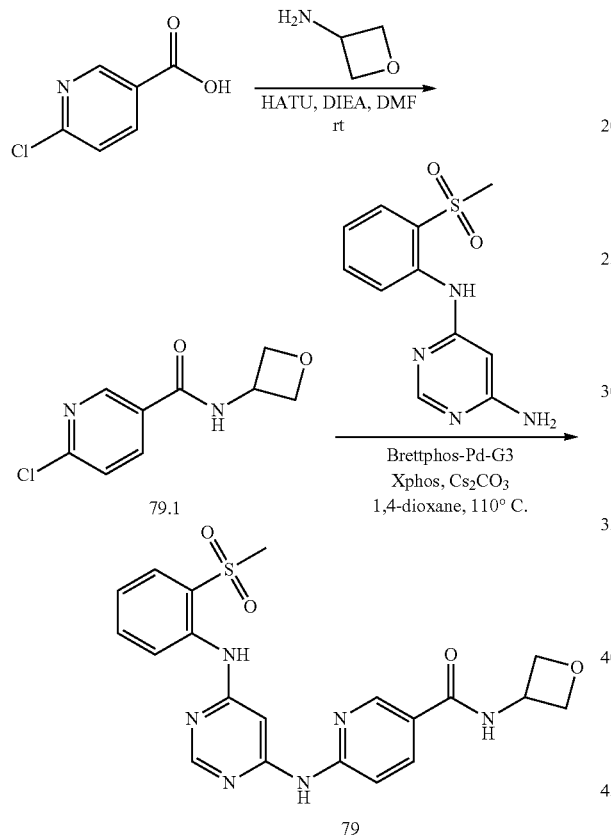

6-chloro-N-(oxetan-3-yl)nicotinamide (79.1). To a mixture of 6-chloronicotinic acid (472 mg, 3.0 mmol), oxetan-3-amine (263 mg, 3.6 mmol) and HATU (1.71 g, 4.5 mmol) in DMF (40 mL) was added 176yri (1.16 g, 9.0 mmol), the reaction mixture was stirred at room temperature overnight. After the reaction was completed, the mixture was diluted by water (50 mL) and extracted with EtOAc (50 mL×2). The organic extract was washed by water (100 mL×4) and brine (50 mL) successively, dried over Na$_2$SO$_4$, filtered and concentrated to give 79.1 (330 mg, 52% yield) as light brown solid. LC-MS m/z: 213.3 [M+H]$^+$. LCMS purity (214 nm): 96.27%; t$_R$=1.205 min.

6-((6-((2-(methylsulfonyl)phenyl)amino)pyrimidin-4-yl)amino)-N-(oxetan-3-yl)nicotinamide (79). A mixture of 79.1 (120 mg, 0.56 mmol), N$^4$-(2-(methylsulfonyl)phenyl)pyrimidine-4,6-diamine (150 mg, 0.56 mmol), Brettphos-Pd-G3 (51 mg, 0.056 mmol), Xphos (54 mg, 0.12 mmol) and Cs$_2$CO$_3$ (554 mg, 1.70 mmol) in 1,4-dioxane (30 mL) was stirred at 110° C. overnight under argon atmosphere. After the reaction was completed, the mixture was filtered by suction. The filtrate was concentrated and purified by column chromatography on silica gel (CH$_2$Cl$_2$:MeOH=10:1) and then reversed phase prep-HPLC to give 79 (15 mg, 6% yield) as white solid. $^1$H NMR (400 MHz, DMSO-d$_6$) δ 10.32 (s, 1H), 9.08 (d, J=6.4 Hz, 1H), 8.89 (s, 1H), 8.79 (d, J=2.0 Hz, 1H), 8.38 (d, J=0.8 Hz, 1H), 8.13 (dd, J=8.8, 2.4 Hz, 1H), 8.01 (d, J=7.6 Hz, 1H), 7.93 (dd, J=8.0, 1.6 Hz, 1H), 7.77-7.73 (m, 1H), 7.65 (d, J=8.8 Hz, 1H), 7.46 (s, 1H), 7.41-7.37 (m, 1H), 5.04-4.97 (m, 1H), 4.78 (t, J=6.4 Hz, 2H), 4.59 (t, J=6.4 Hz, 2H), 3.23 (s, 3H). LC-MS m/z: 441.1 [M+H]$^+$. HPLC purity (254 nm): 98.28%; t$_R$=6.441 min.

Example 1ca: Preparation of Compound 80

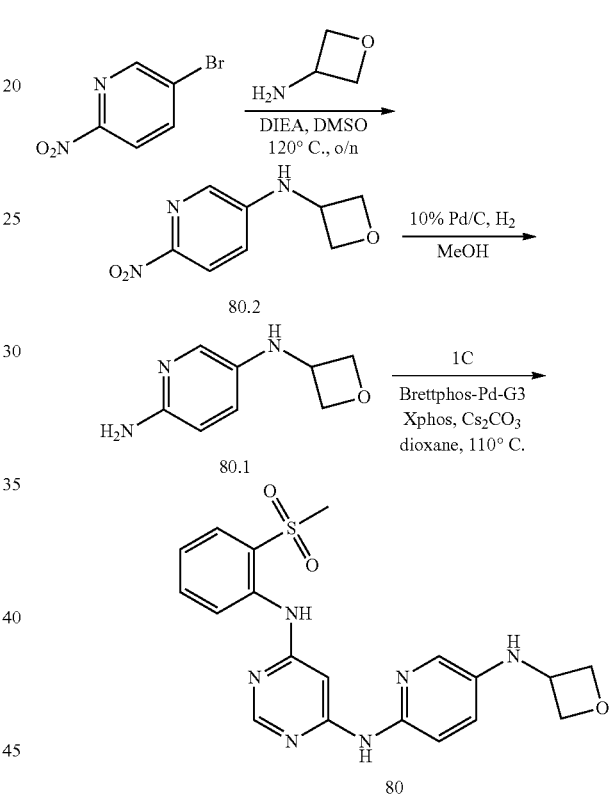

6-nitro-N-(oxetan-3-yl)176yridine-3-amine (80.2). To a mixture of 5-bromo-2-nitropyridine (3.05 g, 15.0 mmol) and oxetan-3-amine (1.10 g, 15.0 mmol) in DMSO (50 mL) was added 176yri (10 mL), the reaction mixture was stirred at 120° C. overnight under argon atmosphere. After the reaction was completed, the mixture was diluted by water (100 mL), extracted with EtOAc (100 mL×2). The organic extract was washed by water (100 mL×4) and brine (100 mL) successively, dried over Na$_2$SO$_4$, concentrated and purified by column chromatography on silica gel (EtOAc:hexane=1:1) to give 80.2 (515 mg, 17.5% yield) as yellow solid. LC-MS m/z: 196.4 [M+H]$^+$. LCMS purity (254 nm): 88.24%; t$_R$=1.531 min.

N$^5$-(oxetan-3-yl)pyridine-2,5-diamine (80.1). To a solution of 80.2 (515 mg, 2.64 mmol) in MeOH (50 mL) was added 10% Pd/C (100 mg), the reaction mixture was stirred at room temperature overnight under hydrogen atmosphere. After the reaction was completed, the mixture was filtered by suction and the filtrate was concentrated to give crude 80.1 (435 mg) as deep brown solid. LC-MS m/z: 166.4 [M+H]⁺. LCMS purity (214 nm): 85%; $t_R$=0.161 min $N^4$-(2-(methylsulfonyl)phenyl)-$N^6$-(5-(oxetan-3-ylamino)177yridine-2-yl) pyrimidine-4,6-diamine (80). A mixture of 80.1 (165 mg, 1.0 mmol), 1C (283 mg, 1.0 mmol), Brettphos-Pd-G3 (91 mg, 0.10 mmol), Xphos (95 mg, 0.20 mmol) and Cs₂CO₃ (975 mg, 3.0 mmol) in 1,4-dioxane (30 mL) was stirred at 110° C. overnight under argon atmosphere. After the reaction was completed, the mixture was filtered by suction. The filtrate was concentrated and purified by column chromatography on silica gel (CH₂Cl₂:MeOH=10:1) and then reversed phase prep-HPLC to give 80 (8 mg, 1.9% yield) as white solid. ¹H NMR (400 MHz, DMSO-d₆) δ 8.87 (s, 1H), 8.50 (s, 1H), 8.16 (d, J=0.8 Hz, 1H), 8.02 (d, J=2.4 Hz, 1H), 7.92-7.87 (m, 2H), 7.71-7.67 (m, 1H), 7.54 (dd, J=8.8, 2.8 Hz, 1H), 7.35-7.31 (m, 1H), 7.14 (d, J=5.6 Hz, 1H), 6.51 (d, J=8.8 Hz, 1H), 6.05 (d, J=0.8 Hz, 1H), 4.87-4.78 (m, 3H), 4.42 (t, 1=5.2 Hz, 2H), 3.18 (s, 3H). LC-MS m/z: 413.2 [M+H]⁺. HPLC purity (214 nm): 92.72%; $t_R$=6.421 min.

Example 1cb: Preparation of Compound 81

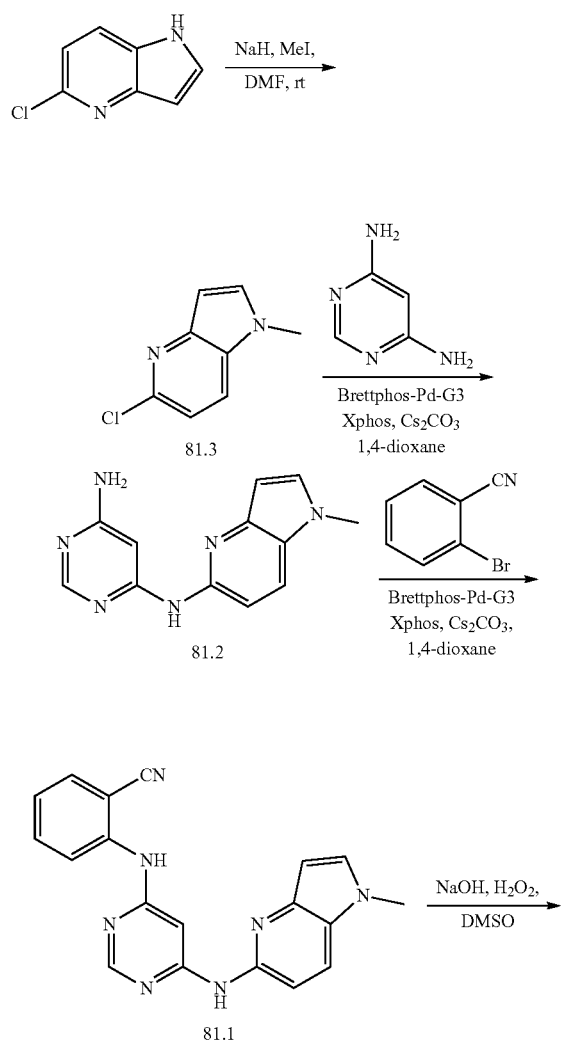

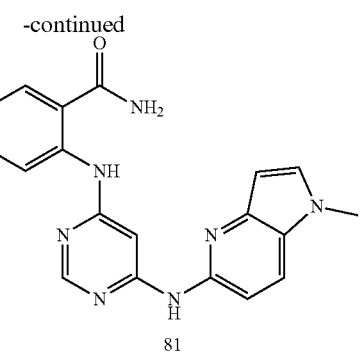

5-chloro-1-methyl-1H-pyrrolo[3,2-b]pyridine (81.3). To a solution of 60% NaH (393 mg, 9.83 mmol) in DMF (20 mL) was added 5-chloro-1H-pyrrolo[3,2-b]pyridine (1.0 g, 6.55 mmol) at 0° C. and stirred for 1 h under Ar. Atmosphere. To the mixture was added CH₃I (1.40 g, 9.83 mmol) and the reaction mixture was stirred at room temperature overnight. After the reaction was completed, the mixture was quenched by water (30 mL) and extracted with EtOAc (30 mL×3). The organic extract was washed by Brine (50 mL×4), dried over Na₂SO₄, concentrated to give 81.3 (1.09 g, 99% yield) as a brown solid. LC-MS m/z: 167.2 [M+1]⁺. LCMS purity (214 nm): >99.9%; $t_R$=1.336 min.

$N^4$-(1-methyl-1H-pyrrolo[3,2-b]178yridine-5-yl)pyrimidine-4,6-diamine (81.2). A mixture of 81.3 (1.20 g, 7.23 mmol), pyrimidine-4,6-diamine (954 mg, 8.66 mmol), Brettphos-Pd-G3 (654 mg, 0.72 mmol), Xphos (688 mg, 1.44 mmol) and Cs₂CO₃ (3.5 g, 21.68 mmol) in 1,4-dioxane (40 mL) was stirred at 100° C. for 5 h under Ar. Atmosphere. After the reaction was completed, the mixture was quenched by water (50 mL) and extracted with EtOAc (50 mL×2). The organic extract was washed with brine (50 mL), dried over Na₂SO₄, concentrated and purified by column chromatography on silica gel (CH₂Cl₂:MeOH=15:1) to give 81.2 (310 mg, 17.2% yield) as a yellow solid. LC-MS m/z: 241.3 [M+1]⁺. LCMS purity (214 nm): 82.67%; $t_R$=1.101 min.

2-((6-((1-methyl-1H-pyrrolo[3,2-b]179yridine-5-yl)amino)pyrimidin-4-yl)amino)benzonitrile (81.1). A mixture of 81.2 (310 mg, 1.29 mmol), 2-bromobenonitrile (282 mg, 1.55 mmol), Brettphos-Pd-G3 (117 mg, 0.13 mmol), Xphos (123 mg, 0.26 mmol) and Cs₂CO₃ (1.26 g, 3.87 mmol) in 1,4-dioxane (30 mL) was stirred at 100° C. for 5 h under Ar. Atmosphere. After the reaction was completed, the mixture was quenched by water (50 mL) and extracted with EtOAc (50 mL×2). The organic extract was washed with brine (50 mL), dried over Na₂SO₄, concentrated and purified by column chromatography on silica gel (EtOAc:hexane=7:3) to give 81.1 (80 mg, 18.1% yield) as a yellow solid. LC-MS m/z: 342.2 [M+1]⁺. LCMS purity (214 nm): 78.24%; $t_R$=1.423 min.

2-((6-((1-methyl-1H-pyrrolo[3,2-b]179yridine-5-yl)amino) pyrimidin-4-yl)amino)benzamide (81). To a solution of 81.1 (80 mg, 0.23 mmol) in DMSO (5 ml) was added NaOH (28 mg, 0.71 mmol) and 30% H₂O₂ (265 mg, 2.34 mmol), the reaction mixture was stirred at room temperature overnight. After the reaction was completed, the mixture was quenched by water (20 mL) and extracted with EtOAc (20 mL×3). The organic extract was washed with Brine (30 mL), dried over Na₂SO₄, concentrated and purified by reversed phase prep-HPLC give 81 (38.06 mg, 45.2% yield) as a yellow solid. ¹H NMR (400 MHz, DMSO-d₆) δ 10.99 (s, 1H), 9.79 (s, 1H), 8.37 (d, J=8.4 Hz, 1H), 8.33 (s, 1H), 8.24 (s, 1H), 7.88 (s, 1H), 7.83 (d, J=8.4 Hz, 1H), 7.77 (dd, J=8.0, 1.2 Hz, 1H), 7.72 (s, 1H), 7.55-7.50 (m, 2H), 7.18 (d, J=8.8 Hz, 2H), 7.05 (t, J=7.6 Hz, 1H), 6.34 (d, J=3.2 Hz, 1H), 3.80 (s, 3H). LC-MS m/z: 360.1 [M+1]$^+$. HPLC purity (254 nm): 99.20%; $t_R$=6.911 min.

Example 2: TYK2-JH2 Binding Assay

The following example describes the TYK2-JH2 HTRF binding assay used to determine the ligand efficiency of the TYK2 inhibitors.

To calculate ligand efficiency, Equation 1 is applied:

$$\text{Ligand Efficiency} = \frac{[1.4\ (-\log IC50)]}{\#\ \text{of heavy atoms}}$$

in which IC$_{50}$ comes from the binding assay used to determine compound potency.

TYK JH2 enzyme mix (ChemPartnec CP20210818A-BV), tracer (ChemPartnec CP-0029472-051) and mAb Anti-6HIS Tb cryptate Gold (Cisbio: Cat No. 61H$_{12}$TLA) mix were prepared in assay buffer (10 mM MgCl$_2$, 20 mM HEPES pH 7.5, 0.01% Triton X-100, 1 mM DTT). Compounds diluted in DMSO (Final Concentrations 0.1 to 0.000005 [µM]) and enzyme mix (0.5 nM Final Concentration) were added to 384 well plates, briefly centrifuged and incubated at room temperature for 10 minutes. After incubation, tracer mix (Tracer-35 nM final concentration); (Mab Anti-6HIS Tb cryptate Gold-0.5× final)) was added, briefly centrifuged then incubate at room temperature 60 minutes. After incubation, plates were read by Envision TR-FRET (Ex340/Em495/520) protocol (PerkinElmer-Envision 2104 multilabel plate reader).

TABLE 2

Ligand efficiency using the TYK-JH2 binding assay.

| Compound No. | Ligand Efficiency |
|---|---|
| 1 | ††† |
| 2 | ††† |
| 3 | †† |
| 4 | ††† |
| 5 | †† |
| 6 | ††† |
| 7 | ††† |
| 8 | ††† |
| 9 | ††† |
| 10 | ††† |
| 11 | †† |
| 12 | ††† |
| 13 | †† |
| 14 | ††† |
| 15 | ††† |
| 16 | †† |
| 17 | †† |
| 18 | ††† |
| 19 | ††† |
| 20 | ††† |
| 21 | ††† |
| 22 | ††† |
| 23 | ††† |
| 24 | †† |
| 25 | ††† |
| 26 | †† |
| 27 | † |
| 28 | †† |
| 29 | †† |
| 30 | †† |
| 31 | †† |
| 32 | ††† |
| 33 | †† |

TABLE 2-continued

Ligand efficiency using the TYK-JH2 binding assay.

| Compound No. | Ligand Efficiency |
|---|---|
| 34 | †† |
| 35 | ††† |
| 36 | ††† |
| 37 | ††† |
| 38 | ††† |
| 39 | †† |
| 40 | ††† |
| 41 | †† |
| 42 | ††† |
| 43 | †† |
| 44 | ††† |
| 45 | ††† |
| 46 | ††† |
| 47 | ††† |
| 48 | ††† |
| 49 | ††† |
| 50 | ††† |
| 51 | ††† |
| 52 | ††† |
| 53 | ††† |
| 54 | † |
| 55 | †† |
| 56 | † |
| 57 | ††† |
| 58 | ††† |
| 59 | ††† |
| 60 | ††† |
| 61 | ††† |
| 62 | †† |
| 63 | ††† |
| 64 | ††† |
| 65 | ††† |
| 66 | ††† |
| 67 | ††† |
| 68 | ††† |
| 69 | ††† |
| 70 | ††† |
| 71 | ††† |
| 72 | † |
| 73 | ††† |
| 74 | ††† |
| 75 | † |
| 76 | † |
| 77 | †† |
| 78 | † |
| 79 | †† |
| 80 | † |

†††: >0.39;
††: 0.37-0.39;
†: <0.37

Example 3a: IL-12 Induced pSTAT4 Assay

The following example describes the IL-12 induced pSTAT4 assay used to determine the cellular potency (IL-12/pSTAT4) of the TYK2 inhibitors.

NK-92 cells (human natural killer lymphoma cell line) were cultured in MEM α, nucleosides (Life Technologies, 22571020) 12.5% heat inactivated FBS (Dominique Dutscher, S1810), 12.5% heat inactivated Horse serum (Life Technologies, 26050088) and 1% Penicillin-Streptomycin (Life Technologies, 15140122), 5 ng/mL human IL-2 (R&D systems, 202-II/CF), 0.2 mM inositol (Sigma, PHR1351 lot LRAC4118), 0.1 mM β-mercaptoethanol (Life Technologies, 31350010), and 0.02 mM folic acid (Sigma, F8758).

NK-92 cells were starved overnight in starvation medium (Opti-MEM (ThermoFisher, 11058-021), 10% charcoal stripped FBS (ThermoFisher 12676-029), and 1% Penicillin (100U/ml)-Streptomycin (100 µg/ml) (ThermoFisher, ref 15140122)), then plated in a 96-well tissue culture plate (20K cells/well) prior to pre-incubation with test compounds (Final Concentration [nM] 1000 to 0.05) for 30 minutes at 37° C. Cells were stimulated with IL-12 (Final Concentration 10 ng/ml) for 30 minutes at 37° C., and terminated by addition of lysis buffer (MSD K150PAD-2). pSTAT4 (Tyr693) was detected using the Mesa Scale Discovery platform (MSD K150PAD-2), according to manufacturer's instruction. Briefly, cell lysates were added to pre-blocked plates and incubated for 1 hour at room temperature. Plates were washed and incubated with detection antibody for 1 hour at room temperature. Plates were washed and Read Buffer was added prior to measurement on the MSD (1300 MSD Quickplex SQ 120). Cellular potency of an exemplary compound of the invention is shown in FIG. 4B.

TABLE 3

Cellular potency using the IL-12 induced pSTAT4 assay (IL-12/pSTAT4).

| Compound No. | Cellular potency (nM) |
|---|---|
| 1 | ††† |
| 2 | ††† |
| 3 | ††† |
| 4 | ††† |
| 5 | ††† |
| 6 | ††† |
| 7 | ††† |
| 8 | ††† |
| 9 | ††† |
| 10 | ††† |
| 11 | ††† |
| 12 | ††† |
| 13 | ††† |
| 14 | ††† |
| 15 | ††† |
| 16 | ††† |
| 17 | ††† |
| 18 | ††† |
| 19 | ††† |
| 20 | ††† |
| 21 | ††† |
| 22 | ††† |
| 23 | ††† |
| 24 | ††† |
| 25 | ††† |
| 26 | ††† |
| 27 | ††† |
| 28 | ††† |
| 29 | ††† |
| 30 | ††† |
| 31 | ††† |
| 32 | ††† |
| 33 | ††† |
| 34 | ††† |
| 35 | ††† |
| 36 | ††† |
| 37 | ††† |
| 38 | ††† |
| 39 | ††† |
| 40 | †† |
| 41 | †† |
| 42 | †† |
| 43 | † |
| 44 | ††† |
| 45 | ††† |
| 46 | ††† |
| 47 | ††† |
| 48 | †† |
| 49 | †† |
| 50 | †† |
| 51 | † |
| 52 | †† |
| 53 | †† |
| 54 | † |
| 55 | N.D. |
| 56 | N.D. |
| 57 | N.D. |
| 58 | † |
| 59 | † |
| 60 | † |
| 61 | †† |
| 62 | † |
| 63 | †† |
| 64 | † |
| 65 | † |
| 66 | † |
| 67 | † |
| 68 | † |
| 69 | † |
| 70 | † |
| 71 | † |
| 72 | † |
| 73 | N.D. |
| 74 | †† |
| 75 | N.D. |
| 76 | †† |
| 77 | † |
| 78 | † |
| 79 | † |
| 80 | † |

†††: <100;
††: 100-1000;
†: >1000;
N.D.: No Data

Example 3b: IL-6 Induced pSTAT3 Assay

The following example describes the IL-6 induced pSTAT3 assay used to determine the cellular selectivity (IL-6/pSTAT3) of the TYK2 inhibitors.

TF-1 (ATCC®, CRL-2003™) cells were cultured in RPMI 1640 Medium, with GlutaMAX™ Supplement, HEPES for Cell Culture (Life Technologies, 72400047), 10% Fetal Bovine Serum (Life Technologies, 26400044), 2 ng/mL human recombinant GM-CSF (Life Technologies, PHC2013), 1 mM Sodium pyruvate (Life Technologies, 11360039), 1% MEM NEAA (Life Technologies, 11140-035), 1% Penicillin/Streptomycin (Life Technologies, 15140-122).

TF-1 (70×10⁶) cells were starved overnight in T01 50 flasks (Opti-MEM™ I Reduced Serum Medium, no phenol red (Life Technologies, 11058-021), 1 mM Na pyruvate (Life Technologies, 11360039), 1% MEM NEAA (Life Technologies, 11140-035), and 1% Penicillin/Streptomycin (Life Technologies, 15140-122)) then seeded into 96-well TPP plates (150 000 cell/well) and incubated with test compounds (Final Concentration [nM] 10000-0.05) for 30 minutes at 37° C. After incubation, cells were stimulated with 100 ng/ml human recombinant IL-4 (ThermoFisher, PHC0066) for 30 minutes at 37° C. Stimulation was terminated by addition of lysis buffer (MSD K150SVD) and pSTAT3 detection was measured with Phospho-STAT3 (Tyr705) Kit MSD K150SVD)) according to manufacturer's instruction. Briefly, cell lysates were added to pre-blocked plates, sealed, and shake for 1 hour at room temperature. Plates were then washed and incubated with detection antibody for 1 hour at room temperature. After washing, Read Buffer was added, and plates were read on MSD instrument (Model 1300 MSD Quickplex SQ 120). Cellular selectivity of an exemplary compound of the invention is shown in FIG. 4B.

TABLE 4

Cellular selectivity using the IL-6 induced pSTAT3 assay (IL-6/pSTAT3).

| Compound No. | Cellular selectivity (nM) |
|---|---|
| 1 | ††† |
| 2 | ††† |
| 3 | †† |
| 4 | †† |
| 5 | †† |
| 6 | †† |
| 8 | †† |
| 9 | ††† |
| 10 | †† |
| 11 | † |
| 12 | † |
| 13 | †† |
| 17 | ††† |
| 18 | † |
| 19 | ††† |
| 21 | †† |
| 22 | †† |
| 23 | ††† |
| 26 | ††† |
| 27 | ††† |
| 28 | ††† |
| 35 | ††† |
| 39 | ††† |
| 44 | ††† |
| 45 | † |
| 46 | † |
| 47 | † |
| 49 | † |
| 53 | † |

†††: >10,000;
††: 4,000-10,000;
†: <4,000;
N.D.: No Data

Example 3c: Cellular Selectivity (GM-CSF/pSTAT5)

The CellSensor irf1-bla TF-1 cell line (LifeTechnologies, K1657) was cultured in RPMI 1640 Medium (Invitrogen 72400-047), 10% Fetal Bovine Serum (Invitrogen, 26400044), 1 mM Sodium pyruvate (Life Technologies, 11360039), 1% MEM NEAA (Life Technologies, 11140-035), 2 ng/ml of human recombinant GM-CSF (Fisher, PHC2015), 1% Penicillin/Streptomycin (Life Technologies, 15140-122) and 5 µg/ml of Blasticidin (ThermoFisher, A1113903).

The cell line was seeded in a T75 flask at 13×10$^6$ cells/50 mL in starvation medium (Opti-MEM™ I Reduced Serum Medium, no phenol red (Life Technologies, 11058-021), 1 mM Na pyruvate (Life Technologies, 11360039), 1% MEM NEAA (Life Technologies, 11140-035), and 1% Penicillin/Streptomycin (Life Technologies, 15140-122)) for 16 hours at 37° C. under 5% CO$_2$ the day before the assay.

For the assay, CellSensor irf1-bla TF-1 cells were seeded at 30 000 cells/32 µL (starvation medium)/well in a 384-well plate.

Compounds were added on the cells in 4 µL (starvation medium)/well at 10× the final concentration. They were incubated for 30 minutes at 37° C.

Human recombinant carrier-free GM-CSF (ThermoFisher, ref PHC2015) was added to the wells in 4 µL (starvation medium)/well at 10×. The final concentration was 1 ng/mL. Control wells without GM-CSF treatment were added. Plates were incubated for 5 hours at 37° C.

6× LiveBlazer-FRET substrate (Invitrogen, K1085) was added to the wells at 8 µL/well. The substrate was prepared shortly before use by mixing 6 µL of solution A and 60 µL of solution B to 934 µL of solution C. Plates were incubated for 2.5 hours at room temperature in the dark. The plates were read on an Envision (Perkin Elmer) with an excitation at a wavelength of 409 nm and two wavelengths for the emission 520 nm and 450 nm. The ratio between the acceptor (450 nm) and donor (520 nm) emission was used to calculate the IC50s.

The IC$_{50}$ for the inhibition of pSTAT5 was calculated with the Xlfit software using the 4 Parameter Logistic Model or Sigmoidal Dose-Response Model (model 205).

TABLE 5

Cellular selectivity using the GM-CSF induced pSTAT5 assay

| Compound No. | Cellular selectivity (nM) |
|---|---|
| 1 | †† |
| 2 | ††† |
| 3 | ††† |
| 4 | ††† |
| 5 | ††† |
| 6 | ††† |
| 8 | † |
| 9 | ††† |
| 10 | ††† |
| 11 | ††† |
| 12 | † |
| 13 | ††† |
| 17 | †††† |
| 18 | ††† |
| 19 | ††† |
| 21 | ††† |
| 22 | ††† |
| 23 | ††† |
| 26 | ††† |
| 27 | ††† |
| 28 | ††† |
| 35 | ††† |
| 39 | ††† |
| 44 | ††† |
| 45 | † |
| 46 | † |
| 47 | ††† |
| 49 | ††† |
| 53 | †† |

†††: >10,000 nM;
††: 4,000-10,000 nM;
†: <4,000 nM;

Example 3d: Cellular Selectivity (IL-10/pSTAT3)

PBMCs from 4 donors were thawed at 37° C. and resuspended in RPMI+5% FBS. The cells were washed twice with RPMI+5% FBS then incubated for 1-hour 37° C. 90 ul of the PBMCs were seeded in 96-well plates for the assay.

Compounds were diluted in DMSO, titrated in PBS and added to prepared cells (final compound concentrations 10 to 0.0005 [µM], in 0.5% DMSO, and 4.5% PBS). They were incubated for 30-minutes at 37° C.

Cells were stimulated with the addition of the IL-10 cytokine (final assay concentration [35 pM], Biolegend #571002) and incubated for 30-minutes at 37° C. Samples were fixed by adding 10 ul of 16% paraformaldehyde (EMS) and incubated for 10-minutes at room temperature.

Cells were thawed and washed once with Wash Buffer (PBS+0.3% BSA) prior to the addition of the CD14 (Biolegend #325612) and CD45RA (Biolegend #304106) antibodies and incubated for 30 min. Cells were washed twice in Wash Buffer followed by permeabilization in 100% cold methanol for 15 min. Cells were washed three times in Wash Buffer prior to the addition of the pSTAT3-PE antibody (eBioscience #501122408) and incubated for 90 min at 4° C. Cells were washed twice in Wash Buffer and resuspended in 90 µl Wash Buffer prior to running on a LSRII flow cytometer (BD Biosciences, San Jose, CA).

Total Monocytes were gated, and the Mean Fluorescence Intensity (MFI) was determined from the PE channel to quantify pSTAT3 signal. Data was analyzed using the CellEngine flow cytometry software. The pSTAT3 MFI was used to calculated Activity (% Control):

Activity = 100 ∗ [(Test Compound Signal − Background)/
(*DMSO* Control Signal − Background)].

Data were then analyzed by non-linear regression to determine inhibitory potencies using the following equation in Collaborative Drug Discovery (Burlingame, CA):

$Y = \text{Bottom} + (\text{Top} - \text{Bottom})/(1 + 10[(-pIC50 - X) * HillSlope])$ where X: log concentration in Molar; Y: Activity (% Control); Top: curve top plateau; Bottom: curve bottom plateau, fixed range from −20-20%; Hill Slope: unconstrained. Potency data are reported as pIC50 or pIC90 values ±SD. IC90 values are defined from the fitted IC50 values:

$IC90 = (1/9)(1/HillSlope) * IC50.$

Example 3e: Cellular Selectivity (IL-4/pSTAT6)

PBMCs from 4 donors were thawed at 37° C. and resuspended in RPMI+5% FBS. The cells were washed twice with RPMI+5% FBS then incubated for 1-hour 37° C. 90 ul of the PBMCs were seeded in 96-well plates for the assay.

Compounds were diluted in DMSO, titrated in PBS and added to prepared cells (final compound concentrations 10 to 0.0005 [µM], in 0.5% DMSO, and 4.5% PBS). They were incubated for 30-minutes at 37° C.

Cells were stimulated with the addition of the IL-4 cytokine (final assay concentration [4 pM], Biolegend #766202) and incubated for 30-minutes at 37° C. Samples were fixed by adding 10 ul of 16% paraformaldehyde (EMS) and incubated for 10-minutes at room temperature.

Cells were thawed and washed once with Wash Buffer (PBS+0.3% BSA) prior to the addition of the CD14 (Biolegend #325612) and CD45RA (Biolegend #304106) antibodies and incubated for 30 min. Cells were washed twice in Wash Buffer followed by permeabilization in 100% cold methanol for 15 min. Cells were washed three times in Wash Buffer prior to the addition of the pSTAT6-PE antibody (Biolegend #686004) and incubated for 90 min at 4° C. Cells were washed twice in Wash Buffer and resuspended in 90 µl Wash Buffer prior to running on a LSRII flow cytometer (BD Biosciences, San Jose, CA).

Total Monocytes were gated, and the Mean Fluorescence Intensity (MFI) was determined from the PE channel to quantify pSTAT6 signal. Data was analyzed using the CellEngine flow cytometry software. The pSTAT6 MFI was used to calculated Activity (% Control):

Activity=100∗[(Test Compound Signal−Background)/(DMSO Control Signal−Background)]

Data were then analyzed by non-linear regression to determine inhibitory potencies using the following equation in Collaborative Drug Discovery (Burlingame, CA):

$Y = \text{Bottom} + (\text{Top} - \text{Bottom})/(1 + 10[(-pIC50 - X) * HillSlope])$ where X: log concentration in Molar; Y: Activity (% Control); Top: curve top plateau; Bottom: curve bottom plateau, fixed range from −20-20%; Hill Slope: unconstrained. Potency data are reported as pIC50 or pIC90 values ±SD. IC90 values are defined from the fitted IC50 values:

$IC90 = (1/9)(1/HillSlope) * IC50.$

Example 3f: Cellular Selectivity (IFN-γ/nSTAT1)

PBMCs from 4 donors were thawed at 37° C. and resuspended in RPMI+5% FBS. The cells were washed twice with RPMI+5% FBS then incubated for 1-hour 37° C. 90 ul of the PBMCs were seeded in 96-well plates for the assay.

Compounds were diluted in DMSO, titrated in PBS and added to prepared cells (final compound concentrations 10 to 0.0005 [µM], in 0.5% DMSO, and 4.5% PBS). They were incubated for 30-minutes at 37° C.

Cells were stimulated with the addition of the IFN-γ cytokine (final assay concentration [3 pM], Biolegend #766202) and incubated for 30-minutes at 37° C. Samples were fixed by adding 10 ul of 16% paraformaldehyde (EMS) and incubated for 10-minutes at room temperature.

Cells were thawed and washed once with Wash Buffer (PBS+0.3% BSA) prior to the addition of the CD14 (Biolegend #325612) and CD45RA (Biolegend #304106) antibodies and incubated for 30 min. Cells were washed twice in Wash Buffer followed by permeabilization in 100% cold methanol for 15 min. Cells were washed three times in Wash Buffer prior to the addition of the pSTAT1-PE antibody (Biolegend #666404) and incubated for 90 min at 4° C. Cells were washed twice in Wash Buffer and resuspended in 90 µl Wash Buffer prior to running on a LSRII flow cytometer (BD Biosciences, San Jose, CA).

Total Monocytes were gated, and the Mean Fluorescence Intensity (MFI) was determined from the PE channel to quantify pSTAT1 signal. Data was analyzed using the CellEngine flow cytometry software. The pSTAT1 ME was used to calculated Activity (% Control):

Activity = 100 ∗ [(Test Compound Signal − Background)/
(*DMSO* Control Signal − Background)]

Data were then analyzed by non-linear regression to determine inhibitory potencies using the following equation in Collaborative Drug Discovery (Burlingame, CA):

$$Y = \text{Bottom} + (\text{Top} - \text{Bottom})/)(1 + 10[(-pIC50 - X)*HillSlope])$$

where X: log concentration in Molar; Y: Activity (% Control); Top: curve top plateau; Bottom: curve bottom plateau, fixed range from −20-20%; Hill Slope: unconstrained. Potency data are reported as pIC50 or pIC90 values ±SD. IC90 values are defined from the fitted IC50 values:

$$IC90 = (1/9)(1/HillSlope) * IC50.$$

TABLE 6

Summary of selectivity in all cellular assays

|  | EC |
|---|---|
| IL-12/pSTAT4 IC$_{50}$ (nM) | 18 |
| IL-6/pSTAT3 IC$_{50}$ (nM) | >8,500 |
| Selectivity over IL-6[†] | >470x |
| GM-CSF/pSTAT6 IC$_{50}$ (nM) | >8,300 |
| Selectivity over GM-CSF[†] | >460x |
| IL-10/pSTAT3 IC$_{50}$ (nM) | >740 |
| Selectivity over IL-10[†] | >40x |
| IL-4/pSTAT6 IC$_{50}$ (nM) | >3,800 |
| Selectivity over IL-4[†] | >210x |
| IFNγ/pSTAT1 IC$_{50}$ (nM) | >10,000 |
| Selectivity over IFNγ[†] | >550x |

[†]Fold selectivity = (IL-6 or GM-CSF IC$_{50}$)/(IL-12 IC$_{50}$)

Example 4: Selectivity for TYK2-JH2. Biochemical Competitive Binding Assays Against the JAK Family Assay Protocol These studies were conducted at Eurofins-DiscoverX (San Diego, CA) using the KINOMEscan platform (KdELECT Kinase Assay Panel). Binding of recombinant DNA-tagged JAK partial construct proteins (containing either JH1 or JH2 domains) to biotinylated ligands immobilized on streptavidin-coated beads was measured in a competition binding assay format. Test compounds were diluted serially in DMSO and mixed with JAK protein and beads to initiate the assay, generating final assay concentrations covering >4-log range for the test compounds. Assays were incubated at room temperature for 1 h, followed by elution of bound kinases from the beads.

Parameters Measured and Calculated

Bound JAK proteins were quantified by qPCR, and Activity (% Control) (POC) was calculated as:

Activity = 100 * [(Test Compound Signal − Background)/

(DMSO Control Signal − Background)].

Data were then analyzed by non-linear regression to determine inhibitory potencies (reported as pIC50values) using the following equation in Collaborative Drug Discovery (Burlingame, CA):

$$Y = \text{Bottom} + (\text{Top} - \text{Bottom})/)(1 + 10[(-pIC50 - X)*HillSlope])$$

where X: log concentration in Molar; Y: Activity (% Control); Top: curve top plateau, fixed range from 80-120%; Bottom: curve bottom plateau, fixed range from −20-20%; Hill Slope: fixed value=−1. Potency data are reported as pIC50 values. Selectivity for TYK2-JH2 over other family members was calculated as: Fold selectivity=JAK-X IC50 (nM)/TYK2-JH2 IC50 (nM). Where JAK-X IC50 (nM): the mean potency for the off-target JAK family member; TYK2-JH2 IC50 (nM): mean potency for TYK2-JH2.

Figure 4A:
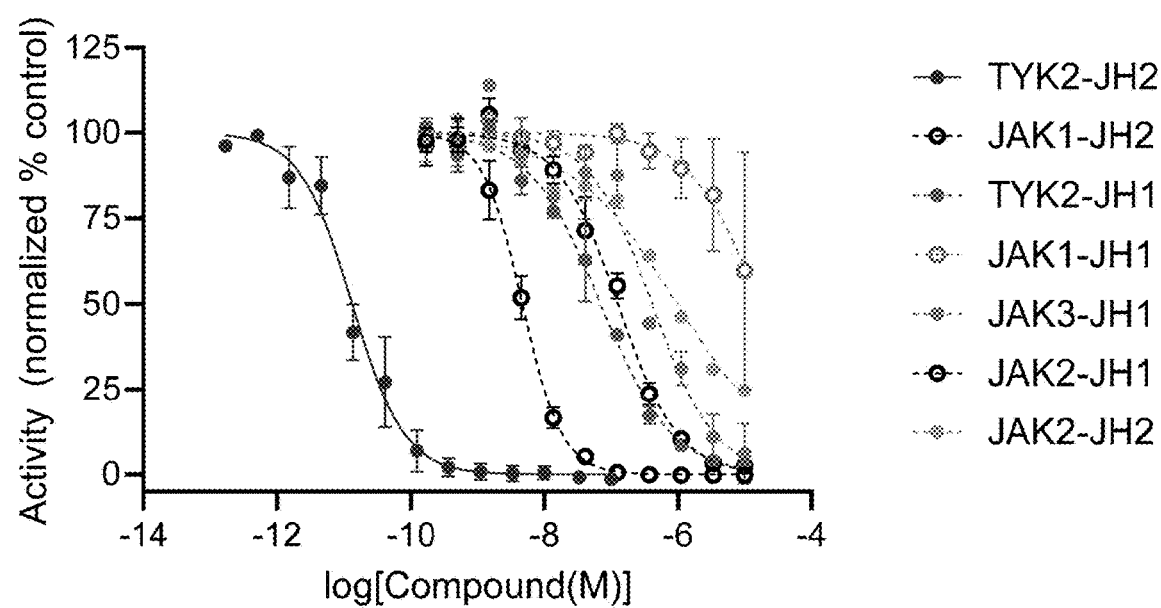
FIG. 4A-FIG. 4B. Exemplary compounds of the invention demonstrate selectivity for TYK2-JH2. (A) Selectivity for TYK2-JH2 measured against individual members of the JAK family (JH1 kinase domains and JH2 pseudokinase domains) in biochemical binding assays. Cellular selectivity demonstrated in cytokine-induced phosphorylation assays for (B) TYK2-JH2 (IL-12/pSTAT4) against the JAK 1/JAK2 (IL-6/pSTAT3) pathway.
Figure 4B:
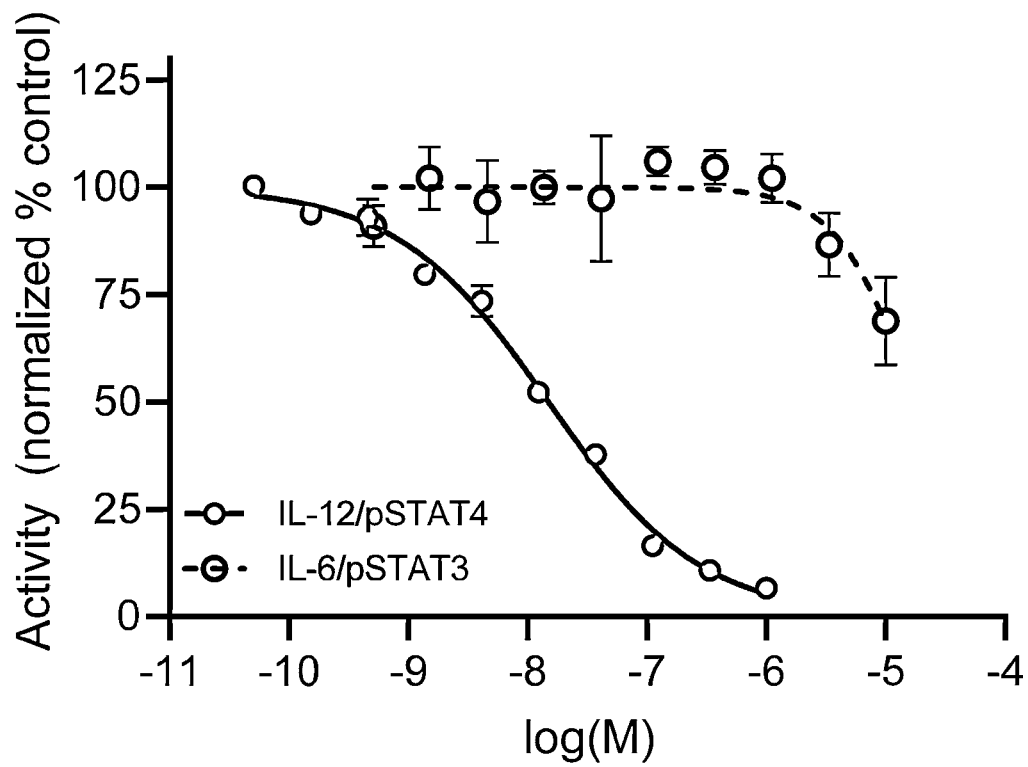

Selectivity of an exemplary compound of the invention is shown in Table 7, and in FIG. 4A.

TABLE 7

Selectivity for TYK-2-JH2 against the JAK family

|  | EC |
|---|---|
| TYK2-JH2 IC$_{50}$ (pM) | 12 |
| TYK2-JH1 (selectivity) | 5,700x |
| JAK1-JH2 (selectivity) | 350x |
| JAK1-JH1 (selectivity) | >10,000x |
| JAK2-JH1 (selectivity) | 10,000x |
| JAK2-JH2 (selectivity) | >10,000x |
| JAK3-JH1 (selectivity) | >10,000x |

Example 5 Pharmacokinetic Studies

The following example describes the methods used to evaluate the pharmacokinetics of TYK2 inhibitors in vivo following dosing of a compound of the invention.

The pharmacokinetics of test compounds were evaluated in either male CD-1 mice or male C57BL/6 mice when administered by oral gavage and IV bolus injection. The formulation for each test compound is summarized in Table 8. The animals were allowed free access to food and water before administration. Plasma samples were collected as shown in Table 8. The plasma samples were analyzed by LC-MS/MS and the concentration of test compound at each time point was determined by linear regression. Pharmacokinetic parameters were calculated from the plasma concentrations by non-compartmental modeling using WinNonlin 8.2.

Parenteral composition. To prepare a parenteral pharmaceutical composition suitable for administration by injection, the test articles described herein were dissolved in DMSO and then mixed with necessary volumes of PEG400 followed by 0.9% saline or 5% dextrose in water or 5% Kolliphor HS 15 in saline to provide the final concentrations of 0.2 mg/mL or 0.4 mg/mL test article as shown in Table 8. The resultant mixtures were solutions suitable for administration by injection.

Oral composition. To prepare a pharmaceutical composition for oral delivery, the test articles described herein were dissolved in DMSO and then mixed with necessary volume of PEG400 followed by 0.9% sterile saline or 5% dextrose in water or 5% Kolliphor HS 15 in saline to provide the final concentrations of 0.5 mg/mL or 1 mg/mL (Table 8). The resultant mixtures were suitable for oral administration.

TABLE 8

Test Articles and PK Protocol

| Test Article | Mouse Strain | IV Formulation | PO Formulation | Plasma Sampling Timepoints (semi-serial sampling, n = 9) |
|---|---|---|---|---|
| 1 | CD1 | 0.4 mg/mL in 5% DMSO, 10% PEG400 in saline | 1 mg/mL in 10% DMSO, 40% PEG400, 50% D5W | 0.0333 hr, 0.083 hr, 0.167 hr, 0.5 hr, 1 hr, 2 hr, 3 hr, 5 hr, 8 hr, and 24 hr |
| 2 | CD1 | 0.4 mg/mL in 5% DMSO, 10% PEG400 in saline | 1 mg/mL in 10% DMSO, 40% PEG400, 50% D5W | 0.0333 hr, 0.083 hr, 0.167 hr, 0.5 hr, 1 hr, 2 hr, 3 hr, 5 hr, 8 hr, and 24 hr |
| 3 | CD1 | 0.4 mg/mL in 5% DMSO, 10% PEG400 in saline | 1 mg/mL in 10% DMSO, 40% PEG400, 50% D5W | 0.0333 hr, 0.083 hr, 0.167 hr, 0.5 hr, 1 hr, 2 hr, 3 hr, 5 hr, 8 hr, and 24 hr |
| 4 | CD1 | 0.4 mg/mL in 5% DMSO, 10% PEG400 in saline | 1 mg/mL in 10% DMSO, 40% PEG400, 50% D5W | 0.0333 hr, 0.083 hr, 0.167 hr, 0.5 hr, 1 hr, 2 hr, 3 hr, 5 hr, 8 hr, and 24 hr |
| 5 | CD1 | 0.2 mg/mL in 5% DMSO + 10% PEG400 in saline | none | 0.0333 hr, 0.083 hr, 0.167 hr, 0.5 hr, 1 hr, 2 hr, 3 hr, 5 hr, 8 hr, and 24 hr |
| 6 | CD1 | 0.4 mg/mL in 5% DMSO, 10% PEG400 in saline | 1 mg/mL in 5% DMSO, 10% PEG400 in saline | 0.0333 hr, 0.083 hr, 0.167 hr, 0.5 hr, 1 hr, 2 hr, 3 hr, 5 hr, 8 hr, and 24 hr |
| 8 | CD1 | 0.4 mg/mL in 5% DMSO, 5% Kolliphor HS 15 in saline | 0.5 mg/mL in 5% DMSO, 5% Kolliphor HS 15 in saline | 0.0333 hr, 0.083 hr, 0.167 hr, 0.5 hr, 1 hr, 2 hr, 3 hr, 5 hr, 8 hr, and 24 hr |
| 9 | CD1 | 0.2 mg/mL in 5% DMSO, 10% PEG400 in saline | none | 0.0333 hr, 0.083 hr, 0.167 hr, 0.5 hr, 1 hr, 2 hr, 3 hr, 5 hr, 8 hr, and 24 hr |
| 11 | CD1 | 0.4 mg/mL in 5% DMSO, 10% PEG400 in saline | 1 mg/mL in 5% DMSO, 10% PEG400 in saline | 0.0333 hr, 0.083 hr, 0.167 hr, 0.5 hr, 1 hr, 2 hr, 3 hr, 5 hr, 8 hr, and 24 hr |
| 12 | CD1 | 0.4 mg/mL in 5% DMSO, 10% PEG400 in saline | 1 mg/mL in 5% DMSO, 10% PEG400 in saline | 0.0333 hr, 0.083 hr, 0.167 hr, 0.5 hr, 1 hr, 2 hr, 3 hr, 5 hr, 8 hr, and 24 hr |
| 15 | CD1 | 0.4 mg/mL in 5% DMSO, 10% PEG400 in saline | none | 0.0333 hr, 0.083 hr, 0.167 hr, 0.5 hr, 1 hr, 2 hr, 3 hr, 5 hr, 8 hr, and 24 hr |
| 17 | C57BL/6 | 0.4 mg/mL in 10% DMSO, 40% PEG400, 50% D5W | 0.5 mg/mL in 10% DMSO, 40% PEG400, 50% D5W | 0 hr, 0.083 hr, 0.25 hr, 0.5 hr, 1 hr, 2 hr, 4 hr |
| 18 | C57BL/6 | 0.4 mg/mL in 10% DMSO, 40% PEG400, 50% D5W | 0.5 mg/mL in 10% DMSO, 40% PEG400, 50% D5W | 0 hr, 0.083 hr, 0.25 hr, 0.5 hr, 1 hr, 2 hr, 4 hr |
| 20 | C57BL/6 | 0.4 mg/mL in 10% DMSO, 40% PEG400, 50% D5W | 0.5 mg/mL in 10% DMSO, 40% PEG400, 50% D5W | 0 hr, 0.083 hr, 0.25 hr, 0.5 hr, 1 hr, 2 hr, 4 hr |
| 21 | C57BL/6 | 0.4 mg/mL in 10% DMSO, 40% PEG400, 50% D5W | 0.5 mg/mL in 10% DMSO, 40% PEG400, 50% D5W | 0 hr, 0.083 hr, 0.25 hr, 0.5 hr, 1 hr, 2 hr, 4 hr |
| 22 | C57BL/6 | 0.4 mg/mL in 10% DMSO, 40% PEG400, 50% D5W | 0.5 mg/mL in 10% DMSO, 40% PEG400, 50% D5W | 0 hr, 0.083 hr, 0.25 hr, 0.5 hr, 1 hr, 2 hr, 4 hr |
| 25 | CD1 | 0.2 mg/mL in 5% DMSO, 10% PEG400 in saline | none | 0.0333 hr, 0.083 hr, 0.167 hr, 0.5 hr, 1 hr, 2 hr, 3 hr, 5 hr, 8 hr, and 24 hr |
| 26 | C57BL/6 | 0.4 mg/mL in 10% DMSO, 40% PEG400, 50% D5W | 1 mg/mL in 10% DMSO, 40% PEG400, 50% D5W | 0 hr, 0.083 hr, 0.25 hr, 0.5 hr, 1 hr, 2 hr, 4 hr |
| 27 | C57BL/6 | 0.4 mg/mL in 10% DMSO, 40% PEG400, 50% D5W | 1 mg/mL in 10% DMSO, 40% PEG400, 50% D5W | 0 hr, 0.083 hr, 0.25 hr, 0.5 hr, 1 hr, 2 hr, 4 hr |
| 28 | C57BL/6 | 0.4 mg/mL in 10% DMSO, 40% PEG400, 50% D5W | 1 mg/mL in 10% DMSO, 40% PEG400, 50% D5W | 0 hr, 0.083 hr, 0.25 hr, 0.5 hr, 1 hr, 2 hr, 4 hr |

TABLE 8-continued

Test Articles and PK Protocol

| Test Article | Mouse Strain | IV Formulation | PO Formulation | Plasma Sampling Timepoints (semi-serial sampling, n = 9) |
|---|---|---|---|---|
| 39 | C57BL/6 | 0.4 mg/mL in 10% DMSO, 40% PEG400, 50% D5W | 0.5 mg/mL in 10% DMSO, 40% PEG400, 50% D5W | 0 hr, 0.083 hr, 0.25 hr, 0.5 hr, 1 hr, 2 hr, 4 hr |
| 42 | C57BL/6 | 0.4 mg/mL in 10% DMSO, 40% PEG400, 50% D5W | 1 mg/mL in 10% DMSO, 40% PEG400, 50% D5W | 0 hr, 0.083 hr, 0.25 hr, 0.5 hr, 1 hr, 2 hr, 4 hr |
| 44 | C57BL/6 | 0.4 mg/mL in 10% DMSO, 40% PEG400, 50% D5W | 1 mg/mL in 10% DMSO, 40% PEG400, 50% D5W | 0 hr, 0.083 hr, 0.25 hr, 0.5 hr, 1 hr, 2 hr, 4 hr |
| 45 | C57BL/6 | 0.4 mg/mL in 10% DMSO, 40% PEG400, 50% D5W | 0.5 mg/mL in 10% DMSO, 40% PEG400, 50% D5W | 0 hr, 0.083 hr, 0.25 hr, 0.5 hr, 1 hr, 2 hr, 4 hr |
| 46 | C57BL/6 | 0.4 mg/mL in 10% DMSO, 40% PEG400, 50% D5W | 1 mg/mL in 10% DMSO, 40% PEG400, 50% D5W | 0 hr, 0.083 hr, 0.25 hr, 0.5 hr, 1 hr, 2 hr, 4 hr |
| 56 | C57BL/6 | 0.4 mg/mL in 10% DMSO, 40% PEG400, 50% D5W | 1 mg/mL in 10% DMSO, 40% PEG400, 50% D5W | 0 hr, 0.083 hr, 0.25 hr, 0.5 hr, 1 hr, 2 hr, 4 hr |

DMSO = dimethyl sulfoxide, D5W = 5% dextrose in water, hr = hour

The PK parameters measured in mouse plasma after treatment with TYK2 inhibitor compounds via PO (oral administration) at 5 mg/kg are summarized below in Tables 9-11.

TABLE 9

Maximum plasma concentration ($C_{max}$).

| Compound No. | $C_{max}$ (ng/mL) |
|---|---|
| 1 | † |
| 2 | ††† |
| 4 | † |
| 5 | ††† |
| 6 | ††† |
| 8 | †† |
| 11 | †† |
| 12 | ††† |
| 44 | † |

†††: >1500;
††: 800-1500;
†: <800

TABLE 10

Half-life ($t_{1/2}$).

| Compound No. | $t_{1/2}$ (hr) |
|---|---|
| 1 | †† |
| 2 | †† |
| 4 | †† |
| 5 | ††† |
| 6 | † |
| 8 | ††† |
| 11 | ††† |
| 12 | † |
| 44 | ††† |

†††: >1.5;
††: 1.0-1.5;
†: <1.0

TABLE 11

Total systemic exposure ($AUC_{inf}$).

| Compound No. | $AUC_{inf}$ (hr*ng/mL) |
|---|---|
| 1 | †† |
| 2 | ††† |
| 4 | † |
| 5 | ††† |
| 6 | ††† |
| 8 | †† |
| 11 | ††† |
| 12 | †† |
| 44 | † |

†††: >2000;
††: 1000-2000;
†: <1000

Example 6: Brain Exposure Pharmacokinetic Studies

The brain exposure of exemplary compounds, e.g., 1, 2, and 4 were evaluated in male Sprague Dawley rats after oral gavage administration at 10 mg/kg. The formulation was 5% DMSO+10% PEG400 in saline. Rats were fasted overnight with food returned 4 hours post-dose. CSF was collected by direct needle puncture into the cisterna *magna*.

The brain exposure of 18 was evaluated in male C57BL/6 mice after oral gavage administration at 5 mg/kg. The formulation was 10% DMSO+40% PEG400 in saline. Mice were provided free access to food and water without fasting. Terminal sample collection of plasma and brain tissue were collected at 0, 0.83, 0.25, 0.5, 1, 2, and 4 hours post-dose with n=3 at each timepoint.

For both rat and mouse studies, brain tissue was washed with 3 volumes of saline prior to homogenization. Brain tissue was homogenized with 3 volumes (v/w) of phosphate buffered saline. Plasma, brain homogenate, and CSF samples (rat only) were analyzed by LC-MS/MS and the concentration of test compound at each time point was determined by linear regression.

Pharmacokinetic parameters were calculated from the plasma, brain, and CSF concentrations by non-compartmental modeling using WinNonlin 8.2. The PK parameters are summarized in Table 12.

TABLE 12

Plasma, Brain, and CSF PK Parameters

| Test Article | Matrix | Brain[a, b] $Kp_{u, u}$ |
|---|---|---|
| 4 | Plasma | ††† |
|  | Brain |  |
|  | CSF |  |
| 2 | Plasma | † |
|  | Brain |  |
|  | CSF |  |
| 1 | Plasma | †† |
|  | Brain |  |
|  | CSF |  |
| 18 | Plasma | ††† |
|  | Brain |  |

[a](CSF $AUC_{inf}$)/(Plasma $AUC_{inf}$)($f_{u, plasma}$)
[b](Brain $AUC_{inf}$)($f_{u, brain}$)/(Plasma $AUC_{last}$)($f_{u, plasma}$)
††† >0.2$_u$;
†† 0.1-0.2$_u$;
† <0.1$_u$ Example 7: IMQ-Induced Psoriasis Model This study was conducted in accordance with the Inotiv Boulder test facility standard operating procedures (SOPs), the World Health Organization Quality Practices in Basic Biomedical Research guidelines, and in compliance with all state and federal regulations, including USDA Animal Welfare Act 9 CFR Parts 1-3. Federal Register 39129, Jul. 22, 1993. This study was conducted in accordance with The Guide for the Care & Use of Laboratory Animals (8th Edition) and therefore in accordance with all Inotiv Boulder IACUC approved policies.

Prior to the start of the study, 9-10 week old, BALB/c mice (CRL) were acclimated for 4 days. On study day 0, animals were randomized into treatment groups based on body weight, anesthetized with 3% isoflurane and their backs shaved and depilated. Baseline measurements for PASI (psoriasis area severity index) and caliper (skin thickness via spring-loaded micrometer calipers (Mitutuyo 700-118)) were performed.

On study days 1-8, disease was induced with approximately 50 μl of 5% imiquimod (Pencol Pharmacy, MWI) cream applied to the hair-free skin of the back and rubbed in until absorbed. Test articles were dosed orally BID (the exception was deucravacitinib at 3 mpk, which was dosed QD, with vehicle administered as the second daily dose). On study days 2, 4, 6, and 8, caliper (skin thickness) and PASI (independent scoring (0-5) of erythema, scaling, and skin thickness) measurements were performed.

On day 8, the study was terminated following the final PASI and caliper measurements. The spleen (for measurements of change in weight), whole blood (for PK), and back skin (for histology and cytokine measurements) samples were collected. Histopathology samples were evaluated for epidermal thickness, dermal inflammation, epidermal inflammation/hyperkeratosis, epidermal erosion, and epidermal hyperplasia.

Figure 2A:
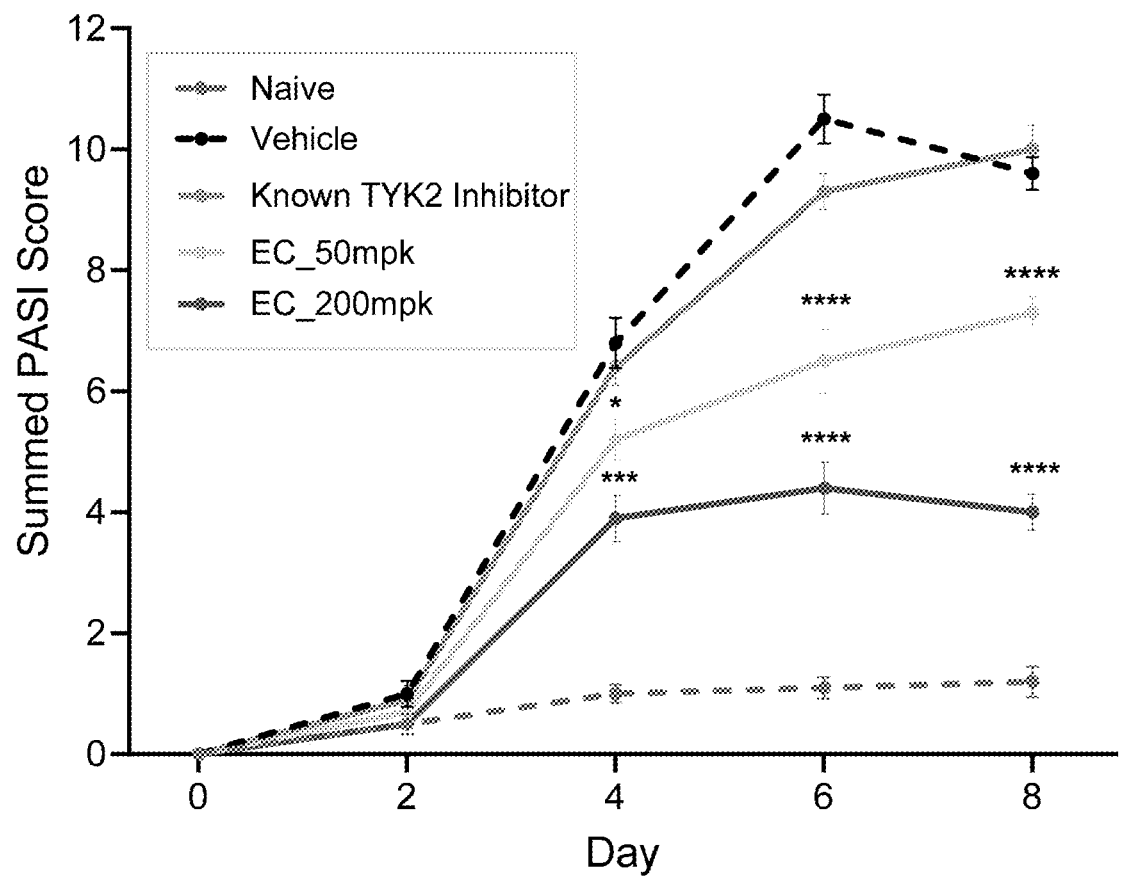
FIG. 2A-FIG. 2H. Exemplary compound of the invention demonstrated dose-dependent inhibition of psoriasis scores (PASI), back skin histopathology scores and relative spleen weight in a 7-day imiquimod-induced mouse model of psoriasis. (A) PASI score. **$p<0.0001$; *$p<0.001$; *$p<0.05$ v. Vehicle (two-way ANOVA with Dunnett's multiple comparisons test). (B) Histopathology score. **$p<0.0001$ v. Naive (two-tailed t-test); ††††$p<0.0001$ v. Vehicle (one-way ANOVA with Dunnett's multiple comparisons test). (C) Relative spleen weight. **$p<0.0001$ v. Naive (two-tailed t-test); ††††$p<0.0001$; †$p<0.05$ v. Vehicle (one-way ANOVA with Dunnett's multiple comparisons test). (D) Representative sections of H&E-stained skin tissue show IMQ-induced mild epidermal inflammation (small arrow), marked dermal inflammation (*), and marked epidermal hyperplasia (large arrow), and improvement in animals treated with exemplary compound. Improvement in disease was also seen with back skin tissue proinflammatory cytokine/chemokine levels for (E) IL-17A (pg/mL); (F) GM-CSF (pg/mL); (G) TNF-α (pg/mL); and (H) MIP1a (pg/mL). **$p<0.0001$; *$p<0.001$; **$p<0.01$ v. Naive (two-tailed t-test); ††††$p<0.0001$; †††$p<0.001$; †$p<0.05$ v. Vehicle (one-way ANOVA with Dunnett's multiple comparisons test).
Figure 2B:
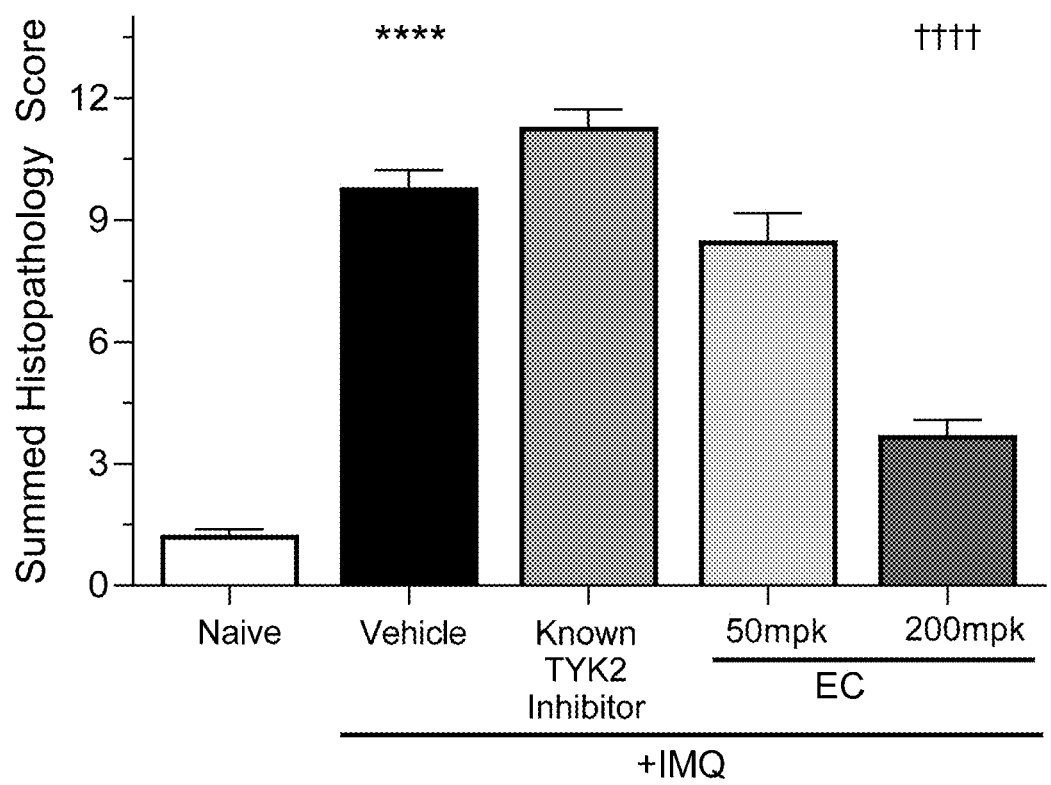
Figure 2C:
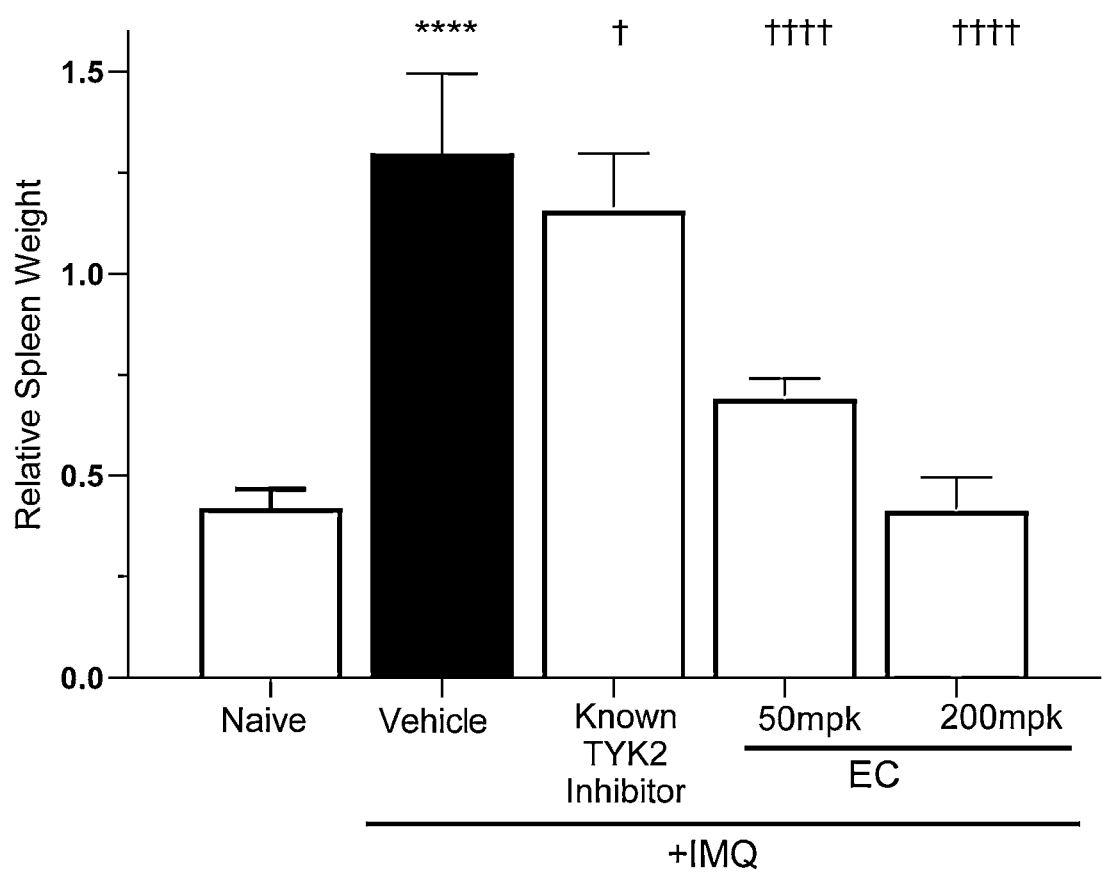
Figure 2D:
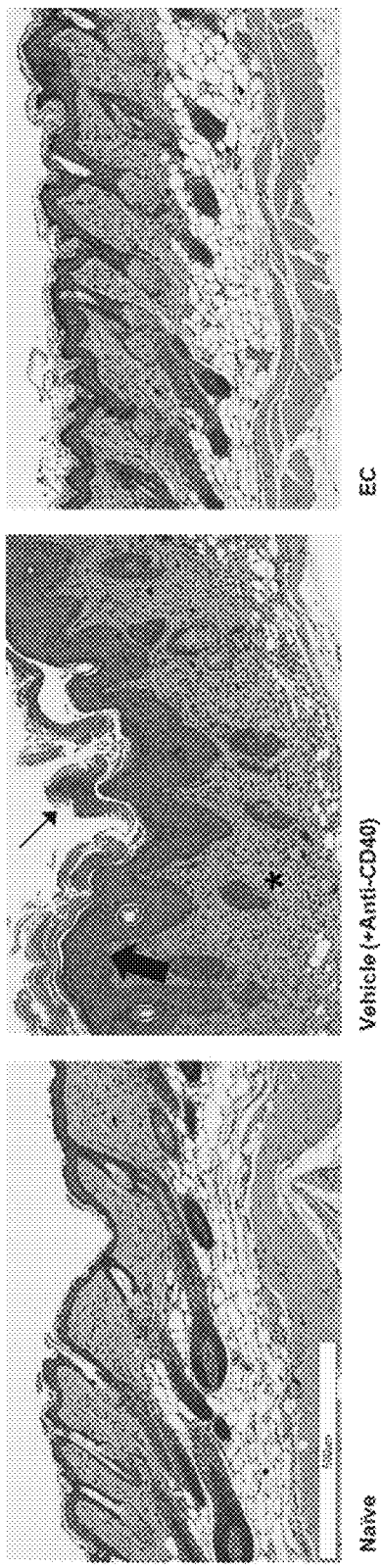
Figure 2E:
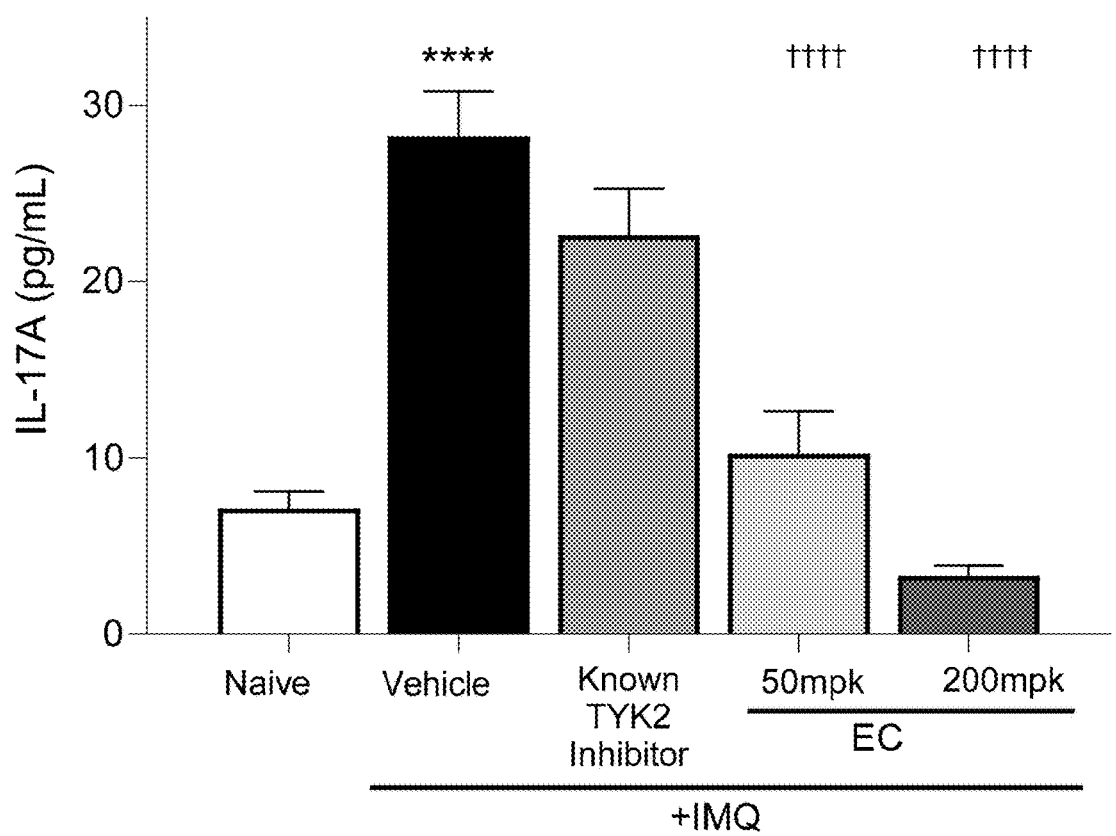
Figure 2F:
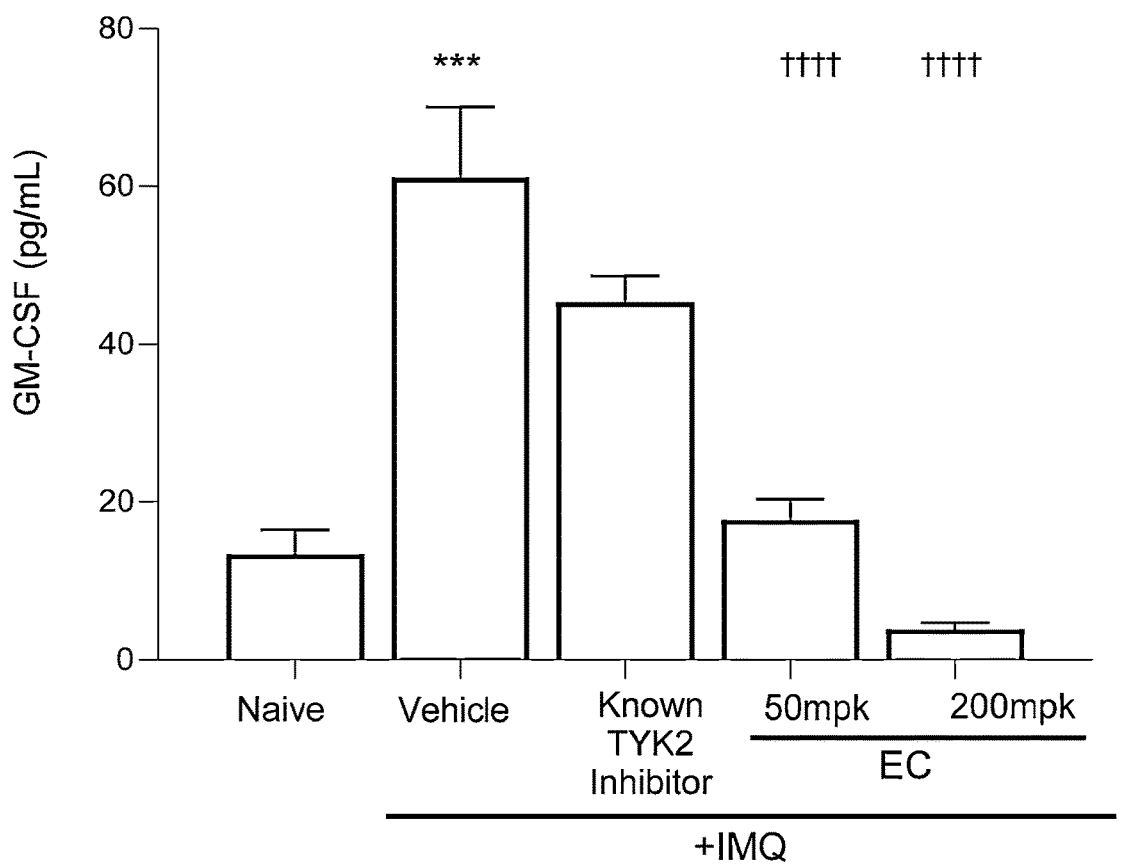
Figure 2G:
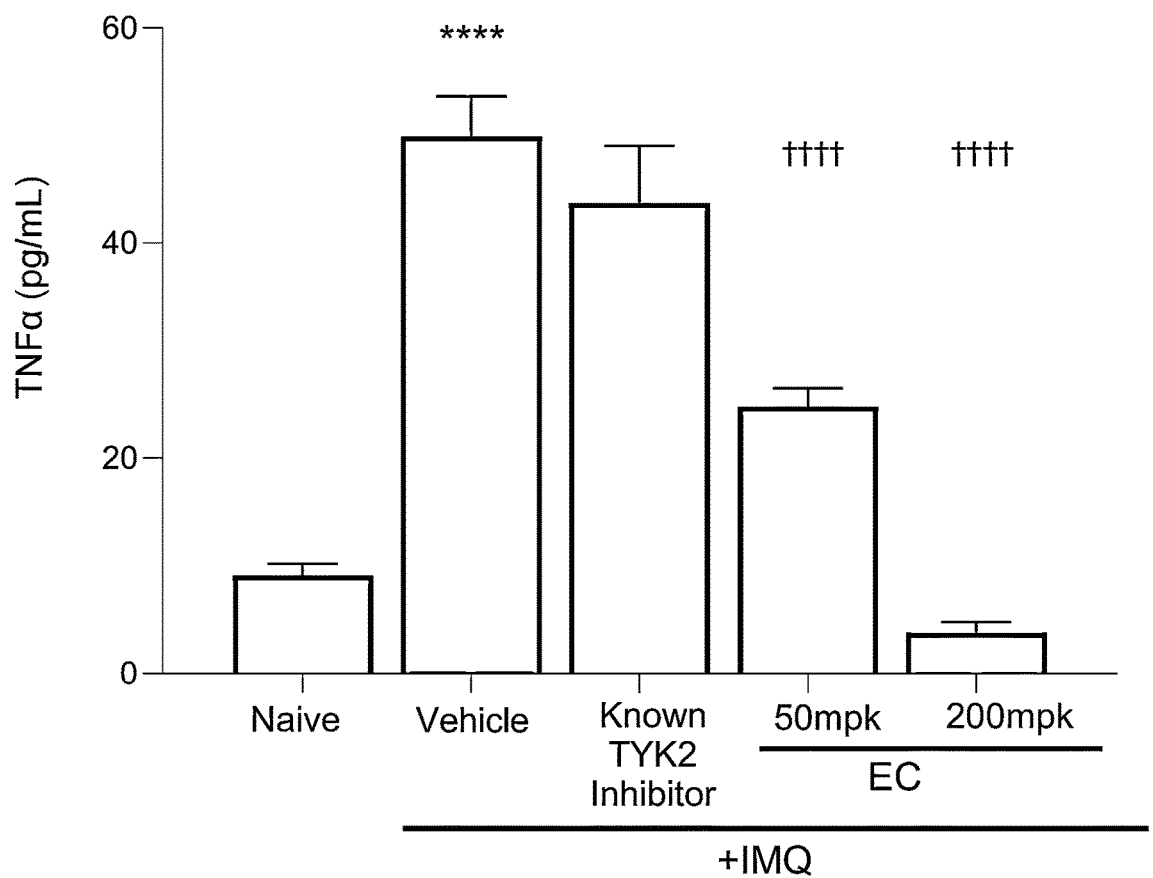
Figure 2H:
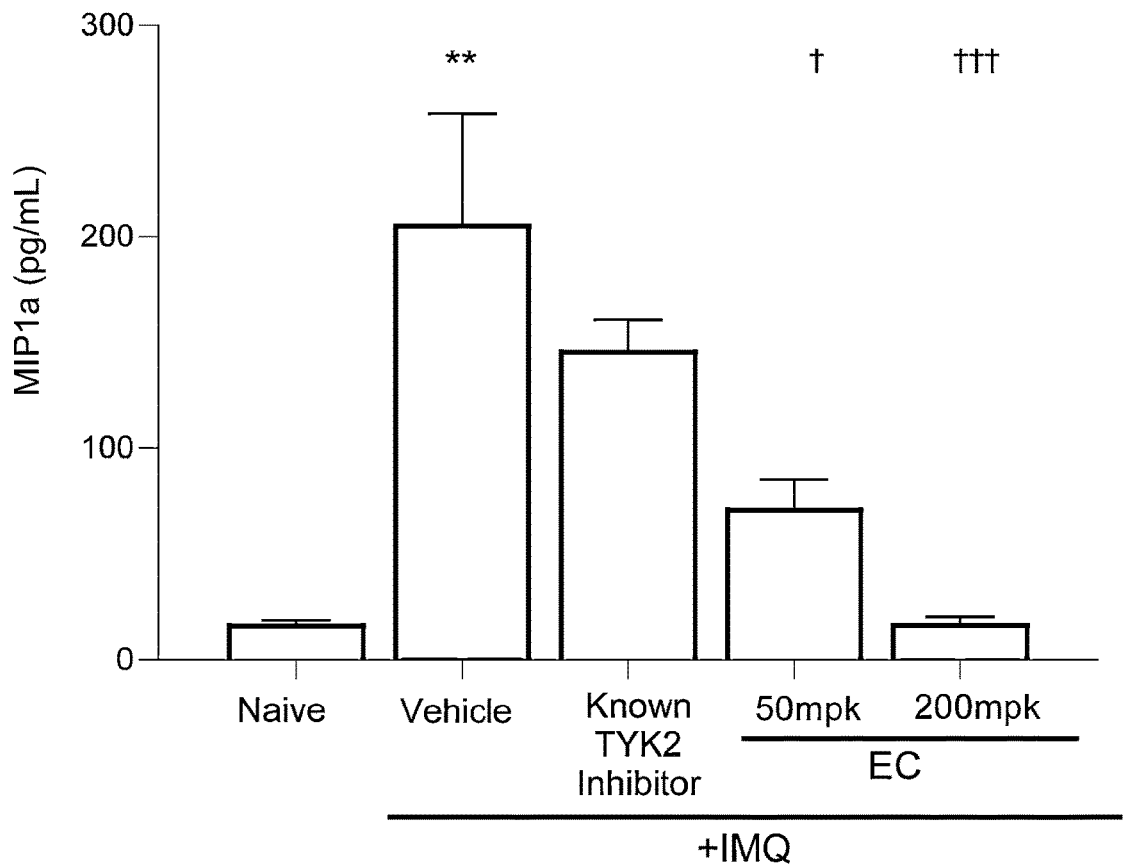

Overall efficacy of test articles is based on the summed PASI scores and back skin histopathology. FIGS. 2A and 2B. Additional readouts of the model support activity of an exemplary compound in psoriasis (FIG. 2C-2H).

Example 8: IL-23-Induced Ear Edema and IL-17A

Experimental Design: All studies were conducted in C57BL/6 mice (7-9 w) at ChemPartner (Shanghai, China) with IACUC approval and following guidelines established by AAALAC. IL-23 was injected (QD for 4 days) into the right ears of mice to induce inflammation. The left ears (and both ears of the naïve group) were given vehicle injections. Mice were dosed orally with test compounds either BID or QD, with the first (or only) compound dose administered 1 h prior to IL-23 injection. Body weight was measured daily, and at study termination, ear thickness was measured by micrometer and ear pinna were weighed. Plasma was collected for test compound concentration measurement, and ear skin was harvested for IL-17A measurements by ELISA.

Parameters Measured and Calculated

Body weight. Daily change in body weight (reported as change from Day 0) was calculated as:

Body weight change (from Day 0)(%)=100*Body weight/Group mean Day 0 body weight

All study treatment groups were then tested by two-way ANOVA (factors: Group and Day) with Dunnett's multiple comparisons test against the Naïve group.

Plasma exposure. Compound concentrations in terminal plasma samples are reported as ng/ml.

Day 4 terminal endpoints. Ear swelling (reported as the thickness change in mm) was calculated as:

Thickness difference(mm)=Right ear thickness(mm)− Left ear thickness(mm).

Ear weight is reported in g. Ear IL-17A levels (reported in pgIpg protein) were calculated as:

$$[IL-17A]\ (pg/\mu g) =$$

measured $IL-17A\ (pg/ml)$/homogenate protein concentration $(\mu g/ml)$.

Figure 1B:
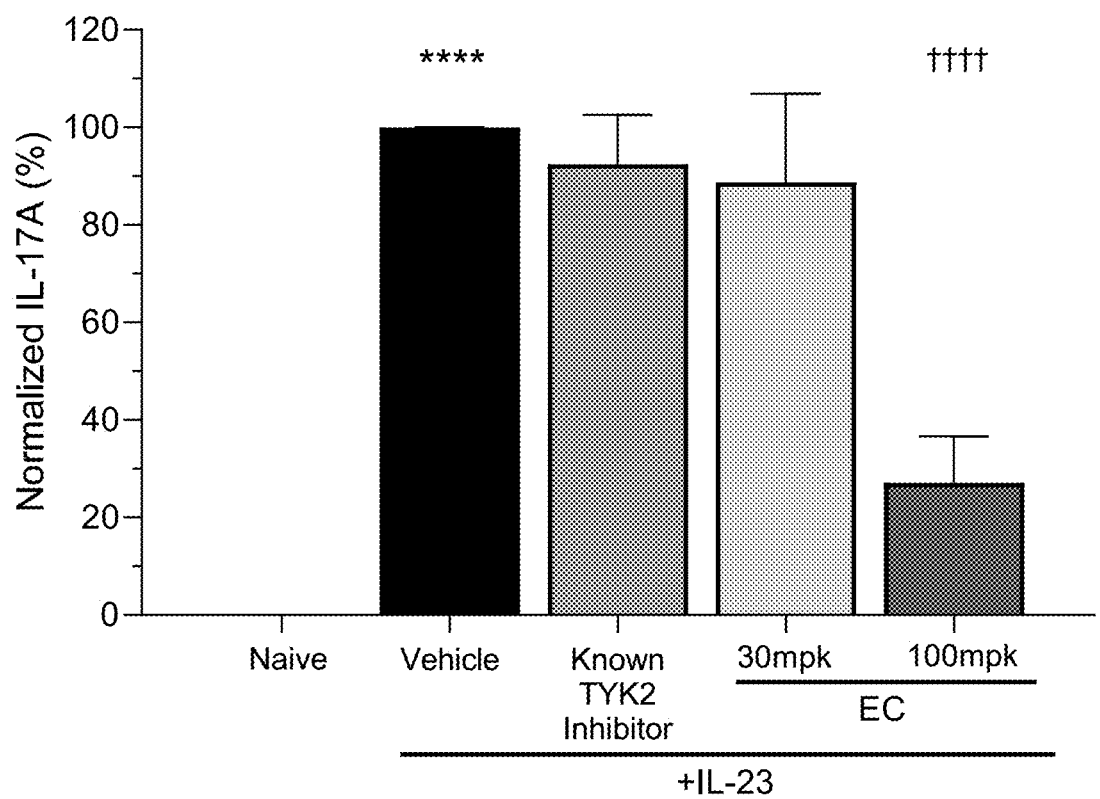

For each Day 4 endpoint, Naïve and Vehicle groups were compared by two-tailed t-test to confirm IL-23induction for individual studies. All study treatment groups were then tested by one-way ANOVA with Dunnett's multiple comparisons test against the Vehicle group. Final analysis of combined study data was performed using values normalized for each study prior to aggregation. Ear thickness, ear weight, and IL-17A levels were normalized as:

Normalized endpoint (%) =

$$100 * [1 - (X - \text{Mean Vehicle})/(\text{Mean Naïve} - \text{Mean Vehicle})]$$

where X: individual datapoint for the study animal and endpoint; Mean Vehicle: Mean endpoint value for the study Vehicle group; Mean Naïve: Mean endpoint value for the study Naïve group. Normalized and combined values for Naïve and Vehicle groups were compared by two-way ANOVA (factors: Group and Study) to confirm IL-23 induction. Normalized data for all studies and study groups (including those not reported here) were combined and compared by two-way ANOVA (factors: Group and Study) with Dunnett's multiple comparisons test against the Vehicle group. Overall combined mean values for ear endpoints (swelling (FIG. 1A)), weight, IL-17A (FIG. 1B) levels) and plasma exposures are reported.

Example 9. Screening Against scanEDGE Kinome

Assay Protocol

Figure 3:
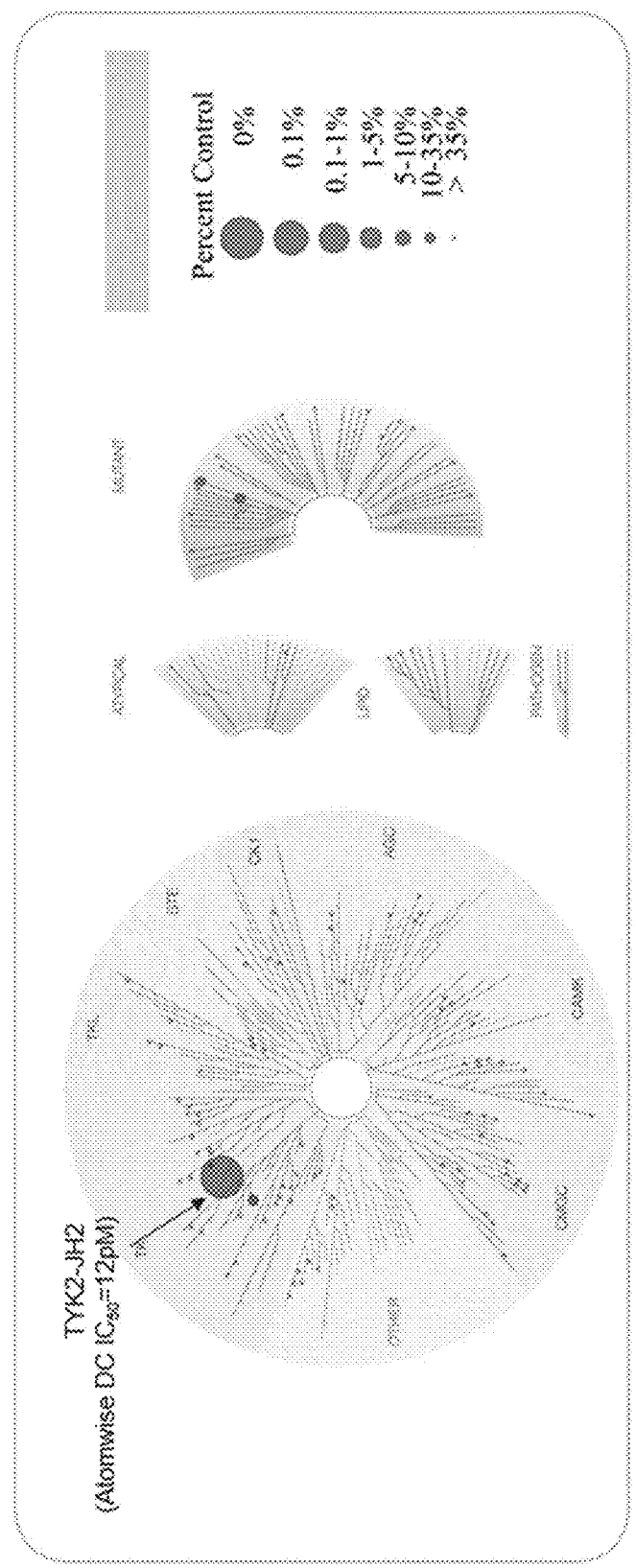
FIG. 3. Exemplary compounds of the invention demonstrate selectivity v. kinome panel. (A) Screening against scanEDGE kinome panel: TYK2-JH2 selectivity over $IC_{50(app)}$ for pABL1(E255K), pABL1(T315I), pABL1, and ABL1=580×, 1300×, 370×, and 200×, respectively. Kinome partition index*(PTYK2-JH2)=0.98. Selectivity also measured v. safety47 Panel: $IC_{50}>1$ μM across a panel of GPCRs, ion channels, enzymes and receptors [$IC_{50}$ for LCK=20 nM, incorporated into kinome $P_{TYK2-JH2}$]. *Cheng et al, JMC, 2010. $IC_{50(app)}$=2-point IC50 approximation.

This study was conducted at Eurofins-DiscoverX (San Diego, CA) using the KINOMEscan® platform. Binding of recombinant DNA-tagged kinases to biotinylated ligands immobilized on streptavidin-coated beads was measured in a competition binding assay format. Test compound was diluted and mixed with kinase proteins and beads to initiate the assay, generating final assay concentrations of 10 and 100 nM for the test compound. Assays were incubated at room temperature for 1 h, followed by elution of bound kinases from the beads. Kinome selectivity of an exemplary compound of the invention is shown in FIG. 3.

Parameters Measured and Calculated

Bound kinases were quantified by qPCR, and Activity (% Control) was calculated as:

Activity=100*[(Test Compound Signal−Positive Control)/(DMSO Control−Positive Control)].

Data were then analyzed by non-linear regression to approximate inhibitory potencies (reported as pIC50(app) values) using the following equation in GraphPad Prism (Boston, MA):

$$Y = \text{Bottom} + (\text{Top} - \text{Bottom})/)(1 + 10[(-pIC50 - X) * \text{HillSlope}])$$

where X: log concentration in Molar; Y: Activity (% Control); Top: curve top plateau, constrained to 100%; Bottom: curve bottom plateau, constrained 0%; Hill Slope: fixed value=−1. Potency data are reported aspIC50(app) values.

For kinases with no detectable inhibitory activity (Activity (% Control)=100% at both 10 and 100 nM), pIC50(app) is reported as <4. If inhibitory activity was similar at 10 and 100 nM an exemplary compound and at least one datapoint >75%, pIC50(app) is reported as <7 (the highest test concentration). If inhibitory activity was similar at 10 and 100 nM and both datapoints <75%, pIC50(app) is not calculated and reported as Not Determined (ND). For kinases with data that did not adhere to the assumption of greater inhibitory activity at 100 nM an exemplary compound as compared to 10 nM test concentration (20% threshold), pIC50(app) is reported as ND.

The TYK2-JH2 partition index for an exemplary compound was calculated using the pIC50(app) from scanEDGE panel screening, JAK family pIC50 values, and the LCK pIC50 determined in the SAFETYscan47 panel. Calculations followed those previously described (3). Briefly, the potencies for an exemplary compound binding for all kinase targets were used to calculate individual kinase occupancies (zKinaseX=1/IC50(app) (M)) and summed to generate a ztotal. For kinases where pIC50(app)<4 or <7, IC50 values of 10−4 (M) or 10−7 (M) were used, respectively. The partition index for TYK2-JH2 was then calculated as:PTYK2-JH2=zTYK2-JH2/z total Example 10. Safety47 Panels Assay Protocol These studies were conducted at Eurofins-DiscoverX (San Diego, CA) using target-specific assay platforms, including Hit Hunter® cAMP, Calcium No WashPLUS, PathHunter® NHR Pro and NHR NT, KINOMEscan®, and FLIPR®. Where appropriate, activity of the test compound was tested in bothinhibition/antagonist and stimulation/agonist modes. An exemplary compound was tested with a final assay concentration range from 50 pM to 1 µM.

Parameters Measured and Calculated

For inhibition/antagonist assays, Response (%) was calculated as:

$$\text{Response} = 100 * [1 - (\text{Test Compound Signal} - \text{Background})/$$
$$(EC80 \text{ Control Signal} - \text{Background})]$$

For stimulation/agonist assays, Response (%) was calculated as: Response=

$$100 * [(\text{Test Compound Signal} - \text{Background})/$$
$$(\text{Control Ligand Max Signal} - \text{Background})]$$

Data were then analyzed by non-linear regression to determine potencies using the following equation in Collaborative Drug Discovery (Burlingame, CA):

$$Y = \text{Bottom} + (\text{Top} - \text{Bottom})/)(1 + 10[(-pIC50 - X) * \text{HillSlope}])$$

where X: log concentration in Molar; Y: Activity (% Control); Top: curve top plateau, fixed range from 80-120%; Bottom: curve bottom plateau, fixed range from −20-20%; Hill Slope: unconstrained. Potency data are reported as pIC50 or pEC50 values.

Example 11a. Whole Blood Potency (IFNα/pSTAT5)

Heparinized human whole blood (5 different donors) was acquired from the Stanford Blood Center and used fresh for each experiment. Whole blood was plated (90 µl per well) into a 96-well assay plate immediately prior to initiation of the assay.

Test compounds were diluted serially (3-fold) in DMSO to generate a series of 10 concentrations (at 200× final assay concentrations). The highest concentration was 667 µM, to generate a dilution series from 3.4 nM to 66.7 µM in DMSO. DMSO dilutions were diluted 10-fold in PBS to generate 20× final assay concentrations.

Pre-incubation of compounds and whole blood was initiated by adding 5 µl of the compound dilutions to the assay plates and incubated for 30 min at 37° C. Blood was then stimulated by the addition of IFN-α (5 µl of 200 ng/ml) (Miltenyi #130-093-873) followed by incubation at 37° C. for 15 min. Assays were terminated by the addition of Lyse/Fix (BD Biosciences #558049) (60 µl treated blood+1 ml Lyse/Fix) and incubated for 10 min. Cells were diluted 1:1 with Wash Buffer (PBS+0.3% BSA) and centrifuged to pellet white blood cells. Fixed cells were washed once with Wash Buffer and the pelleted cell plate was frozen at −80° C.

Cells were thawed and washed once with Wash Buffer prior to the addition of the α-CD3-Blue520 antibody (2 µg/ml final concentration; Biolegend #300481) and incubated for 30 min. Cells were washed twice in Wash Buffer followed by permeabilization in 100% cold methanol for 15 min. Cells were washed three times in Wash Buffer prior to the addition of the α-CD4-APC antibody (0.5 µg/ml final concentration; Biolegend #300514) and the α-pSTAT5-PE antibody (0.67 µg/ml final concentration; Biolegend #936904) and incubated for 90 min. Cells were washed twice in Wash Buffer and resuspended in 90 µl Wash Buffer prior to running on a LSRII flow cytometer (BD Biosciences, San Jose, CA). Total T cells (CD3+) and CD4+ cells were gated, and the Mean Fluorescence Intensity (MFI) was determined from the PE channel to quantify pSTAT5 signal.

The pSTAT5 MFI in the CD4+ gate was used to calculated Activity (% Control):

$$\text{Activity} = 100 * [(\text{Test Compound Signal} - \text{Background})/(DMSO \text{ Control Signal} - \text{Background})]$$

Figure 5A:
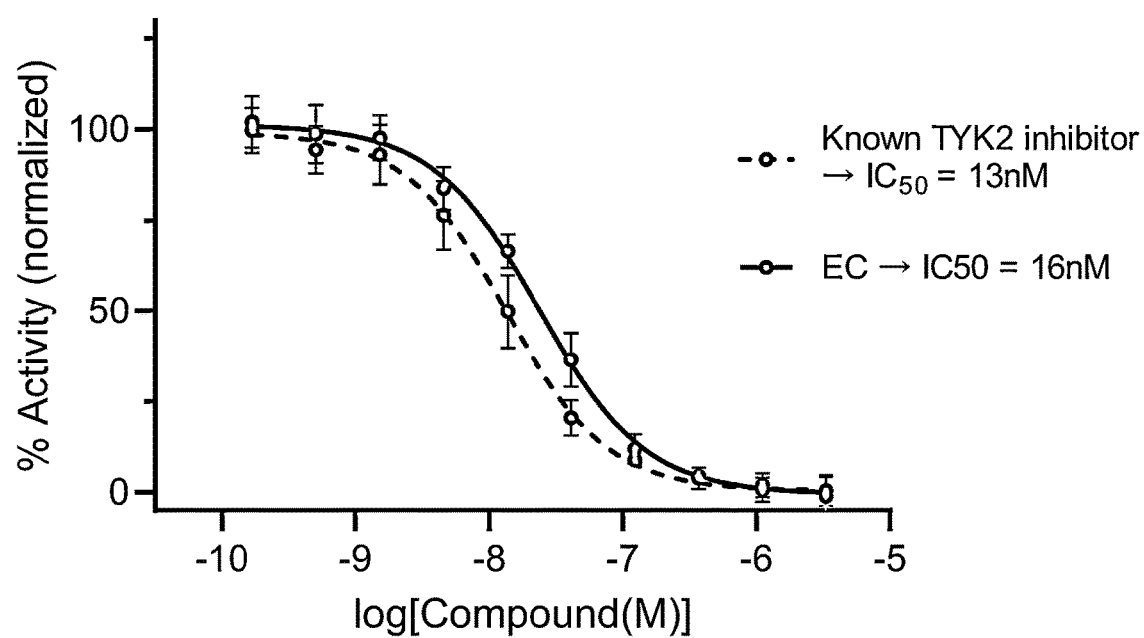
FIG. 5A-FIG. 5B. Exemplary compounds of the invention demonstrated potency for TYK2-JH2 in whole blood in the (A) IFNα/pSTAT5 and (B) IL-23/pSTAT3 signaling pathways.

Data were then analyzed by non-linear regression to determine inhibitory potencies using the following equation in Collaborative Drug Discovery (Burlingame, CA):

$$Y = \text{Bottom} + (\text{Top} - \text{Bottom})/(1 + 10[(-pIC50 - X) * HillSlope])$$

where X: log concentration in Molar; Y: Activity (% Control); Top: curve top plateau; Bottom: curve bottom plateau, fixed range from −20-20%; Hill Slope: unconstrained. Potency data are reported as pIC50 or pIC90 values ±SD. IC90 values are defined from the fitted IC50 values: IC90= (1/9)(1/HillSlope)*IC50. FIG. 5A.

Example 11b. Whole Blood Potency (IL-23/pSTAT3)

Heparinized human whole blood (4 different donors) was acquired from the Stanford Blood Center and used fresh for each experiment. Whole blood was plated (90 µl per well) into a 96-well assay plate immediately prior to initiation of the assay.

Test compounds were diluted serially (3-fold) in DMSO to generate a series of 10 concentrations (final compound concentrations 10 to 0.0005 [µM], in 0.5% DMSO, and 4.5% PBS).

Pre-incubation of compounds and whole blood was initiated by adding 5 µl of the compound dilutions to the assay plates and incubated for 30 min at 37° C. Blood was then stimulated by the addition of IL-23 (3 pM final concentration) (Biotechne #1290-IL-010/CF) followed by incubation at 37° C. for 30 min. Assays were terminated by the addition of Lyse/Fix (BD Biosciences #558049) (80 µl treated blood+1 ml Lyse/Fix) and incubated for 10 min. Cells were diluted 1:1 with Wash Buffer (PBS+0.3% BSA) and centrifuged to pellet white blood cells. Fixed cells were washed once with Wash Buffer.

Cells were washed once with Wash Buffer prior to the addition of the CD3 (BD Biosciences #BDB570237), CD161 (Biolegend #339910), and CD45 (Biolegend #304106) antibodies and incubated for 30 min. Cells were washed twice in Wash Buffer followed by permeabilization in 100% cold methanol for 15 min. Cells were washed three times in Wash Buffer prior to the addition of pSTAT3-PE antibody (eBioscience #501122408) and incubated for 90 min at 4° C. Cells were washed twice in Wash Buffer and resuspended in 90 µl Wash Buffer prior to running on a LSRII flow cytometer (BD Biosciences, San Jose, CA). CD161+ and CD45RA− T-cells were gated, and the Mean Fluorescence Intensity (MFI) was determined from the PE channel to quantify pSTAT3 signal.

Figure 5B:
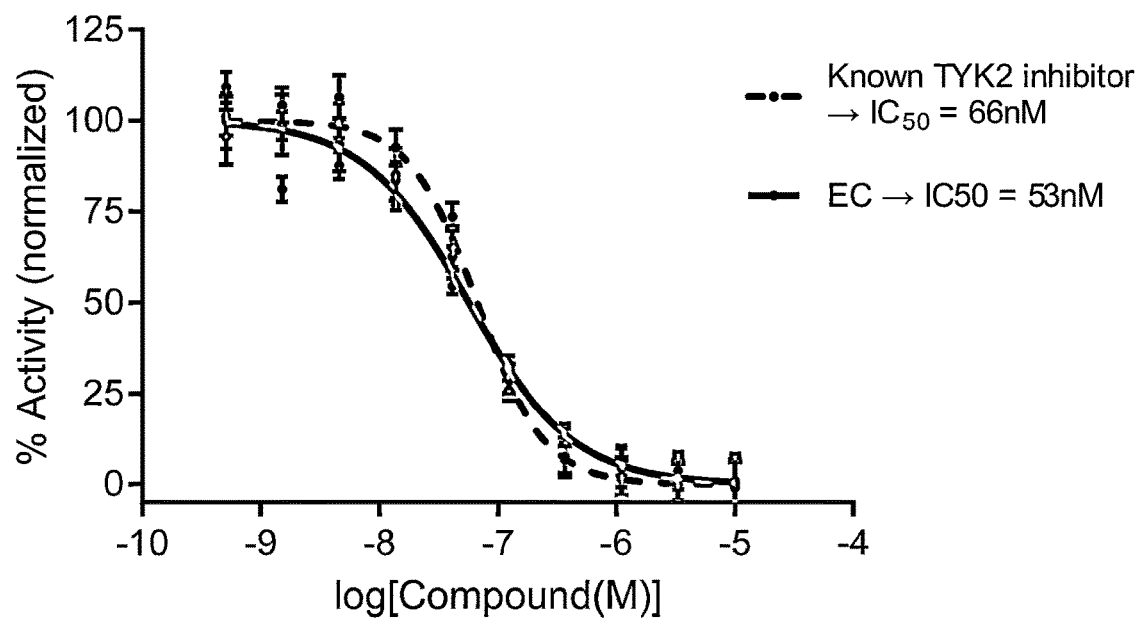

Data were then analyzed by non-linear regression to determine inhibitory potencies using the following equation in Collaborative Drug Discovery (Burlingame, CA):

$$Y = \text{Bottom} + (\text{Top} - \text{Bottom})/(1 + 10[(-pIC50 - X) * HillSlope])$$

where X: log concentration in Molar; Y: Activity (% Control); Top: curve top plateau; Bottom: curve bottom plateau, fixed range from −20-20%; Hill Slope: unconstrained. Potency data are reported as pIC50 or pIC90 values ±SD. IC90 values are defined from the fitted IC50 values: IC90= (1/9)(1/HillSlope)*IC50. FIG. 5B.

Example 12. Anti-CD-Induced Mouse Model of Inflammatory Bowel Disease (IBD)

This study was conducted in accordance with the Inotiv Boulder test facility standard operating procedures (SOPs), the World Health Organization Quality Practices in Basic Biomedical Research guidelines, and in compliance with all state and federal regulations, including USDA Animal Welfare Act 9 CFR Parts 1-3. Federal Register 39129, Jul. 22, 1993. This study was conducted in accordance with The Guide for the Care & Use of Laboratory Animals (8th Edition) and therefore in accordance with all Inotiv Boulder IACUC approved policies.

Prior to the start of the study, 6-7 week old, RAGN 12 mice (Taconics) were acclimated for approximately 4 days. On study day −1, mice were weighed and randomized into treatment groups based on body weight. On study day 0, 200 µg of anti-CD40 monoclonal antibody (BioXcell) was administered intraperitoneally to induce disease. Test articles were dosed orally BID (the exception was the known TYK2 inhibitor at 3 mpk, which was dosed QD, with vehicle administered as the second daily dose). Bodyweight was measured daily on study days 1-6.

On day 7, the study was terminated; mice were anesthetized with Isoflurane and bled to exsanguination followed by cervical dislocation. The entire colon was removed, measured, and weighed. The plasma (for PK) and colon (for histology and cytokine measurements) samples were collected. Histopathology samples were evaluated for edema, inflammation (extent of macrophage, lymphocyte and polymorphonuclear (PMN) cell infiltration), gland loss, erosion, and hyperplasia.

Figure 6A:
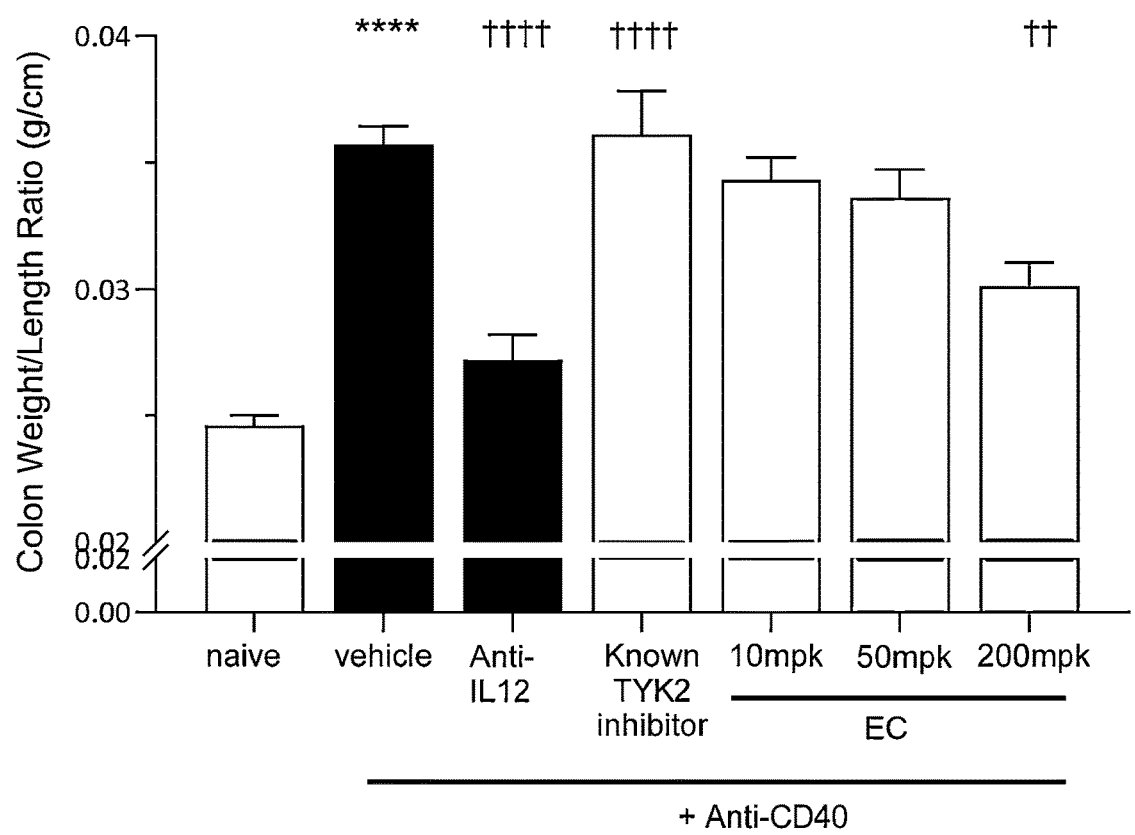
Figure 6B:
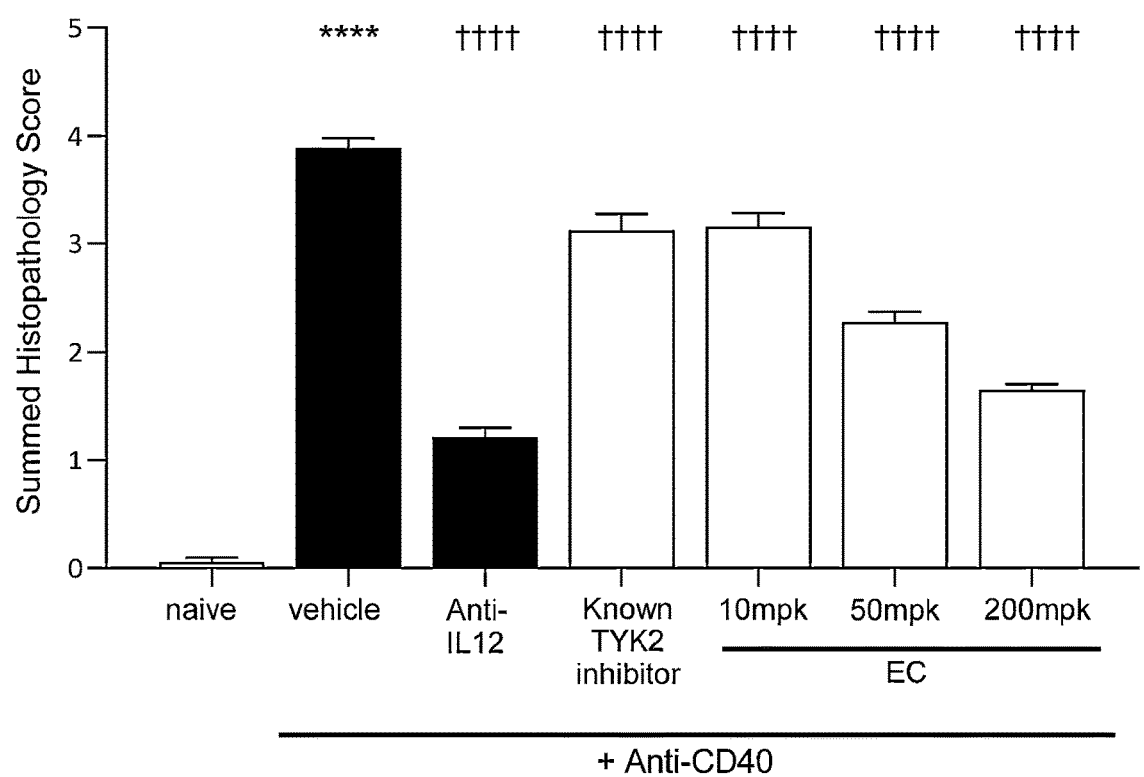
Figure 6C:
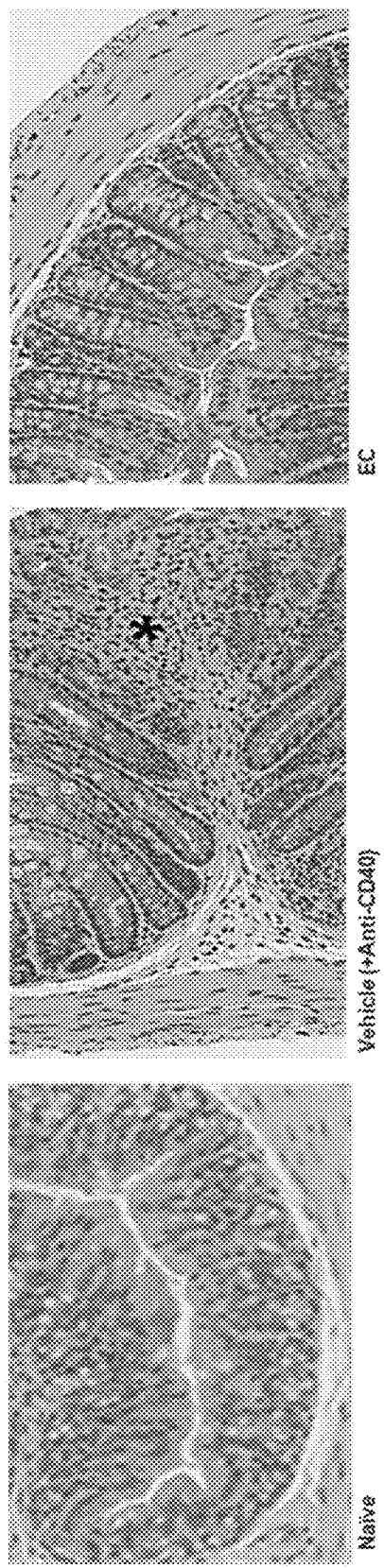
Figure 6D:
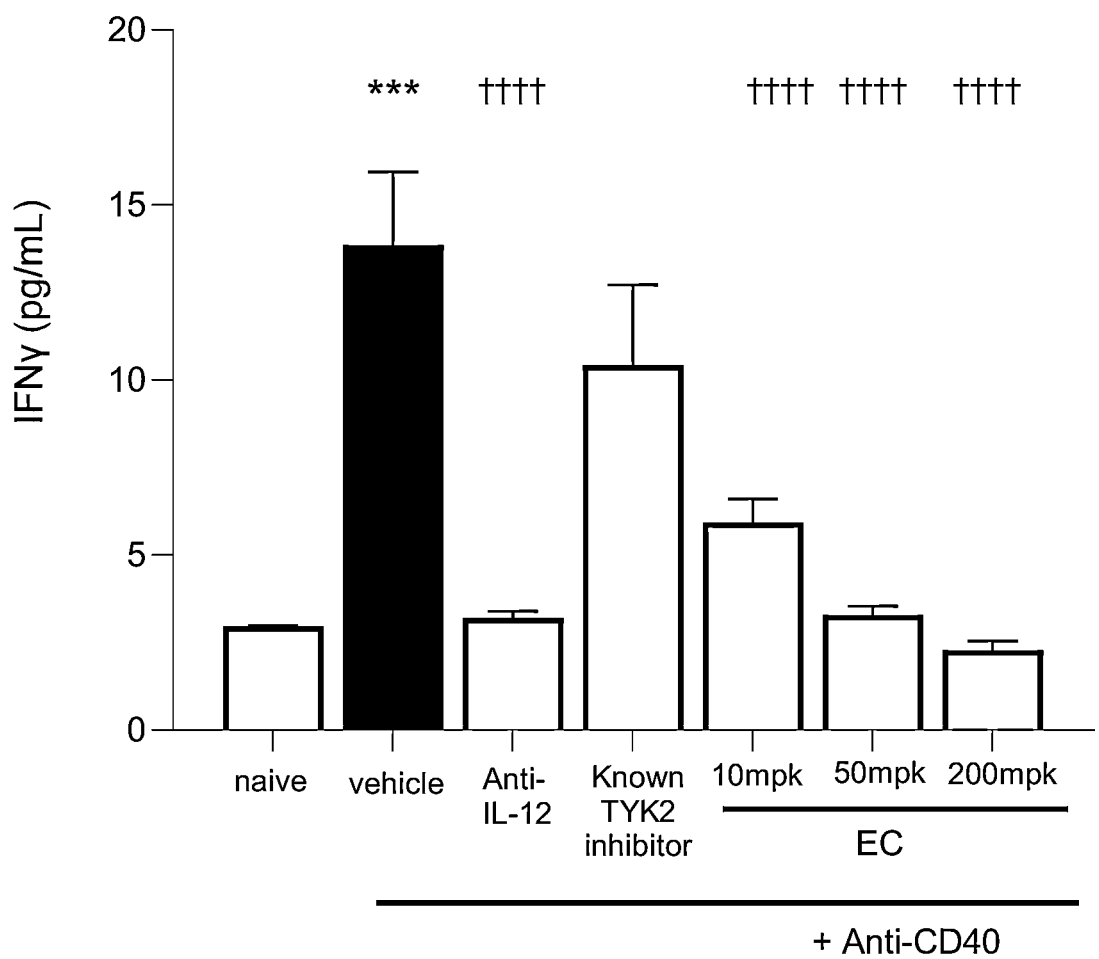
Figure 6E:
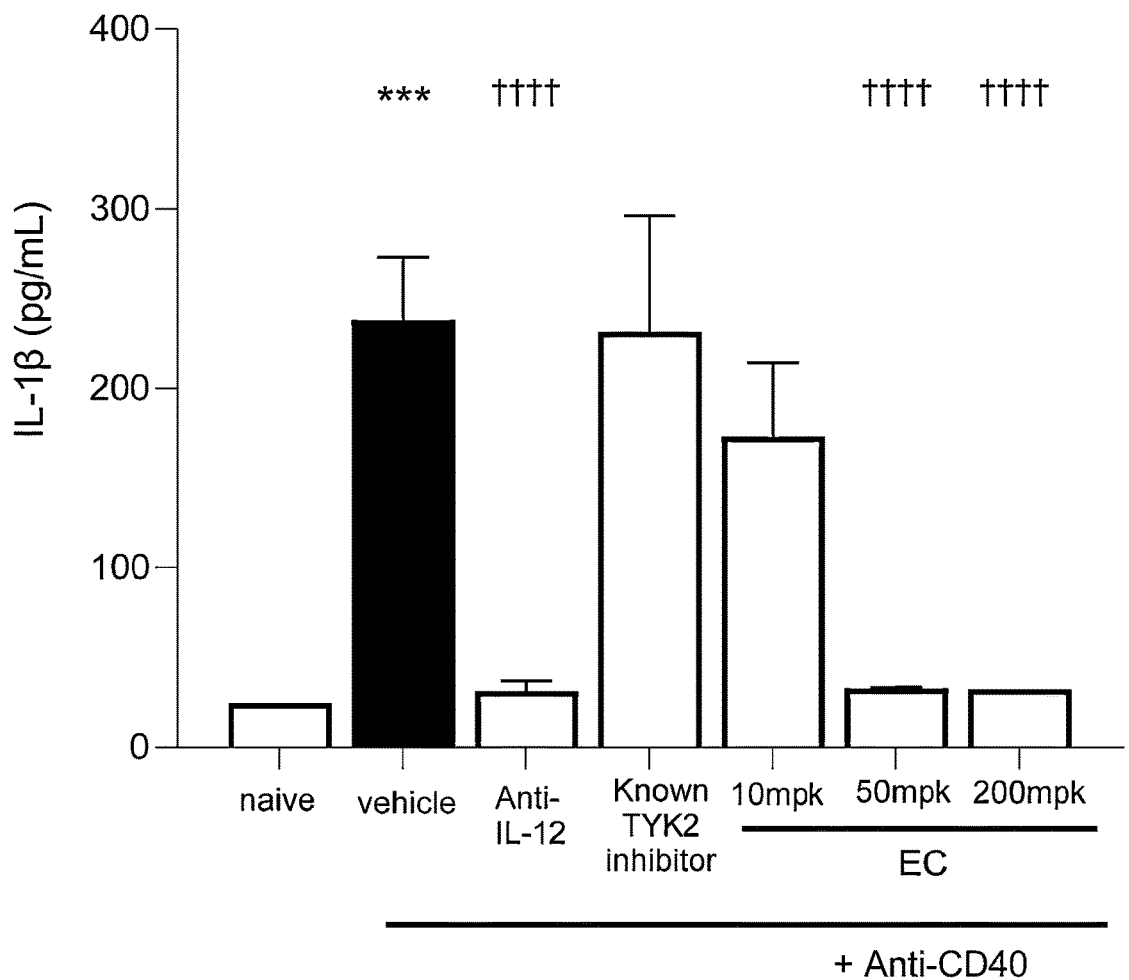
Figure 6F:
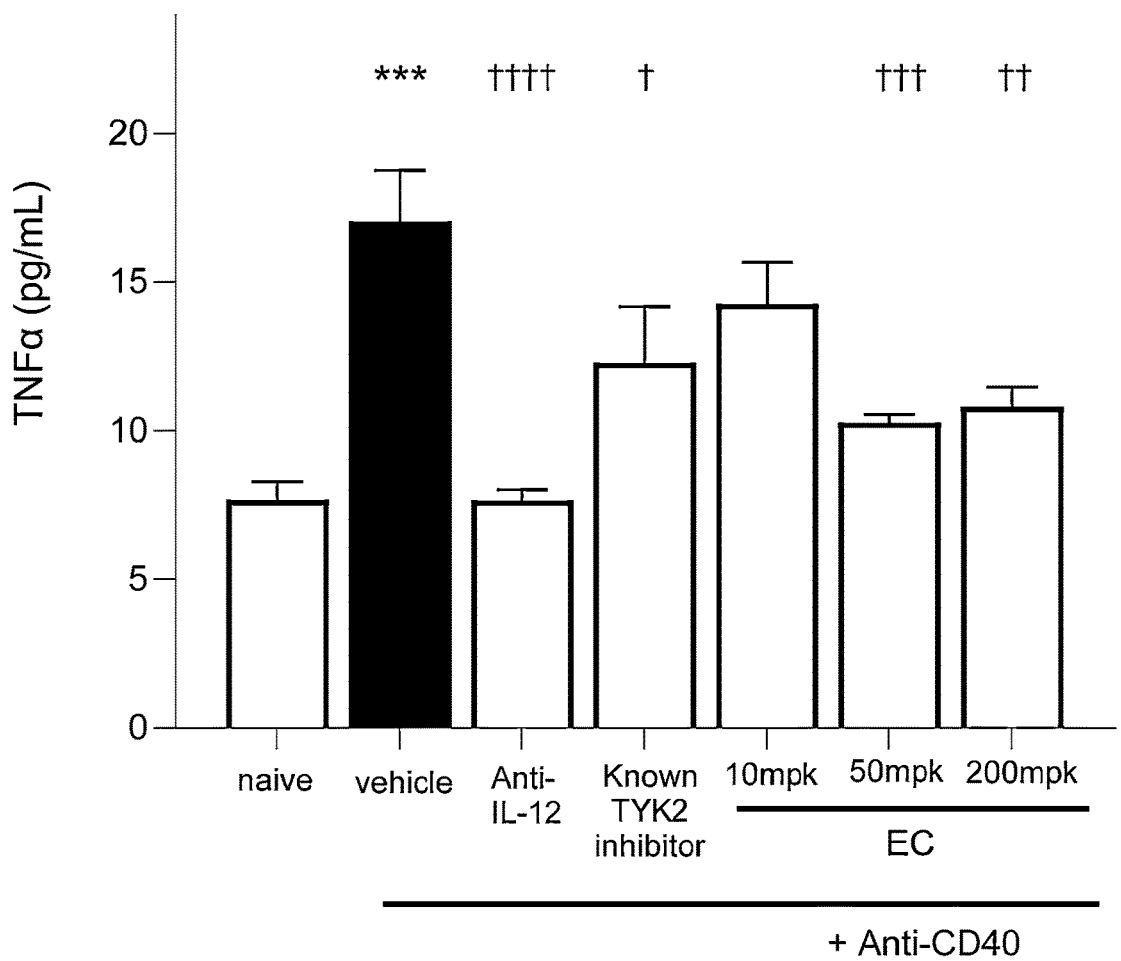
Figure 6G:
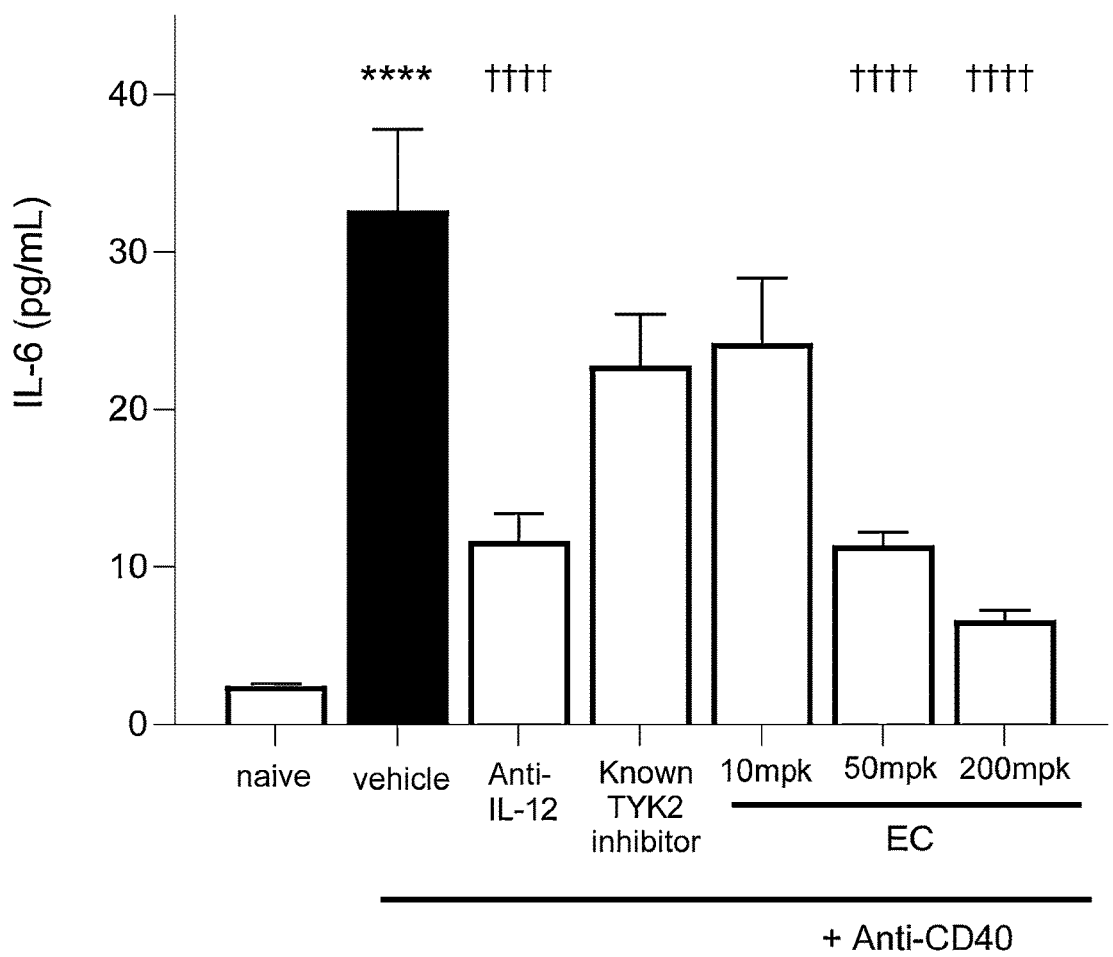
Figure 6H:
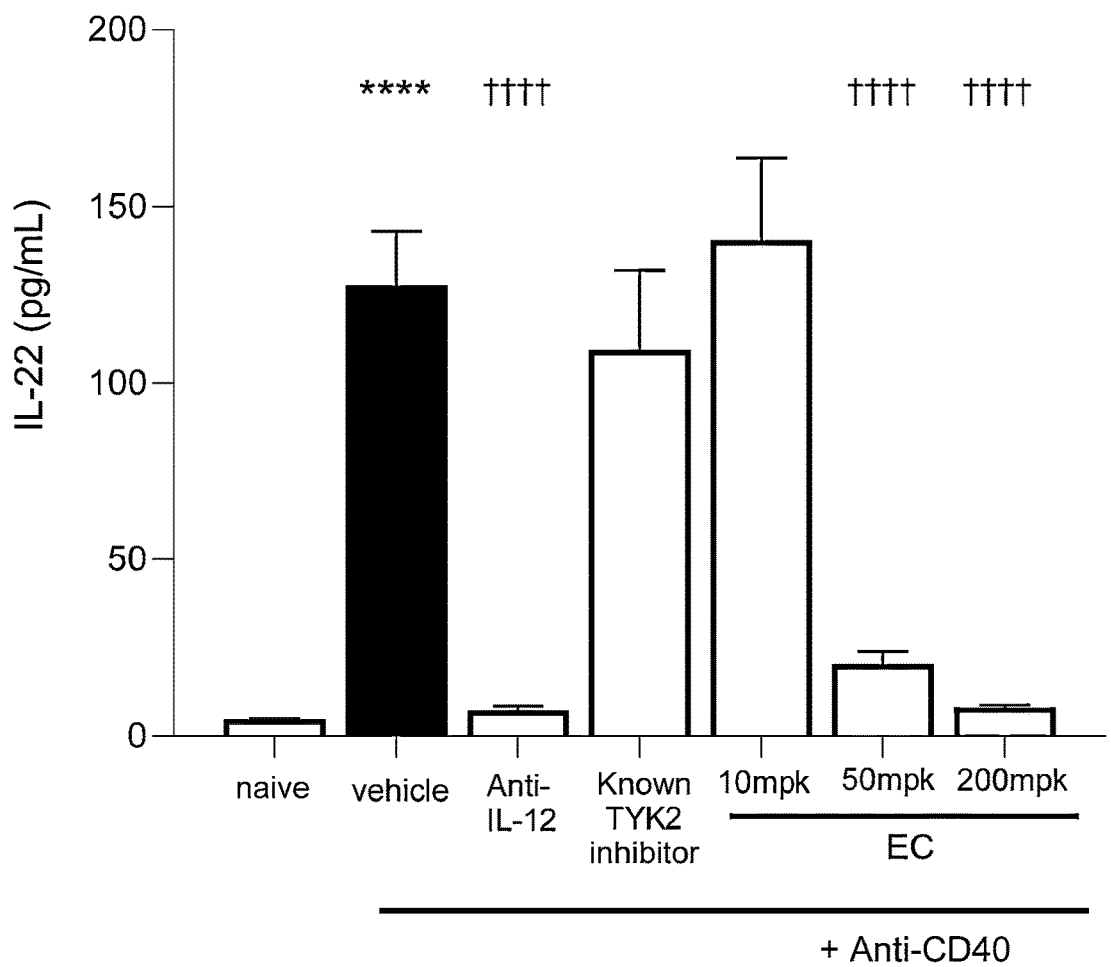
Figure 6I:
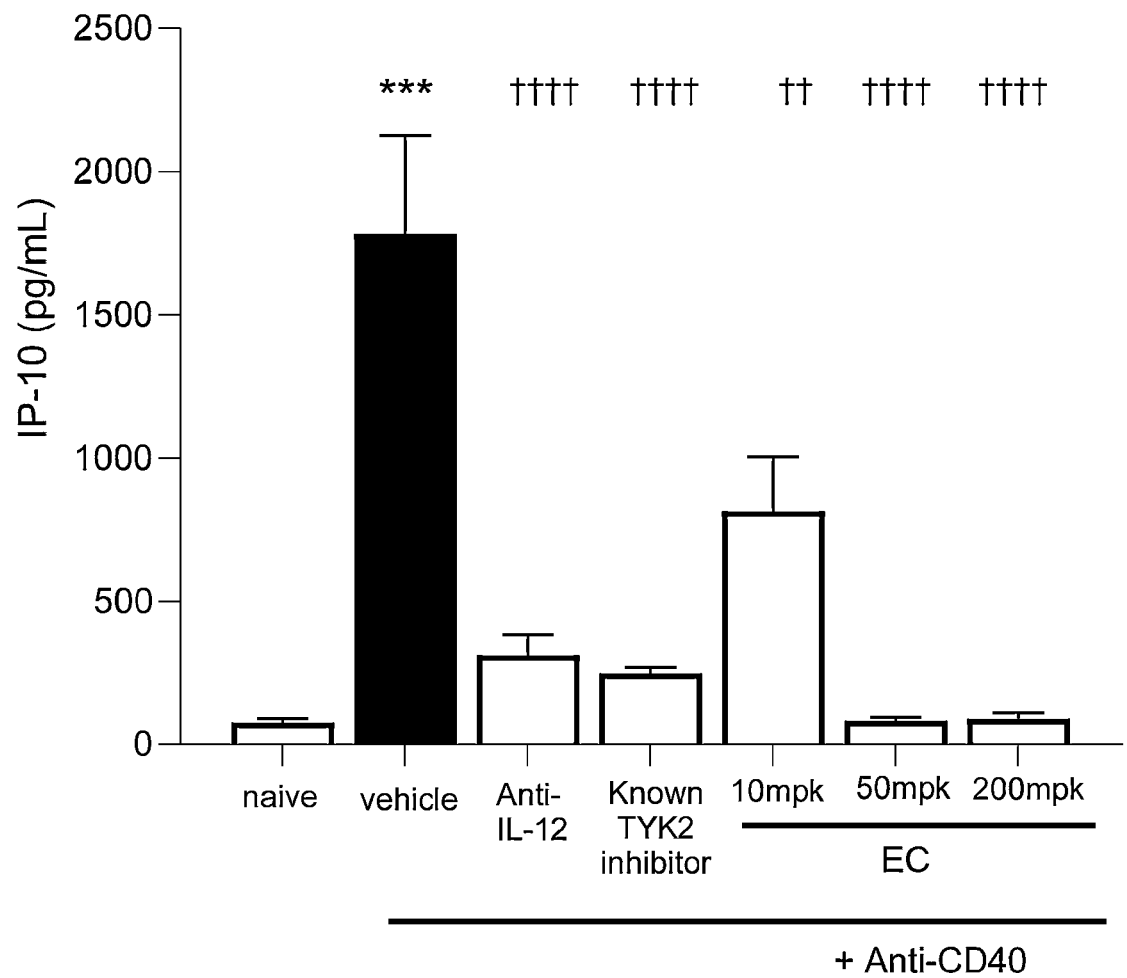

Overall efficacy of test articles is based on a ratio of colon weight to length, and colon histopathology (FIGS. 6A and 6B). Additional readouts of the model support activity of an exemplary compound in IBD (FIG. 6C-6I).

Example 13. MOG(35-55)-Induced Chronic Experimental Autoimmune Encephalomyelitis (EAE)

This study was conducted in accordance with the Inotiv Boulder test facility standard operating procedures (SOPs), the World Health Organization Quality Practices in Basic Biomedical Research guidelines, and in compliance with all state and federal regulations, including USDA Animal Welfare Act 9 CFR Parts 1-3. Federal Register 39129, Jul. 22, 1993. This study was conducted in accordance with The Guide for the Care & Use of Laboratory Animals (8th Edition) and therefore in accordance with all Inotiv Boulder IACUC approved policies and procedures. A "blanket" IACUC protocol for this specific working protocol was approved by the Inotiv Boulder IACUC (IB-054).

Prior to the start of the study, 11-13 week old, C57BL/6J mice (JAX) were acclimated for at least 7 days. On study day −1, mice in the naïve, vehicle, disease control, and prophylactic treatment groups were weighed and randomized into treatment groups based on body weight. On study day 0, all animals were anesthetized with isoflurane to inject MOG(35-55) in CFA SC; 2 hours post MOG(35-55) injection mice were administered PTX IP. A second IP injection of PTX was given approximately 24 hours post immunization.

Dosing was initiated for the naïve, vehicle, disease control, and prophylactic treatment groups on day 0. For the therapeutic treatment groups, mice were randomized into treatment groups on day 11 when at least 20% of all animals exhibited disease. Dosing for the therapeutic groups was initiated on day 11.

Figure 7A:
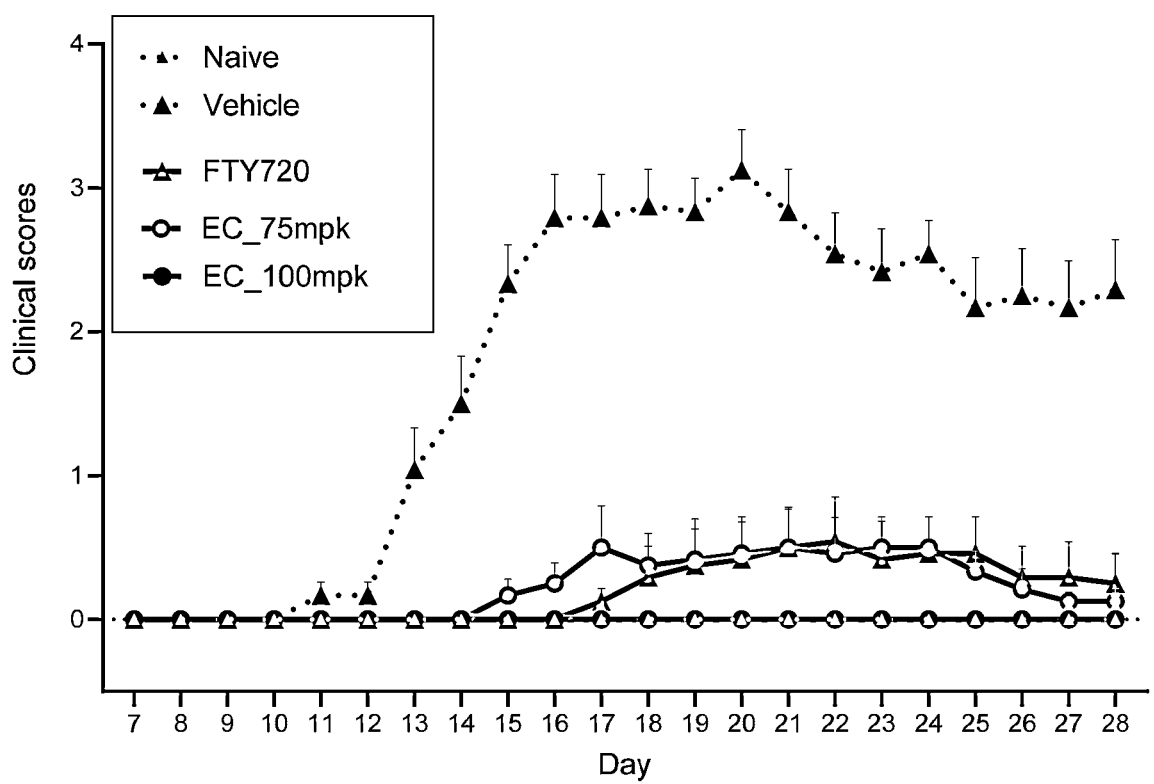
FIG. 7A-7B. Exemplary compounds of the invention demonstrated dose-dependent inhibition of clinical scores in a 28-day MOG (35-55)-induced chronic experimental autoimmune encephalomyelitis (EAE) model in C57BLJ6 mice. Inhibition observed with both (A) prophylactic and (B) therapeutic dosing of exemplary compound.
Figure 7B:
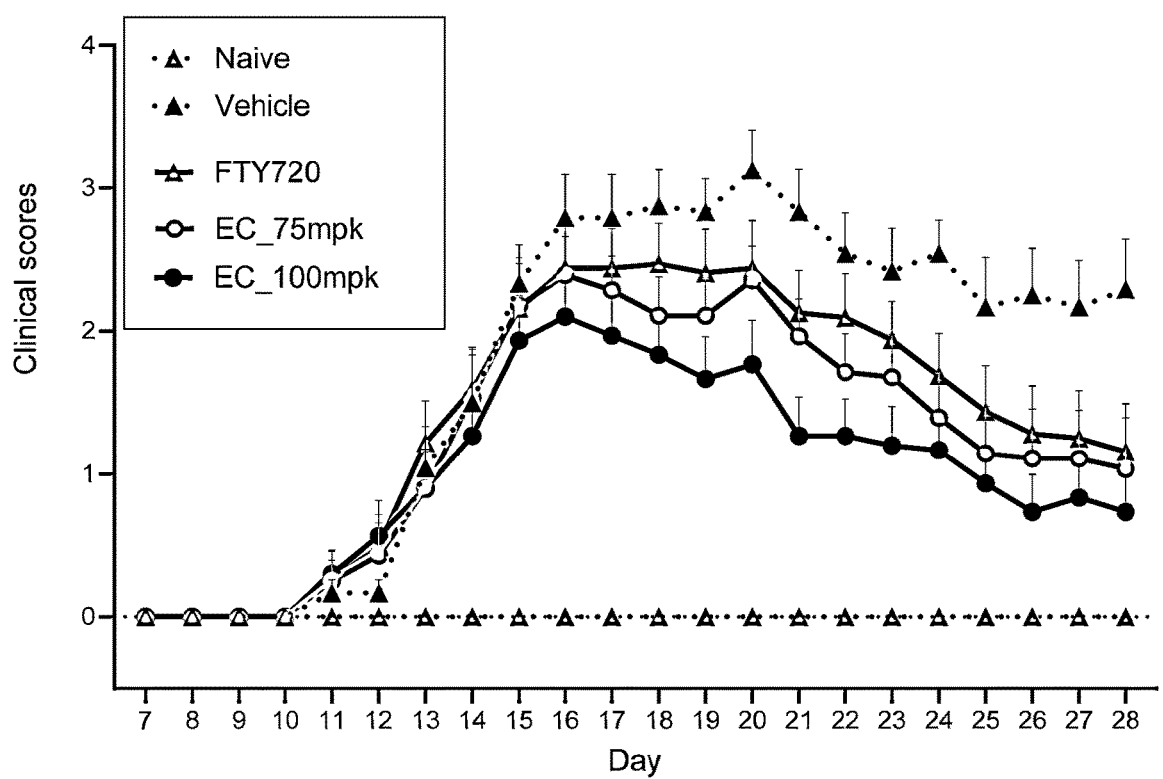

Bodyweight was measured daily for all mice starting on day 0. Clinical scoring was initiated for all mice starting on day 7. On day 28, the study was terminated for all groups. The mice were bled to exsanguination followed by bilateral penurmothoracotamy. The spinal cord was removed for histopathology. The plasma (for PK) samples were collected. Histopathology samples will be evaluated for inflammation and demyelination using hematoxylin and eosin (H&E)+Luxol Fast Blue (LFB) dual stain. Overall efficacy of test articles is based on clinical scores and histopathology scores (FIGS. 7A and 7B). The EAE animal model is most frequently used to measure inflammation in the CNS. The clinical scores support dose-dependent inhibition of inflammation in the CNS by an exemplary compound.

While certain embodiments of the present invention have been described and/or exemplified above, various other embodiments will be apparent to those skilled in the art from the foregoing disclosure. The present invention is, therefore, not limited to the particular embodiments described and/or exemplified but is capable of considerable variation and modification without departure from the scope and spirit of the appended claims.

A number of patent and non-patent publications are cited herein in order to describe the state of the art to which this invention pertains. The entire disclosure of each of these publications is incorporated by reference herein for all purposes.

What is claimed is:

1. A compound of Formula I:

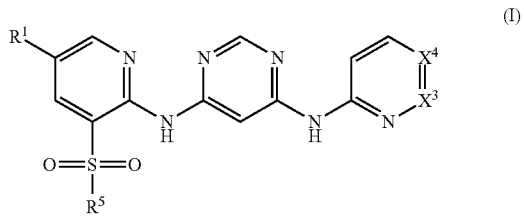

wherein
$R^1$ is a member selected from H, halogen, substituted or unsubstituted straight- or branched-chain $C_1$-$C_6$ alkyl, and substituted or unsubstituted straight- or branched-chain $C_1$-$C_6$ alkoxy;
$R^5$ is $C_1$-$C_6$ alkyl; and
$X^3$ is selected from N and $CR^7$;
$X^4$ is selected from and $CR^8$, wherein
$R^7$ is selected from H, substituted or unsubstituted $C_1$-$C_6$ alkyl, and substituted or unsubstituted $C_1$-$C_6$ aminoalkyl, wherein $R^7$ and $R^8$, together with the carbon atoms to which they are joined, are optionally joined to form a ring selected from substituted or unsubstituted cycloalkyl and substituted or unsubstituted heterocycloalkyl,
$R^8$ is selected from;
substituted or unsubstituted $C_1$-$C_6$ alkyl,

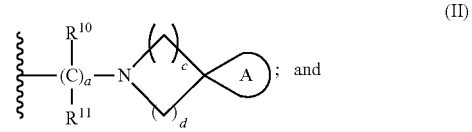

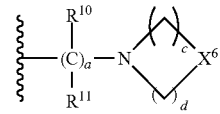

wherein
one or more carbon atom of a ring in Formula II or Formula III is optionally substituted with a member independently selected from halogen, and substituted or unsubstituted alkyl;
a is selected from the integers 0 and 1;
$R^{10}$ and $R^{11}$ are independently selected from H, halogen and substituted or unsubstituted $C_1$-$C_6$ alkyl;
c and d are independently selected from the integers 0, 1, 2, 3 and 4 with the proviso that the sum c+d is selected from the integers 3, 4, 5, and 6;
A is a ring system selected from substituted or unsubstituted cycloalkyl and substituted or unsubstituted heterocylcoalkyl; and
$X^6$ is selected from O, $NR^{12}$, and $CR^{12}R^{13}$ in which
$R^{12}$ and $R^{13}$ are independently selected from H and substituted or unsubstituted alkyl,
or a pharmaceutically acceptable salt, tautomer, solvate or hydrate thereof.

2. The compound according to claim 1, wherein the ring system includes an oxygen and a nitrogen.

3. The compound according to claim 1, wherein $R^8$ is selected from:

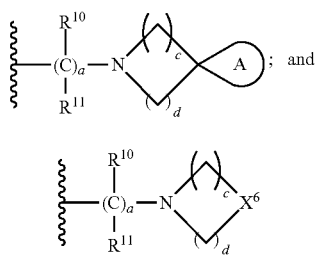

wherein
A is a ring system selected from substituted or unsubstituted cycloalkyl and substituted or unsubstituted heterocycloalkyl, wherein one or more carbon atom is substituted with halogen;
$R^{10}$ and $R^{11}$ are independently selected from H, halogen and substituted or unsubstituted $C_1$-$C_6$ alkyl;
a is selected from the integers 0 and 1;
c and d are independently selected from the integers 0, 1, 2, 3 and 4 with the proviso that the sum c+d is selected from the integers 3, 4, 5, and 6; and
$X^6$ is selected from O, $NR^{12}$, and CR 12R 13
in which
$R^{12}$ and $R^{13}$ are independently selected from H, halogen, and substituted or unsubstituted alkyl.

4. The compound according to claim 3, wherein $R^{13}$ is selected from H and halogen.

5. The compound according to claim 1, wherein $X^3$ is $CR^7$.

6. The compound according to claim 3, wherein one of $R^{10}$ or $R^{11}$ is $CF_3$.

7. The compound according to claim 1 in which $R^1$ is F.

8. A pharmaceutical formulation comprising the compound the pharmaceutically acceptable salt, tautomer, solvate or hydrate thereof according to claim 1, and a pharmaceutically acceptable carrier.

9. The pharmaceutical formulation of claim 8, formulated for parenteral or oral administration.

10. The pharmaceutical formulation of claim 8, formulated for intravenous, subcutaneous or intraperitoneal injection.

11. A method of treating a TYK2-mediated disease in a subject in need thereof, comprising; administering to the subject a therapeutically effective amount of the compound, pharmaceutically acceptable salt, tautomer, solvate or hydrate thereof according to claim 1, wherein the TYK2-mediated disease is susceptible to treatment with a TYK2 inhibitor.

12. The method according to claim 11, wherein the compound, salt, tautomer, hydrate or solvate is administered to the subject as a pharmaceutically acceptable formulation.

13. The method according to claim 12, wherein the pharmaceutically acceptable formulation is formulated for intravenous, subcutaneous, intrathecal, intracerebral ventricular or intraperitoneal injection.

14. A method of treating an autoimmune or inflammatory disease in a subject in need thereof by inhibiting TYK2 kinase in the subject, the method comprising administering to the subject a therapeutically effective amount of the compound, pharmaceutically acceptable salt, tautomer, solvate or hydrate thereof according to claim 1, wherein the autoimmune/autoinflammatory disease is susceptible to treatment with a TYK2 inhibitor.

15. The method according to claim 14, wherein the disease is a member selected from Plaque Psoriasis, Psoriatic Arthritis, Lupus, and Inflammatory Bowel Disease.

16. A method of inhibiting TYK2, the method comprising bringing into contact with the TYK2 an effective TYK2-inhibiting amount of the compound, tautomer, solvate, hydrate, or a salt thereof.

17. The method according to claim 16, wherein the inhibition of the TYK2 kinase takes place in vivo or in vitro.

18. The method according to claim 15, wherein the Inflammatory Bowel Disease is a member selected from Crohn's, Ulcerative Colitis and a combination thereof.

* * * * *